(12) United States Patent
Wagner et al.

(10) Patent No.: US 11,053,301 B2
(45) Date of Patent: Jul. 6, 2021

(54) METHODS AND COMPOSITIONS RELATING TO COVALENTLY CIRCULARIZED NANODISCS

(71) Applicant: PRESIDENT AND FELLOWS OF HARVARD COLLEGE, Cambridge, MA (US)

(72) Inventors: Gerhard Wagner, Chestnut Hill, MA (US); Mahmoud Nasr, Boston, MA (US)

(73) Assignee: PRESIDENT AND FELLOWS OF HARVARD COLLEGE, Cambridge, MA (US)

(*) Notice: Subject to any disclaimer, the term of this patent is extended or adjusted under 35 U.S.C. 154(b) by 0 days.

(21) Appl. No.: 16/317,924

(22) PCT Filed: Jul. 17, 2017

(86) PCT No.: PCT/US2017/042307
§ 371 (c)(1),
(2) Date: Jan. 15, 2019

(87) PCT Pub. No.: WO2018/017442
PCT Pub. Date: Jan. 25, 2018

(65) Prior Publication Data
US 2019/0233501 A1 Aug. 1, 2019

Related U.S. Application Data

(60) Provisional application No. 62/363,395, filed on Jul. 18, 2016.

(51) Int. Cl.
*C07K 14/775* (2006.01)
*B82Y 5/00* (2011.01)
(Continued)

(52) U.S. Cl.
CPC ............ *C07K 14/775* (2013.01); *A61K 39/12* (2013.01); *A61K 39/39* (2013.01); *B82Y 5/00* (2013.01);
(Continued)

(58) Field of Classification Search
CPC .......... A61P 35/00; A61P 37/02; A61P 37/08; A61K 48/0075; A61K 38/00;
(Continued)

(56) References Cited

U.S. PATENT DOCUMENTS

| 7,048,949 | B2 | 5/2006 | Sligar et al. |
| 7,083,958 | B2 | 8/2006 | Sligar et al. |

(Continued)

FOREIGN PATENT DOCUMENTS

| EP | 2832741 A1 | 2/2015 |
| WO | 2018213372 A1 | 11/2018 |

OTHER PUBLICATIONS

Law et al. Tangier Disease. The Complete mRNA Sequence Encoding for Preproapo-A-I. JBC. 1985; 260(23): 12810-12814. (Year: 1985).*

(Continued)

*Primary Examiner* — Soren Harward
*Assistant Examiner* — Jia-Hai Lee
(74) *Attorney, Agent, or Firm* — Nixon Peabody LLP

(57) ABSTRACT

Described herein are methods and compositions relating to nanodiscs, e.g., phospholipid bilayers with a proteinaceous belt or border. Further provided herein are loopable membrane scaffold proteins, e.g., for forming nanodiscs.

4 Claims, 29 Drawing Sheets

Specification includes a Sequence Listing.

(51) Int. Cl.
- *A61K 39/39* (2006.01)
- *A61K 39/12* (2006.01)
- *B82Y 40/00* (2011.01)
- *C07K 1/04* (2006.01)
- *C07K 14/47* (2006.01)
- *C07K 14/705* (2006.01)
- *C12N 9/48* (2006.01)
- *C12N 9/80* (2006.01)
- *A61K 39/00* (2006.01)

(52) U.S. Cl.
CPC .............. *B82Y 40/00* (2013.01); *C07K 1/045* (2013.01); *C07K 1/047* (2013.01); *C07K 14/47* (2013.01); *C07K 14/705* (2013.01); *C12N 9/48* (2013.01); *C12N 9/80* (2013.01); *A61K 2039/55555* (2013.01); *C12N 2740/16134* (2013.01)

(58) Field of Classification Search
CPC ............ A61K 2039/6031; A61K 38/12; C07K 14/47; C07K 14/705; C07K 16/28; C07K 2317/94; C07K 2319/00; C07K 19/00; C07K 2319/50; C07K 5/06165; C07K 1/13; C07K 17/00; C07K 17/06; C07K 1/006; A61L 27/54; A61L 2300/252
See application file for complete search history.

(56) References Cited

U.S. PATENT DOCUMENTS

| | | | |
|---|---|---|---|
| 7,575,763 B2 | 8/2009 | Sligar et al. | |
| 7,592,008 B2 | 9/2009 | Sligar et al. | |
| 7,622,437 B2 | 11/2009 | Morrissey | |
| 7,662,410 B2 | 2/2010 | Sligar et al. | |
| 7,691,414 B2 | 4/2010 | Sligar et al. | |
| 2005/0182243 A1* | 8/2005 | Sligar .................... | C07K 14/47 530/350 |
| 2006/0057662 A1* | 3/2006 | Sligar .................... | C07K 14/47 435/69.1 |
| 2011/0305723 A1 | 12/2011 | Renner et al. | |
| 2011/0321183 A1 | 12/2011 | Ploegh et al. | |
| 2013/0337002 A1 | 12/2013 | Lange et al. | |

OTHER PUBLICATIONS

Antos et al. Site-Specific Protein Labeling via Sortase-Mediated Transpeptidation. Curr Protoc Protein Sci. Apr. 2009 ; Chapter 15: Unit-15.3, pp. 1-23. (Year: 2009).*

Scott et al. A Functioning Chimera of the Cyclic Nucleotide-Binding Domain From the Bovine Retinal Rod Ion Channel and the DNA-binding Domain From Catabolite Gene-Activating Protein. Biochemistry 2001, 40, 7464-7473. (Year: 2001).*

Miehling et al. "A Split-Intein-Based Method for the Efficient Production of Circularized Nanodiscs for Structural Studies of Membrane Proteins." ChemBioChem 19(18): 1927-1933 (2018).

Nasr et al. "Covalently circularized nanodiscs for studying membrane proteins and viral entry." Nature Methods 14(1): 49-52 (2017).

Nasr et al. "Creating large covalently circularized nanodiscs and their application in studying viral entry and genome translocation." Protein Science 24: 192-193 (2015).

Bayburt et al., "Membrane protein assembly into Nanodiscs", FEBS Letters 584(9):1721-1727 (2010).

Hagn et al., "Optimized phospholipid bilayer nanodiscs facilitate high-resolution structure determination of membrane proteins", J Am Chem Soc. 135(5):1919-1925 (2013).

Nath et al., "Single-molecule fluorescence spectroscopy using phospholipid bilayer nanodiscs", Methods Enzymol. 472:89-117 (2010).

Raschle et al., "Structural and functional characterization of the integral membrane protein VDAC-1 in lipid bilayer nanodiscs", J. Am. Chem. Soc. 131(49):17777-17779 (2009).

Sachse et al., "Membrane protein synthesis in cell-free systems: from bio-mimetic systems to bio-membranes", FEBS Letters 588(17):2774-2781 (2014).

Schuler et al., "Nanodiscs as a new tool to examine lipid-protein interactions", Methods Mol Biol. 974:415-433 (2013).

Sheng et al., "In vivo adsorption of autoantibodies in myasthenia gravis using Nanodisc-incorporated acetylcholine receptor", Exp. Neurol. 225(2):320-327 (2010).

Tapaneeyakorn et al., "Solution- and solid-state NMR studies of GPCRs and their ligands", Biochim Biophys Acta. 1808(6):1462-1475 (2011).

Tzitzilonis et al., "Detergent/nanodisc screening for high-resolution NMR studies of an integral membrane protein containing a cytoplasmic domain", PLoS One 8(1):e54378 (2013).

Xu et al., "Three-dimensional structure of Bax-mediated pores in membrane bilayers", Cell Death and Disease 4:e683 (2013).

Bayburt et al., "Self-assembly of discoidal phospholipid bilayer nanoparticles with membrane scaffold proteins", Nano Letters 2(8):853-856 (2002).

Denisov et al., "Directed self-assembly of monodisperse phospholipid bilayer Nanodiscs with controlled size", J. Am. Chem. Soc. 126(11):3477-3487 (2004).

Gluck et al., "Integral membrane proteins in nanodiscs can be studied by solution NMR spectroscopy", J Am Chem Soc. 131(34):12060-12061 (2009).

Langecker et al., "DNA nanostructures interacting with lipid bilayer membranes", Acc Chem Res. 47(6):1807-1815 (2014).

Mitra, "Nanodiscs: Membrane Protein Research in Near Native Conditions", Mater Methods 3:177 (2013).

Wang et al., "Smaller Nanodiscs are Suitable for Studying Protein Lipid Interactions by Solution NMR", Protein J 34 (3):205-211 (2015).

\* cited by examiner

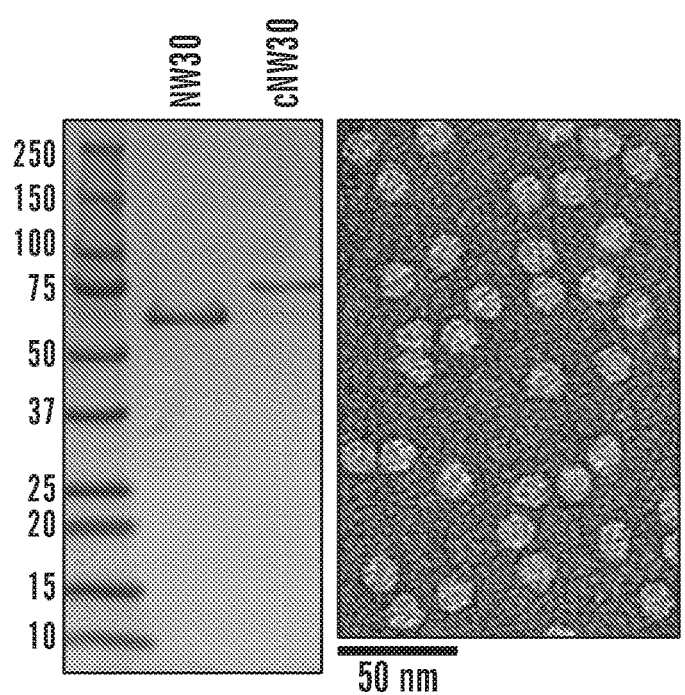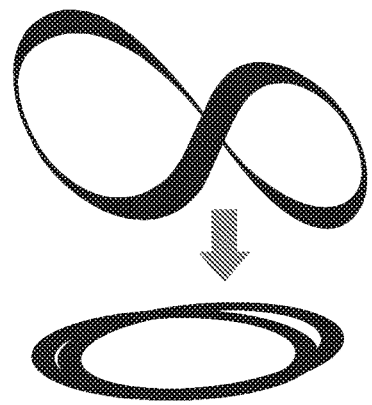
FIG. 3A
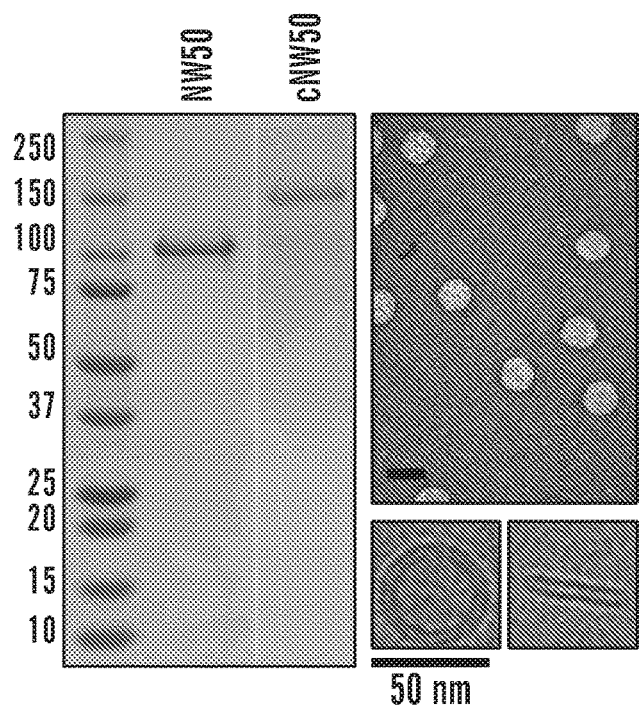
FIG. 3B  FIG. 3C

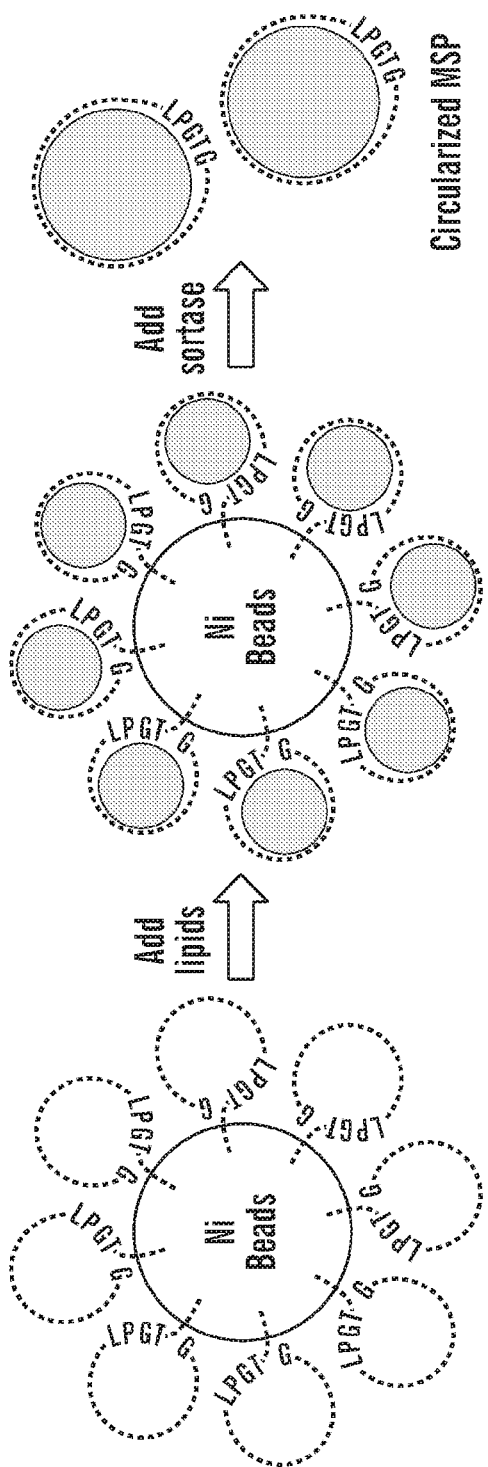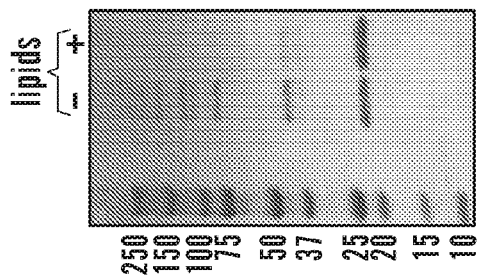
FIG. 9A
FIG. 9B

NW50 (amino acid sequence after TEV cleavage)
GSTFSKLREQLGPVTQEFWDNLEKETEGLRQEMSKDLEEVKAKVQPYLDDFQKKWQEEM
ELYRQKVEPLRAELQEGARQKLHELQEKLSPLGEEMRDRARAHVDALRTHLAPYSDELRQ
RLAARLEALKENGGARLAEYHAKATEHLSTLSEKAKPALEDLRQGLLPVLESFKVSFLSALE
EYTKKLNTQGTPVTQEFWDNLEKETEGLRQEMSKDLEEVKAKVQPYLDDFQKKWQEEMEL
YRQKVEPLRAELQEGARQKLHELQEKLSPLGEEMRDRARAHVDALRTHLAPYSDELRQRL
AARLEALKENGGARLAEYHAKATEHLSTLSEKAKPALEDLRQGLLPVLESFKVSFLSALEEY
TKKLNTQGTPVTQEFWDNLEKETEGLRQEMSKDLEEVKAKVQPYLDDFQKKWQEEMELY
RQKVEPLRAELQEGARQKLHELQEKLSPLGEEMRDRARAHVDALRTHLAPYSDELRQRLA
ARLEALKENGGARLAEYHAKATEHLSTLSEKAKPALEDLRQGLLPVLESFKVSFLSALEEYT
KKLNTQGTPVTQEFWDNLEKETEGLRQEMSKDLEEVKAKVQPYLDDFQKKWQEEMELYR
QKVEPLRAELQEGARQKLHELQEKLSPLGEEMRDRARAHVDALRTHLAPYSDELRQRLAA
RLEALKENGGARLAEYHAKATEHLSTLSEKAKPALEDLRQGLLPVLESFKVSFLSALEEYTK
KLNTQGTPVTQEFWDNLEKETEGLRQEMSKDLEEVKAKVQPYLDDFQKKWQEEMELYRQ
KVEPLRAELQEGARQKLHELQEKLSPLGEEMRDRARAHVDALRTHLAPYSDELRQRLAARL
EALKENGGARLAEYHAKATEHLSTLSEKAKPALEDLRQGLLPVLESFKVSFLSALEEYTKK<u>L
NTQLPGT</u>GAAALEHHHHHH

*FIG. 16*

METHODS AND COMPOSITIONS RELATING TO COVALENTLY CIRCULARIZED NANODISCS

CROSS-REFERENCE TO RELATED APPLICATIONS

This application is a 35 U.S.C. § 371 National Phase Entry Application of International Application No. PCT/US2017/042307 filed Jul. 17, 2017, which designates the U.S. and claims benefit under 35 U.S.C. § 119(e) of U.S. Provisional Application No. 62/363,395 filed Jul. 18, 2016, the contents of which are incorporated herein by reference in their entireties.

GOVERNMENT SUPPORT

This invention was made with government support under GM113406; GM047467; GM075879; and AI037581 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 13, 2017, is named 002806-086591-PCT_SL.txt and is 199,362 bytes in size.

TECHNICAL FIELD

The technology described herein relates to nanodiscs, proteins used to assemble the nanodiscs, and methods of making nanodiscs.

BACKGROUND

Small models of the cell membrane can be used to study the structure and behavior of cell membrane proteins, e.g., as part of the development of drugs and/or vaccines. Traditionally, such models were produced by creating micelles or liposomes. Micelles are small spheres which require the use of significant levels of detergents for their creation. These detergents can destabilize and/or inhibit any associated cell membrane proteins, limiting the utility of the micelles. Liposomes do not require detergent use, but tend to aggregate and are irregular in size, making them unsuitable for analysis by crystallization and NMR.

A more recent development is nanodiscs. Nanodiscs do not contain detergents and are not prone to aggregation. A conventional nanodisc is composed of a nanometer-sized phospholipid bilayer encircled by two copies of a helical, amphipathic membrane scaffold proteins (MSPs) (Denisov et al. J Am Chem Soc. 2004; 126:3477-87 and Bayburt et al. Nano Lett. 2002; 2:853-6). These conventional nanodiscs are limited in size from 7-17 nm. In addition to this limited range of possible sizes, the size of each conventional nanodisc in a given preparation tends to vary significantly. This lack of uniformity is undesirable for, e.g., crystallazation and causes variation in the number of membrane proteins found in each individual nanodisc.

SUMMARY

As described herein, the inventors have found that by circularizing the membrane scaffold protein, it is possible to obtain nanodiscs of up to 100 nm in diameter with extremely high consistency in the size of each individual nanodisc. Additionally, the nanodiscs made with such circularized membrane scaffold proteins can be designed to be either circular or polygonal in shape. The polygonal nanodiscs are of particular interest as they can increase the likelihood of crystallization.

In one aspect of any of the embodiments, described herein is a loopable membrane scaffold protein comprising, from N-terminus to C-terminus: i) an N-terminal circularization domain; ii) a plurality of amphipathic alpha helix domains; and iii) a C-terminal circularization domain.

In some embodiments of any of the aspects, one circularization domain comprises: a non-polar amino acid sequence comprising at least one N-terminal glycine or alanine residue; and the other circularization domain comprises: a sequence LPXTG/A; wherein X represents any amino acid. In some embodiments of any of the aspects, the N-terminal circularization domain comprises: a non-polar amino acid sequence comprising at least one N-terminal glycine or alanine residue; and the C-terminal circularization domain comprises: a sequence LPXTG/A; wherein X represents any amino acid. In some embodiments of any of the aspects, the non-polar amino acid sequence is from 1 to 10 amino acids in length and comprises amino acids selected from the group consisting of: glycine and alanine. In some embodiments of any of the aspects, the non-polar amino acid sequence consists of 1-5 glycine residues. In some embodiments of any of the aspects, the non-polar amino acid sequence consists of 1-5 alanine residues. In some embodiments of any of the aspects, the sequence LPXTG/A is covalently bound to the at least one glycine or alanine residue of (i). In some embodiments of any of the aspects, the sequence LPXTG/A is LPGTG/A (SEQ ID NO: 24); LPSTG/A (SEQ ID NO: 25); LPETG/A (SEQ ID NO: 26).

In some embodiments of any of the aspects, one circularization domain comprises an intein separated from the domain of (ii) by a Cys; and the other circularization domain comprises an intein separated from the domain of (ii) by a dipeptide sequence of Asn-Cys, with the Asn being closest to the intein. In some embodiments of any of the aspects, the N-terminal circularization domain comprises an intein separated from the domain of (ii) by a Cys; and the C-terminal circularization domain comprises an intein separated from the domain of (ii) by a dipeptide sequence of Asn-Cys, with the Asn being closest to the intein. In some embodiments of any of the aspects, at least one intein is flanked by a chitin binding domain (CBD).

In some embodiments of any of the aspects, each circularization domain comprises a Cys.

In some embodiments of any of the aspects, the amphipathic alpha helix domain comprises: a) an ApoA-I polypeptide; or b) at least one alpha helical polypeptide with secondary amphipathicity or a repeat thereof; c) at least one amphipathic proline-rich polypeptide or a repeat thereof; or d) at least one repeat of the sequence XZXPPP; wherein X is any hydrophobic residue and Z is any hydrophilic residue. In some embodiments of any of the aspects, the alpha helical polypeptide has a sequence selected from the group consisting of: DWFKAFYDKLAEKFKEAF (SEQ ID NO: 27); DFLKAFYDKVAEKFKEAAPDWFKAFYDK-VAEKFKEAF (SEQ ID NO: 28): KLALRLALKAF-KAALKLA (SEQ ID NO: 29); RLALDLALRAF-KAAWKLA (SEQ ID NO: 30); ELAWDLAFEALDAELKLD (SEQ ID NO: 31); FLKLLKKFLKLFKKLLKLF (SEQ ID NO: 32); WLKLLKKWLKLWKKLLKL (SEQ ID NO: 33);

LLKFLKRLLKLLKDLWKLL (SEQ ID NO: 34); WEAAF-AEALAEAWAEHLAEALAEAVEALAA (SEQ ID NO: 35); WEAKLAKALAKALAKHLAKALAKALKACEA (SEQ ID NO: 36); RAFARALARALKALARALKALAR (SEQ ID NO: 37); GLFEALLELLESLWELLLEA (SEQ ID NO: 38); KLLKLLLKLWKKLLKLLK (SEQ ID NO: 39); DWLKAFYDKVAEKLKEAF (SEQ ID NO: 40); and DWFKAFYDKVAEKFKEAF (SEQ ID NO: 41).

In some embodiments of any of the aspects, the protein further comprises a cap sequence N-terminal of the N-terminal circularization domain that can be cleaved to expose the N-terminal circularization domain as the N-terminus of the protein. In some embodiments of any of the aspects, the cap sequence comprises as sequence selected from the group consisting of: a) Leu-Val-Pro-Arg-Gly-Ser (SEQ ID NO: 42); and b) Glu-X-Leu-Tyr-Φ-Gln-φ where X is any residue, Φ is any large or medium hydrophobic residue and φ is glycine or alanine (SEQ ID NO: 43). In some embodiments of any of the aspects, the cap sequence further comprises an affinity purification tag N-terminal of the cleavage site. In some embodiments of any of the aspects, the protein further comprises a His tag flanking one of the circularization domains. In some embodiments of any of the aspects, the His tag is located C-terminal of the C-terminal circularization domain. In some embodiments of any of the aspects, the protein further comprises a linker flanking one of the circularization domains. In some embodiments of any of the aspects, the linker is located C-terminal of the C-terminal circularization domain.

In some embodiments of any of the aspects, the plurality of amphipathic alpha helix domains are separated by flexible linker sequences. In some embodiments of any of the aspects, the flexible linker sequence is selected from the group consisting of: LPGTGS (SEQ ID NO: 44); LPGTSG (SEQ ID NO: 45); LPSTGS (SEQ ID NO: 46); and LPSTSG (SEQ ID NO: 47).

In some embodiments of any of the aspects, the protein has the sequence of any of SEQ ID NOs: 1-4 and 6-23.

In one aspect of any of the embodiments, described herein is a covalently circularized nanodisc comprising: a) a phospholipid bilayer; and b) a looped membrane scaffold protein forming a belt around the bilayer, wherein the looped membrane scaffold protein comprises: i) an N-terminal circularization domain covalently linked to a C-terminal circularization domain; and ii) a plurality of amphipathic alpha helix domains.

In some embodiments of any of the aspects, an N-terminal circularization domain covalently linked to a C-terminal circularization domain comprises the sequence LPXT followed by a non-polar amino acid sequence comprising at least one N-terminal glycine or alanine residue; wherein X represents any amino acid. In some embodiments of any of the aspects, the non-polar amino acid sequence is from 1 to 10 amino acids in length and comprises amino acids selected from the group consisting of: glycine and alanine. In some embodiments of any of the aspects, the non-polar amino acid sequence consists of 1-5 glycine residues. In some embodiments of any of the aspects, the non-polar amino acid sequence consists of 1-5 alanine residues. In some embodiments of any of the aspects, the sequence LPXT is LPGT (SEQ ID NO: 48); LPST (SEQ ID NO: 49); or LPET (SEQ ID NO: 50).

In some embodiments of any of the aspects, the N-terminal circularization domain covalently linked to a C-terminal circularization domain is a cysteine residue.

In some embodiments of any of the aspects, the diameter is greater than about 6 nm. In some embodiments of any of the aspects, the diameter is greater than about 15 nm. In some embodiments of any of the aspects, the diameter is greater than about 50 nm. In some embodiments of any of the aspects, the diameter is about 80 nm.

In one aspect of any of the embodiments, described herein is a method of making a nanodisc as described herein, the method comprising: contacting the loopable membrane scaffold protein described herein with a sortase enzyme; and contacting the looped protein produced in step (a) with solubilized phospholipids. In some embodiments of any of the aspects, the sortase is selected from the group consisting of: *Staphylococcus aureus* wild type sortase A (Srt A); evolved sortase; eSrtA; eSrtA(2A-9); eSrtA(4S-9); and *Streptococcus pyogenes* sortase A. In some embodiments of any of the aspects, the contacting step is stopped by quenching the reaction with a sortase inhibitor. In some embodiments of any of the aspects, the sortase inhibitor is AAEK2 or high concentrations of EDTA. In some embodiments of any of the aspects, the sortase is bound to a substrate. In some embodiments of any of the aspects, the sortase further comprises a His tag.

In one aspect of any of the embodiments, described herein is a method of making a nanodisc as described herein, the method comprising: a) contacting the loopable membrane scaffold protein described herein with a solution having a pH low enough to induce cleavage of the dipeptide sequence of Asn-Cys; and a thiol reagent to induce cleavage at the Cys residue, resulting in circularization of the protein; and b) contacting the looped protein produced in step (a) with solubilized phospholipids. In some embodiments of any of the aspects, the thiol reagent is DTT.

In one aspect of any of the embodiments, described herein is a method of making a nanodisc as described herein, the method comprising a) contacting the loopable membrane scaffold protein described herein with a thiol reagent, resulting in circularization of the protein; and b) contacting the looped protein produced in step (a) with solubilized phospholipids.

In some embodiments of any of the aspects, the phospholipids are solubilized in detergent. In some embodiments of any of the aspects, step (b) occurs at a temperature of from about 0 C to about 42 C. In some embodiments of any of the aspects, step (b) occurs at a temperature of from about 0 C to about 37 C. In some embodiments of any of the aspects, the ratio of loopable membrane scaffold protein to phospholipids is from about 1:2000 to about 1:5000. In some embodiments of any of the aspects, the ratio of loopable membrane scaffold protein to phospholipids is from about 1:3500 to about 1:4500; and circular nanodiscs are formed. In some embodiments of any of the aspects, the ratio of loopable membrane scaffold protein to phospholipids is from about 1:4000; and circular nanodiscs are formed. In some embodiments of any of the aspects, the ratio of loopable membrane scaffold protein to phospholipids is from about 1:2500 to about 1:3700; and non-circular nanodiscs are formed. In some embodiments of any of the aspects, the ratio of loopable membrane scaffold protein to phospholipids is from about 1:3100 to about 1:3400; and non-circular nanodiscs are formed.

In some embodiments of any of the aspects, the protein further comprises a cap sequence N-terminal of the N-terminal circularization domain and the method comprises a first step of contacting the protein with an enzyme to cleave the cap sequence. In some embodiments of any of the aspects, the protein further comprises a C-terminal His tag and the method comprises a first step of binding the protein to a substrate. In some embodiments of any of the aspects, the substrate comprises Cu2+, Ni2+ or Co2+. In some embodiments of any of the aspects, the substrate is a chip or bead. In some embodiments of any of the aspects, the substrate is a bead and step (a) is performed in the presence of phospholipids. In some embodiments of any of the aspects, the substrate is a bead and the steps (a) and (b) are performed concurrently. In some embodiments of any of the aspects, the method further comprises, after step (a), a step of eluting the looped protein produced in step (a) from the substrate.

In some embodiments of any of the aspects, the loopable membrane scaffold protein is in solution at a concentration of less than 100 uM prior to the contacting step. In some embodiments of any of the aspects, the looped protein formed in step (a) is passed through a column, substrate, and/or solution comprising Cu2+, Co2+ or Ni2+.

BRIEF DESCRIPTION OF THE DRAWINGS

FIG. 2A depicts a general outline of the constructs that are used for making covalently circularized nanodiscs. Constructs containing a sortase A recognition sequence (LPXTG (SEQ ID NO: 51)) and N-terminal glycine can undergo circularization (intramolecular transpeptidation) after exposing the N-terminal glycine and incubating with evolved sortase. FIG. 2A discloses "HHHHHH" as SEQ ID NO: 54. FIG. 2B depicts an outline of the procedure for creating circularized proteins over a Cu+2 chip. FIG. 2B discloses "GSTFSKL" as SEQ ID NO: 80, "KLNTQLPGTAAALEHHHHHH" as SEQ ID NO: 81, "KLNTQLPGTGSTFSKLR" as SEQ ID NO: 82 and "AALEHHHHHH" as SEQ ID NO: 83. FIG. 2C shows SDS-PAGE analysis of NW11 before (lane 1) and after (lane 2) circularization. FIG. 2C discloses "LPXTG" as SEQ ID NO: 51 and "HHHHHH" as SEQ ID NO: 54. FIG. 2D depicts MS/MS spectrum of a tryptic peptide of cNW11 confirming the ligation of the N-terminal residues (GSTFSK (SEQ ID NO: 52)) to the C-terminal LPGTG motif (SEQ ID NO: 53). The b and y ions that were identified in the MS/MS spectrum are highlighted in blue and red. FIG. 2D discloses "KLNTQLPGTGSTFSK" as SEQ ID NO: 84. FIG. 2E depicts the diameter distribution for nanodiscs made using linear MSP (top) and circularized MSP (bottom) and their representative negative stain images. FIG. 2E discloses "NTQLPGTAA" as SEQ ID NO: 85 and "NTQLPGTGST" as SEQ ID NO: 86.

FIGS. 3A-3C demonstrate the production of large covalently circularized nanodiscs. FIG. 3A demonstrate SDS-PAGE analysis of NW30 before and after circularization. The circularized NW30 migrates slower than the linear form. Right: negative-stain EM analysis of the nanodiscs made using circularized NW30 (cNW30) shows the formation of ~15 nm nanodiscs. FIG. 3B demonstrate SDS-PAGE analysis of NW50 before and after circularization. Right: negative-stain EM analysis of the nanodiscs made using circularized NW50 (cNW50) shows the formation of ~50 nm nanodiscs. Bottom: cryo-EM images for individual nanodiscs showing top and side views. FIG. 3C depicts negative stain images showing single nanodisc particles with increasing sizes as indicated.

FIG. 5 discloses "LPXTG" as SEQ ID NO: 51 and "HHHHHH" as SEQ ID NO: 54.

FIG. 6A depicts negative-stain EM of 50-nm circularized nanodiscs plus poliovirus. A control (nanodiscs without CD155) is shown to illustrate the relative dimensions of the 30-nm poliovirus and the 50-nm nanodisc. FIG. 6B depicts an outline of the procedure used to initiate poliovirus bridging and fusion with nanodiscs decorated with CD155. FIG. 6C depicts negative-stain EM images showing individual viruses tethered to nanodiscs. FIG. 6D depicts cryo-EM image of 50-nm nanodiscs plus poliovirus. FIG. 6E depicts cryo-EM image showing a tilted view of 50-nm nanodisc. FIG. 6F depicts cryo-EM images showing individual viruses tethered to nanodiscs. FIG. 6G-6H depict cryo-EM images showing the creation of a putative pore in the nanodisc by the poliovirus. FIG. 6I depicts cryo-EM image showing three viral particles around a 15-nm nanodisc. FIG. 6J depicts cryo-EM image showing individual viruses ejecting RNA after incubation with CD155-decorated 15-nm nanodiscs.

FIG. 7A depicts 2D-[$^1$H,$^{15}$N]-TROSY spectrum of $^2$H,$^{15}$N-labeled VDAC-1 in cNW9 nanodiscs. FIG. 7B depicts representative image of negatively stained cNW9 nanodiscs containing single VDAC-1 channel. The stain-filled channels appear as dark spot inside the nanodisc. Right: SDS-PAGE analysis of cNW9 nanodiscs containing VDAC-1. FIG. 7C depicts 2D-[$^1$H,$^{15}$N]-TROSY spectrum of $^2$H,$^{15}$N-labeled VDAC-1 in cNW11 nanodiscs. FIG. 7D depicts representative image of negatively stained cNW11 nanodiscs containing VDAC-1 channels. Each nanodisc appear to contain 2 channels. Right: SDS-PAGE analysis of cNW11 nanodiscs containing VDAC-1.

FIG. 8 discloses "GSTFSKL" as SEQ ID NO: 80, "KLNTQLPGTAAALEHHHHHH" as SEQ ID NO: 81, "AALEHHHHHH" as SEQ ID NO: 83 and "LEEYTKKLNTQLPGTGSTFSKLREQL" as SEQ ID NO: 87.

FIG. 9A depicts a schematic of circularization of NW proteins over Ni2+ beads. His6-tagged linear NW ("His6" disclosed as SEQ ID NO: 54) is attached to Ni-beads followed by adding lipids to NW. Addition of lipids to NW helps to bring the C and N terminal ends close so the circularization pathway will dominate. Adding His6-tagged sortase ("His6" disclosed as SEQ ID NO: 54) creates circularized non-tagged NW (cNW), which can be eluted while cleaved His6-tagged cleavage product ("His6" disclosed as SEQ ID NO: 54) and sortase remain bound to the beads. FIG. 9A discloses "KLNTQLPGTGSTFSK" as SEQ ID NO: 84. FIG. 9B SDS-PAGE gel showing the final products after circularization over Ni beads with or without lipids.

FIG. 11 discloses "LEEKLNTQLPXTGSTFSKL-RELEEKLNTQLPXTGSTFSKLRELEEKLNTQLPXTG-STFSKLRE" as SEQ ID NO: 88 and "LEEYTKKLNTQLPGTGSTFSKL-RELEEKLNTQLPGTGSTFSKLRE" as SEQ ID NO: 89.

FIG. 12C demonstrates that placement in MSP1D1 nanodiscs increases the melting temperature of VDAC1 by 9.2 degrees over that of VDAC1 in an LDAO micelle environment, and covalent circularization of the scaffold protein (cNW11) raises Tm by additional 9.2 degrees. Thermal unfolding of human VDAC-1 was followed by CD spectroscopy at 218 nm, the wavelength most characteristic of β-sheet secondary structure. Orange: VDAC1 in 0.1% LDAO. Depicted are VDAC1 reconstituted into conventional nanodiscs (assembled using MSP1D1), and VDAC1 reconstituted into circularized nanodiscs (assembled using cNW11). Nanodiscs were made with POPC/POPG 3:2 lipids. FIG. 12D depicts thermal unfolding of VDAC1 reconstituted into circularized nanodiscs (assembled using cNW9) followed by CD spectroscopy at 218 nm. Nanodiscs were made with POPC/POPG lipids at a molar ratio of 3:2. All samples were in 20 mM Tris-HCl, pH 7.5, 100 mM NaCl. FIG. 12E depicts analysis of the VDAC1 nanodisc assembly reaction. Top: size-exclusion chromatography and negative-stain EM of VDAC1 in cNW9 nanodiscs. Negative-stain image shows nanodiscs containing a single channel. The stain-filled channels appear as dark spots inside nanodiscs. Bottom: SDS-PAGE analysis of the nanodisc assembly. Fractions 1-6 were collected and analyzed.

FIGS. 13A-13B depict SDS-PAGE analysis of the proteolysis of lipid-free MSPΔH5 and cNW9. Samples were treated with V8 protease for 0 min (before addition of V8), and for 1, 3 and 18 hours. Lanes are labeled with times of protease treatment. Proteolysis was performed in 20 mM Tris-HCl, pH 7.5, 100 mM NaCl at 37° C. and using a protein:protease ratio (w/w) of 1000:1. Treatment of MSPΔH5 with V8 resulted in the appearance of a large peptide, which is close in size to MSPΔH5 and is not discernible until about 18 hours after addition of V8; this peptide may be generated earlier but is not visible due to the low amount or overlap with uncleaved MSPΔH5. The intensity of the MSPΔH5 band decreased by 75% after 3 hours and by 93% after 18 hours. On the other hand, the intensity of the cNW9 band decreased by only 20% after 18 hours. A band that corresponds to linearized NW9 was observed after 3 hours and increased in intensity after 18 hours. FIGS. 13C-13D depict SDS-PAGE analysis of the proteolysis of nanodiscs assembled with MSPΔH5 and cNW9. Samples were treated with V8 protease for 0 min (before addition of V8), and for 20 min, 1, 3 and 18 hours. Proteolysis was performed at 37° C. at pH 7.5 in 20 mM Tris-HCl, 100 mM NaCl using a 100:1 protein:protease (w/w). The band intensity of MSPΔH5 decreased by 81% after 3 hours. There were no decreases in cNW9 band intensity up to 3 hours. ImageJ™ software was for analyzing band intensities.

DETAILED DESCRIPTION

Figure 1:
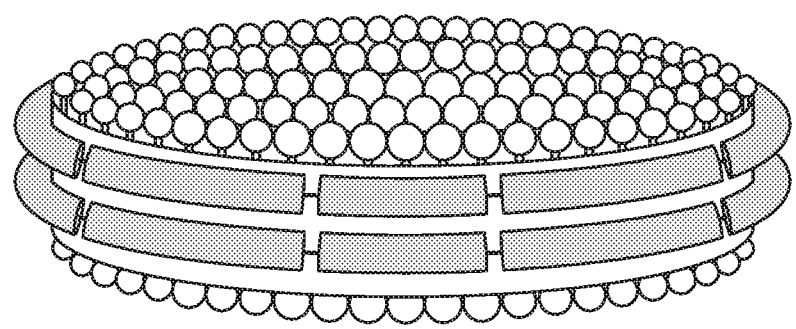
FIG. 1 depicts a schematic representation of a nanodisc.

The inventors have discovered methods of making nanodisc which permit previously unachievable sizes, uniformity, and geometry. This new approach to nanodisc construction involves the use of circularized membrane scaffold proteins, as opposed to the linear membrane scaffold proteins previously described. Provided herein are loopable membrane scaffold proteins, nanodiscs comprising such proteins, and methods of producing these nanodiscs.

Described herein are covalently circularized nanodiscs and the loopable membrane scaffold proteins used to construct these nanodiscs. As used herein, "nanodisc" refers to a discoidal, nanoscale phospholipid bilayer which is "belted" or "ringed" by a membrane scaffold protein. The membrane scaffold protein comprises amphipathic alpha helices which provide an hydrophobic surface next to the hydrocarbon tails of the phospholipid bilayer and an external hydrophilic surface. As used herein, "covalently circularized nanodisc" refers to a nanodisc in which the membrane scaffold protein has been covalently bonded to itself to form continuous polypeptide loop (i.e. it has been circularized).

In one aspect of any of the embodiments, described herein is a loopable membrane scaffold protein comprising, from N-terminus to C-terminus: i) an N-terminal circularization domain; ii) at least one amphipathic alpha helix domain; and iii) a C-terminal circularization domain. In one aspect of any of the embodiments, described herein is a loopable membrane scaffold protein comprising, from N-terminus to C-terminus: i) an N-terminal circularization domain; ii) a plurality of amphipathic alpha helix domains; and iii) a C-terminal circularization domain. As used herein, "loopable membrane scaffold protein" refers to a protein which is capable of being circularized by a covalent bond in such as way that the interior circumference of the protein provides a hydrophobic environment and the exterior circumference forms a hydrophilic environment. Once circularized, the protein is referred to herein as a "looped membrane scaffold protein." This circularized protein can accommodate a phospholipid bilayer within the interior circumference.

As used herein, "circularized" or "looped" when used in reference to a polypeptide refers to the fact that the peptide sequence is not linear in nature, e.g., it does not have an N-terminus or C-terminus. A polypeptide which is circularized or looped can form any shape, e.g., a circle, an oval, or a polygon. In contrast, a polypeptide or nanodisc referred to herein which is "circular in shape," has a shape or cross-section which forms the shape of a circle.

As used herein, "a circularization domain" refers to a section of a linear polypeptide which upon interaction with a corresponding second circularization domain in the same polypeptide, can cause circularization of the polypeptide. The circularization domain can comprise one or more amino acid residues. A number of circularization technologies are known in the art and any such technology can be applied to the proteins described herein. Exemplary circularization domains are described below.

Proteins can be circularized by the action of a sortase enzyme. Sortase recognizes a LPXTG/A (e.g., LPXTG (SEQ ID NO: 51) or LPXTA (SEQ ID NO: 56)) sequence, cleaving the sequence after the threonine. The threonine residue can then form a new peptide bond with a glycine or alanine residue found at a second, more N-terminal location in the polypeptide, causing it to be circularized. The use of sortase enzymes to circularize polypeptide is described in more detail in, e.g., Cowper et al. ChemBioChem 2013 14:809-812; Antos et al., Journal of Biological Chemistry 2009 284:16028-36; and Tsukiji et al. ChemBioChem 2009 10:787-798; each of which is incorporated by reference herein in its entirety. In some embodiments of any of the aspects described herein, one circularization domain comprises: a non-polar amino acid sequence comprising at least one N-terminal glycine or alanine residue; and the other circularization domain comprises: a sequence LPXTG/A; wherein X represents any amino acid. In some embodiments of any of the aspects described herein, the N-terminal circularization domain comprises: a non-polar amino acid sequence comprising at least one N-terminal glycine or alanine residue; and the C-terminal circularization domain comprises: a sequence LPXTG/A; wherein X represents any amino acid.

As used herein, "non-polar amino acid sequence" refers to a sequence comprising non-polar amino acids, the sequence being at least one amino acid in length. In some embodiments of any of the aspects, the non-polar amino acid sequence is from 1 to 20 amino acids in length. In some embodiments of any of the aspects, the non-polar amino acid sequence is from 1 to about 10 amino acids in length. In some embodiments of any of the aspects, the non-polar amino acid sequence is from 1 to 10 amino acids in length. In some embodiments of any of the aspects, the non-polar amino acid sequence comprises glycine and alanine residues. In some embodiments of any of the aspects, the non-polar amino acid sequence consists of glycine and alanine residues. In some embodiments of any of the aspects, the non-polar amino acid sequence is from 1 to 10 amino acids in length and comprises amino acids selected from the group consisting of: glycine and alanine. In some embodiments of any of the aspects, the non-polar amino acid sequence is from 1 to 10 amino acids in length and consists of amino acids selected from the group consisting of: glycine and alanine. In some embodiments of any of the aspects, the non-polar amino acid sequence consists of 1-5 residues selected from glycine and alanine. In some embodiments of any of the aspects, the non-polar amino acid sequence consists of 1-5 glycine residues. In some embodiments of any of the aspects, the non-polar amino acid sequence consists of 1-5 alanine residues.

In some embodiments of any of the aspects, the sequence LPXTG/A can be covalently bound to the at least one glycine or alanine residue of (i).

In some embodiments of any of the aspects, the LPXTG/A is LPGTG/A (SEQ ID NO: 24); LPSTG/A (SEQ ID NO: 25); or LPETG/A (SEQ ID NO: 26). In some embodiments of any of the aspects, the LPXTG/A is LPGTG (SEQ ID NO: 53); LPGTA (SEQ ID NO: 57); LPSTG (SEQ ID NO: 58); LPSTA (SEQ ID NO: 59); LPETG (SEQ ID NO: 60); or LPETA (SEQ ID NO: 61).

Proteins can also be circularized by use of two intein domains (e.g., using the pTWIN vectors commercially available from New England Biolabs; Ipswich, Mass. (e.g., Cat. No. N6951S)). Inteins can excise themselves from a polypeptide, causing splicing of the remaining sequence (e.g., exteins). When inteins are used to flank a central sequence, the central sequence can be circularized when the inteins excise themselves. Various inteins and their use are described in more detail in, e.g. Elleuche et al. Applied Microbiology and Biotechnology. 2010 87:479-489; Cowper et al. ChemBioChem 2013 14:809-812; Ahlmann-Eltze et al. 2015 hdl.handle.net/1721.1/96071; Evans et al. Journal of Biological Chemistry 1999 274:18359-18363; and Evans et al. Biopoly 1999 51: 333-342; each of which is incorporated by reference herein in its entirety.

In some embodiments of any of the aspects, one circularization domain comprises an intein separated from the domain of (ii) by a Cys; and the other circularization domain comprises an intein separated from the domain of (ii) by a dipeptide sequence of Asn-Cys, with the Asn being closest to the intein. In some embodiments of any of the aspects, the N-terminal circularization domain comprises an intein separated from the domain of (ii) by a Cys; and the C-terminal circularization domain comprises an intein separated from the domain of (ii) by a dipeptide sequence of Asn-Cys, with the Asn being closest to the intein. In some embodiments of any of the aspects, at least one intein is flanked by a chitin binding domain (CBD). Intein-mediated cyclization is described further in, e.g., Xu et al. Methods. 2001 July; 24(3):257-77; which is incorporated by reference herein in its entirety.

Proteins can also be circularized by utilizing 2 cysteine residues, one at each end of the sequence to be circularized. The C-terminal cysteine is capable of initiating an intramolecular N→S acyl shift. This results in an S-acyl intermediate that can be intercepted by an added thiol, yielding a C-terminal thioester and liberating cysteine. The cysteine at the N terminus interacts with the C-terminal thioester and leads to spontaneous backbone circularization, through intramolecular transthioesterification. Next, an S→N acyl shift rearrangement occurs that lead to formation of a peptide bond. The final circularized product will have a cysteine next to the newly formed peptide bond. Such methods of circularization are described in more detail at, e.g., Cowper, B et. al. ChemBioChem 2013, 14, 809-812; which is incorporated by reference herein in its entirety. In some embodiments of any of the aspects, each circularization domain comprises a Cys. In some embodiments of any of the aspects, one of the Cys residues is preceded by a Gly residue. In some embodiments of any of the aspects, one of the Cys residues is the C-terminal residue of the linear polypeptide.

As used herein, "amphipathic alpha helix domain" refers to a domain comprising a continuous amphipathic alpha helix, e.g., an alpha helix with a face which is hydrophobic/non-polar and a second face which is hydrophilic/polar. In some embodiments, a loopable membrane scaffold protein can comprise a plurality of amphipathic alpha helix domains, e.g., multiple domains separated by non-helical sequences. Several exemplary amphipathic alpha helix domains are provided herein. By way of non-limiting example, an amphipathic alpha helix can comprise an ApoA-I polypeptide or repeats thereof; at least one alpha helical polypeptide with secondary amphipathicity or a repeat thereof; at least one amphipathic proline-rich polypeptide or a repeat thereof; or at least one repeat of the sequence XZXPPP; wherein X is any hydrophobic residue (e.g., any of A, I, L, F, V, P, W, M, Y and G) and Z is any hydrophilic residue (e.g., any of R, K, D, E, Q, N, H, S, T, or C). A given amphipathic alpha helix domain and/or loopable membrane scaffold protein can comprise a combination of any of the specific sequences and domains described herein.

ApoA-I (e.g., NCBI Gene ID: 335), also referred to as ApoA1, refers to the major protein component of high density lipoprotein (HDL) in plasma, which also serves a cofactor for lecithin cholesterolacyltransferase (LCAT). The sequences for ApoA-I are known for a number of species, e.g., human ApoA-I mRNA (e.g., NCBI Ref Seq: NM_000039.2) and protein (e.g., NCBI Ref Seq: NP_000030.1; SEQ ID NO: 5) sequences. The native ApoA-1 protein comprises a 43 residue N-terminal globular domain and a 200 residue C-terminal lipid binding domain (e.g., residues 68-267 of SEQ ID NO: 5) which forms an ampipathic alpha helix. As used herein, "ApoA-I polypeptide" refers to a polypeptide comprising at least one repeat of the ApoA-I C-terminal lipid binding domain (e.g., residues 68-267 of SEQ ID NO: 5). In some embodiments of any of the aspects, an ApoA-I polypeptide comprises from 1 to 10 repeats of the ApoA-I C-terminal lipid binding domain (e.g., residues 68-267 of SEQ ID NO: 5).

As used herein, "secondary amphipathicity" refers to amphipathicity existing in the secondary structure of a polypeptide, e.g., the polar residues are found on one face of the secondary structure and the nonpolar residues are found on the opposite face of the secondary structure.

In some embodiments of any of the aspects described herein, an alpha helical polypeptide with secondary amphipathicity can have a sequence selected from the group consisting of: DWFKAFYDKLAEKFKEAF (SEQ ID NO: 27); DFLKAFYDKVAEKFKEAAPDWFKAFYDK-VAEKFKEAF (SEQ ID NO: 28); KLALRLALKAF-KAALKLA (SEQ ID NO: 29); RLALDLALRAF-KAAWKLA (SEQ ID NO: 30); ELAWDLAFEALDAELKLD (SEQ ID NO: 31); FLKLLKKFLKLFKKLLKLF (SEQ ID NO: 32); WLKLLKKWLKLWKKLLKL (SEQ ID NO: 33); LLKFLKRLLKLLKDLWKLL (SEQ ID NO: 34); WEAAF-AEALAEAWAEHLAEALAEAVEALAA (SEQ ID NO: 35); WEAKLAKALAKALAKHLAKALAKALKACEA (SEQ ID NO: 36); RAFARALARALKALARALKALAR (SEQ ID NO: 37); GLFEALLELLESLWELLLEA (JTS1 peptide) (SEQ ID NO: 38); KLLKLLLKLWKKLLKLLK (SEQ ID NO: 39); DWLKAFYDKVAEKLKEAF (18A peptide) (SEQ ID NO: 40); DWFKAFYDKVAEKFKEAF (4F peptide) (SEQ ID NO: 41); or variants thereof. Alpha helical polypeptide with secondary amphipathicity are readily identified by one of skill in the art, e.g., the Helical Wheel Prediction algorithm available at rzlab.ucr.edu/scripts/wheel/can be used to characterize the secondary amphipathicity of a query polypeptide sequence. Secondary amphipathic peptides are described further in the art at, e.g., S. Gottschalk et al., Gene Ther. 1996; 3: 448-457; T. Niidome et al. Bioconjugate Chem. 1999; 10(5): 773-780); B. Chung et al., J. Bio. Chem. 1985; 260:10256-10262; and H. Kariyazono et al. J. Pept. Sci. 2016; 22: 116-122; each of which is incorporated by reference herein in its entirety.

The loopable membrane scaffold proteins described herein can further comprise sequences useful for preparation of the covalently circularized nanodiscs, but which will not be present in the covalently circularized nanodisc itself. For example, sequences flanking the N- or C-terminal circularization domains can be used to purify the loopable membrane scaffold proteins and/or to tether them to a substrate or surface for the circularization process. Circularization itself will necessarily remove such flanking sequences from the membrane scaffold protein as it is looped at the circulariation domains.

In some embodiments of any of the aspects, the loopable membrane scaffold protein can comprise a cap sequence N-terminal of the N-terminal circularization domain that can be cleaved to expose the N-terminal circularization domain as the N-terminus of the protein. In some embodiments of any of the aspects, the loopable membrane scaffold protein can comprise a a cap sequence N-terminal of the N-terminal circularization domain comprising a non-polar amino acid sequence that can be cleaved to expose the N-terminal circularization domain a non-polar amino acid sequence as the N-terminus of the protein. Such cap sequences can comprise and be cleaved by means of any sequence recognized by a protease. By way of non-limiting example, the cap sequence can comprise the recognition sequence Leu-Val-Pro-Arg-Gly-Ser (SEQ ID NO: 42). This recognition sequence can be cleaved by thrombin between Arg and Gly. By way of further non-limiting example, the cap sequence can comprise the recognition sequence Glu-X-Leu-Tyr-Φ-

Gln-φ where X is any residue, Φ is any large or medium hydrophobic residue (e.g., W, F, M, Y, L, I, or V) and φ is glycine or alanine (SEQ ID NO: 43). Glu-X-Leu-Tyr-Φ-Gln-φ (SEQ ID NO: 43) is recognized by TEV protease and cleaved after the Gln residue.

In some embodiments of any of the aspects, the cap sequence, or any sequence flanking the circularization domains can further comprise an affinity purification tag. In some embodiments of any of the aspects, the cap sequence can further comprise an affinity purification tag N-terminal of the cleavage site. In some embodiments of any of the aspects, the loopable membrane scaffold protein can comprise an affinity tag flanking one of the circularization domains. In some embodiments of any of the aspects, the loopable membrane scaffold protein can comprise an affinity tag C-terminal of the C-terminal circularization domain. In some embodiments of any of the aspects, the loopable membrane scaffold protein can comprise an affinity tag N-terminal of the N-terminal circularization domain.

Affinity tags can be used for, e.g., affinity purification or to bind a protein to a desired substrate or surface. Affinity tags can be used to bind the loopable membrane scaffold tag to a surface or substrate prior to circularization, or to remove flanking sequences (e.g. cleaved N-terminal cap sequences) after they have been cleaved. A number of affinity tags and their binding partner ligands are well known in the art and are described, e.g., in Lichty et al. Protein Expr Purif 2005 41:98-105; Zhao et al. J Analytical Methods in Chemistry 2013; Kimple et al. Current Protocols in Protein Science 2004 36:939:9.1-9.9.19; and Giannone et al. Methods and Protocols "Protein Affinity Tags" Humana Press 2014; each of which is incorporated by reference herein in its entirety. Non-limiting examples of affinity tags can include His tags, Flag tags, or Strep tags.

Affinity tags can be separated from a circularization domain by a linker. Accordingly, a linker can be located C-terminal of the C-terminal circularization domain and N-terminal of an affinity tag, or N-terminal of the N-terminal circularization domain and C-terminal of an affinity tag.

Illustrative examples of linkers include glycine polymers $(G)_n$; glycine-serine polymers $(G_{1-5}S_{1-5})_n$. (SEQ ID NO: 63), where n is an integer of at least one, two, three, four, or five; glycine-alanine polymers; alanine-serine polymers; and other flexible linkers known in the art. Glycine and glycine-serine polymers are relatively unstructured, and therefore may be able to serve as a neutral tether between domains of the proteins described herein. Glycine accesses significantly more phi-psi space than even alanine, and is much less restricted than residues with longer side chains (see Scheraga, *Rev. Computational Chem.* 11173-142 (1992)). The ordinarily skilled artisan will recognize that design of a protein in particular embodiments can include linkers that are all or partially flexible, such that the linker can include a flexible linker as well as one or more portions that confer less flexible structure to provide for a desired nanodisc structure.

Other exemplary linkers include, but are not limited to the following amino acid sequences: GGG; DGGGS (SEQ ID NO: 64); TGEKP (SEQ ID NO: 65) (see, e.g., Liu et al., PNAS 5525-5530 (1997)); GGRR (SEQ ID NO: 66) (Pomerantz et al. 1995, supra); (GGGGS)$_n$ wherein=1, 2, 3, 4 or 5 (SEQ ID NO: 67) (Kim et al., PNAS 93, 1156-1160 (1996); EGKSSGSGSESKVD (SEQ ID NO: 68) (Chaudhary et al., 1990, Proc. Natl. Acad. Sci. U.S.A. 87:1066-1070); KESGSVSSEQLAQFRSLD (SEQ ID NO: 69) (Bird et al., 1988, Science 242:423-426), GGRRGGGS (SEQ ID NO: 70); LRQRDGERP (SEQ ID NO: 71); LRQKDGGGSERP (SEQ ID NO: 72); LRQKD(GGGS)$_2$ ERP (SEQ ID NO: 73). Alternatively, flexible linkers can be rationally designed using a computer program capable of modeling both DNA-binding sites and the peptides themselves (Desjarlais & Berg, PNAS 90:2256-2260 (1993), PNAS 91:11099-11103 (1994) or by phage display methods. In one embodiment, the linker comprises the following amino acid sequence: GSTSGSGKPGSGEGSTKG (SEQ ID NO: 74) (Cooper et al., *Blood,* 101(4): 1637-1644 (2003)).

In some embodiments of any of the aspects, a covalently circularized nanodisc can, when viewed from an angle which is perpendicular to a hydrophilic surface of the phospholipid layer, be circular in shape. In some embodiments of any of the aspects, a covalently circularized nanodisc can, when viewed from an angle which is perpendicular to a hydrophilic surface of the phospholipid layer, be polygonal (e.g., triangular, rectangular, pentagonal, etc) in shape.

In some embodiments of any of the aspects, the shape of the nanodisc can be directed by the ratio of phospholipids to looped scaffold membrane protein. In some embodiments of any of the aspects, the shape of the nanodisc can be directed by the structure of the looped scaffold membrane protein. A looped scaffold membrane protein comprising a single amphipathic alpha helix domain or multiple amphipathic alpha helix domains which are joined by sequences with constrained geometry will tend to form nanodiscs which, when viewed from an angle which is perpendicular to a hydrophilic surface of the phospholipid layer, are circular in shape.

In some embodiments of any of the aspects, the loopable scaffold membrane protein can comprise a plurality of amphipathic alpha helix domains separated by flexible linker sequences. Each linker sequence will tend to allow a sharper bend to be assumed by a looped scaffold membrane protein at that location. Accordingly, such variants of the looped scaffold membrane protein can, when viewed from an angle which is perpendicular to a hydrophilic surface of the phospholipid layer, be polygonal in shape. The particular polygon assumed by the assembled nanodisc can be directed by the number of separate flexible linker sequences present in the looped scaffold membrane protein, with each forming a corner of a polygon. Linker sequences are known to those of skill in the art and can be any sequence of less than about 30 amino acids in length which do not assume a secondary structure. In some embodiments of any of the aspects, the linker sequence can be less than 30 amino acids in length. In some embodiments of any of the aspects, the linker sequence can be less than about 25 amino acids in length. In some embodiments of any of the aspects, the linker sequence can be less than 25 amino acids in length. In some embodiments of any of the aspects, the linker sequence can be less than about 20 amino acids in length. In some embodiments of any of the aspects, the linker sequence can be less than 20 amino acids in length.

In some embodiments of any of the aspects, the flexible linker sequence is selected from the group consisting of: LPGTGS (SEQ ID NO: 44); LPGTSG (SEQ ID NO: 45); LPSTGS (SEQ ID NO: 46); and LPSTSG (SEQ ID NO: 47).

In some embodiments of any of the aspects, the loopable scaffold membrane protein has the sequence of any of SEQ ID NOs: 1-4 and 6-23.

Mutation of certain residues to cysteine can, e.g., permit immobilizing nanodiscs to surfaces and/or solid substrates, e.g., by surface plasmon resonance or with use of resins or beads configured to bind to cysteine residues. Provision of cysteine residues can further permit attachment of tags, e.g., small molecule or protein tags for NMR or crystallization applications). Accordingly, in some embodiments, the loopable scaffold membrane protein can comprise substitution with cysteine at one or more residues.

In some embodiments of any of the aspects, the loopable scaffold membrane protein can further comprise a substitution with cysteine at one or more residues corresponding to positions 31, 36, 137, and 153 of SEQ ID NO: 1 or 6, or positions 31, 36, 93, 110, 159, and 175 of SEQ ID NO: 2 or 7. In some embodiments of any of the aspects, the loopable scaffold membrane protein can further comprise a substitution with cysteine at one residue corresponding to positions 31, 36, 137, and 153 of SEQ ID NO: 1 or 6. In some embodiments of any of the aspects, the loopable scaffold membrane protein can further comprise a substitution with cysteine at two residues corresponding to positions 31, 36, 137, and/or 153 of SEQ ID NO: 1 or 6. In some embodiments of any of the aspects, the loopable scaffold membrane protein can further comprise a substitution with cysteine at three residues corresponding to positions 31, 36, 137, and/or 153 of SEQ ID NO: 1 or 6. In some embodiments of any of the aspects, the loopable scaffold membrane protein can further comprise a substitution with cysteine at the four residues corresponding to positions 31, 36, 137, and 153 of SEQ ID NO: 1 or 6.

In some embodiments of any of the aspects, the loopable scaffold membrane protein can further comprise a substitution with cysteine at the residue corresponding to positions 31, 36, 93, 110, 159, or 175 of SEQ ID NO: 2 or 7. In some embodiments of any of the aspects, the loopable scaffold membrane protein can further comprise a substitution with cysteine at the two residues corresponding to positions 31, 36, 93, 110, 159, and/or 175 of SEQ ID NO: 2 or 7. In some embodiments of any of the aspects, the loopable scaffold membrane protein can further comprise a substitution with cysteine at the three residues corresponding to positions 31, 36, 93, 110, 159, and/or 175 of SEQ ID NO: 2 or 7. In some embodiments of any of the aspects, the loopable scaffold membrane protein can further comprise a substitution with cysteine at the four residues corresponding to positions 31, 36, 93, 110, 159, and/or 175 of SEQ ID NO: 2 or 7. In some embodiments of any of the aspects, the loopable scaffold membrane protein can further comprise a substitution with cysteine at the five residues corresponding to positions 31, 36, 93, 110, 159, and/or 175 of SEQ ID NO: 2 or 7. In some embodiments of any of the aspects, the loopable scaffold membrane protein can further comprise a substitution with cysteine at the six residues corresponding to positions 31, 36, 93, 110, 159, and 175 of SEQ ID NO: 2 or 7.

In some embodiments of any of the aspects, the loopable scaffold membrane protein can comprise a sequence of SEQ ID NO: 1 or 6 with a substitution with cysteine at one or more residues corresponding to positions 31, 36, 137, and 153 of SEQ ID NO: 1 or 6. In some embodiments of any of the aspects, the loopable scaffold membrane protein can comprise a sequence of SEQ ID NO: 2 or 7 with a substitution with cysteine at one or more residues corresponding to positions 31, 36, 93, 110, 159, and 175 of SEQ ID NO: 2 or 7.

In some embodiments of any of the aspects, the loopable scaffold membrane protein can have or comprise the sequence of SEQ ID NO: 62.

NW11_3C

SEQ ID NO: 62

MGSSHHHHHHENLYFQGSTFSKLREQLGPVTQEFWCNLEKETEGLRQ

EMSKDLEEVKAKVQPYLDDFQKKWQEEMELYRQKVEPLRAELQEGAR

QKLHELQEKLSPLGECMRDRARAHVDALRTHLAPYSDELRQRLAARL

EALKENGGARLAEYHAKATEHLSTLSEKAKPALCDLRQGLLPVLESF

KVSFLSALEEYTKKLNTQLPGTGAAALEHHHHHH

In one aspect of any of the embodiments, described herein is a nucleic acid encoding a loopable membrane scaffold protein as described herein. In one aspect of any of the embodiments, described herein is a vector comprising a nucleic acid encoding a loopable membrane scaffold protein as described herein.

The loopable scaffold membrane proteins described herein can be circularized and combined with phospholipids to form a covalently circularized nanodisc. In one aspect of any of the embodiments, described herein is a covalently circularized nanodisc comprising: a) a phospholipid bilayer; and b) a looped membrane scaffold protein forming a belt around the bilayer, wherein the looped membrane scaffold protein comprises: i) an N-terminal circularization domain covalently linked to a C-terminal circularization domain; and ii) at least one amphipathic alpha helix domains. In one aspect of any of the embodiments, described herein is a covalently circularized nanodisc comprising: a) a phospholipid bilayer; and b) a looped membrane scaffold protein forming a belt around the bilayer, wherein the looped membrane scaffold protein comprises: i) an N-terminal circularization domain covalently linked to a C-terminal circularization domain; and ii) a plurality of amphipathic alpha helix domains.

Suitable exemplary circularization domains and methods of circularizing proteins comprising them are described elsewhere herein. The looped proteins that result from use of these exemplary circularization domains are described herein.

In some embodiments of any of the aspects, a loopable membrane scaffold protein can comprise one circularization domain comprising: a non-polar amino acid sequence comprising at least one N-terminal glycine or alanine residue; and a second circularization domain comprising: a sequence LPXTG/A; wherein X represents any amino acid. In the resulting looped membrane scaffold protein a first circularization domain covalently linked to a second circularization domain comprises the sequence LPXT followed by a non-polar amino acid sequence comprising at least one N-terminal glycine or alanine residue; wherein X represents any amino acid. In some embodiments, the sequence LPXT is LPGT (SEQ ID NO: 48); LPST (SEQ ID NO: 49); or LPET (SEQ ID NO: 50).

In some embodiments of any of the aspects, a loopable membrane scaffold protein can comprise one circularization domain comprising an intein separated from the domain of (ii) by a Cys; and a second circularization domain comprising an intein separated from the domain of (ii) by a dipeptide sequence of Asn-Cys, with the Asn being closest to the intein. In the resulting looped membrane scaffold protein a first circularization domain covalently linked to a second circularization domain comprises a cysteine residue.

In some embodiments of any of the aspects, each circularization domain of a loopable membrane scaffold protein can comprise a Cys residue. In some embodiments of any of the aspects, one of the Cys residues is preceded by a Gly residue. In some embodiments of any of the aspects, one of the Cys residues is the C-terminal residue of the linear polypeptide. In the resulting looped membrane scaffold protein a first circularization domain covalently linked to a second circularization domain comprises a cysteine residue.

In some embodiments of any of the aspects, the diameter of the nanodisc is greater than about 6 nm. In some embodiments of any of the aspects, the diameter of the nanodisc is greater than 6 nm. In some embodiments of any of the aspects, the diameter of the nanodisc is greater than about 15 nm. In some embodiments of any of the aspects, the diameter of the nanodisc is greater than 15 nm. In some embodiments of any of the aspects, the diameter of the nanodisc is greater than about 50 nm. In some embodiments of any of the aspects, the diameter of the nanodisc is greater than 50 nm. In some embodiments of any of the aspects, the diameter of the nanodisc is about 80 nm. In some embodiments of any of the aspects, the diameter of the nanodisc is 80 nm.

In some embodiments of any of the aspects, the diameter of the nanodisc is about 6 nm to about 80 nm. In some embodiments of any of the aspects, the diameter of the nanodisc is 6 nm to 80 nm. In some embodiments of any of the aspects, the diameter of the nanodisc is about 15 nm to about 80 nm. In some embodiments of any of the aspects, the diameter of the nanodisc is 15 nm to 80 nm. In some embodiments of any of the aspects, the diameter of the nanodisc is about 50 nm to about 80 nm. In some embodiments of any of the aspects, the diameter of the nanodisc is 50 nm to 80 nm.

The nanodiscs described herein comprise phospholipids. As used herein, the term "phospholipid" refers to phosphatidic acids, phosphoglycerides, and phosphosphingolipids. Phosphatidic acids include a phosphate group coupled to a glycerol group, which may be mono- or diacylated. Phosphoglycerides (or glycerophospholipids) include a phosphate group intermediate an organic group (e.g., choline, ethanolamine, serine, inositol) and a glycerol group, which may be mono- or diacylated. Phosphosphingolipids (or sphingomyelins) include a phosphate group intermediate an organic group (e.g., choline, ethanolamine) and a sphingosine (non-acylated) or ceramide (acylated) group. It will be appreciated that in certain embodiments, the phospholipids useful in the compositions and methods of the invention include their salts (e.g., sodium, ammonium). For phospholipids that include carbon-carbon double bonds, individual geometrical isomers (cis, trans) and mixtures of isomers are included.

Representative phospholipids include phosphatidylcholines, phosphatidylethanolamines, phosphatidylglycerols, phosphatidylserines, phosphatidylinositols, and phosphatidic acids, and their lysophosphatidyl (e.g., lysophosphatidylcholines and lysophosphatidylethanolamine) and diacyl phospholipid (e.g., diacylphosphatidylcholines, diacylphosphatidylethanolamines, diacylphosphatidylglycerols, diacylphosphatidylserines, diacylphosphatidylinositols, and diacylphosphatidic acids) counterparts.

The acyl groups of the phospholipids may be the same or different. In certain embodiments, the acyl groups are derived from fatty acids having C10-C24 carbon chains (e.g., acyl groups such as lauroyl, myristoyl, palmitoyl, stearoyl or oleoyl groups). Representative diacylphosphatidylcholines (i.e., 1,2-diacyl-sn-glycero-3-phosphocholines) include distearoylphosphatidylcholine (DSPC), dioleoylphosphatidylcholine (DOPC), dipalmitoylphosphatidylcholine (DPPC), dilinoleoylphosphatidylcholine DLPC), palmitoyloleoylphosphatidylcholine (POPC), palmitoyllinoleoylphosphatidylcholine, stearoyllinoleoylphosphatidylcholine stearoyloleoylphosphatidylcholine, stearoylarachidoylphosphatidylcholine, didecanoylphosphatidylcholine (DDPC), dierucoylphosphatidylcholine (DEPC), dilinoleoylphosphatidylcholine (DLOPC), dimyristoylphosphatidylcholine (DMPC), myristoylpalmitoylphosphatidylcholine (MPPC), myristoylstearoylphosphatidylcholine (MSPC), stearoylmyristoylphosphatidylcholine (SMPC), palmitoylmyristoylphosphatidylcholine (PMPC), palmitoylstearoylphosphatidylcholine (PSPC), stearoylpalmitoylphosphatidylcholine (SPPC), and stearoyloleoylphosphatidylcholine (SOPC).

Representative diacylphosphatidylethanolamines (i.e., 1,2-diacyl-sn-glycero-3-phosphoethanolamines) include dioleoylphosphatidylethanolamine (DOPE), dipalmitoylphosphatidylethanolamine (DPPE), distearoylphosphatidylethanolamine (DSPE), dilauroylphosphatidylethanolamine (DLPE), dimyristoylphosphatidylethanolamine (DMPE), dierucoylphosphatidylethanolamine (DEPE), and palmitoyloleoylphosphatidylethanolamine (POPE).

Representative diacylphosphatidylglycerols (i.e., 1,2-diacyl-sn-glycero-3-phosphoglycerols) include dioleoylphosphatidylglycerol (DOPG), dipalmitoylphosphatidylglycerol (DPPG), dierucoylphosphatidylglycerol (DEPG), dilauroylphosphatidylglycerol (DLPG), dimyristoylphosphatidylglycerol (DMPG), distearoylphosphatidylglycerol (DSPG), and palmitoyloleoylphosphatidylglycerol (POPG).

Representative diacylphosphatidylserines (i.e., 1,2-diacyl-sn-glycero-3-phosphoserines) include dilauroylphosphatidylserine (DLPS), dioleoylphosphatidylserine (DOPS), dipalmitoylphosphatidylserine (DPPS), and distearoylphosphatidylserine (DSPS).

Representative diacylphosphatidic acids (i.e., 1,2-diacyl-sn-glycero-3-phosphates) include dierucoylphosphatidic acid (DEPA), dilauroylphosphatidic acid (DLPA), dimyristoylphosphatidic acid (DMPA), dioleoylphosphatidic acid (DOPA), dipalmitoylphosphatidic acid (DPPA), and distearoylphosphatidic acid (DSPA).

Representative phospholipids include phosphosphingolipids such as ceramide phosphoryllipid, ceramide phosphorylcholine, and ceramide phosphorylethanolamine.

In some embodiments of any of the aspects, the nanodics of the invention can comprise one type of phospholipid. In some embodiments of any of the aspects, the nanodics of the invention can comprise two or more different phospholipids. In some embodiments of any of the aspects, the nanodics of the invention can comprise two different phospholipids. In some embodiments of any of the aspects, the nanodics of the invention can comprise three different phospholipids. In some embodiments of any of the aspects, the nanodics of the invention can comprise four different phospholipids.

In some embodiments of any of the aspects, the phospholipid can be a native lipid extract. In some embodiments of any of the aspects, the phospholipid can be a headgroup modified lipid, e.g., alkyl phosphates (e.g. 16:0 Monomethyl PE; 18:1 Monomethyl PE; 16:0 Dimethyl PE; 18:1 Dimethyl PE; 16:0 Phosphatidylmethanol; 18:1 Phosphatidylmethanol; 16:0 Phosphatidylethanol; 18:1 Phosphatidylethanol; 16:0-18:1 Phosphatidylethanol; 16:0 Phosphatidylpropanol; 18:1 Phosphatidylpropanol; 16:0 Phosphatidylbutanol; and 18:1 Phosphatidylbutanol); MRI imaging reagents (e.g. 14:0 PE-DTPA (Gd); DTPA-BSA (Gd); 16:0 PE-DTPA (Gd); 18:0 PE-DTPA (Gd); bis(14:0 PE)-DTPA (Gd); bis(16:0 PE)-DTPA (Gd); and bis(18:0 PE)-DTPA (Gd)); chelators (e.g., 14:0 PE-DTPA (Gd); DTPA-BSA (Gd); 16:0 PE-DTPA (Gd); 18:0 PE-DTPA (Gd); bis(14:0 PE)-DTPA (Gd); bis(16:0 PE)-DTPA (Gd); and bis(18:0 PE)-DTPA (Gd)); glycosylated lipids (e.g., 18:1 Lactosyl PE); pH sensitive lipids (e.g., N-palmitoyl homocysteine; 18:1 DGS; 16:0 DGS; and DOBAQ); antigenic lipids (e.g., DNP PE and DNP Cap PE); adhesive lipids (e.g., 16:0 DG Galloyl); and functionalized lipids (e.g., 16:0 PA-PEGS-mannose; 16:0 Caproylamine PE; 18:1 Caproylamine PE; 16:0 MPB PE; 18:1 MPB PE; 16:0 Ptd Ethylene Glycol; 18:1 Ptd Ethylene Glycol; 16:0 Folate Cap PE; 16:0 Cyanur PE; 16:0 Biotinyl PE; 18:1 Biotinyl PE; 16:0 Biotinyl Cap PE; 16:0 Cyanur Cap PE; 18:1 Biotinyl Cap PE; 16:0 Dodecanoyl PE; 18:1 Dodecanyl PE; 16:0 Glutaryl PE; 18:1 Glutaryl PE; 16:0 Succinyl PE; 18:1 Succinyl PE; 16:0 PDP PE; 18:1 PDP PE; 16:0 Ptd Thioethanol; 18:1 Dodecanylamine PE; 16:0 Dodecanylamine PE; 16:0 PE MCC; 18:1 PE MCC; 16:0 hexynoyl PE; and 16:0 azidocaproyl PE).

In some embodiments of any of the aspects described herein, the phospholipids can further comprise a molecule of interest, e.g., a membrane protein, a receptor, a transmembrane protein or channel, hydrophobic small molecules, hydrophobic drugs, RNA, peptides, and the like. In some embodiments of any of the aspects described herein, the covalently circularized nanodiscs described herein can be or be utilized as a drug delivery vehicle.

Provided herein are methods of making the covalently circularized nanodiscs described herein. In one aspect of any of the embodiments, described herein is a method comprising: a) circularizing the loopable membrane scaffold protein described herein; b) contacting the looped protein produced in step (a) with solubilized phospholipids.

In one aspect of any of the embodiments, described herein is a method comprising: a) contacting the loopable membrane scaffold protein described herein with a sortase enzyme; b) contacting the looped protein produced in step (a) with solubilized phospholipids. A number of sortase enzymes are known in the art, e.g., ones that recognize the various exemplary circularization domain sequences provided herein. By way of non-limiting example, the sortase can be Staphylococcus aureus wild type sortase A (Srt A); evolved sortase; eSrtA; eSrtA(2A-9); eSrtA(4S-9); or Streptococcus pyogenes sortase A. Wild type SrtA and eSrtA recognize LPXTG (SEQ ID NO: 51) while eSrtA(2A-9) recognizes LAXTG (SEQ ID NO: 75), LSETG (SEQ ID NO: 76) and accepts glycine nucleophiles and eSrt A(4S-9) recognizes LPXSG (SEQ ID NO: 77), LPXCG (SEQ ID NO: 78), LPXAG (SEQ ID NO: 79) and accepts glycine nucleophiles. Evolved sortases are described further in, e.g., Don et al. PNAS 2014 111(37):13343-8 and Chen et al. PNAS 2011 108(28):11399-404; each of which is incorporated by reference herein in its entirety. Streptococcus sortase A recognizes the LPXTA motif (SEQ ID NO: 56) and accepts alanine nucleophiles (see, e.g., P. Race, J Biol. Chem. 284: 6924-6933; which is incorporated by reference herein in its entirety).

In some embodiments of any of the aspects, the contacting step can be stopped by quenching the reaction with a sortase inhibitor. Sortase inhibition is known in the art and can include the use of AAEK2 or a high concentration of EDTA. As used herein, a high concentration of EDTA can be from about 100 uM to about 400 mM, e.g., 100 uM to 400 mM, about 1 mM to about 300 mM, 1 mM to 300 mM, about 1 mM to about 200 mM, or 1 mM to 200 mM.

In one aspect of any of the embodiments, described herein is a method comprising a) contacting the loopable membrane scaffold protein comprising intein circularization domains with: i) a solution having a pH low enough to induce cleavage of the dipeptide sequence of Asn-Cys; ii) and a thiol reagent to induce cleavage at the Cys residue; resulting in circularization of the protein; and b) contacting the looped protein produced in step (a) with solubilized phospholipids. In some embodiments of any of the aspects, the thiol reagent is DTT.

In some embodiments of any of the aspects, the loopable membrane scaffold protein comprises a chitin binding domain flanking each circularization domain and is first purified by chitin binding prior to circularization (e.g., the loopable membrane scaffold protein is expressed from a pTWIN vector in E. coli and purified by binding to chitin beads).

In one aspect of any of the embodiments, described herein is a method comprising a) contacting a loopable membrane scaffold protein comprising circularization domains comprising cysteine residues with a thiol reagent or thiol donor, resulting in circularization of the protein; and b) contacting the looped protein produced in step (a) with solubilized phospholipids. In some embodiments of any of the aspects, the thiol can be DTT, sodium 2-mercaptoethane sulfonate (MESNa) or guanidinium hydrocholoride. Circularization via two cysteine residues is described in the art, e.g., Cowper, B et. al. ChemBioChem 2013, 14, 809-812; which is incorporated by reference herein in its entirety. Briefly, the C-terminal cysteine initiates an intramolecular N→S acyl shift. This results in an S-acyl intermediate that can be intercepted by an added thiol, yielding a C-terminal thioester and liberating cysteine. The cysteine at the N terminus interacts with the C-terminal thioester and leads to spontaneous backbone circularization, through intramolecular transthioesterification. Next, an S→N acyl shift rearrangement occurs that lead to formation of a peptide bond. The final circularized product has a cysteine next to the newly formed peptide bond.

In some embodiments of any of the aspects, a reagent and/or enzyme used to catalyze or permit circularization (e.g., a sortase enzyme) can be bound to a substrate or surface.

In some embodiments of any of the aspects, a reagent and/or enzyme used to catalyze or permit circularization (e.g., a sortase enzyme) can further comprise an affinity tag to, e.g., permit binding a substrate or to assist in removal of the reagent and/or enzyme when the reaction is to be stopped. In some embodiments of any of the aspects, the affinity tag is a His tag. In some embodiments of any of the aspects, a sortase can further comprise a His tag.

In some embodiments of any of the aspects, the loopable membrane scaffold protein can further comprise an affinity tag that permits the protein to be bound to a substrate or surface. In some embodiments of any of the aspects, the loopable membrane scaffold protein can further comprise a His tag that permits the protein to be bound to a substrate or surface. In some embodiments of any of the aspects, the loopable membrane scaffold protein can further comprise a C-terminal affinity tag that permits the protein to be bound to a substrate or surface. In some embodiments of any of the aspects, the method described herein can further comprise a first step of binding a loopable membrane scaffold protein comprising an affinity tag to a substrate or surface.

In some embodiments of any of the aspects, the substrate comprises $Cu^{2+}$, $Ni^{2+}$ or $Co^{2+}$. In some embodiments of any of the aspects, the substrate is a column, chip, or bead.

In some embodiments of any of the aspects, the loopable membrane scaffold protein is bound to a substrate, e.g., a bead, and the first contacting step is performed in the presence of phospholipids. In some embodiments of any of the aspects, the loopable membrane scaffold protein is bound to a substrate, e.g., a bead, and the first and second contacting steps are performed concurrently.

In some embodiments of any of the aspects, the loopable membrane scaffold protein is bound to a substrate, e.g., a bead, and after the first contacting step, the looped membrane scaffold protein is eluted from the substrate.

In some embodiments of any of the aspects, the loopable membrane scaffold protein is in solution prior to the first contacting step. In some embodiments of any of the aspects, the loopable membrane scaffold protein is in solution at a concentration of less than about 100 uM prior to the first contacting step. In some embodiments of any of the aspects, the loopable membrane scaffold protein is in solution at a concentration of less than 100 uM prior to the first contacting step. In some embodiments of any of the aspects, the loopable membrane scaffold protein is in solution at a concentration of from about 1 uM to about 1 mM prior to the first contacting step. In some embodiments of any of the aspects, the loopable membrane scaffold protein is in solution at a concentration of from 1 uM to 1 mM prior to the first contacting step. In some embodiments of any of the aspects, the loopable membrane scaffold protein is in solution at a concentration of from about 1 uM to about 100 uM prior to the first contacting step. In some embodiments of any of the aspects, the loopable membrane scaffold protein is in solution at a concentration of from 1 uM to 100 uM prior to the first contacting step. In some embodiments of any of the aspects, the looped membrane scaffold protein formed after the first contacting step is passed through a column, substrate, and/or solution which can be bound by an affinity tag found on the loopable membrane scaffold protein. In some embodiments of any of the aspects, the looped membrane scaffold protein formed after the first contacting step is passed through a column, substrate, and/or solution Cu2+, Co2+ or Ni2+, which can be bound by an affinity tag (e.g. a His tag) found on the loopable membrane scaffold protein.

In some embodiments of any of the aspects, the loopable membrane protein further comprises a cap sequence N-terminal of the N-terminal circularization domain and the method comprises a first step of contacting the protein with an enzyme to cleave the cap sequence.

In some embodiments of any of the aspects, the phospholipids of the second contacting step are solubilized in detergent. Exemplary detergents can include, but are not limited to Decyl β-D-maltopyranoside, Deoxycholic acid, Digitonin, n-Dodecyl β-D-glucopyranoside, n-Dodecyl β-D-maltoside, N-Lauroylsarcosine sodium salt, Sodium cholate, Sodium deoxycholate, Undecyl β-D-maltoside, Triton X-100, CHAPS, 5-Cyclohexylpentyl β-D-maltoside, n-dodecyl phosphatidylcholine, n-octyl-β-d-glucoside, and Brij 97.

In some embodiments of any of the aspects, the second contacting step occurs at a temperature of from about 0 C to about 42 C. In some embodiments of any of the aspects, the second contacting step occurs at a temperature of from 0 C to 42 C. In some embodiments of any of the aspects, the second contacting step occurs at a temperature of from about 0 C to about 37 C. In some embodiments of any of the aspects, the second contacting step occurs at a temperature of from 0 C to 37 C.

In some embodiments of any of the aspects, the ratio of loopable membrane scaffold protein to phospholipids is from about 1:1000 to about 1:10,000. In some embodiments of any of the aspects, the ratio of loopable membrane scaffold protein to phospholipids is from 1:1000 to 1:10,000. In some embodiments of any of the aspects, the ratio of loopable membrane scaffold protein to phospholipids is from about 1:2000 to about 1:5000. In some embodiments of any of the aspects, the ratio of loopable membrane scaffold protein to phospholipids is from 1:2000 to 1:5000.

In some embodiments of any of the aspects, the loopable membrane scaffold protein has the sequence of SEQ ID NO: 4; the ratio of loopable membrane scaffold protein to phospholipids is from about 1:3500 to about 1:4500; and nanodiscs which are circular in shape formed. In some embodiments of any of the aspects, the loopable membrane scaffold protein has the sequence of SEQ ID NO: 4; the ratio of loopable membrane scaffold protein to phospholipids is about 1:4000; and nanodiscs which are circular in shape are formed. In some embodiments of any of the aspects, the loopable membrane scaffold protein has the sequence of SEQ ID NO: 4; the ratio of loopable membrane scaffold protein to phospholipids is from 1:3500 to 1:4500; and nanodiscs which are circular in shape are formed. In some embodiments of any of the aspects, the loopable membrane scaffold protein has the sequence of SEQ ID NO: 4; the ratio of loopable membrane scaffold protein to phospholipids is 1:4000; and nanodiscs which are circular in shape are formed. In some embodiments of any of the aspects, the phospholipids are POPC/POPG lipids.

In some embodiments of any of the aspects, the loopable membrane scaffold protein has the sequence of SEQ ID NO: 4; the ratio of loopable membrane scaffold protein to phospholipids is from about 1:2500 to about 1:3700; and nanodiscs which are polygonal in shape are formed. In some embodiments of any of the aspects, the loopable membrane scaffold protein has the sequence of SEQ ID NO: 4; the ratio of loopable membrane scaffold protein to phospholipids is from about 1:3100 to about 1:3400; and nanodiscs which are polygonal in shape are formed. In some embodiments of any of the aspects, the loopable membrane scaffold protein has the sequence of SEQ ID NO: 4; the ratio of loopable membrane scaffold protein to phospholipids is from 1:2500 to 1:3700; and nanodiscs which are polygonal in shape are formed. In some embodiments of any of the aspects, the loopable membrane scaffold protein has the sequence of SEQ ID NO: 4; the ratio of loopable membrane scaffold protein to phospholipids is from 1:3100 to 1:3400; and nanodiscs which are polygonal in shape are formed. In some embodiments of any of the aspects, the phospholipids are POPC/POPG lipids.

The nanodiscs described herein can be used, e.g., in structural and/or functional studies of membrane proteins or as vaccine platforms. It is specifically contemplated that the nanodiscs described herein can be used for solution NMR, cryo-EM studies, crystallization, and 2D lattice of, e.g., membrane proteins in or on the bilayer. Membrane proteins can be studied to examine, e.g., protein-protein interactions with other membrane proteins, or cytosolic or extracellular proteins; behavior and structure of membrane pores; virus entry and inhibition thereof; and cell-free expression of membrane proteins. The nanodiscs described herein can also permit study of, e.g., lipid rafts themselves, vesicle fusion, and Residual Dipolar Coupling (RDC) measurements (detergent free, homogenous effect, charge tunable).

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

In some embodiments, a nucleic acid encoding a polypeptide as described herein (e.g. a loopable membrane scaffold protein) is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence, which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding encoding a polypeptide as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A loopable membrane scaffold protein comprising, from N-terminus to C-terminus:
   i. an N-terminal circularization domain;
   ii. a plurality of amphipathic alpha helix domains; and
   iii. a C-terminal circularization domain.
2. The protein of paragraph 1, wherein one circularization domain comprises:
   a non-polar amino acid sequence comprising at least one N-terminal glycine or alanine residue; and
   the other circularization domain comprises:
   a sequence LPXTG/A; wherein X represents any amino acid.
3. The protein of paragraph 1, wherein the N-terminal circularization domain comprises:
   a non-polar amino acid sequence comprising at least one N-terminal glycine or alanine residue; and
   the C-terminal circularization domain comprises:
   a sequence LPXTG/A; wherein X represents any amino acid.
4. The protein of any of paragraphs 1-3, wherein the non-polar amino acid sequence is from 1 to 10 amino acids in length and comprises amino acids selected from the group consisting of: glycine and alanine.
5. The protein of any of paragraphs 1-4, wherein the non-polar amino acid sequence consists of 1-5 glycine residues.

6. The protein of any of paragraphs 1-4, wherein the non-polar amino acid sequence consists of 1-5 alanine residues.
7. The protein of paragraph 1-6, wherein the sequence LPXTG/A is covalently bound to the at least one glycine or alanine residue of (i).
8. The protein of any of paragraphs 1-7, wherein the sequence LPXTG/A is LPGTG/A (SEQ ID NO: 24); LPSTG/A (SEQ ID NO: 25); or LPETG/A (SEQ ID NO: 26).
9. The protein of paragraph 1, wherein one circularization domain comprises an intein separated from the domain of (ii) by a Cys; and the other circularization domain comprises an intein separated from the domain of (ii) by a dipeptide sequence of Asn-Cys, with the Asn being closest to the intein.
10. The protein of paragraph 1, wherein the N-terminal circularization domain comprises an intein separated from the domain of (ii) by a Cys; and the C-terminal circularization domain comprises an intein separated from the domain of (ii) by a dipeptide sequence of Asn-Cys, with the Asn being closest to the intein.
11. The protein of any of paragraphs 9-10, wherein at least one intein is flanked by a chitin binding domain (CBD).
12. A protein of paragraph 1, wherein each circularization domain comprises a Cys.
13. The protein of any of paragraphs 1-12, wherein the amphipathic alpha helix domain comprises:
    (a) an ApoA-I polypeptide; or
    (b) at least one alpha helical polypeptide with secondary amphipathicity or a repeat thereof;
    (c) at least one amphipathic proline-rich polypeptide or a repeat thereof; or
    (d) at least one repeat of the sequence XZXPPP; wherein X is any hydrophobic residue and Z is any hydrophilic residue.
14. The protein of paragraph 13, wherein the alpha helical polypeptide has a sequence selected from the group consisting of:

```
                                (SEQ ID NO: 27)
DWFKAFYDKLAEKFKEAF;

(SEQ ID NO: 28)
DFLKAFYDKVAEKFKEAAPDWFKAFYDKVAEKFKEAF:

(SEQ ID NO: 29)
KLALRLALKAFKAALKLA;

(SEQ ID NO: 30)
RLALDLALRAFKAAWKLA;

(SEQ ID NO: 31)
ELAWDLAFEALDAELKLD;

(SEQ ID NO: 32)
FLKLLKKFLKLFKKLLKLF;

(SEQ ID NO: 33)
WLKLLKKWLKLWKKLLKL;

(SEQ ID NO: 34)
LLKFLKRLLKLLKDLWKLL;

(SEQ ID NO: 35)
WEAAFAEALAEAWAEHLAEALAEAVEALAA;

(SEQ ID NO: 36)
WEAKLAKALAKALAKHLAKALAKALKACEA;
```

-continued
```
                                (SEQ ID NO: 37)
RAFARALARALKALARALKALAR;

(SEQ ID NO: 38)
GLFEALLELLESLWELLLEA;

(SEQ ID NO: 39)
KLLKLLLKLWKKLLKLLK;

(SEQ ID NO: 40)
DWLKAFYDKVAEKLKEAF;
and (SEQ ID NO: 41)
DWFKAFYDKVAEKFKEAF.
```

15. The protein of any of paragraphs 1-14, further comprising a cap sequence N-terminal of the N-terminal circularization domain that can be cleaved to expose the N-terminal circularization domain as the N-terminus of the protein.
16. The protein of paragraph 15, wherein the cap sequence comprises as sequence selected from the group consisting of:
    a. Leu-Val-Pro-Arg-Gly-Ser (SEQ ID NO: 42); and
    b. Glu-X-Leu-Tyr-Φ-Gln-φ where X is any residue, Φ is any large or medium hydrophobic residue and φ is glycine or alanine (SEQ ID NO: 43).
17. The protein of any of paragraphs 1-16, wherein the cap sequence further comprises an affinity purification tag N-terminal of the cleavage site.
18. The protein of any of paragraphs 1-17, further comprising a His tag flanking one of the circularization domains.
19. The protein of paragraph 18, wherein the His tag is located C-terminal of the C-terminal circularization domain.
20. The protein of any of paragraphs 1-19, further comprising a linker flanking one of the circularization domains.
21. The protein of any of paragraphs 1-20, wherein the linker is located C-terminal of the C-terminal circularization domain.
22. The protein of any of paragraphs 1-21, wherein the plurality of amphipathic alpha helix domains are separated by flexible linker sequences;
23. The protein of paragraph 22, wherein the flexible linker sequence is selected from the group consisting of:

```
                                (SEQ ID NO: 44)
        LPGTGS;

(SEQ ID NO: 45)
        LPGTSG;

(SEQ ID NO: 46)
        LPSTGS;
        and (SEQ ID NO: 47)
        LPSTSG.
```

24. The protein of any of paragraphs 1-23, having the sequence of any of SEQ ID NOs: 1-4 and 6-23.
25. A covalently circularized nanodisc comprising:
    a. a phospholipid bilayer; and
    b. a looped membrane scaffold protein forming a belt around the bilayer, wherein the looped membrane scaffold protein comprises:

iv. an N-terminal circularization domain covalently linked to a C-terminal circularization domain; and
v. a plurality of amphipathic alpha helix domains.

26. The nanodisc of paragraph 25, wherein an N-terminal circularization domain covalently linked to a C-terminal circularization domain comprises the sequence LPXT followed by a non-polar amino acid sequence comprising at least one N-terminal glycine or alanine residue;
wherein X represents any amino acid.

27. The nanodisc of any of paragraphs 25-26, wherein the non-polar amino acid sequence is from 1 to 10 amino acids in length and comprises amino acids selected from the group consisting of: glycine and alanine.

28. The nanodisc of any of paragraphs 25-27, wherein the non-polar amino acid sequence consists of 1-5 glycine residues.

29. The nanodisc of any of paragraphs 25-27, wherein the non-polar amino acid sequence consists of 1-5 alanine residues.

30. The nanodisc of any of paragraphs 25-29, wherein the sequence LPXT is LPGT (SEQ ID NO: 48); LPST (SEQ ID NO: 49); or LPET (SEQ ID NO: 50).

31. The nanodisc of any paragraph 25, wherein the N-terminal circularization domain covalently linked to a C-terminal circularization domain is a cysteine residue.

32. The nanodisc of any of paragraphs 25-31, wherein amphipathic alpha helix domain comprises:
(a) an ApoA-I polypeptide; or
(b) at least one alpha helical polypeptide with secondary amphipathicity or a repeat thereof;
(c) at least one amphipathic proline-rich polypeptide or a repeat thereof; or
(d) at least one repeat of the sequence XZXPPP; wherein X is any hydrophobic residue and Z is any hydrophilic residue.

33. The nanodisc of paragraph 32, wherein the alpha helical polypeptide has a sequence selected from the group consisting of:

DWFKAFYDKLAEKFKEAF; (SEQ ID NO: 27)

DFLKAFYDKVAEKFKEAAPDWFKAFYDKVAEKFKEAF; (SEQ ID NO: 28)

KLALRLALKAFKAALKLA; (SEQ ID NO: 29)

RLALDLALRAFKAAWKLA; (SEQ ID NO: 30)

ELAWDLAFEALDAELKLD; (SEQ ID NO: 31)

FLKLLKKFLKLFKKLLKLF; (SEQ ID NO: 32)

WLKLLKKWLKLWKKLLKL; (SEQ ID NO: 33)

LLKFLKRLLKLLKDLWKLL; (SEQ ID NO: 34)

WEAAFAEALAEAWAEHLAEALAEAVEALAA; (SEQ ID NO: 35)

WEAKLAKALAKALAKHLAKALAKALKACEA; (SEQ ID NO: 36)

RAFARALARALKALARALKALAR; (SEQ ID NO: 37)

GLFEALLELLESLWELLLEA; (SEQ ID NO: 38)

KLLKLLLKLWKKLLKLLK; (SEQ ID NO: 39)

DWLKAFYDKVAEKLKEAF; (SEQ ID NO: 40)
and

DWFKAFYDKVAEKFKEAF. (SEQ ID NO: 41)

34. The nanodisc of any of paragraphs 25-33, wherein the plurality of amphipathic alpha helix domains are separated by flexible linker sequences;

35. The nanodisc of paragraph 25-34, wherein the flexible linker sequence is selected from the group consisting of:

LPGTGS; (SEQ ID NO: 44)

LPGTSG; (SEQ ID NO: 45)

LPSTGS; (SEQ ID NO: 46)
and

LPSTSG. (SEQ ID NO: 47)

36. The nanodisc of any of paragraphs 25-35, wherein the protein has the sequence of any of SEQ ID NOs: 1-4 and 6-23.

37. The nanodisc of any of paragraphs 25-36, wherein the diameter is greater than about 6 nm.

38. The nanodisc of any of paragraphs 25-37, wherein the diameter is greater than about 15 nm.

39. The nanodisc of any of paragraphs 25-38, wherein the diameter is greater than about 50 nm.

40. The nanodisc of any of paragraphs 25-39, wherein the diameter is about 80 nm.

41. A method of making a nanodisc of any of paragraphs 25-30 or 32-40, the method comprising:
a. contacting the loopable membrane scaffold protein of any of paragraphs 1-8 or 13-24 with a sortase enzyme;
b. contacting the looped protein produced in step (a) with solubilized phospholipids.

42. The method of paragraph 41, wherein the sortase is selected from the group consisting of:
*Staphylococcus aureus* wild type sortase A (Srt A); evolved sortase; eSrtA; eSrtA(2A-9); eSrtA(4S-9); and *Streptococcus pyogenes* sortase A.

43. The method of any of paragraphs 41-42, wherein the contacting step is stopped by quenching the reaction with a sortase inhibitor.

44. The method of paragraph 43, wherein the sortase inhibitor is AAEK2 or high concentrations of EDTA.

45. The method of any of paragraphs 41-44, wherein the sortase is bound to a substrate.

46. The method of any of paragraphs 41-45, wherein the sortase further comprises a His tag.

47. A method of making a nanodisc of any of paragraphs 31-40, the method comprising:

a. contacting the loopable membrane scaffold protein of any of paragraphs 9-11 or 13-24 with:
   a. a solution having a pH low enough to induce cleavage of the dipeptide sequence of Asn-Cys;
   b. and a thiol reagent to induce cleavage at the Cys residue;
   resulting in circularization of the protein; and
b. contacting the looped protein produced in step (a) with solubilized phospholipids.

48. The method of paragraph 47, wherein the thiol reagent is DTT.
49. A method of making a nanodisc of any of paragraphs 31-40, the method comprising:
   a. contacting the loopable membrane scaffold protein of any of paragraphs 12-24 with a thiol reagent, resulting in circularization of the protein; and
   b. contacting the looped protein produced in step (a) with solubilized phospholipids.
50. The method of any of paragraphs 41-49, wherein the phospholipids are solubilized in detergent.
51. The method of any of paragraphs 41-50, wherein step (b) occurs at a temperature of from about 0 C to about 42 C.
52. The method of any of paragraphs 41-51, wherein step (b) occurs at a temperature of from about 0 C to about 37 C.
53. The method of any of paragraphs 41-52, wherein the ratio of loopable membrane scaffold protein to phospholipids is from about 1:2000 to about 1:5000.
54. The method of any of paragraphs 41-53, wherein the ratio of loopable membrane scaffold protein of any of paragraphs 1-21 and 24 to phospholipids is from about 1:3500 to about 1:4500; and circular nanodiscs are formed.
55. The method of any of paragraphs 41-54, wherein the ratio of loopable membrane scaffold protein of any of paragraphs 1-21 and 24 to phospholipids is from about 1:4000; and circular nanodiscs are formed.
56. The method of any of paragraphs 41-55, wherein the ratio of loopable membrane scaffold protein of any of paragraphs 22-23, to phospholipids is from about 1:2500 to about 1:3700; and non-circular nanodiscs are formed.
57. The method of any of paragraphs 41-56, wherein the ratio of loopable membrane scaffold protein of any of paragraphs 22-23 to phospholipids is from about 1:3100 to about 1:3400; and non-circular nanodiscs are formed.
58. The method of any of paragraphs 41-57, wherein the protein further comprises a cap sequence N-terminal of the N-terminal circularization domain and the method comprises a first step of contacting the protein with an enzyme to cleave the cap sequence.
59. The method of any of paragraphs 41-58, wherein the protein further comprises a C-terminal His tag and the method comprises a first step of binding the protein to a substrate.
60. The method of any of paragraphs 41-59, wherein the substrate comprises Cu2+, Ni2+ or Co2+.
61. The method of any of paragraphs 41-60, wherein the substrate is a chip or bead.
62. The method of any of paragraphs 41-61, wherein the substrate is a bead and step (a) is performed in the presence of phospholipids.
63. The method of any of paragraphs 41-62, wherein the substrate is a bead and the steps (a) and (b) are performed concurrently.
64. The method of any of paragraphs 41-63, further comprising, after step (a), a step of eluting the looped protein produced in step (a) from the substrate.
65. The method of any of paragraphs 41-64, wherein the loopable membrane scaffold protein is in solution at a concentration of less than 100 uM prior to the contacting step.
66. The method of paragraph 65, wherein the looped protein formed in step (a) is passed through a column, substrate, and/or solution comprising Cu2+, Co2+ or Ni2+.

Some embodiments of the technology described herein can be defined according to any of the following numbered paragraphs:

1. A loopable membrane scaffold protein comprising, from N-terminus to C-terminus:
   i. an N-terminal circularization domain;
   ii. a plurality of amphipathic alpha helix domains; and
   iii. a C-terminal circularization domain.
2. The protein of paragraph 1, wherein one circularization domain comprises:
   a non-polar amino acid sequence comprising at least one N-terminal glycine or alanine residue; and
   the other circularization domain comprises:
   a sequence LPXTG/A; wherein X represents any amino acid.
3. The protein of paragraph 1, wherein the N-terminal circularization domain comprises:
   a non-polar amino acid sequence comprising at least one N-terminal glycine or alanine residue; and
   the C-terminal circularization domain comprises:
   a sequence LPXTG/A; wherein X represents any amino acid.
4. The protein of any of paragraphs 1-3, wherein the non-polar amino acid sequence is from 1 to 10 amino acids in length and comprises amino acids selected from the group consisting of: glycine and alanine.
5. The protein of any of paragraphs 1-4, wherein the non-polar amino acid sequence consists of 1-5 glycine residues.
6. The protein of any of paragraphs 1-4, wherein the non-polar amino acid sequence consists of 1-5 alanine residues.
7. The protein of paragraph 1-6, wherein the sequence LPXTG/A is covalently bound to the at least one glycine or alanine residue of (i).
8. The protein of any of paragraphs 1-7, wherein the sequence LPXTG/A is LPGTG/A (SEQ ID NO: 24); LPSTG/A (SEQ ID NO: 25); or LPETG/A (SEQ ID NO: 26).
9. The protein of paragraph 1, wherein one circularization domain comprises an intein separated from the domain of (ii) by a Cys; and the other circularization domain comprises an intein separated from the domain of (ii) by a dipeptide sequence of Asn-Cys, with the Asn being closest to the intein.
10. The protein of paragraph 1, wherein the N-terminal circularization domain comprises an intein separated from the domain of (ii) by a Cys; and the C-terminal circularization domain comprises an intein separated from the domain of (ii) by a dipeptide sequence of Asn-Cys, with the Asn being closest to the intein.
11. The protein of any of paragraphs 9-10, wherein at least one intein is flanked by a chitin binding domain (CBD).
12. A protein of paragraph 1, wherein each circularization domain comprises a Cys.

13. The protein of any of paragraphs 1-12, wherein the amphipathic alpha helix domain comprises:
   (a) an ApoA-I polypeptide; or
   (b) at least one alpha helical polypeptide with secondary amphipathicity or a repeat thereof;
   (c) at least one amphipathic proline-rich polypeptide or a repeat thereof; or
   (d) at least one repeat of the sequence XZXPPP; wherein X is any hydrophobic residue and Z is any hydrophilic residue.
14. The protein of paragraph 13, wherein the alpha helical polypeptide has a sequence selected from the group consisting of:

DWFKAFYDKLAEKFKEAF; (SEQ ID NO: 27)

DFLKAFYDKVAEKFKEAAPDWFKAFYDKVAEKFKEAF; (SEQ ID NO: 28)

KLALRLALKAFKAALKLA; (SEQ ID NO: 29)

RLALDLALRAFKAAWKLA; (SEQ ID NO: 30)

ELAWDLAFEALDAELKLD; (SEQ ID NO: 31)

FLKLLKKFLKLFKKLLKLF; (SEQ ID NO: 32)

WLKLLKKWLKLWKKLLKL; (SEQ ID NO: 33)

LLKFLKRLLKLLKDLWKLL; (SEQ ID NO: 34)

WEAAFAEALAEAWAEHLAEALAEAVEALAA; (SEQ ID NO: 35)

WEAKLAKALAKALAKHLAKALAKALKACEA; (SEQ ID NO: 36)

RAFARALARALKALARALKALAR; (SEQ ID NO: 37)

GLFEALLELLESLWELLLEA; (SEQ ID NO: 38)

KLLKLLLKLWKKLLKLLK; (SEQ ID NO: 39)

DWLKAFYDKVAEKLKEAF; (SEQ ID NO: 40)
    and

DWFKAFYDKVAEKFKEAF. (SEQ ID NO: 41)

15. The protein of any of paragraphs 1-14, further comprising a cap sequence N-terminal of the N-terminal circularization domain that can be cleaved to expose the N-terminal circularization domain as the N-terminus of the protein.
16. The protein of paragraph 15, wherein the cap sequence comprises as sequence selected from the group consisting of:
    a. Leu-Val-Pro-Arg-Gly-Ser (SEQ ID NO: 42); and
    b. Glu-X-Leu-Tyr-Φ-Gln-φ where X is any residue, Φ is any large or medium hydrophobic residue and φ is glycine or alanine (SEQ ID NO: 43).
17. The protein of any of paragraphs 1-16, wherein the cap sequence further comprises an affinity purification tag N-terminal of the cleavage site.
18. The protein of any of paragraphs 1-17, further comprising a His tag flanking one of the circularization domains.
19. The protein of paragraph 18, wherein the His tag is located C-terminal of the C-terminal circularization domain.
20. The protein of any of paragraphs 1-19, further comprising a linker flanking one of the circularization domains.
21. The protein of any of paragraphs 1-20, wherein the linker is located C-terminal of the C-terminal circularization domain.
22. The protein of any of paragraphs 1-21, wherein the plurality of amphipathic alpha helix domains are separated by flexible linker sequences;
23. The protein of paragraph 22, wherein the flexible linker sequence is selected from the group consisting of:

LPGTGS; (SEQ ID NO: 44)

LPGTSG; (SEQ ID NO: 45)

LPSTGS; (SEQ ID NO: 46)
    and

LPSTSG. (SEQ ID NO: 47)

24. The protein of any of paragraphs 1-23, having the sequence of any of SEQ ID NOs: 1-4 and 6-23.
25. The protein of paragraph 24, further comprising a substitution with cysteine at one or more residues corresponding to positions 31, 36, 137, and 153 of SEQ ID NO: 1 or 6, or positions 31, 36, 93, 110, 159, and 175 of SEQ ID NO: 2 or 7.
26. The protein of any of paragraphs 1-23, having the sequence of SEQ ID NO: 62.
27. A covalently circularized nanodisc comprising:
    a. a phospholipid bilayer; and
    b. a looped membrane scaffold protein forming a belt around the bilayer, wherein the looped membrane scaffold protein comprises:
       i. an N-terminal circularization domain covalently linked to a C-terminal circularization domain; and
       ii. a plurality of amphipathic alpha helix domains.
28. The nanodisc of paragraph 27, wherein an N-terminal circularization domain covalently linked to a C-terminal circularization domain comprises the sequence LPXT followed by a non-polar amino acid sequence comprising at least one N-terminal glycine or alanine residue;
    wherein X represents any amino acid.
29. The nanodisc of any of paragraphs 27-28, wherein the non-polar amino acid sequence is from 1 to 10 amino acids in length and comprises amino acids selected from the group consisting of: glycine and alanine.
30. The nanodisc of any of paragraphs 27-29, wherein the non-polar amino acid sequence consists of 1-5 glycine residues.
31. The nanodisc of any of paragraphs 27-30, wherein the non-polar amino acid sequence consists of 1-5 alanine residues.
32. The nanodisc of any of paragraphs 27-31, wherein the sequence LPXT is LPGT (SEQ ID NO: 48); LPST (SEQ ID NO: 49); or LPET (SEQ ID NO: 50).

33. The nanodisc of any paragraph 32, wherein the N-terminal circularization domain covalently linked to a C-terminal circularization domain is a cysteine residue.
34. The nanodisc of any of paragraphs 27-33, wherein amphipathic alpha helix domain comprises:
    (a) an ApoA-I polypeptide; or
    (b) at least one alpha helical polypeptide with secondary amphipathicity or a repeat thereof;
    (c) at least one amphipathic proline-rich polypeptide or a repeat thereof; or
    (d) at least one repeat of the sequence XZXPPP; wherein X is any hydrophobic residue and Z is any hydrophilic residue.
35. The nanodisc of paragraph 34, wherein the alpha helical polypeptide has a sequence selected from the group consisting of:

DWFKAFYDKLAEKFKEAF; (SEQ ID NO: 27)

DFLKAFYDKVAEKFKEAAPDWFKAFYDKVAEKFKEAF; (SEQ ID NO: 28)

KLALRLALKAFKAALKLA; (SEQ ID NO: 29)

RLALDLALRAFKAAWKLA; (SEQ ID NO: 30)

ELAWDLAFEALDAELKLD; (SEQ ID NO: 31)

FLKLLKKFLKLFKKLLKLF; (SEQ ID NO: 32)

WLKLLKKWLKLWKKLLKL; (SEQ ID NO: 33)

LLKFLKRLLKLLKDLWKLL; (SEQ ID NO: 34)

WEAAFAEALAEAWAEHLAEALAEAVEALAA; (SEQ ID NO: 35)

WEAKLAKALAKALAKHLAKALAKALKACEA; (SEQ ID NO: 36)

RAFARALARALKALARALKALAR; (SEQ ID NO: 37)

GLFEALLELLESLWELLLEA; (SEQ ID NO: 38)

KLLKLLLKLWKKLLKLLK; (SEQ ID NO: 39)

DWLKAFYDKVAEKLKEAF; (SEQ ID NO: 40)
and

DWFKAFYDKVAEKFKEAF. (SEQ ID NO: 41)

36. The nanodisc of any of paragraphs 27-35, wherein the plurality of amphipathic alpha helix domains are separated by flexible linker sequences; 37. The nanodisc of paragraph 27-36, wherein the flexible linker sequence is selected from the group consisting of:

LPGTGS; (SEQ ID NO: 44)

LPGTSG; (SEQ ID NO: 45)

LPSTGS; (SEQ ID NO: 46)
and

LPSTSG. (SEQ ID NO: 47)

38. The nanodisc of any of paragraphs 27-37, wherein the protein has the sequence of any of SEQ ID NOs: 1-4 and 6-23.
39. The nanodics of paragraph 38, wherein the protein further comprises a substitution with cysteine at one or more residues corresponding to positions 31, 36, 137, and 153 of SEQ ID NO: 1 or 6, or positions 31, 36, 93, 110, 159, and 175 of SEQ ID NO: 2 or 7.
40. The nanodisc of any of paragraphs 27-39, wherein the protein has the sequence of SEQ ID NO: 62.
41. The nanodisc of any of paragraphs 27-40, wherein the diameter is greater than about 6 nm.
42. The nanodisc of any of paragraphs 27-41, wherein the diameter is greater than about 15 nm.
43. The nanodisc of any of paragraphs 27-42, wherein the diameter is greater than about 50 nm.
44. The nanodisc of any of paragraphs 27-43, wherein the diameter is about 80 nm.
45. A method of making a nanodisc of any of paragraphs 27-32 or 34-44, the method comprising:
    a. contacting the loopable membrane scaffold protein of any of paragraphs 1-8 or 13-26 with a sortase enzyme;
    b. contacting the looped protein produced in step (a) with solubilized phospholipids.
46. The method of paragraph 45, wherein the sortase is selected from the group consisting of:
    *Staphylococcus aureus* wild type sortase A (Srt A); evolved sortase; eSrtA; eSrtA(2A-9); eSrtA(4S-9); and *Streptococcus pyogenes* sortase A.
47. The method of any of paragraphs 45-46, wherein the contacting step is stopped by quenching the reaction with a sortase inhibitor.
48. The method of paragraph 47, wherein the sortase inhibitor is AAEK2 or high concentrations of EDTA.
49. The method of any of paragraphs 45-48, wherein the sortase is bound to a substrate.
50. The method of any of paragraphs 45-49, wherein the sortase further comprises a His tag.
51. A method of making a nanodisc of any of paragraphs 33-44, the method comprising:
    a. contacting the loopable membrane scaffold protein of any of paragraphs 9-11 or 13-26 with:
        i. a solution having a pH low enough to induce cleavage of the dipeptide sequence of Asn-Cys;
        ii. and a thiol reagent to induce cleavage at the Cys residue;
    resulting in circularization of the protein; and
    b. contacting the looped protein produced in step (a) with solubilized phospholipids.
52. The method of paragraph 51, wherein the thiol reagent is DTT.
53. A method of making a nanodisc of any of paragraphs 33-44, the method comprising:
    a. contacting the loopable membrane scaffold protein of any of paragraphs 12-26 with a thiol reagent, resulting in circularization of the protein; and b. contacting the looped protein produced in step (a) with solubilized phospholipids.
54. The method of any of paragraphs 45-53, wherein the phospholipids are solubilized in detergent.
55. The method of any of paragraphs 45-54, wherein step (b) occurs at a temperature of from about 0 C to about 42 C.
56. The method of any of paragraphs 45-55, wherein step (b) occurs at a temperature of from about 0 C to about 37 C.
57. The method of any of paragraphs 45-56, wherein the ratio of loopable membrane scaffold protein to phospholipids is from about 1:2000 to about 1:5000.
58. The method of any of paragraphs 45-57, wherein the ratio of loopable membrane scaffold protein of any of paragraphs 1-21 and 24-26 to phospholipids is from about 1:3500 to about 1:4500; and circular nanodiscs are formed.
59. The method of any of paragraphs 45-58, wherein the ratio of loopable membrane scaffold protein of any of paragraphs 1-21 and 24-26 to phospholipids is from about 1:4000; and circular nanodiscs are formed.
60. The method of any of paragraphs 45-59, wherein the ratio of loopable membrane scaffold protein of any of paragraphs 22-26, to phospholipids is from about 1:2500 to about 1:3700; and non-circular nanodiscs are formed.
61. The method of any of paragraphs 45-60, wherein the ratio of loopable membrane scaffold protein of any of paragraphs 22-26 to phospholipids is from about 1:3100 to about 1:3400; and non-circular nanodiscs are formed.
62. The method of any of paragraphs 45-61, wherein the protein further comprises a cap sequence N-terminal of the N-terminal circularization domain and the method comprises a first step of contacting the protein with an enzyme to cleave the cap sequence.
63. The method of any of paragraphs 45-62, wherein the protein further comprises a C-terminal His tag and the method comprises a first step of binding the protein to a substrate.
64. The method of any of paragraphs 45-63, wherein the substrate comprises $Cu^{2+}$, $Ni^{2+}$ or $Co^{2+}$.
65. The method of any of paragraphs 45-64, wherein the substrate is a chip or bead.
66. The method of any of paragraphs 45-65, wherein the substrate is a bead and step (a) is performed in the presence of phospholipids.
67. The method of any of paragraphs 45-66, wherein the substrate is a bead and the steps (a) and (b) are performed concurrently.
68. The method of any of paragraphs 45-67, further comprising, after step (a), a step of eluting the looped protein produced in step (a) from the substrate.
69. The method of any of paragraphs 45-68, wherein the loopable membrane scaffold protein is in solution at a concentration of less than 100 uM prior to the contacting step.
70. The method of paragraph 69, wherein the looped protein formed in step (a) is passed through a column, substrate, and/or solution comprising $Cu^{2+}$, $Co^{2+}$ or $Ni^{2+}$.

EXAMPLES

Example 1

Described herein are three different nanodics embodiments and/or structures: (1) covalently circularized nanodiscs (cNDs); and (2) polygonal nanodiscs). Specifically contemplated herein are the use of these nanodics for, e.g., facilitating solution NMR and Cryo-EM studies, permitting structural and functional studies of large membrane proteins, and the use of the nanodiscs as vaccine platforms.

Nanodiscs have been designed to conduct in vitro biophysical studies of membrane proteins. A nanodisc is an assembly of a phospholipid bilayer surrounded or "belted" by two copies of an amphipathic helical membrane scaffold protein (MSP). A schematic representation of a nanodisc is depicted in FIG. 1.

The size of the MSP (e.g., circumference) defines the size of the nanodiscs and various lipids that can be incorporated to form the discoidal bilayer construct. Nanodiscs have been shown to provide a stable and more biologically relevant, "native-like" lipid bilayer environment compared to agents such as detergents or liposomes. Numerous proteins have been assembled into nanodiscs and these constructs have proven to be useful in studying membrane protein structure and function by solution NMR and Cryo-electron microscopy (Cryo-EM).

As used herein, the term "conventional nanodiscs" refers to discoidal, nanoscale phospholipid bilayers encompassed by a membrane scaffold protein (MSP) e.g., two molecules of amphipathic alpha-helical protein wrapped around the perimeter of the disc in an anti-parallel fashion. The hydrophobic face of the scaffold protein serves to sequester the hydrocarbon tails of the phospholipids away from the solvent and limits the size of the disc. In some embodiments, the membrane scaffold protein can be apolipoprotein. These conventional nanodiscs are lipid-protein nanoparticles roughly 10 nm in diameter.

Described herein are three "non-conventional" nanodiscs: covalently circularized nanodiscs (cNDs) and polygonal nanodiscs.

Covalently circularized nanodiscs (cNDs): Described herein is the covalently linkage of the N and C termini of ApoA-I protein variants and circularization of the proteins on a $Cu^{2+}$ chip to produce uniformly sized nanodiscs. To accommodate the analysis of larger membrane proteins, it is also demonstrated herein that high molecular weight circularized variants can be used to prepare circularized nanodiscs of up to 80 nm in diameter.

Polygonal nanodiscs: The present technology also relates to the production of polygonal nanodiscs. The inventors determined that at suboptimal lipid concentrations, the circularized high molecular weight variants could form nanodiscs having non-circular shapes and that these can increase the chance for crystallization.

Described herein are several applications for the nanodisc structures including their use in solution NMR and Cryo-EM studies, permitting structural and functional studies of larger membrane proteins, permitting the study of membrane protein interactions with other proteins, permitting the study of viral entry into cells, and their use as vaccine platforms.

Example 2

Described herein are covalently circularized phospholipid bilayer nanodiscs (cNDs) of various sizes up to 80 nm in diameter with a very narrow size distribution. Producing nanodiscs of increased size is highly desirable for incorporating larger integral membrane proteins (IMP), molecular complexes, oligomers of IMP, and pore-forming proteins into the discoidal bilayer for detailed biophysical investigation. This alone makes the cNDs described herein of interest to chemists engaged in pharmacological, membrane/lipid, and general biophysics research. Also, the cNDs described herein can permit new opportunities in crystallization, drug and nucleic acid delivery, vaccine platform, cell free expression of larger membrane proteins (IMP) and molecular complexes.

In Addition to cNDs, described herein are polygonal nanodiscs that offer numerous exciting applications.

Using an in vitro system that best mimics the in vivo physicochemical environment surrounding an integral membrane protein (IMP) is critical for fully understanding its molecular behavior in a biologically relevant context. Although micelles and bicelles have been used extensively in the study of IMPs, the presence of detergent often causes destabilization and rapid loss of function of the incorporated protein [1]. Furthermore, detergents can hinder interactions between an IMP and its cytosolic partner(s). Until recently, liposomes were the only means to harbor membrane proteins in a detergent-free bilayer environment. However, liposomes have a tendency to aggregate and are heterogeneous in size. Moreover, liposomes are not compatible with crystallization and solution-state NMR.

Nanodiscs on the other hand provide a detergent-free lipid bilayer model that is compatible with solution NMR, are not prone to aggregation, and do not suffer from the geometric distortion often inherent in other membrane substitutes. A conventional nanodisc is composed of a nanometer-sized phospholipid bilayer encircled by two copies of a helical, amphipathic membrane scaffold proteins (MSPs) [2, 3]. MSPs are truncated forms of apolipoprotein A1, which is the major protein component of high-density lipoprotein. There are several different variants of MSP that can be used to assemble nanodiscs of various sizes ranging from 7-17 nm average diameter [4,5]. These different variants of MSP are commercially available (cube-biotech.com) and have been used for over a decade to study a variety of IMPs.

The use of nanodiscs for multidimensional NMR experiments, as required for complete three-dimensional structural assignment, remains challenging and is still in its early stages. Furthermore, to the best of our knowledge, there has been no membrane proteins successfully crystallized in nanodiscs. A challenging hurdle is that the diameter of the nanodisc particle can vary broadly independent of the MSP chain length in a single preparation [5, 6]. This size heterogeneity can result in a variable number of membrane proteins being incorporated into each disc [6].

Figure 2A:
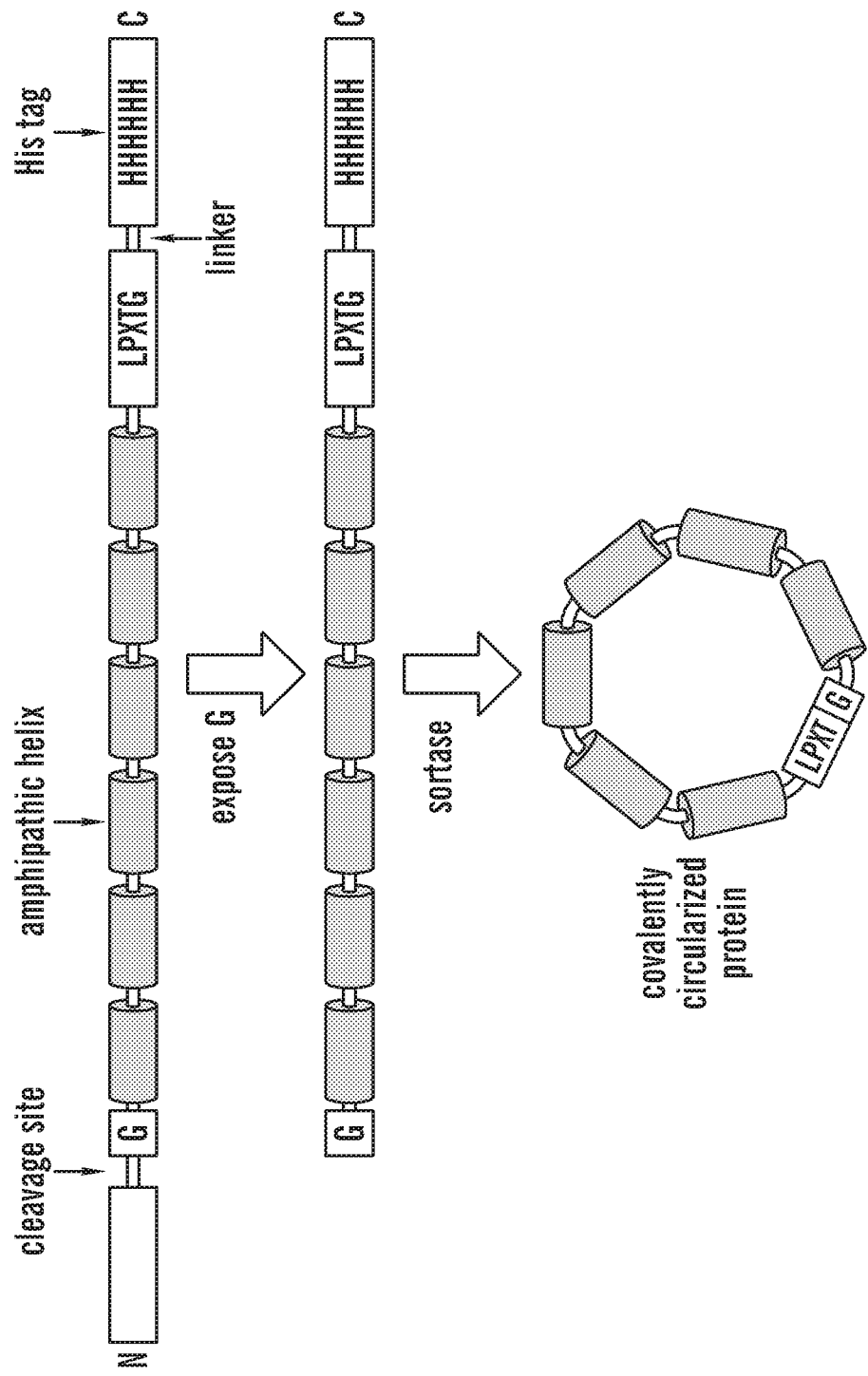
FIGS. 2A-2E depict schematics of the production of covalently circularized MSP and nanodiscs.

Covalently circularized nanodiscs (cNDs). To improve homogeneity, stability and expand the sizes of nanodiscs, sortase A [7] was used to covalently link the N and C termini of several apoA1 variants. As shown in FIG. 2A, the protein constructs contain the consensus sequence recognized by sortase A, which are a LPXTG sequence (SEQ ID NO: 51) near the C terminus and a single glycine residue at the N terminus. These two sites are sufficient to ensure covalent linkage between the N and C termini of a protein [8] while still conserving the function to form nanodiscs.

Figure 2B:
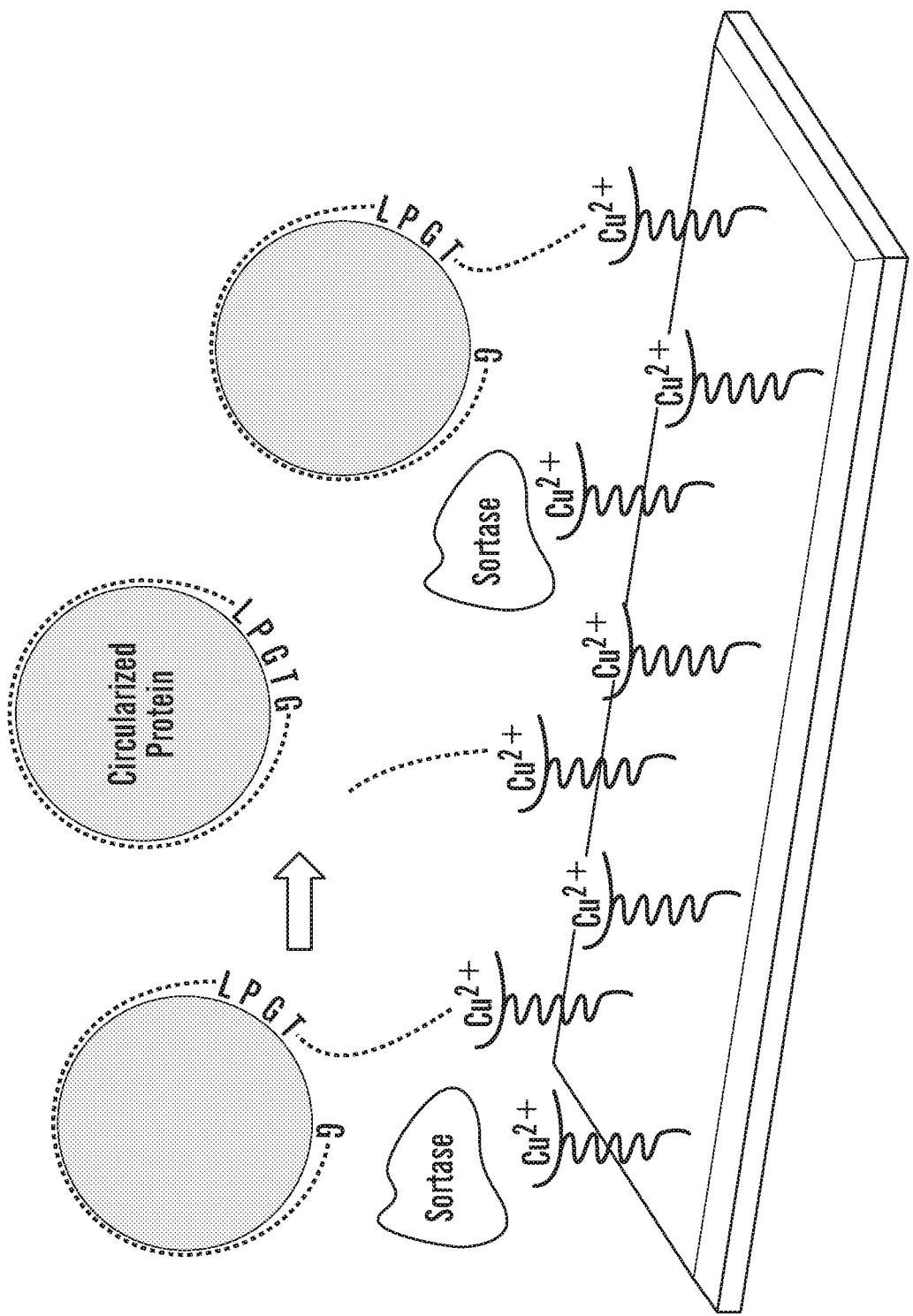

Initially, circularization was performed over a Cu+2 chip (FIG. 2B). Immobilizing proteins on the Cu+2 chip for circularization reduces the chances of intermolecular head-to-tail linkage between two different molecules and decreases reaction time. Negative stain EM was used to confirm that circularized protein retains its ability to assemble into nanodiscs and to assess the size-homogeneity of the discs. The acquired EM images revealed uniformly sized nanodiscs and approximately 90% of the nanodiscs were found to have a diameter between 11-12 nm, as opposed to 32% of nanodiscs assembled with the un-circularized construct (FIG. 1E). Using these circularization methods, several high molecular weight (MW) circularized variants were produced and used to prepare circularized nanodiscs (cND) of up to 80 nm in diameter (FIG. 3C). To scale up the circularization reaction, we a method for circularization in solution and also over nickel beads was developed, permitting production of milligram quantities of circularized proteins.

Polygonal nanodiscs. It was observed that while performing screens to optimize the lipid-to-scaffold-protein ratio, at suboptimal lipid concentrations the circularized high MW variants could also form large nanodiscs of well-defined geometric non-circular shapes (FIGS. 4A-4D). The 3X-, 4X-, 5X-, and 6X-circularized scaffold proteins spontaneously formed triangular, square, pentagonal, and hexagonal shaped nanodiscs. The flexible linkers (LPGTGS (SEQ ID NO: 44)) between each copy of scaffold protein that result from sortase ligation enable these high MW circularized species to assemble nanodiscs with these atypical but well-defined shapes. Each side of these shapes appears to be formed by one copy of scaffold protein. These polygonal nanodiscs can increase the chance for crystallization by encouraging more efficient crystal packing, reducing the degrees of freedom in the scaffold protein by covalent closure, and increasing the stability and homogeneity of the resulting nanodisc.

Applications for the nanodiscs described herein include:
1—facilitating solution NMR and cryo EM studies of membrane proteins in physiologically relevant conditions (more stable and more homogenous than conventional nanodiscs).
2—Permit structural and functional studies of large membrane proteins (eg. mammalian respiratory complex) in bilayer.
3—Permit studying membrane protein interactions with another membrane protein or cytosolic partner.
4—Permit constructions and studying many membrane pores (eg. proapoptotic proteins BAX and BAK pores, anthrax pore etc)
5—Permit studying virus entry to cells (FIG. 6) and screening for potential inhibitors against virus entry.
6—Cell-free expression for large membrane proteins and complexes.
7—Permit Residual Dipolar Coupling (RDC) measurements (detergent free, homogenous effect, charge tunable).
8—Crystallization and 2D lattice.
9—Vaccination (many copies of membrane proteins per disc).
10—Enable studying lipid rafts.
11—Studying the fusion of synaptic vesicle membranes with planar bilayer membranes.

Described herein is the validation of circularized nanodiscs as a novel vaccine platform: Because cNDs particles permit the functional reconstitution of envelope/membrane proteins, the gp41 transmembrane segment plus the highly conserved membrane proximal region (MPER-TM) of HIV, which is an important target for vaccine development, can be incorporated into cNDs and their potential to elicit an immune response and confer immunity to HIV virus challenge investigated. The improved stability, homogeneity and bigger sizes of cNDs relative to conventional nanodiscs make them an ideal platform for vaccine development.

Figure 5:
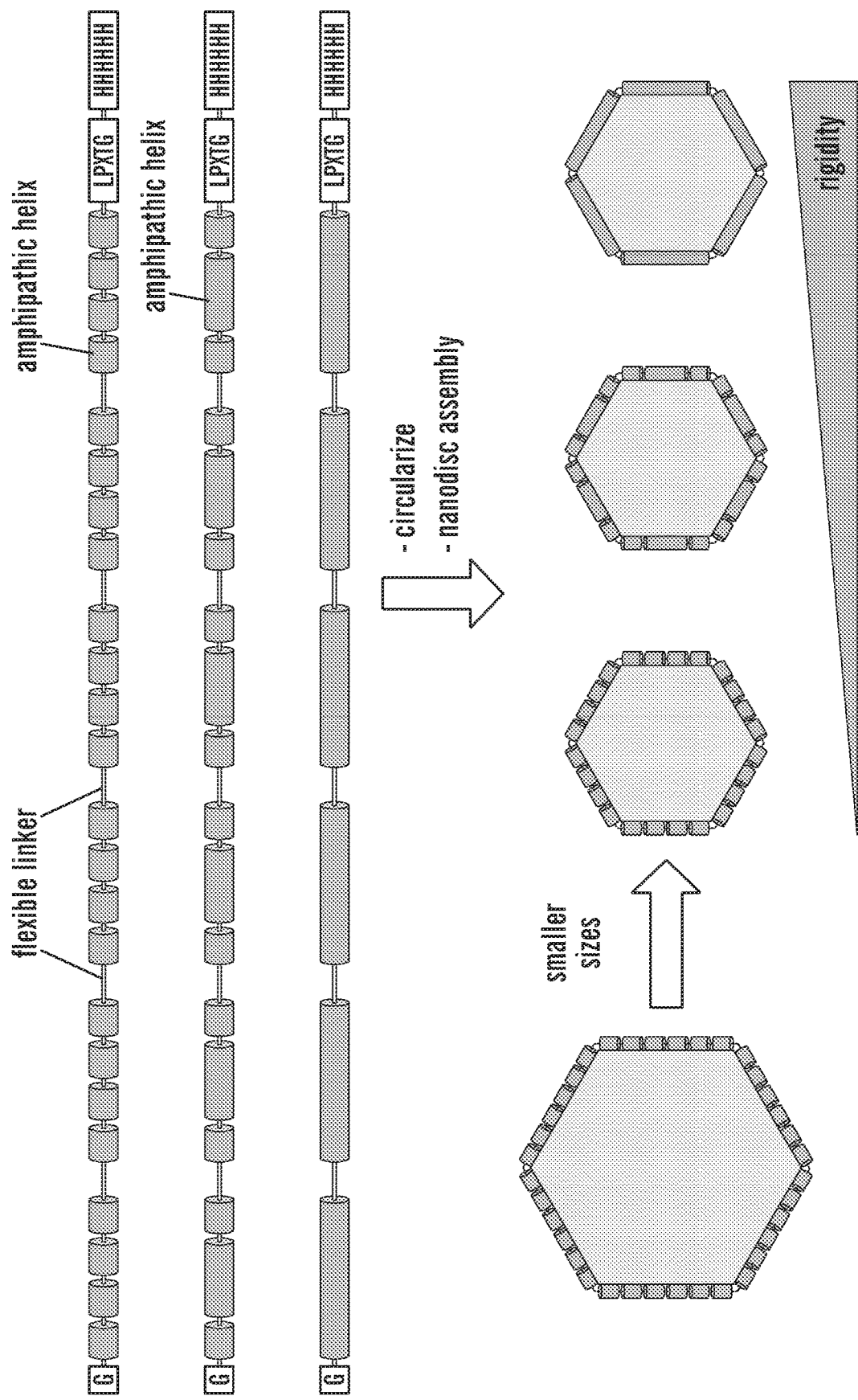
FIG. 5 depicts a schematic of the strategy for making polygonal nanodiscs and the associated scaffold proteins.

Described herein is the design of polygonal nanodiscs and testing for crystallization. To improve the yield and prevent these shapes from becoming circular, a series of constructs can are designed with variable numbers of helices (2-6 helices) between each flexible linker. 2 or 3 helices can be fused together to increase the rigidity (FIG. 5). In addition, a series of constructs can be based on the amphipathic peptide 18A [9]. The assembled nanodiscs can be examined by negative stain. After scaling up the production of polygonal nanodiscs, 2D or 3D crystallization can be performed with or without incorporated membrane protein. Stable and well-characterized membrane protein can be used for crystallization trials.

REFERENCES CITED

[1] Bowie J U. Stabilizing membrane proteins. Current opinion in structural biology. 2001; 11:397-402.
[2] Denisov I G, Grinkova Y V, Lazarides A A, Sligar S G. Directed self-assembly of monodisperse phospholipid bilayer Nanodiscs with controlled size. J Am Chem Soc. 2004; 126:3477-87.
[3] Bayburt T H, Grinkova Y V, Sligar S G. Self-assembly of discoidal phospholipid bilayer nanoparticles with membrane scaffold proteins. Nano Lett. 2002; 2:853-6.
[4] Ritchie T K, Grinkova Y V, Bayburt T H, Denisov I G, Zolnerciks J K, Atkins W M, et al. Chapter 11—Reconstitution of membrane proteins in phospholipid bilayer nanodiscs. Methods in enzymology. 2009; 464:211-31.
[5] Hagn F, Etzkorn M, Raschle T, Wagner G. Optimized phospholipid bilayer nanodiscs facilitate highresolution structure determination of membrane proteins. Journal of the American Chemical Society. 2013; 135:1919-25.
[6] Raschle T, Hiller S, Yu T Y, Rice A J, Walz T, Wagner G. Structural and functional characterization of the integral membrane protein VDAC-1 in lipid bilayer nanodiscs. Journal of the American Chemical Society. 2009; 131: 17777-9.
[7] Chen I, Don B M, Liu D R. A general strategy for the evolution of bond-forming enzymes using yeast display. Proceedings of the National Academy of Sciences of the United States of America. 2011; 108:11399-404.
[8] Antos J M, Popp M W, Ernst R, Chew G L, Spooner E, Ploegh H L. A straight path to circular proteins. The Journal of biological chemistry. 2009; 284:16028-36.
[9] Anantharamaiah G M, Jones J L, Brouillette C G, Schmidt C F, Chung B H, Hughes T A, et al. Studies of synthetic peptide analogs of the amphipathic helix. Structure of complexes with dimyristoyl phosphatidylcholine. The Journal of biological chemistry. 1985; 260:10248-55.

Example 3

Design and applications of circularized nanodiscs for studying membrane proteins and viral entry.

Described herein is a process for producing covalently circularized nanodiscs covering a wide range of defined sizes up to 80 nm in diameter and in a variety of geometric shapes. Further described herein is the use of large nanodiscs to address the poorly understood question of how simple non-enveloped viruses translocate their genomes across membranes to initiate infection, and demonstrate the feasibility of using 50 nm nanodiscs to determine the structure of the RNA translocation pore of poliovirus by cryo-electron microscopy.

Phospholipid bilayer nanodiscs provide a detergent-free lipid bilayer model, enabling biochemical and biophysical characterization of membrane proteins in a physiologically relevant environment[1]. A conventional nanodisc is composed of a nanometer-sized phospholipid bilayer patch encircled by two α-helical, amphipathic membrane scaffold proteins (MSPs)[2, 3]. MSPs are truncated forms of apolipoprotein A1 (apoA1), which is the major protein component of high-density lipoprotein. To date, however, the utility of this system for structural studies has been severely limited by the heterogeneity of size and the number of membrane proteins enclosed, and only small nanodiscs could be constructed with the currently available protein scaffolds[4-7]. To resolve these problems described herein are three different methods to covalently link the N and C termini of newly engineered variants based on apoA1, and the production of nanodiscs with a large range of discrete sizes and defined geometric shapes. The protein constructs described herein contain the consensus sequence recognized by sortase A (LPGTG (SEQ ID NO: 53)) near the C terminus and a single glycine residue at the N terminus (FIG. 2A). These two sites are sufficient to ensure covalent linkage between the N and C termini of a protein[8] while still conserving the function to form nanodiscs.

Figure 2C:
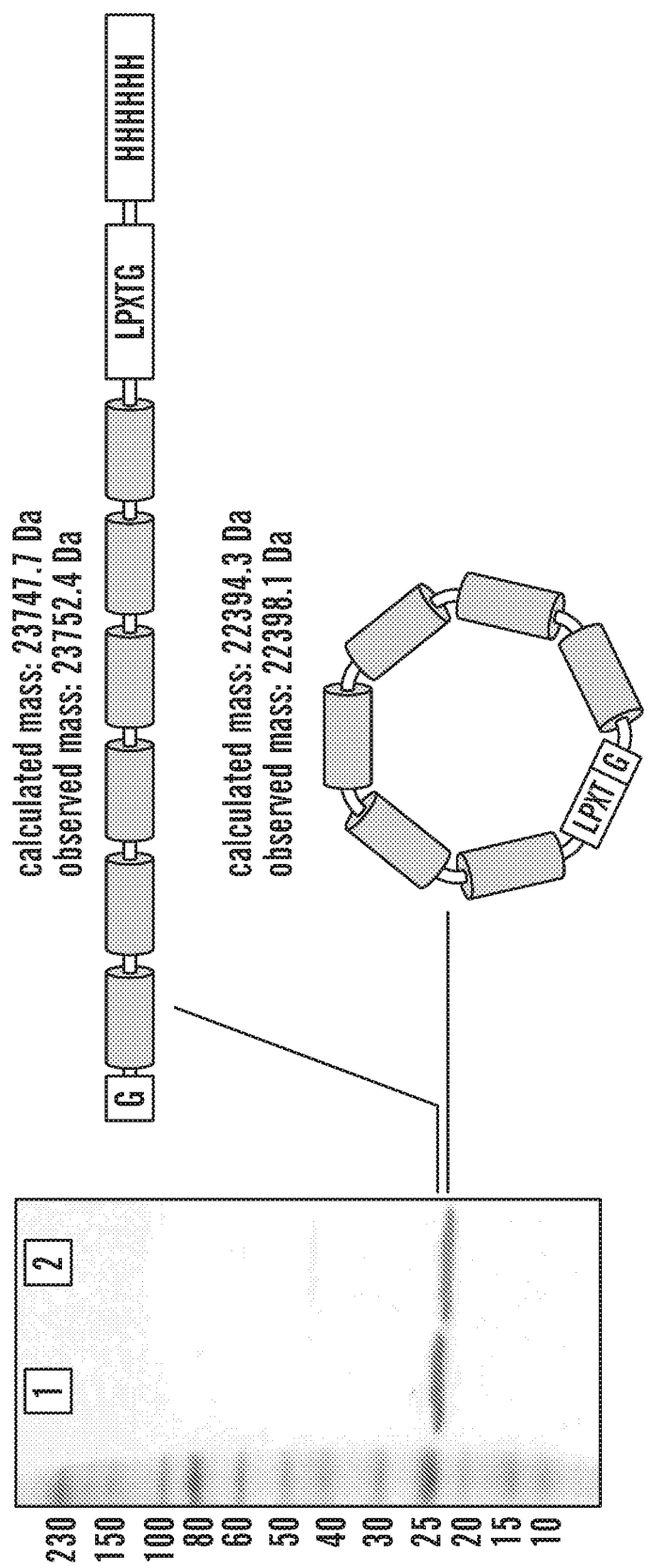
Figure 2D:
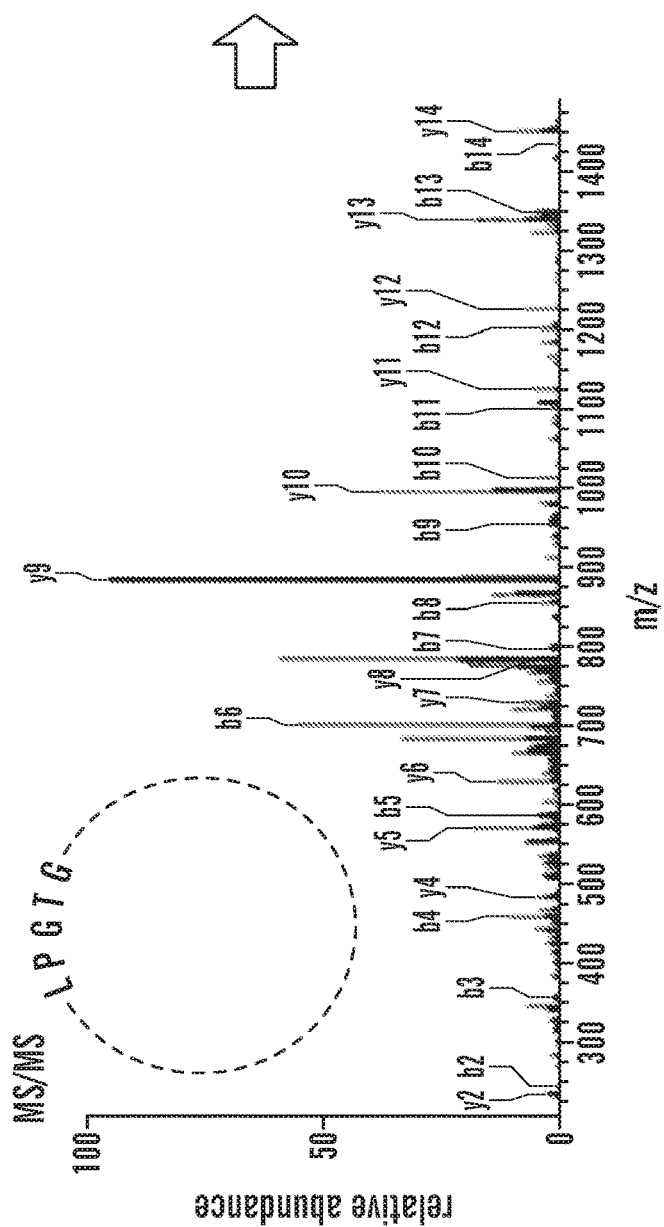
Figure 2E:
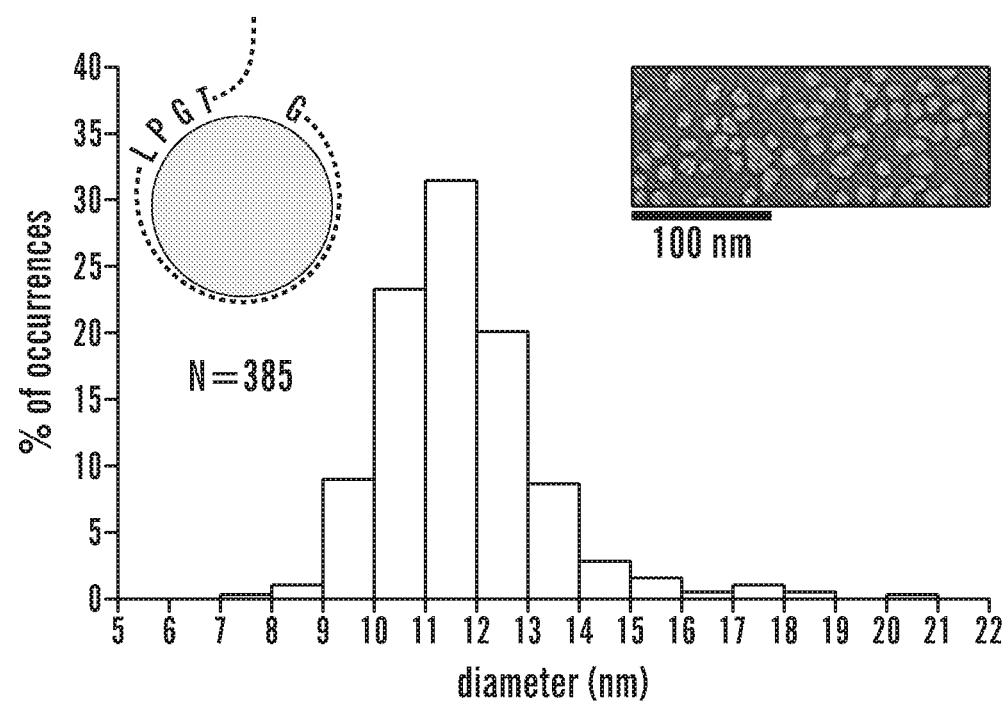
Figure 2E:
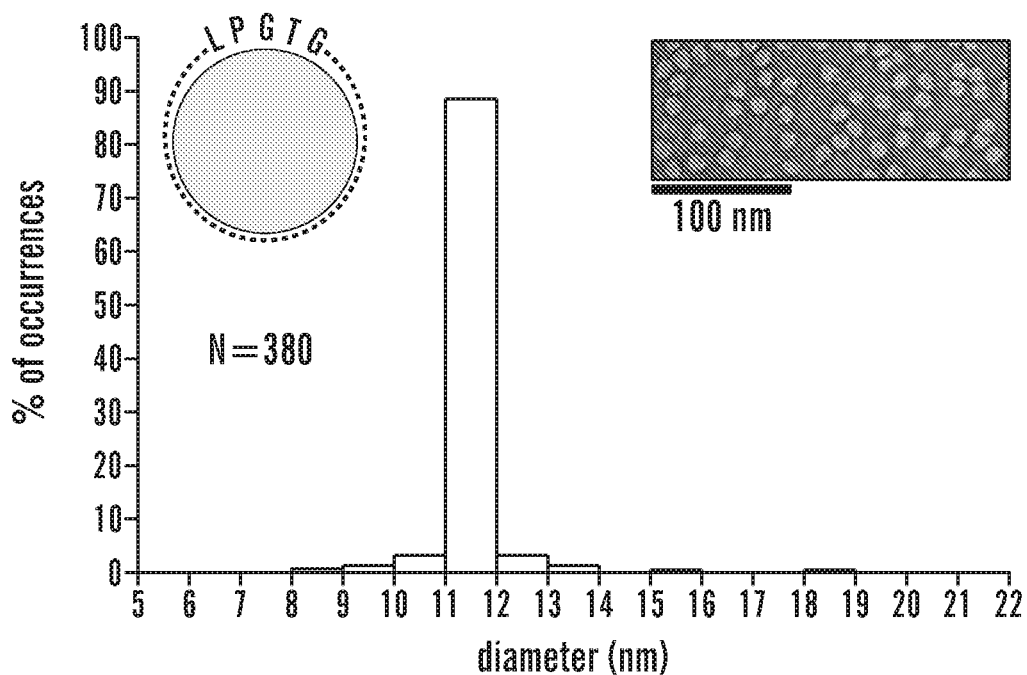
Figures 4A, 4B, 4C, 4D:
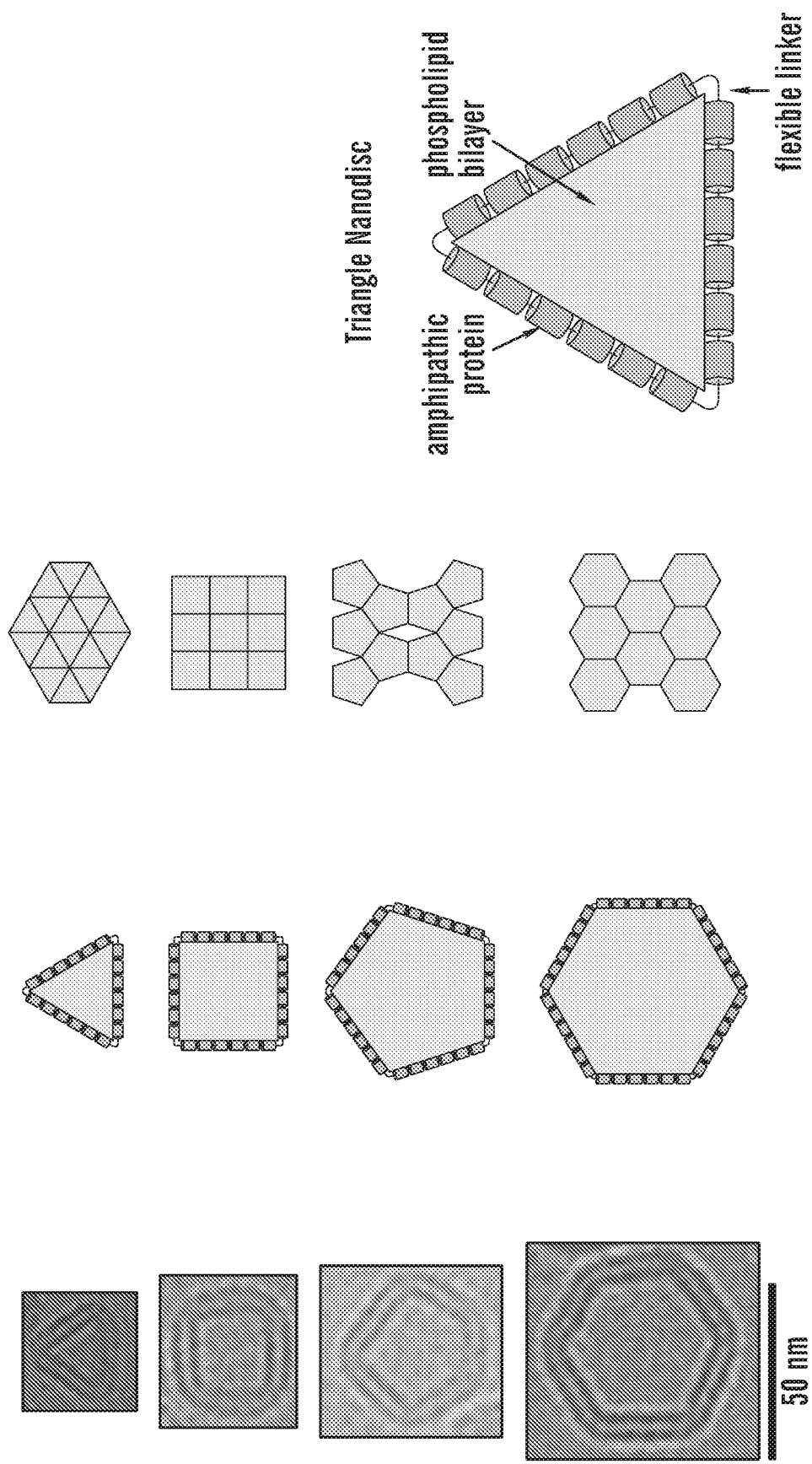
FIG. 4A depicts cryo-EM images of individual nanodiscs with different shapes.
FIG. 4B depicts potential molecular arrangements of scaffold protein molecules in the different shaped nanodiscs.
FIG. 4C depicts possible crystal packing of nanodiscs with the corresponding shapes. The triangular, square and hexagonal shapes should, in principle, provide better crystal packing than pentagonal or circular ones.
FIG. 4D shows that each triangular disc is made of 3 copies of amphipathic protein that are connected together with a long flexible loop.

Initially, the NW11 construct, which assembles an 11 nm nanodisc, was used to optimize the circularization over a $Cu^{+2}$ chip (FIG. 2B). In this scheme, the $Cu^{2+}$ is saturated with un-circularized NW11 protein prior to evolved sortase[9] addition. Upon successful completion, the circularized NW11 (cNW11) is liberated to the solution and can be further purified via nickel affinity chromatography. Immobilizing NW11 on the $Cu^{2+}$ chip for circularization reduces the chances for head-to-tail linkage of two neighboring NW11 molecules and also offers a quick reaction time. Reaction completion was confirmed by SDS-PAGE gel shift (FIG. 2C), and reaction fidelity was confirmed via tandem mass spectrometry (MS/MS) (FIG. 2D). Next, it was tested whether the final circularized product was still capable of assembling nanodiscs. Indeed, cNW11 assembled nanodiscs, and the acquired electron microscopy (EM) images revealed uniformly sized nanodiscs. Nearly 89% of the nanodiscs were found to have a diameter between 11-12 nm as opposed to 32% for nanodiscs assembled with the linear counterpart (FIG. 2E). Even though circularization over a $Cu^{+2}$ chip usually results in a very clean final product, the approach is limited to small-scale production of circularized protein.

In order to scale up the production of cNW11, the circularization reaction was performed over nickel beads (FIG. 9A). SDS-PAGE analysis showed that cNW11 was produced as a mixture with higher molecular weight species that likely arose from head-to-tail ligation of neighboring NW11 monomers followed by circularization (FIG. 9B, lane 1). Adding lipids to the already immobilized NW11 made the intramolecular circularization the dominant pathway, and higher molecular species were only observed in trace quantities (FIG. 9b, lane 2).

Figure 10:
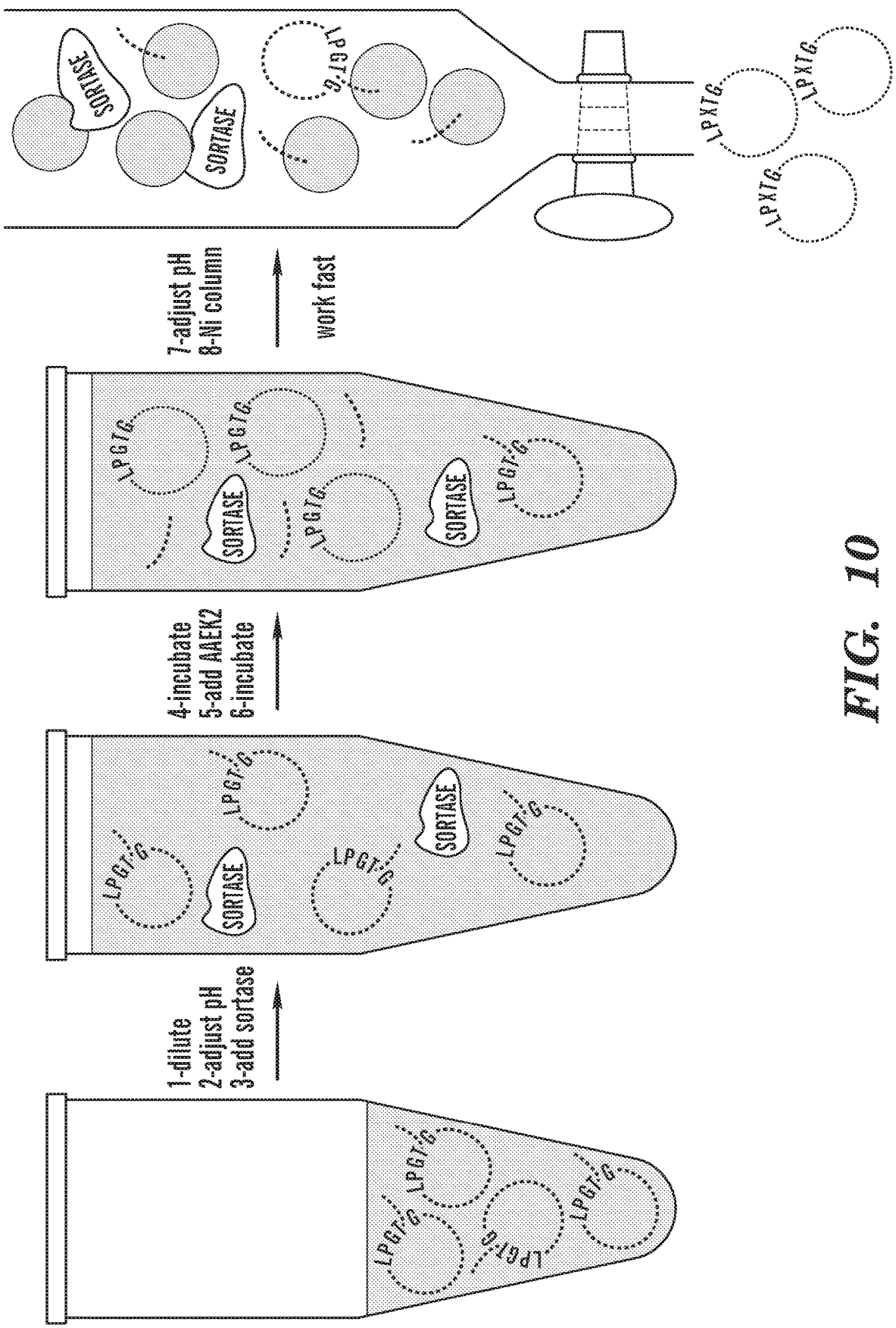
FIG. 10 depicts a schematic outline of the procedure for creating circularized NW in solution. His6-tagged linear NW ("His6" disclosed as SEQ ID NO: 54) is diluted before adding sortase to favor the circularization. Adding the sortase covalent inhibitor AAEK2 quenches the reaction.
Figure 11:
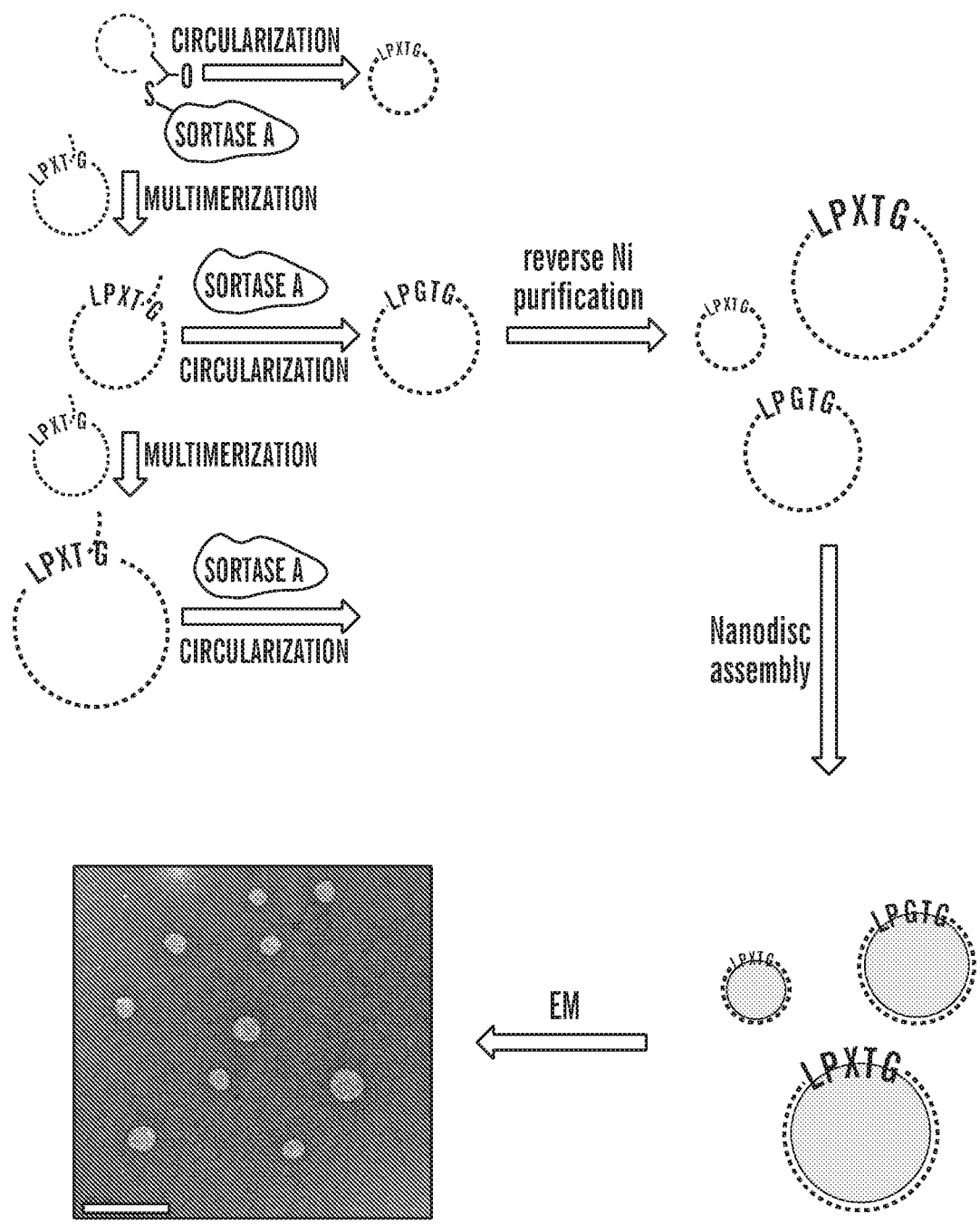
FIG. 11 depicts a schematic of adding evolved sortase to concentrated NW11 solution in order to multimerize NW11, followed by circularization. The oligomeric, circularized species containing variable numbers of NW11 assemble into nanodiscs of various sizes. Bottom: Negative-stain EM image showing large nanodiscs made using oligomeric, circularized NW11. Scale bar represents 100 nm.

To increase the yield of cNW11, the circularization reaction was performed in solution (FIG. 10). Evolved sortase was added to a dilute NW11 solution ([NW11]<15 uM) to suppress linking two or more copies of NW11. The reaction was quenched with a covalent sortase inhibitor AAEK2[10], and cNW11 was purified via reverse nickel affinity chromatography. Reaction completion was readily confirmed by SDS-PAGE analysis. With this method, mg quantities of cNW11 that is >95% monomeric were produced. Also, an array of higher molecular weight circularized species were produced by adding sortase to a concentrated NW11 solution (>100 µM). Indeed larger nanodiscs up to 80 nm in diameter were produced (FIG. 11).

Figure 12A:
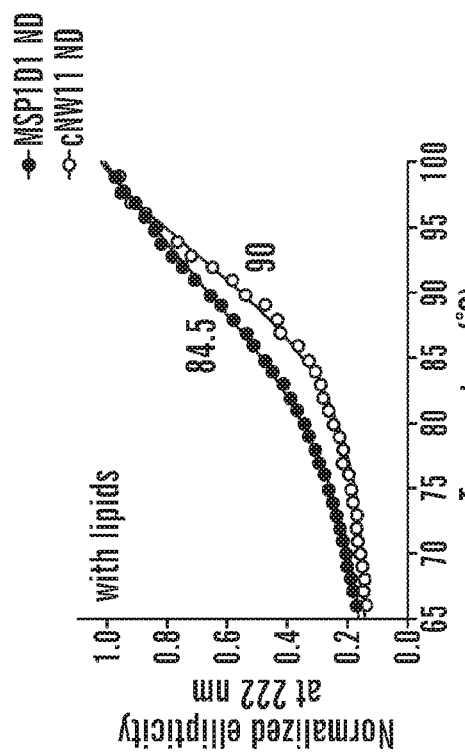
FIGS. 12A-12E demonstrate that covalent circularization stabilizes MSPs against thermal unfolding without and with lipids, stabilizes embedded VDAC1 and allows control of the number of channels embedded. Thermal unfolding of MSP1D1 and cNW11 without (FIG. 12A) and with lipids (FIG. 12B) followed by circular dichroism (CD) spectroscopy at 222 nm, the wavelength most characteristic of helical secondary structure. POPC/POPG lipids at a molar ratio of 3:2 were used to generate nanodiscs.
Figure 12B:
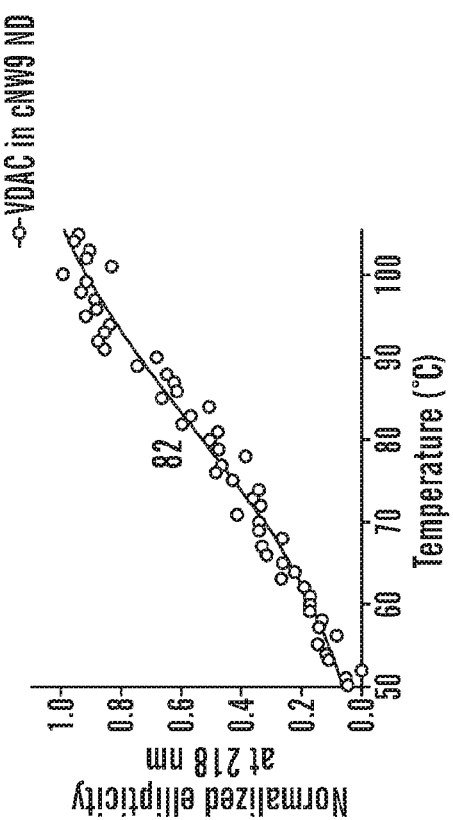
Figure 12C:
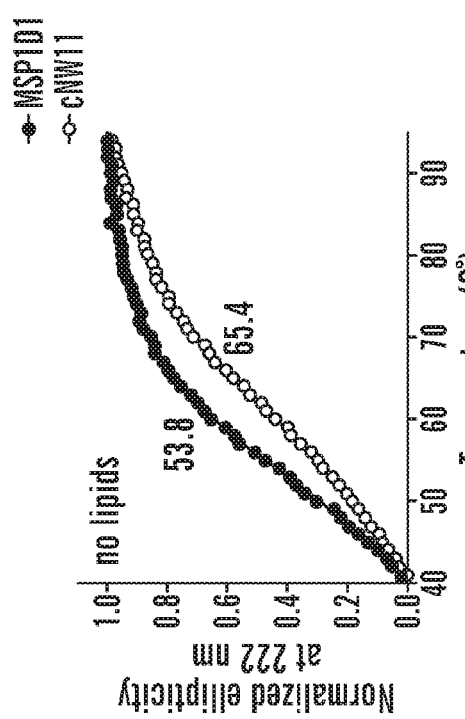
Figure 12D:
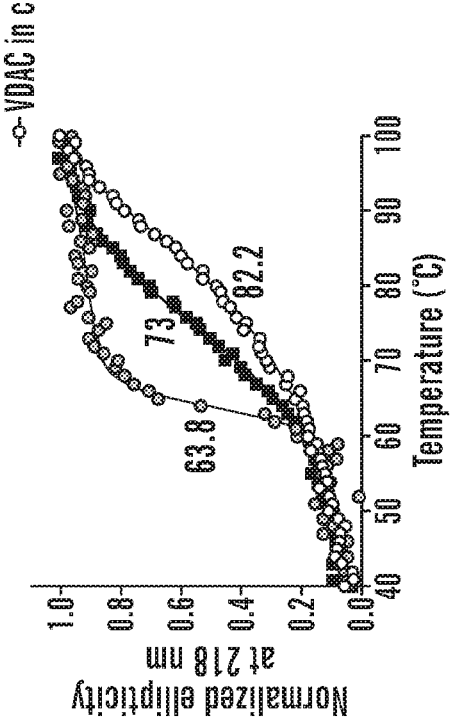
Figure 12E:
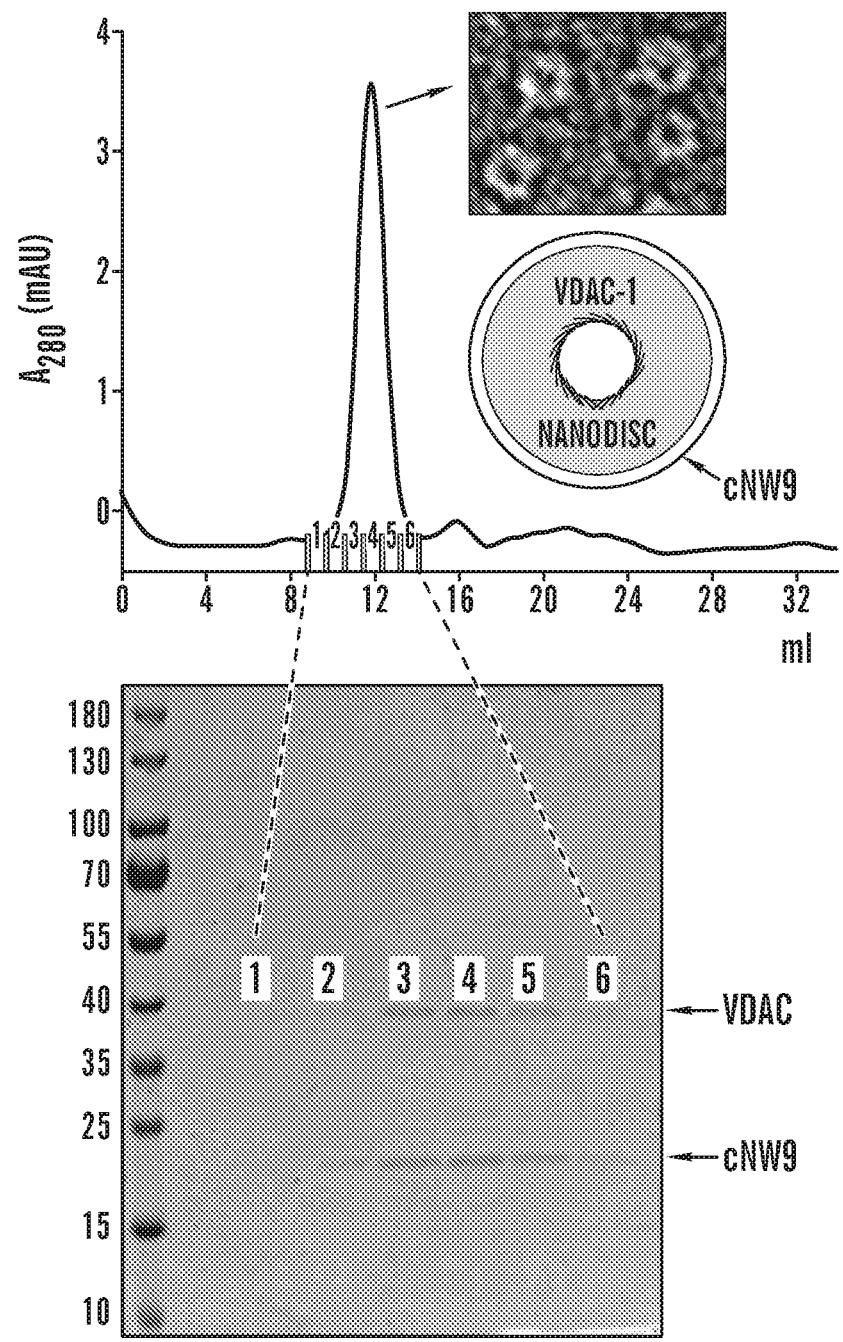
Figure 13A:
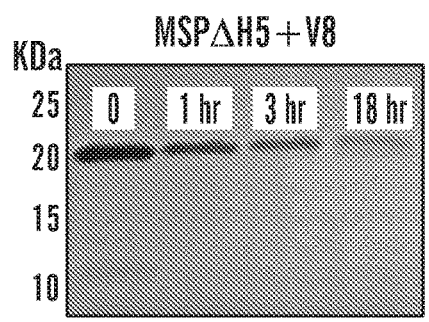
FIGS. 13A-13D demonstrate that covalent circularization stabilizes MSPs against digestion by V8 protease without and with lipids.
Figure 13B:
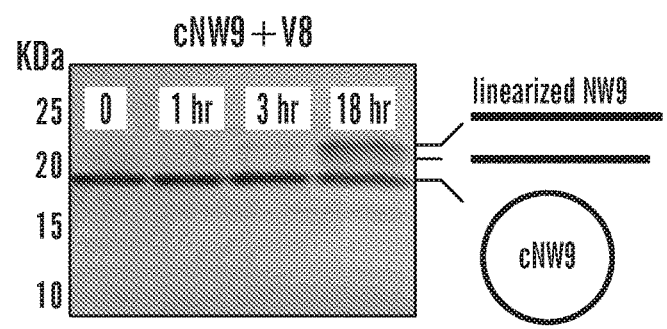
Figure 13C:
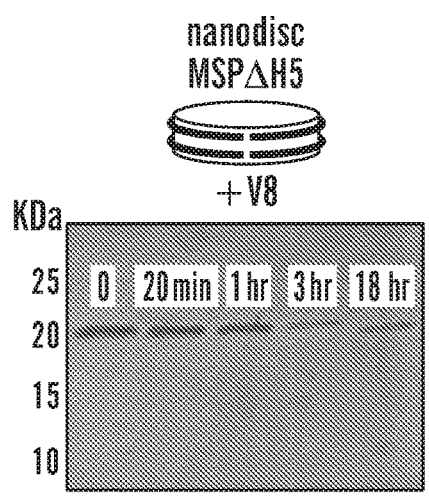
Figure 13D:
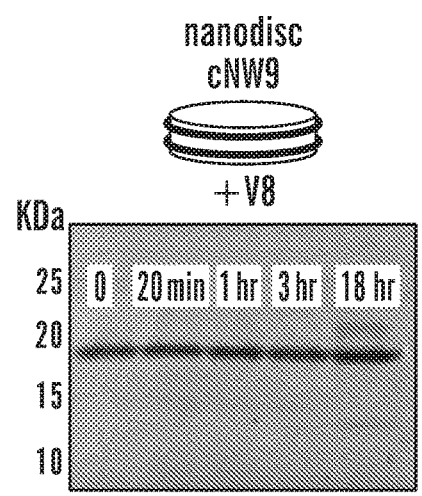
Figure 14:
FIG. 14 depicts characterization of cNW9 by MS/MS confirms the ligation of the C terminus to the N terminus. MS/MS spectrum of a tryptic fragment of cNW9 (SEQ ID NO: 91) showing the ligation of the C-terminal motif (LNTQLPGTG-His6 (SEQ ID NO: 55)) to the N-terminal residues (GSTFSK (SEQ ID NO: 52)). Expected masses for b and y ions along with the peptide sequence are listed in the table (SEQ ID NO: 91). The b and y ions that were identified in the MS/MS spectrum are highlighted. The full amino acid sequence of linear NW9 is shown at the top (SEQ ID NO: 90).
Figure 15:
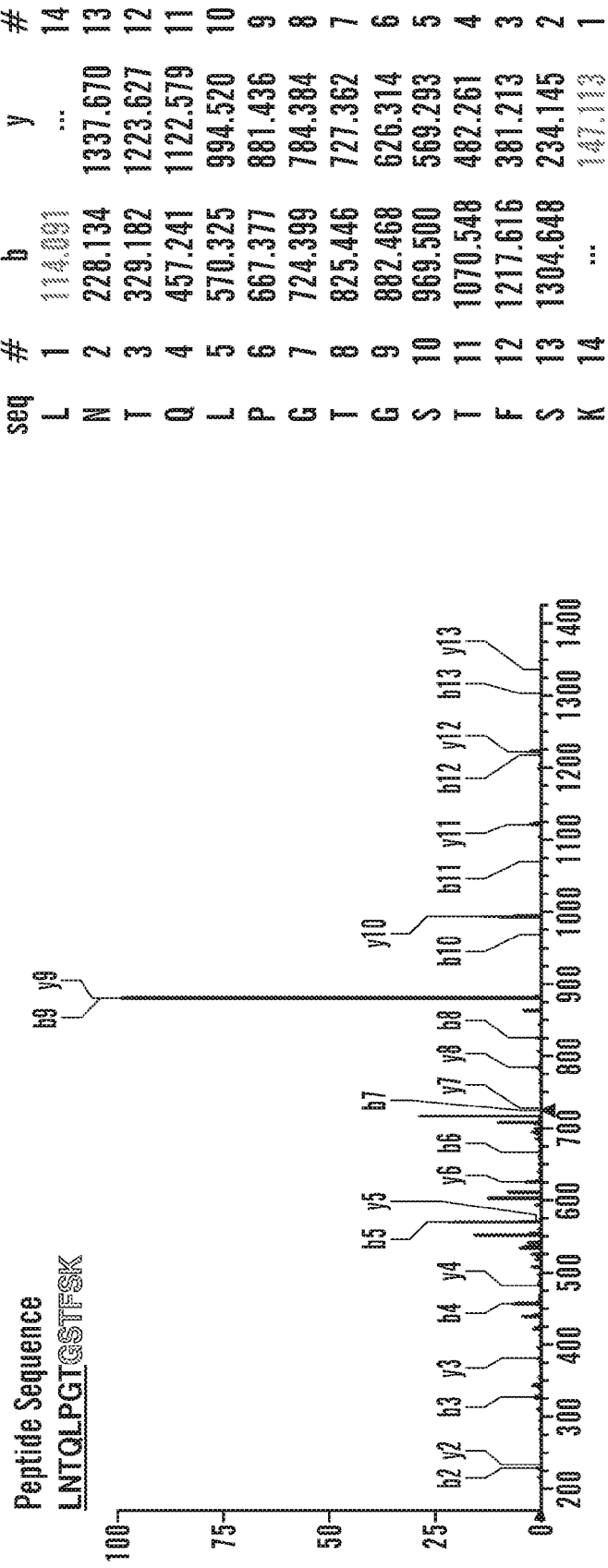
FIG. 15 depicts characterization of cNW30 by MS/MS confirms the ligation of the C terminus to the N terminus. MS/MS spectrum of a tryptic fragment of cNW30 (SEQ ID NO: 91) showing the ligation of the C-terminal motif (LNTQLPGTG-His6 (SEQ ID NO: 55)) to the Nterminal residues (GSTFSK (SEQ ID NO: 52)). Expected masses for b and y ions along with the peptide sequence are listed in the table (SEQ ID NO: 91). The b and y ions that were identified in the MS/MS spectrum are highlighted in. The full amino acid sequence of linear NW30 is shown at the top (SEQ ID NO: 92).
Figure 16:
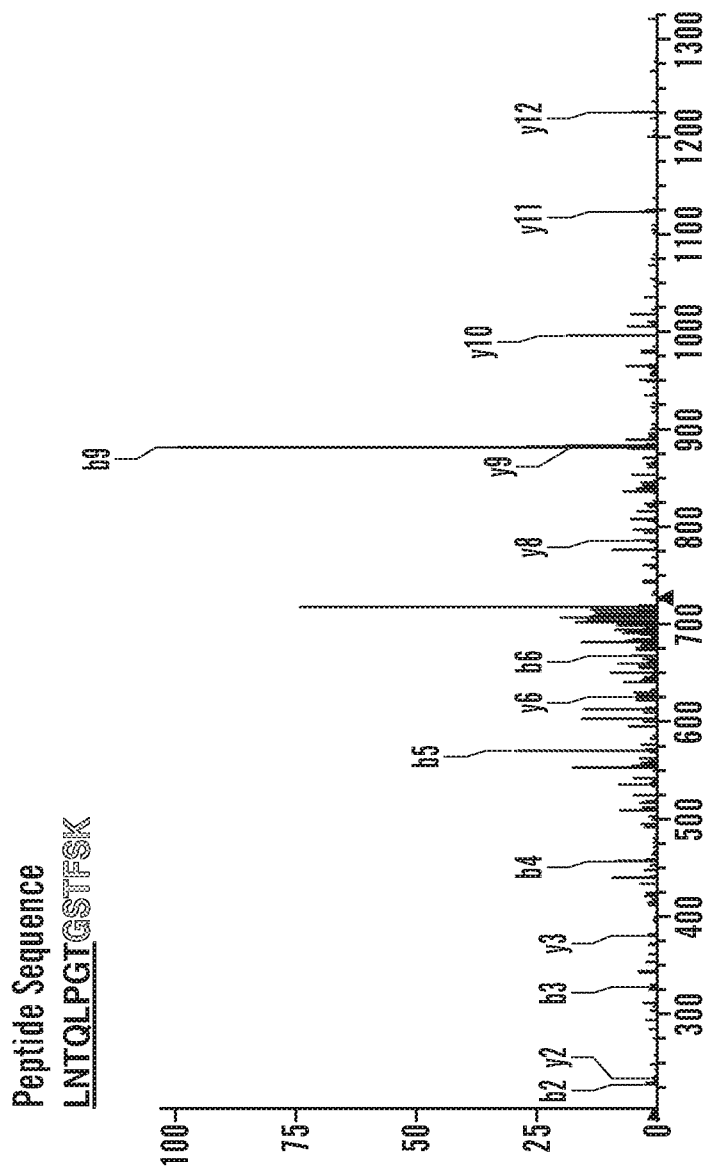
FIG. 16 depicts characterization of cNW50 by MS/MS. Spectrum of a tryptic fragment of cNW50 (SEQ ID NO: 91) showing the ligation of the C-terminal motif (LNTQLPGTG-His6 (SEQ ID NO: 55)) to the N-terminal residues (GSTFSK (SEQ ID NO: 52)). Expected masses for b and y ions along with the peptide sequence are listed in the table (SEQ ID NO: 91). The b and y ions that were positively identified in the MS/MS spectrum are highlighted. The amino acid sequence of linear NW50 (after TEV cleavage) is shown at the top (SEQ ID NO: 93).
Figure 17:
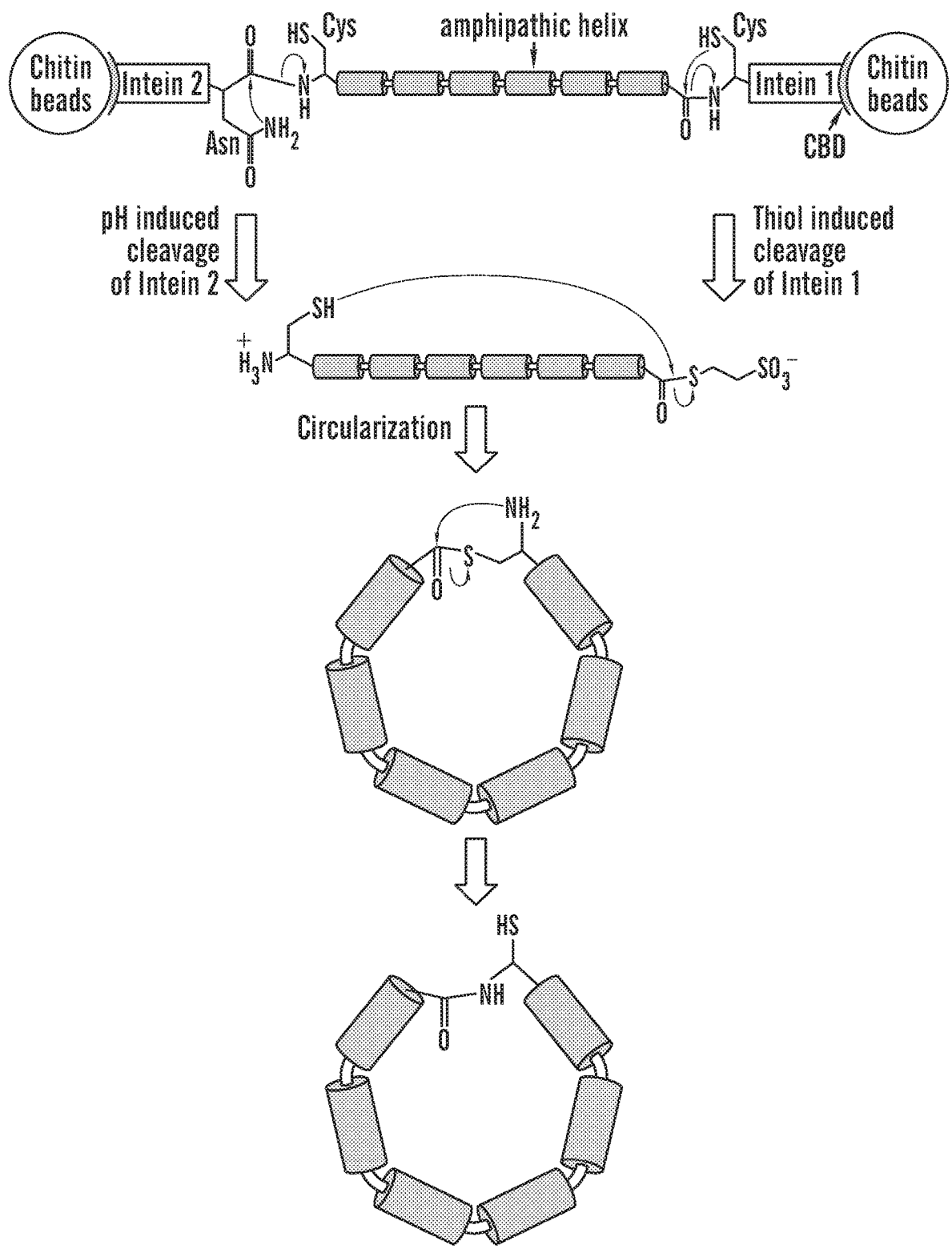
FIG. 17 depict a diagram illustrating the production of circularized proteins or poly peptides using the two-intein system. The intein has a chitin binding domain (CBD) which allows it to bind to chitin beads. The protein splicing of the inteins is then induced by adding DTT and changing the pH. The target protein then released from the chitin bound intein. The exposed N and C termini of the released protein interact together and result in the circularization of the protein.
Figure 18:
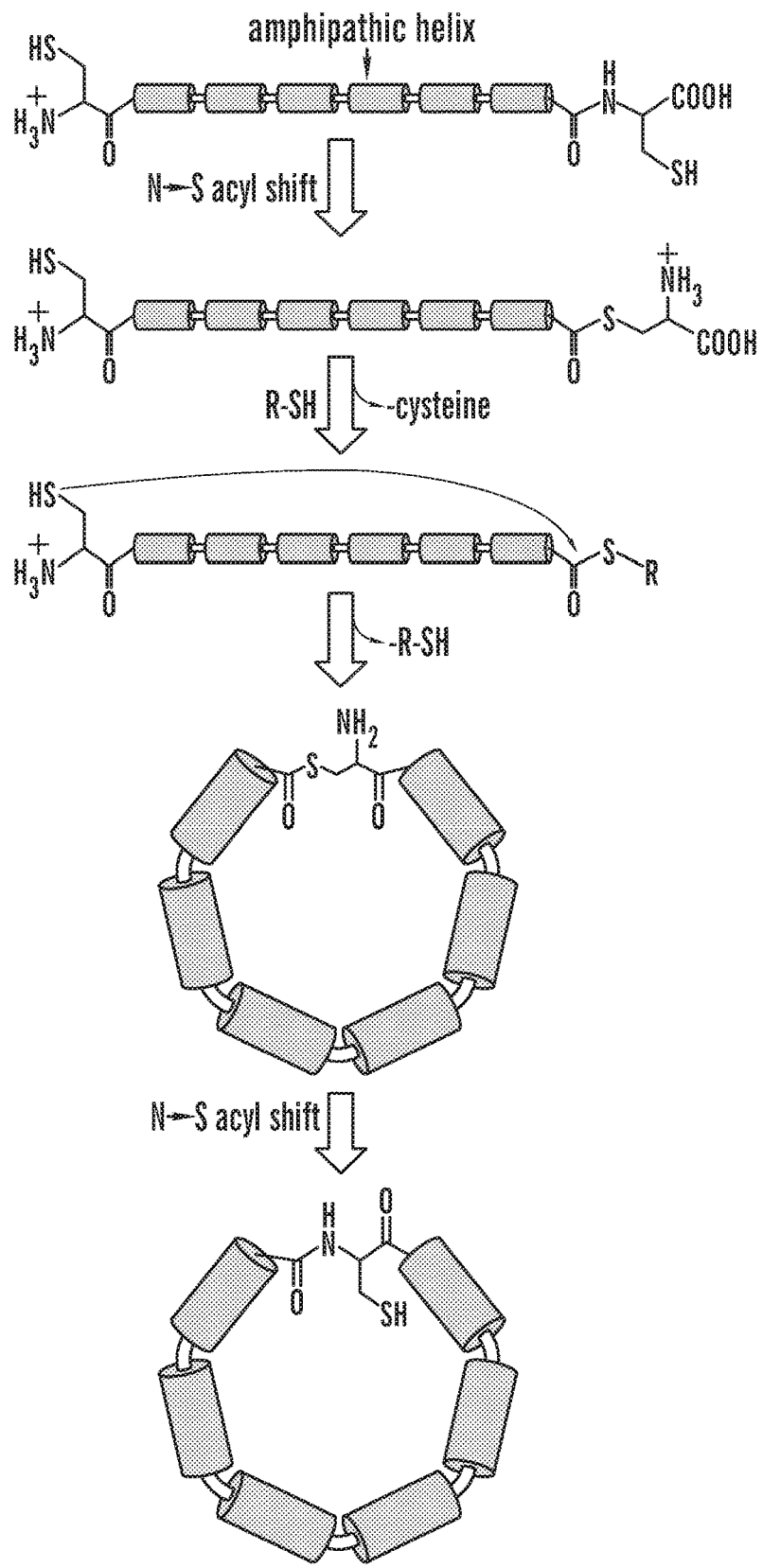
FIG. 18 depicts chemically mediated ligation of scaffold proteins.

Circular dichroism (CD) spectroscopy was used to assess the effect of circularization on the thermal stability of lipid-free and lipid-bound cNW11. cNW11 has increased thermostability with an apparent midpoint melting temperature ($T_m$) of 65.4° C. compared to 53.8° C. for MSP1D1. Similarly, Lipid-bound cNW11 demonstrated better stability compared to lipid-bound MSP1D1 ($T_m$ of 90° C. vs 84.5° C.) (FIG. 12A, 12B). The stability of Voltage-Dependent Anion Channel 1 (VDAC1) in LDAO micelles is increased from 63.8 to 73° C. by insertion into MSP1D1 nanodiscs, and to 82.2° C. when inserted into cNW11 nanodiscs (FIG. 12C). Insertion of VDAC1 into the smaller cNW9 nanodiscs maintains the high $T_m$ of 82° C. (FIG. 12D) and limits the number of embedded channels to a single one (FIG. 12E) avoiding the previously observed problem of undefined numbers of embedded channels[5]. Furthermore, covalent circularization enhances the proteolytic stability of nanodiscs (FIGS. 13A-13D).

During efforts to optimize the lipids/circularized scaffold proteins ratios, it was observed that at suboptimal lipid proportions the circularized high molecular weight variants could also form nanodiscs of well-defined, non-circular shapes (FIG. 4). The 3X-, 4X-, 5X-, and 6X-cNW11 spontaneously formed triangular, square, pentagonal, and hexagonal shaped nanodiscs. The flexible linkers (LPGTGS (SEQ ID NO: 44)) between each copy of NW11 that result from sortase ligation enable these high MW circularized species to assemble nanodiscs with these unusual but well-defined shapes. Each side of these shapes appears to be formed by one copy of NW11. These polygonal nanodiscs are useful for crystallization efforts by encouraging more efficient crystal packing relative to circular nanodiscs.

Inspired by the large nanodiscs resulting from ligation of two or more NW11 molecules, DNA constructs NW30 and NW50 were designed to produce sortaggable variants that assemble 30- and 50-nm nanodiscs, respectively. SDS-PAGE analysis (FIGS. 3A, 3B) illustrates the purification and circularization of NW30 and NW50. Unlike cNW11, the circularized NW30 and NW50 migrate slower than the linear forms. Surprisingly, the cNW30 forms homogenous ~15 nm instead of 30 nm nanodiscs as confirmed by negative-stain (FIG. 3A). It appears that the protein crosses and folds over itself to form a double belt that can support the bilayer with a single polypeptide. On the other hand, as predicted, circularized NW50 assembled homogenous 50 nm nanodiscs.

With the characterization of the circularized nanodiscs (cNDs) in place, the cNW50 nanodiscs were used as a model to study the question of how simple non-enveloped viruses transfer their genomes across membranes to initiate infection. Unlike enveloped viruses, non-enveloped viruses lack an external membrane, and the delivery of their genome into cells requires translocation across a membrane to gain access to the inside of the host cell[11, 12]. Although there are now several model systems being used to study this process, the mechanism of genome translocation remains poorly understood[13], and a more detailed structural analysis of the membrane-associated forms of the cell-entry intermediates is required. So far, mechanistic insights have been limited, due in part to technical difficulties involved in direct visualization of viral gene delivery and sample heterogeneity due to size heterogeneity of liposomes. The availability of large nanodiscs with defined size encouraged structural studies provides resolutions sufficient to gain insights into the mechanism of RNA translocation. As a proof of principal the cNW50 nanodiscs were used to visualize the RNA-translocation pore of poliovirus.

Figure 6A:
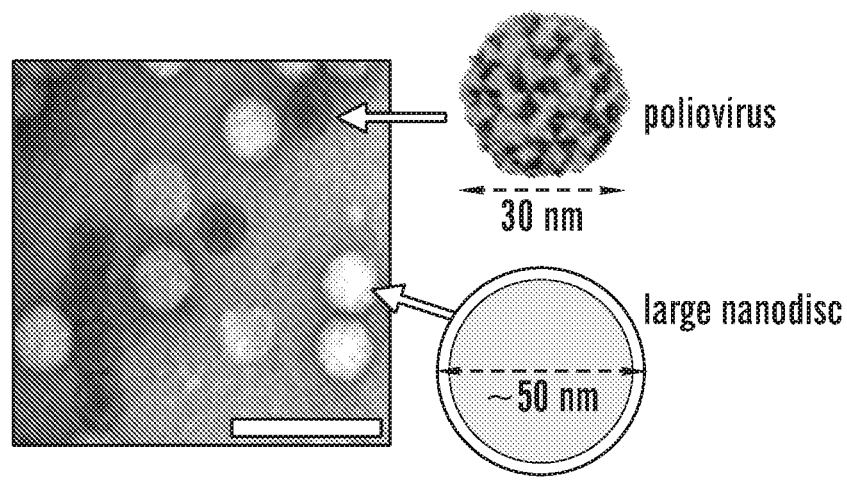
FIGS. 6A-6J depict poliovirus caught in the act.
Figure 6B:
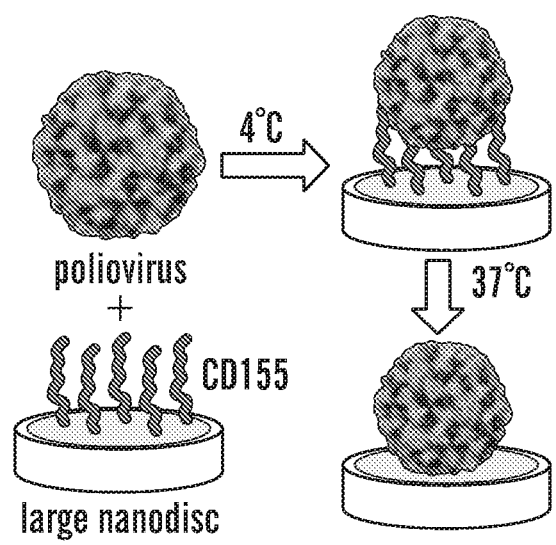
Figure 6C:
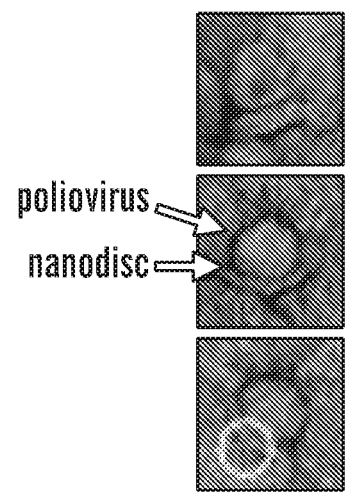
Figure 6D:
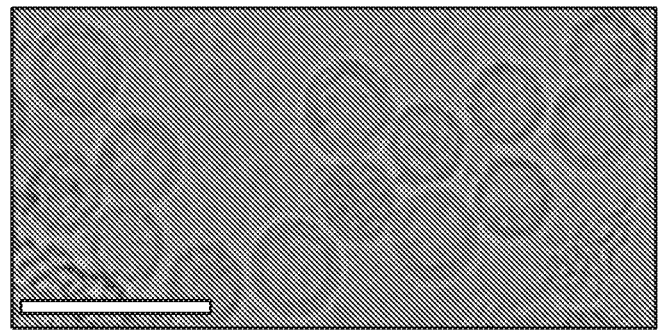
Figure 6E:
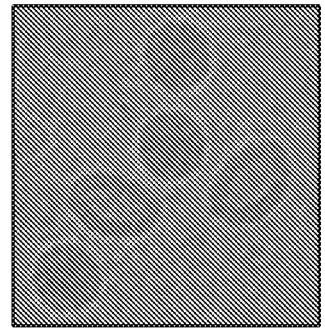
Figure 6F:
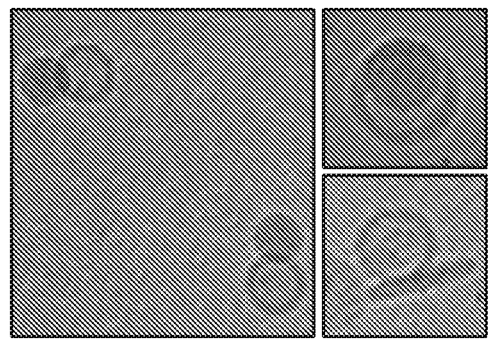
Figure 6G:
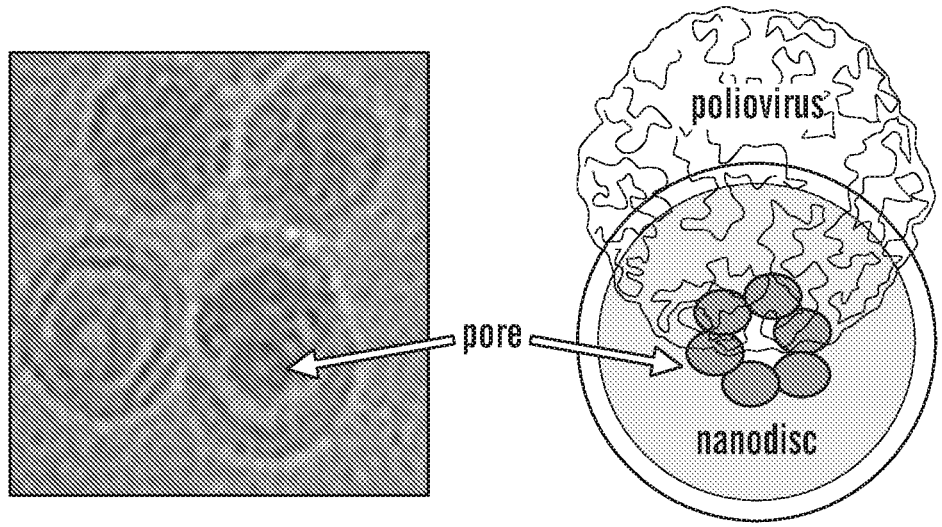
Figure 6H:
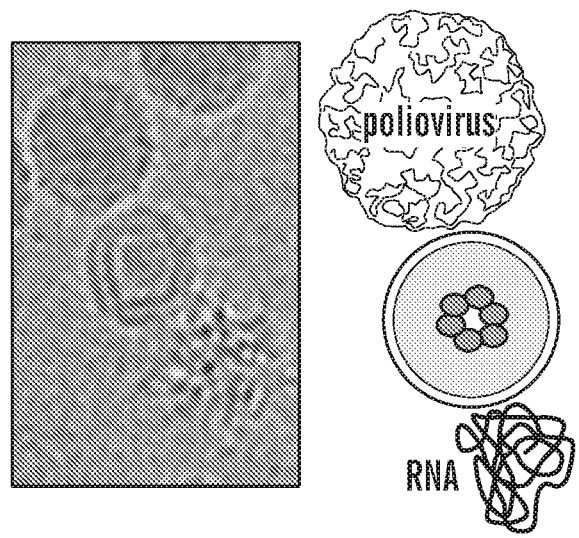
Figure 6I:
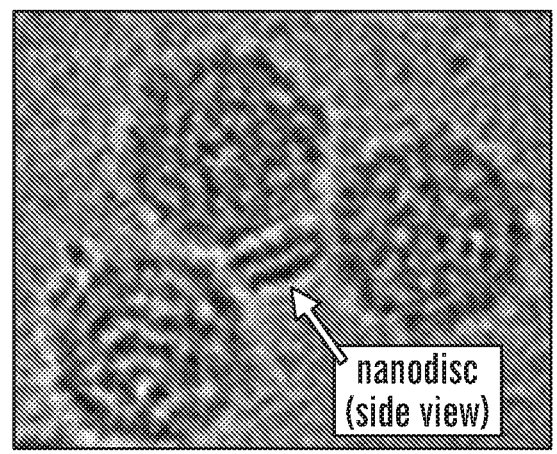
Figure 6J:
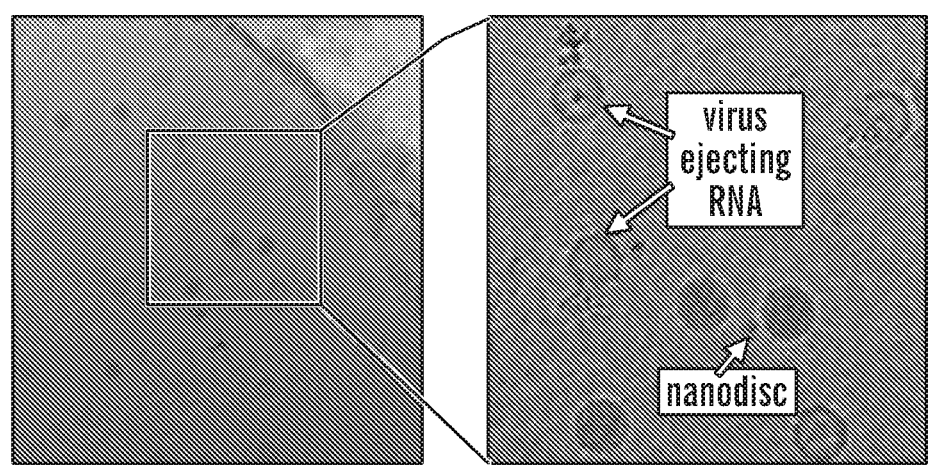
Figure 7A:
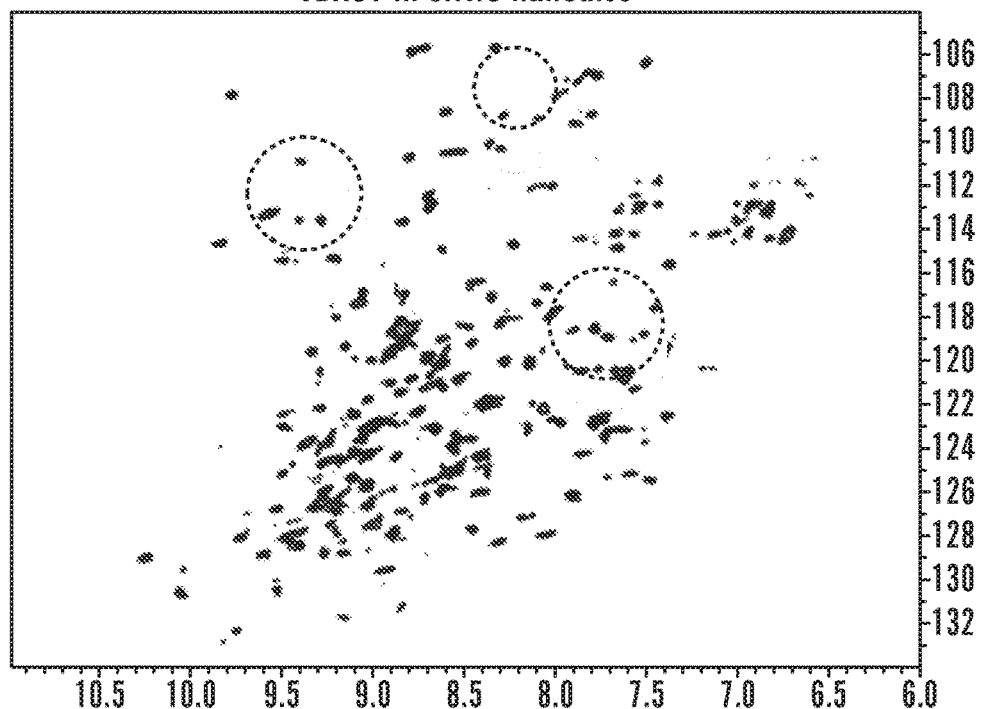
FIGS. 7A-7D demonstrate the analysis of VDAC-1 in different size nanodiscs.
Figure 7B:
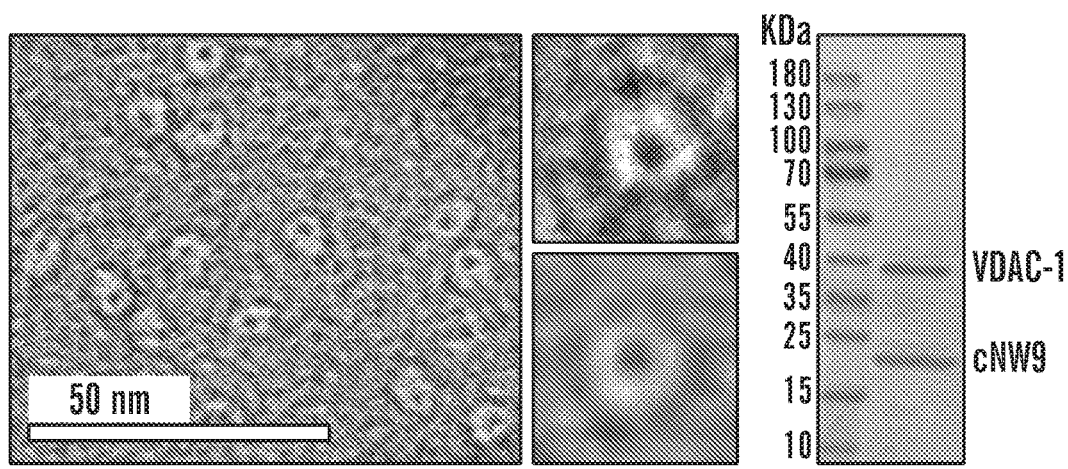
Figure 7C:
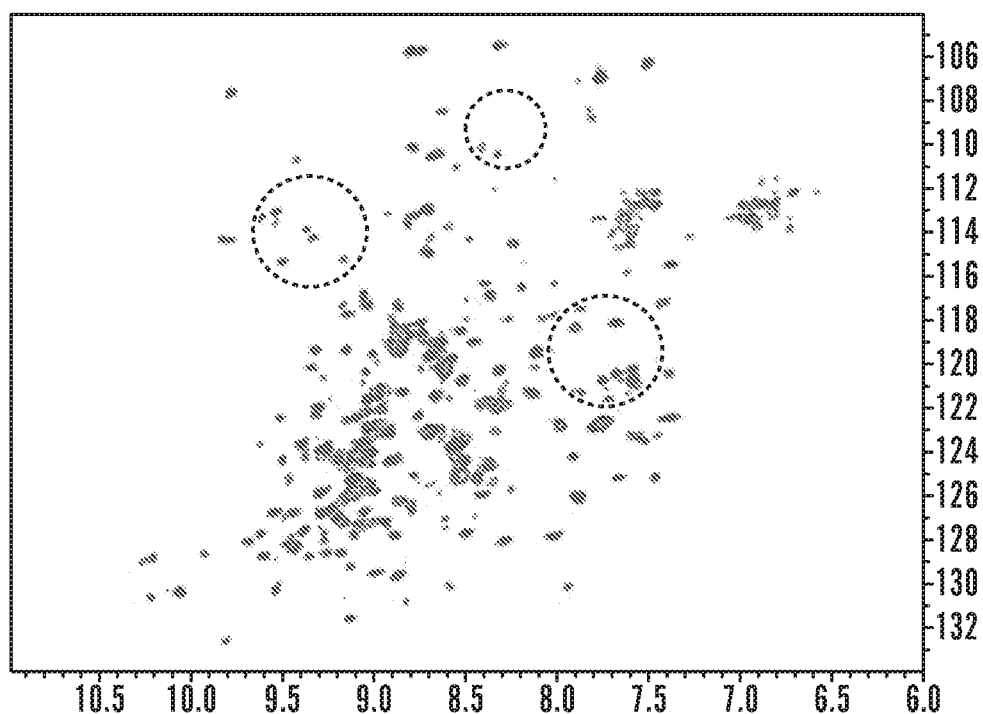
Figure 7D:
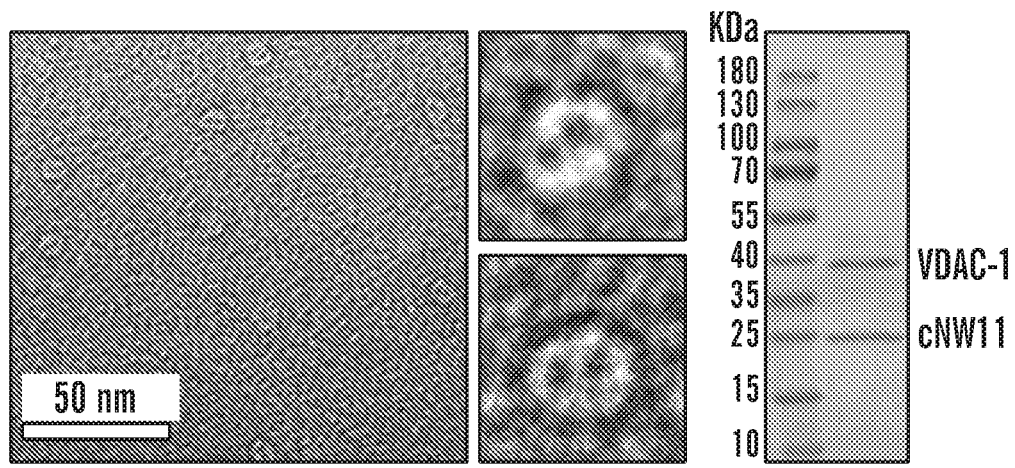

Poliovirus (30 nm diameter) is the prototype member of the enterovirus genus of the picornavirus family, which are positive-sense, single-stranded RNA viruses with ~7500b genomes enclosed by an icosahedral capsid, and lacking an envelope[14]. Viral infection is mediated by a specific receptor, CD155 (also known as the poliovirus receptor, PVR)[15]. Upon raising the temperature from 4° C. to 37° C. the receptor catalyzes a conformational rearrangement and expansion of the virus particle. The expanded virus is then endocytosed by a non-canonical, actin-independent pathway[16], and the RNA is released across the endosomal membrane, leaving an intact empty particle that is then transported to the perinuclear region. A 50-nm nanodisc is sufficiently large to accommodate multiple CD155 copies and has enough surface area to act as a surrogate membrane for the RNA-translocation complex during viral uncoating (FIG. 6A). Similar to studies that used liposomes[17-19], here 50-nm nanodiscs containing lipids derivatized with a NTA nickel-chelating head group were generated and functionalized with the His-tagged CD155 ectodomain. The receptor-decorated nanodiscs were incubated with poliovirus for 5 minutes at 4° C. The complex was then heated to 37° C. for 15 minutes to initiate receptor-mediated viral uncoating (FIG. 6B). Negative-stain EM confirmed virus binding to the CD155-decorated nanodiscs and subsequent insertion of viral components into and across the membrane (FIG. 6C). Additionally, the negative-stain EM images indicated that the virus started to form a pore in the nanodisc. To obtain a view of the molecular interactions involved in the RNA-translocation complex as well as to elucidate in more detail the formation of a pore, cryo-EM studies were conducted using an FEI Polara electron microscope. FIGS. 6D and 13 show the dark RNA-filled virus next to the slightly larger 50 nm nanodisc. The nanodisc is tilted in FIG. 8E and tethered to the virus in FIG. 6F. The formation of a putative pore inside the nanodiscs (FIG. 6G, 6H), through which the virus ejects its RNA was visualized. The images indicate that the pore is formed by several viral proteins whose number and identities are currently being determined. The availability of the circularized 50-nm nanodiscs greatly facilitates imaging as compared to using liposomes because the nanodiscs are more homogenous in size and shape, and allow for the use of a thinner ice layer. Also, RNA can be visualized more easily in the absence of large liposomal membranes. In order to reduce complexity even further, cNW30 nanodiscs (15 nm) decorated with CD155 were used. Surprisingly, the virus also tethers to this smaller nanodisc (FIG. 6I), forms a pore and ejects RNA, leaving an empty viral capsid behind (FIG. 6J). The quality of the data collected on the virus-nanodisc complexes represents a vast improvement over data previously used to obtain low-resolution structural models of the translocation complex using the receptor-decorated liposome model[20], and indicates that the nanodisc model permits determination of structures with greatly improved resolution and quality.

In conclusion, it is demonstrated herein that it is possible to construct covalently circularized nanodiscs with a wide range of geometric shapes and sizes. The ability to make stable cNDs at variable sizes up to 80 nm diameter provides a tool to tightly embed much larger membrane proteins or their intra- and extra-membrane complexes than previous nanodiscs systems have allowed. Moreover, the newly engineered covalently circularized nanodiscs produce nanodiscs with high homogeneity in size and shape and have significantly improved stability compared to non-circularized forms, both of which greatly facilitate their use for cryo-EM and other biophysical approaches. The utility of this model system to probe an outstanding question in the field of virology is demonstrated and the data indicate that the system is suitable for the structural and functional study of other large protein/membrane complexes.

Expression of NW9, NW11, NW30 and NW50.

NW9, NW11, NW30 and NW50 (all in pET-28a) containing a TEV-cleavable N-terminal His6 tag (SEQ ID NO: 54) and a C-terminal sortase-cleavable His6 tag (SEQ ID NO: 54) were transformed into BL21-Gold (DE3) competent E. coli cells (Agilent). 3 L cell cultures were grown at 37° C., 200 rpm in Luria broth (LB) medium supplemented with 50 µg/ml Kanamycin, and expression was induced with 1 mM IPTG at an OD600 of 0.8 for 3 hours at 37° C. (NW9 and NW11) or 16 hours at 18° C. (NW30 and NW50). Cells were harvested by centrifugation (7000×g, 15 minutes, 4° C.) and cell pellets were stored at −80° C.

Purification of NW9 and NW11.

Cell pellets expressing NW9 or NW11 were resuspended in lysis buffer (50 mM Tris-HCl, pH 8.0, 500 mM NaCl, 1% Triton X-100) and lysed by sonication on ice. Lysate was centrifuged (35,000×g, 50 minutes, 4° C.) and the supernatant was filtered and loaded onto Ni2+-NTA column. The column was washed with lysis buffer then with buffer A (50 mM Tris, pH 8.0, 500 mM NaCl). To recover additional protein from the insoluble fractions, the pellets recovered from lysate centrifugation were dissolved in denaturing buffer (50 mM Tris, pH 8.0, 500 mM NaCl, 6M guanidine hydrochloride), centrifuged (35,000×g, 50 minutes, 4° C.), and the supernatant was applied to the same Ni2+-NTA column containing bound protein from the soluble fraction. The column was washed with denaturing buffer, and NW9 and NW11 were refolded on-column with 10 column volumes (CV) buffer A. Resin was then washed with 10 CV of the following: buffer A+1% Triton X-100, buffer A+50 mM sodium cholate, buffer A, and buffer A+20 mM imidazole. Proteins were eluted with buffer A+500 mM imidazole, TEV (His6-tagged (SEQ ID NO: 54); produced in-house) was added to cleave the N-terminal His6 tag (SEQ ID NO: 54), and the samples were dialyzed against 50 mM Tris-HCl, pH 8.0, 20 mM NaCl, 1 mM EDTA, 2 mM DTT at 4° C. for 16 hours. NW9 and NW11 (still containing a C-terminal His6 tag (SEQ ID NO: 54)) were exchanged into nanodisc-assembly buffer (50 mM Tris-HCl, pH 8.0, 500 mM NaCl, 0.02% NaN3) using centricon concentrators (10 kDa MW cutoff, Millipore).

Purification of NW30 and NW50.

NW30 and NW50 were purified under denaturing conditions and refolded as follows. Pellets of cells expressing NW30 or NW50 were resuspended in denaturing lysis buffer (50 mM Tris-HCl, pH 8.0, 500 mM NaCl, 6M guanidine hydrochloride) and lysed by sonication on ice. Lysate was centrifuged (35000×g, 50 minutes, 4° C.) and the supernatant was filtered and loaded onto Ni2+-NTA column. Resin was washed with 10 column volumes (CV) of denaturing lysis buffer to remove unbound proteins, and NW30 and NW50 were refolded on-column with 10 CV buffer A (50 mM Tris HCl, pH 8.0, 500 mM NaCl). Resin was washed with 10 CV of the following: buffer A+1% Triton X-100, buffer A+50 mM sodium cholate, buffer A, and buffer A+20 mM imidazole. Proteins were eluted with buffer A+500 mM imidazole, TEV was added to cleave the N-terminal His6 tag (SEQ ID NO: 54), and samples were dialyzed against 50 mM Tris, pH 8.0, 20 mM NaCl, 1 mM EDTA, 2 mM DTT at 4° C. for 16 hours. NW30 and NW50 (still containing a Cterminal His6 tag (SEQ ID NO: 54)) were further purified by size exclusion chromatography (SEC; Superdex 200 16/60 [GE Healthcare] equilibrated in 20 mM Tris-HCl, pH 7.5, 500 mM NaCl, 50 mM sodium cholate, 0.5 mM EDTA). SEC fractions containing NW30 and NW50 were further purified over Ni2+-NTA resin to remove truncation products (which lack a C-terminal His6 tag (SEQ ID NO: 54)).

Purified proteins were exchanged into nanodisc assembly buffer (50 mM Tris HCl, pH 8.0, 500 mM NaCl, 0.02% NaN3) using centricon concentrators (30 kDa MW cutoff, Millipore).

MSP Circularization.

A 50 mL reaction was prepared with 10 µM NWs and 5 µM (final concentrations) freshly made evolved sortase in 300 mM Tris-HCl, pH 7.5, 150 mM NaCl, and 10 mM CaCl2. The reaction was incubated at 4° C. for 16 hours or at 25° C. for 4 hours with gentle shaking on a rotating platform. A covalent sortase inhibitor AAEK2 was added to a concentration of 500 µM, and the solution was incubated further for 30 minutes at room temperature with gentle shaking. Proteins that did not undergo circularization were removed by binding to Ni2+-NTA column. Circularized NWs (cNWs) were further purified by size-exclusion chromatography (Superdex 75 16/60) equilibrated in 20 mM Tris HCl, pH 7.5, 500 mM NaCl, 50 mM sodium cholate, 0.5 mM EDTA.

Reconstitution of cNW11, cNW30 and cNW50 Nanodiscs.

cNWs:lipid ratios of 1:60, 1:75, 1:1000 and 1:4000 were used to assemble cNW9, cNW11, cNW30, cNW50 nanodiscs respectively. Lipids (POPC:POPG 3:2, solubilized in sodium cholate) and cNWs were incubated on ice for 1 hour. After incubation, sodium cholate was removed by the addition of Bio-beads SM-2 (Bio-Rad) and incubation on ice for 1 hour followed by overnight incubation at 4° C. The nanodisc preparations were filtered through 0.45-µm nitrocellulose-filter tubes to remove the Bio-beads. The nanodisc preparations were further purified by size-exclusion chromatography while monitoring the absorbance at 280 nm on a Superdex 200 10×300 column (for cNW9 and cNW11 nanodiscs) or Superose 6 10/300 column (for cNW30 and cNW50 nanodiscs) equilibrated in 20 mM Tris HCl, pH 7.5, 100 mM NaCl, 0.5 mM EDTA. Fractions corresponding to the size of each nanodisc were collected and concentrated. The purity of nanodisc preparations was checked using SDS-PAGE.

In Vitro Reconstitution of VDAC-1 into POPC/POPG Nanodiscs.

In order to assemble VDAC-1 into POPC/POPG nanodiscs, 15 µM of VDAC-1 (solubilized in LDAO), 150 µM of cNW11 and 8.5 mM lipids (POPC:POPG 3:2, solubilized in sodium cholate) were incubated over ice for 1 hour. After incubation, LDAO and sodium cholate were removed by the addition of Bio-beads SM-2™ (Bio-Rad) and incubation on ice for 1 hour followed by overnight incubation at 4° C. The disc preparation was filtered through 0.45-µm nitrocellulose-filter tubes to remove the Bio-beads™. To remove the VDAC-free nanodiscs, the sample was mixed with Ni2+-NTA resin for 1 hour at 4° C. The resin bed volume was equal to the assembly mixture. The resin was washed with buffer E (20 mM Tris-HCl, pH 8.0, 0.1 M NaCl, 15 mM imidazole). Nanodiscs containing VDAC were eluted with buffer E containing 0.3 M imidazole.

The nanodisc preparation was further purified by size-exclusion chromatography while monitoring the absorbance at 280 nm on a Superdex 200 10×300 column (GE Healthcare) with 20 mM Tris-HCl, pH 7.5, 0.1 mM NaCl at 0.5 mL/minute. Fractions corresponding to the size of the VDAC-nanodisc complex were collected and concentrated. The purity of VDAC containing nanodiscs was checked using SDS-PAGE.

Negative-Stain Electron Microscopy.

Samples were prepared by conventional negative staining as described previously[21]. Briefly, 3.5 µl of nanodisc samples were adsorbed to carbon-coated copper grids and stained with 0.75% (w/v) uranyl formate. EM images were collected with a Philips CM10™ electron microscope (FEI) equipped with a tungsten filament and operated at an acceleration voltage of 100 kV. Images were recorded with a Gatan 1 K×1 K™ CCD camera (Gatan, Inc., Pleasanton, Calif., USA). Images were analyzed with the ImageJ™ software[22].

Cryo-Electron Microscopy.

A 3.5 ul droplet of the poliovirus-nanodisc complex was loaded onto a glow-discharged holey grid (Protochips, Morrisville, N.C.). The excess liquid was removed from the grid surface before it was rapidly plunged into liquid ethane. Grids were transferred to an FEI Polara™ electron microscope operating at an acceleration voltage of 300 keV. Micrographs were acquired on a K2 Summit™ camera (Gatan, Pleasanton, Calif.) in super-resolution mode using SerialEM23™, whereby 25 frames were collected to a total dose of 30 electrons per square angstrom. These frames were aligned and averaged using motioncorr[24].

TABLE 1

Characterization of intact NW proteins by mass spectrometry.

| | Mass, Da | | | |
|---|---|---|---|---|
| | Linear (calculated) | Linear (observed) | Circularized (Calculated) | Circularized (Observed) |
| NW9 | 21191.8 | 21192.8 | 19838.4 | 19838.5 |
| NW11 | 23747.7 | 23752.4 | 22394.3 | 22398.1 |
| NW30 | 65506.9 | 65520.6 | 64153.5 | 64162.4 |
| NW50 | 107266.1 | 107304.7 | 105912.7 | 105940.7 |

REFERENCES

1. Bayburt, T. H., Carlson, J. W. & Sligar, S. G. J Struct Biol 123, 37-44 (1998).
2. Bayburt, T. H., Grinkova, Y. V. & Sligar, S. G. Nano Letters 2, 853-856 (2002).
3. Ritchie, T. K. et al. Methods Enzymol 464, 211-31 (2009).
4. Hagn, F., Etzkorn, M., Raschle, T. & Wagner, G. J Am Chem Soc 135, 1919-25 (2013).
5. Raschle, T. et al. J Am Chem Soc 131, 17777-9 (2009).
6. Grinkova, Y. V., Denisov, I. G. & Sligar, S. G. Protein Eng Des Sel 23, 843-8 (2010).
7. Raschle, T., Hiller, S., Etzkorn, M. & Wagner, G. Current opinion in structural biology 20, 471-9 (2010).
8. Antos, J. M. et al. J Biol Chem 284, 16028-36 (2009).
9. Chen, I., Dorr, B. M. & Liu, D. R. Proc Natl Acad Sci USA 108, 11399-404 (2011).
10. Maresso, A. W. et al. J Biol Chem 282, 23129-39 (2007).
11. Hogle, J. M. Annual Review of Microbiology 56, 677-702 (2002).
12. Tuthill, T. J., Groppelli, E., Hogle, J. M. & Rowlands, D. J. Cell Entry by Non-Enveloped Viruses 343, 43-89 (2010).
13. Marsh, M. & Helenius, A. Cell 124, 729-40 (2006).
14. Tuthill, T. J., Groppelli, E., Hogle, J. M. & Rowlands, D. J. Curr Top Microbiol Immunol 343, 43-89 (2010).
15. Mendelsohn, C. L., Wimmer, E. & Racaniello, V. R. Cell 56, 855-65 (1989).
16. Brandenburg, B. et al. PLoS Biol 5, e183 (2007).
17. Tuthill, T. J., Bubeck, D., Rowlands, D. J. & Hogle, J. M. J Virol 80, 172-80 (2006).
18. Bubeck, D., Filman, D. J. & Hogle, J. M. Nat Struct Mol Biol 12, 615-8 (2005).
19. Strauss, M., Levy, H. C., Bostina, M., Filman, D. J. & Hogle, J. M. J Virol 87, 3903-14 (2013).
20. Strauss, M. et al. J Virol 89, 4143-57 (2015).
21. Ohi, M., Li, Y., Cheng, Y. & Walz, T. Biol Proced Online 6, 23-34 (2004).
22. Schneider, C. A., Rasband, W. S. & Eliceiri, K. W. Nat Methods 9, 671-5 (2012).
23. Mastronarde, D. N. J Struct Biol 152, 36-51 (2005).
24. Li, X., Grigorieff, N. & Cheng, Y. J Struct Biol 172, 407-12 (2010).

Protein sequences

NW9

SEQ ID No: 1

MGSSHHHHHHENLYFQGSTFSKLREQLGPVTQEFWDNLEKETEGLRQEM

SKDLEEVKAKVQPYLDDFQKKWQEEMELYRQKVEPLGEEMRDRARAHVD

ALRTHLAPYSDELRQRLAARLEALKENGGARLAEYHAKATEHLSTLSEK

AKPALEDLRQGLLPVLESFKVSFLSALEEYTKKLNTQLPGTGAAALEHH

HHHH

NW11

SEQ ID NO: 2

MGSSHHHHHHENLYFQGSTFSKLREQLGPVTQEFWDNLEKETEGLRQEM

SKDLEEVKAKVQPYLDDFQKKWQEEMELYRQKVEPLRAELQEGARQKLH

ELQEKLSPLGEEMRDRARAHVDALRTHLAPYSDELRQRLAARLEALKEN

GGARLAEYHAKATEHLSTLSEKAKPALEDLRQGLLPVLESFKVSFLSAL

EEYTKKLNTQLPGTGAAALEHHHHHH

NW30

SEQ ID NO: 3

MGSSHHHHHHENLYFQGSTFSKLREQLGPVTQEFWDNLEKETEGLRQEM

SKDLEEVKAKVQPYLDDFQKKWQEEMELYRQKVEPLRAELQEGARQKLH

ELQEKLSPLGEEMRDRARAHVDALRTHLAPYSDELRQRLAARLEALKEN

GGARLAEYHAKATEHLSTLSEKAKPALEDLRQGLLPVLESFKVSFLSAL

EEYTKKLNTQGTPVTQEFWDNLEKETEGLRQEMSKDLEEVKAKVQPYLD

DFQKKWQEEMELYRQKVEPLRAELQEGARQKLHELQEKLSPLGEEMRDR

ARAHVDALRTHLAPYSDELRQRLAARLEALKENGGARLAEYHAKATEHL

STLSEKAKPALEDLRQGLLPVLESFKVSFLSALEEYTKKLNTQGTPVTQ

EFWDNLEKETEGLRQEMSKDLEEVKAKVQPYLDDFQKKWQEEMELYRQK

VEPLRAELQEGARQKLHELQEKLSPLGEEMRDRARAHVDALRTHLAPYS

DELRQRLAARLEALKENGGARLAEYHAKATEHLSTLSEKAKPALEDLRQ

GLLPVLESFKVSFLSALEEYTKKLNTQLPGTGAAALEHHHHHH

NW50

SEQ ID NO: 4

MGSSHHHHHHENLYFQGSTFSKLREQLGPVTQEFWDNLEKETEGLRQEM

SKDLEEVKAKVQPYLDDFQKKWQEEMELYRQKVEPLRAELQEGARQKLH

ELQEKLSPLGEEMRDRARAHVDALRTHLAPYSDELRQRLAARLEALKEN

GGARLAEYHAKATEHLSTLSEKAKPALEDLRQGLLPVLESFKVSFLSAL

EEYTKKLNTQGTPVTQEFWDNLEKETEGLRQEMSKDLEEVKAKVQPYLD

DFQKKWQEEMELYRQKVEPLRAELQEGARQKLHELQEKLSPLGEEMRDR

ARAHVDALRTHLAPYSDELRQRLAARLEALKENGGARLAEYHAKATEHL

STLSEKAKPALEDLRQGLLPVLESFKVSFLSALEEYTKKLNTQGTPVTQ

EFWDNLEKETEGLRQEMSKDLEEVKAKVQPYLDDFQKKWQEEMELYRQK

-continued

VEPLRAELQEGARQKLHELQEKLSPLGEEMRDRARAHVDALRTHLAPYS

DELRQRLAARLEALKENGGARLAEYHAKATEHLSTLSEKAKPALEDLRQ

GLLPVLESFKVSFLSALEEYTKKLNTQGTPVTQEFWDNLEKETEGLRQE

MSKDLEEVKAKVQPYLDDFQKKWQEEMELYRQKVEPLRAELQEGARQKL

HELQEKLSPLGEEMRDRARAHVDALRTHLAPYSDELRQRLAARLEALKE

NGGARLAEYHAKATEHLSTLSEKAKPALEDLRQGLLPVLESFKVSFLSA

LEEYTKKLNTQGTPVTQEFWDNLEKETEGLRQEMSKDLEEVKAKVQPYL

DDFQKKWQEEMELYRQKVEPLRAELQEGARQKLHELQEKLSPLGEEMRD

RARAHVDALRTHLAPYSDELRQRLAARLEALKENGGARLAEYHAKATEH

LSTLSEKAKPALEDLRQGLLPVLESFKVSFLSALEEYTKKLNTQLPGTG

AAALEHHHHHH

Example 4: Covalently Circularized Nanodiscs for Structural and Functional Studies of Membrane Proteins The physicochemical environment enveloping a membrane protein in vitro is critical to fully understand the molecular behavior in a biologically relevant context. Although micelles and bicelles have produced significant results, detergents can alter dynamic protein behavior and hinder interactions between a membrane protein and its cytosolic partner(s). Conventional nanodiscs are composed of a nanometer-sized phospholipid bilayer encircled by two α helical, amphipathic membrane scaffold proteins (MSPs). These particles provide a unique detergent free lipid bilayer model enabling biochemical and biophysical characterization of membrane proteins in a physiologically relevant medium. Recently, nanodiscs have been used to investigate the structure and function of different membrane proteins using solution NMR.

Although the MSPs used in a particular nanodisc preparation are the same length, the distribution in diameter of an assembled disc can be broad. This can result in a variable number of membrane proteins incorporating into each disc, and obtaining a sample with a mixed population of membrane proteins per nanodisc that lead to confounding results. To overcome these issues described herein are nanodiscs assembled with circularized MSPs (cMSP). Described herein are different methods to covalently link the N and C terminus of an MSP polypeptide using evolved sortase. Sortase reaction fidelity has been confirmed by mass spectrometry of the cMSP polypeptide. The homogeneity in particle diameter was a narrow distribution using negative-stain EM. Using the circularization method, nanodiscs of different sizes up to 100 nm in diameter can be constructed.

Methods

Described herein are three methods to create circularized MSP.

Figure 8:
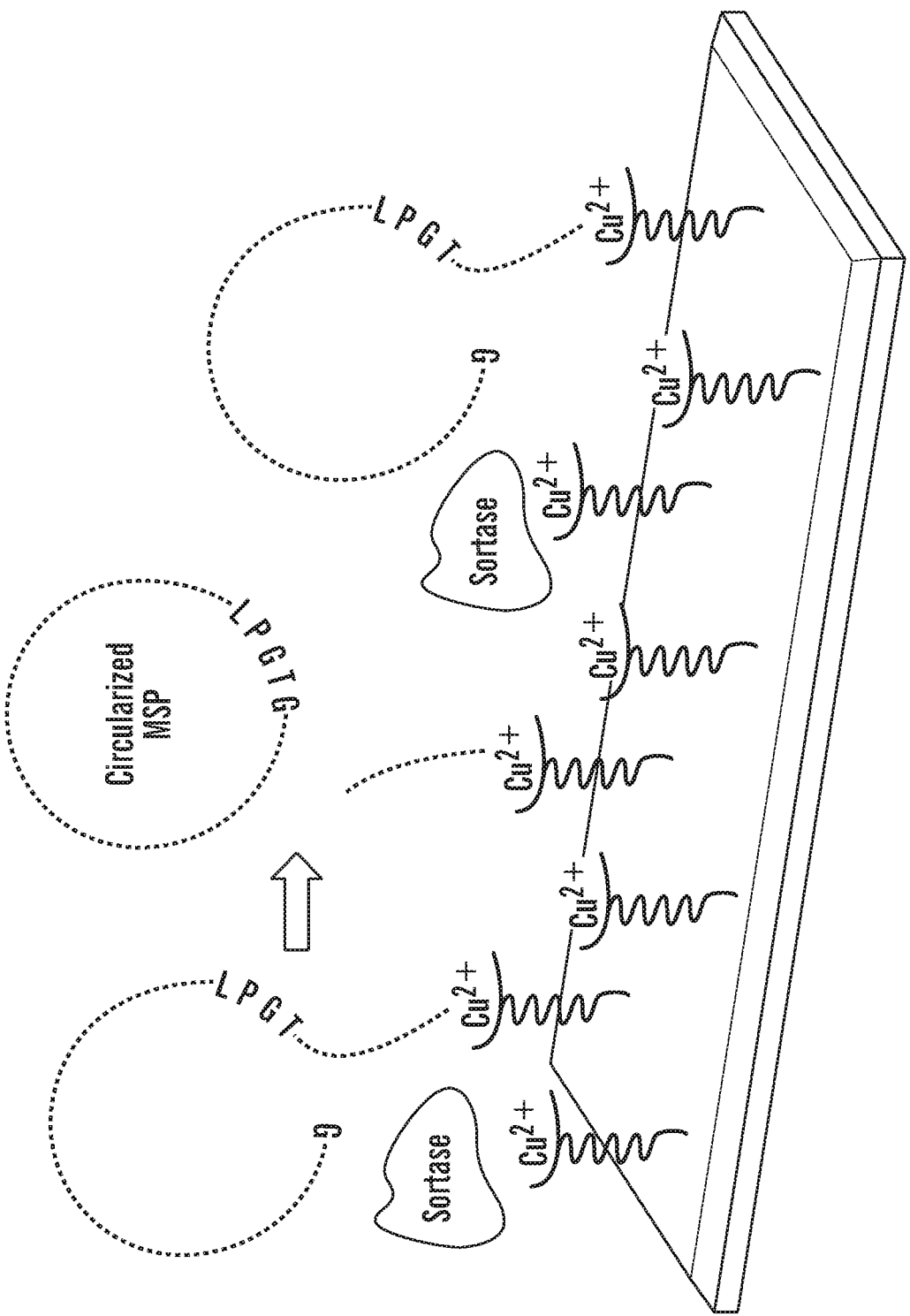
FIG. 8 depicts a schematic outline of the procedure for creating circularized NW proteins over Cu+2 chip. His6-tagged NWs ("His6" disclosed as SEQ ID NO: 54) is attached to Cu+2 chip. Addition of His6-tagged evolved sortase ("His6" disclosed as SEQ ID NO: 54) creates circularized non-His tagged NW (cNW), which can be eluted while cleaved His6-tagged products ("His6" disclosed as SEQ ID NO: 54) and evolved sortase remain bound to the Cu+2 chip. The eluted cMSP is passed through Ni column to get rid of any traces of His6-tagged products ("His6" disclosed as SEQ ID NO: 54) and evolved sortase.

A—creating circularized MSP over Cu+2 (FIG. 8). This method results in the cleanest product. It is suitable for, e.g., small-scale production of circularized MSP.

B—Circularization of MSP over Ni2+ bead. His-tagged MSP is attached to Ni beads then some lipids are added to MSP and finally sortase is added. Adding lipid to MSP first can minimizes the multimerization by-products and maximize the intramolecular circularization. This method is suitable for, e.g., large-scale production of cMSP.

C—Circularization of MSP in solution. His-tagged MSP is diluted in sortase buffer (MSP final conc <15 uM) then sortase is added. The reaction is quenched by adding the sortase covalent inhibitor AAEK2 (final conc 0.5 mM). The reaction mixture is run through Ni column and the flow through collected. This method is suitable for, e.g., large-scale production of cMSP.

Results

FIG. 2E demonstrates, via negative stain EM, that the circularized nanodiscs described herein are more homogenous than conventional nanodiscs. FIGS. 2C-2E depict characterization of the circularized nanodiscs. Large nanodisc sizes can be achieved with the methods described herein (FIG. 3A-3C).

It is specifically contemplated herein that the presently described circularized nanodiscs can be used for the following non-limiting applications: Small circularized nanodiscs (<12 nm)

1—facilitating solution NMR studies of membrane proteins in physiologically relevant conditions (more stable and more homogenous than conventional nanodiscs)

2—Allow for detergent titrations and the transfer of NMR assignments (detergent to nanodisc) because of its high stability.

Large circularized nanodiscs (10-100 nm)

1—Permit structural and functional studies of large membrane proteins (eg. FepA and mammalian respiratory complex) in bilayer 2—Permit studying membrane protein interactions with another membrane protein or cytosolic partner 3—Permit constructions and studying many membrane pores (eg. proapoptotic proteins BAX and BAK pores, anthrax pore etc)

4—Permit studying virus entry to cells (FIGS. 6A-6J) and screening for potential inhibitors against virus entry 5—Cell-free expression for large membrane proteins and complexes.

6—Permit Residual Dipolar Coupling (RDC) measurements (detergent free, homogenous effect, charge tunable)

7—Crystallization and 2D lattice

8—Limited proteolysis of membrane proteins (more stable than conventional nanodisc)

9—Vaccination (many copies of membrane proteins per disc)

10—Studying how Apolipoprotein A-1 interact with lipids since the size of the large nanodisc is suitable for cryo-EM size range.

11—Permit studying lipid rafts.

12—Studying the fusion of synaptic vesicle membranes with planar bilayer membranes.

Protein Sequences

NW9 (assemble ~9 nm nanodisc)

SEQ ID NO: 6

MGSSHHHHHHENLYFQGSTFSKLREQLGPVTQEFWDNLEKETEGLRQEMSKDLEEVKAKVQP

YLDDFQKKWQEEMELYRQKVEPLGEEMRDRARAHVDALRTHLAPYSDELRQRLAARLEALKE

NGGARLAEYHAKATEHLSTLSEKAKPALEDLRQGLLPVLESFKVSFLSALEEYTKKLNTQLP

GTGAAALEHHHHHH

```
NW10 (assemble ~10 nm nanodisc)
                                                         SEQ ID NO: 7
MGSSHHHHHHENLYFQGSTFSKLREQLGPVTQEFWDNLEKETEGLRQEMSKDLEEVKAKVQP

YLDDFQKKWQEEMELYRQKVEPLRAELQEGARQKLHELQEKLSPLGEEMRDRARAHVDALRT

HLAPYSDELRQRLAARLEALKENGGARLAEYHAKATEHLSTLSEKAKPALEDLRQGLLPVLE

SFKVSFLSALEEYTKKLNTQLPGTGAAALEHHHHHH

NW18 (assemble ~18 nm nanodisc)
                                                         SEQ ID NO: 8
MGSSHHHHHHENLYFQGSTFSKLREQLGPVTQEFWDNLEKETEGLRQEMSKDLEEVKAKVQP

YLDDFQKKWQEEMELYRQKVEPLGEEMRDRARAHVDALRTHLAPYSDELRQRLAARLEALKE

NGGARLAEYHAKATEHLSTLSEKAKPALEDLRQGLLPVLESFKVSFLSALEEYTKKLNTQGT

PVTQEFWDNLEKETEGLRQEMSKDLEEVKAKVQPYLDDFQKKWQEEMELYRQKVEPLGEEMR

DRARAHVDALRTHLAPYSDELRQRLAARLEALKENGGARLAEYHAKATEHLSTLSEKAKPAL

EDLRQGLLPVLESFKVSFLSALEEYTKKLNTQLPGTGAAALEHHHHHH

NW20 (assemble ~20 nm nanodisc)
                                                         SEQ ID NO: 9
MGSSHHHHHHENLYFQGSTFSKLREQLGPVTQEFWDNLEKETEGLRQEMSKDLEEVKAKVQP

YLDDFQKKWQEEMELYRQKVEPLRAELQEGARQKLHELQEKLSPLGEEMRDRARAHVDALRT

HLAPYSDELRQRLAARLEALKENGGARLAEYHAKATEHLSTLSEKAKPALEDLRQGLLPVLE

SFKVSFLSALEEYTKKLNTQGTPVTQEFWDNLEKETEGLRQEMSKDLEEVKAKVQPYLDDFQ

KKWQEEMELYRQKVEPLRAELQEGARQKLHELQEKLSPLGEEMRDRARAHVDALRTHLAPYS

DELRQRLAARLEALKENGGARLAEYHAKATEHLSTLSEKAKPALEDLRQGLLPVLESFKVSF

LSALEEYTKKLNTQLPGTGAAALEHHHHHH

NW27 (assemble ~27 nm nanodisc)
                                                         SEQ ID NO: 10
MGSSHHHHHHENLYFQGSTFSKLREQLGPVTQEFWDNLEKETEGLRQEMSKDLEEVKAKVQP

YLDDFQKKWQEEMELYRQKVEPLGEEMRDRARAHVDALRTHLAPYSDELRQRLAARLEALKE

NGGARLAEYHAKATEHLSTLSEKAKPALEDLRQGLLPVLESFKVSFLSALEEYTKKLNTQGT

PVTQEFWDNLEKETEGLRQEMSKDLEEVKAKVQPYLDDFQKKWQEEMELYRQKVEPLGEEMR

DRARAHVDALRTHLAPYSDELRQRLAARLEALKENGGARLAEYHAKATEHLSTLSEKAKPAL

EDLRQGLLPVLESFKVSFLSALEEYTKKLNTQGTPVTQEFWDNLEKETEGLRQEMSKDLEEV

KAKVQPYLDDFQKKWQEEMELYRQKVEPLGEEMRDRARAHVDALRTHLAPYSDELRQRLAAR

LEALKENGGARLAEYHAKATEHLSTLSEKAKPALEDLRQGLLPVLESFKVSFLSALEEYTKK

LNTQLPGTGAAALEHHHHHH

NW30 (assemble ~30 nm nanodisc)
                                                         SEQ ID NO: 11
MGSSHHHHHHENLYFQGSTFSKLREQLGPVTQEFWDNLEKETEGLRQEMSKDLEEVKAKVQP

YLDDFQKKWQEEMELYRQKVEPLRAELQEGARQKLHELQEKLSPLGEEMRDRARAHVDALRT

HLAPYSDELRQRLAARLEALKENGGARLAEYHAKATEHLSTLSEKAKPALEDLRQGLLPVLE

SFKVSFLSALEEYTKKLNTQGTPVTQEFWDNLEKETEGLRQEMSKDLEEVKAKVQPYLDDFQ

KKWQEEMELYRQKVEPLRAELQEGARQKLHELQEKLSPLGEEMRDRARAHVDALRTHLAPYS

DELRQRLAARLEALKENGGARLAEYHAKATEHLSTLSEKAKPALEDLRQGLLPVLESFKVSF

LSALEEYTKKLNTQGTPVTQEFWDNLEKETEGLRQEMSKDLEEVKAKVQPYLDDFQKKWQEE

MELYRQKVEPLRAELQEGARQKLHELQEKLSPLGEEMRDRARAHVDALRTHLAPYSDELRQR
```

-continued

LAARLEALKENGGARLAEYHAKATEHLSTLSEKAKPALEDLRQGLLPVLESFKVSFLSALEE

YTKKLNTQLPGTGAAALEHHHHHH

NW36 (assemble ~36 nm nanodisc)
SEQ ID NO: 12

MGSSHHHHHHENLYFQGSTFSKLREQLGPVTQEFWDNLEKETEGLRQEMSKDLEEVKAKVQP

YLDDFQKKWQEEMELYRQKVEPLGEEMRDRARAHVDALRTHLAPYSDELRQRLAARLEALKE

NGGARLAEYHAKATEHLSTLSEKAKPALEDLRQGLLPVLESFKVSFLSALEEYTKKLNTQGT

PVTQEFWDNLEKETEGLRQEMSKDLEEVKAKVQPYLDDFQKKWQEEMELYRQKVEPLGEEMR

DRARAHVDALRTHLAPYSDELRQRLAARLEALKENGGARLAEYHAKATEHLSTLSEKAKPAL

EDLRQGLLPVLESFKVSFLSALEEYTKKLNTQGTPVTQEFWDNLEKETEGLRQEMSKDLEEV

KAKVQPYLDDFQKKWQEEMELYRQKVEPLGEEMRDRARAHVDALRTHLAPYSDELRQRLAAR

LEALKENGGARLAEYHAKATEHLSTLSEKAKPALEDLRQGLLPVLESFKVSFLSALEEYTKK

LNTQGTPVTQEFWDNLEKETEGLRQEMSKDLEEVKAKVQPYLDDFQKKWQEEMELYRQKVEP

LGEEMRDRARAHVDALRTHLAPYSDELRQRLAARLEALKENGGARLAEYHAKATEHLSTLSE

KAKPALEDLRQGLLPVLESFKVSFLSALEEYTKKLNTQLPGTGAAALEHHHHHH

NW40 (assemble ~40 nm nanodisc)
SEQ ID NO: 13

MGSSHHHHHHENLYFQGSTFSKLREQLGPVTQEFWDNLEKETEGLRQEMSKDLEEVKAKVQP

YLDDFQKKWQEEMELYRQKVEPLRAELQEGARQKLHELQEKLSPLGEEMRDRARAHVDALRT

HLAPYSDELRQRLAARLEALKENGGARLAEYHAKATEHLSTLSEKAKPALEDLRQGLLPVLE

SFKVSFLSALEEYTKKLNTQGTPVTQEFWDNLEKETEGLRQEMSKDLEEVKAKVQPYLDDFQ

KKWQEEMELYRQKVEPLRAELQEGARQKLHELQEKLSPLGEEMRDRARAHVDALRTHLAPYS

DELRQRLAARLEALKENGGARLAEYHAKATEHLSTLSEKAKPALEDLRQGLLPVLESFKVSF

LSALEEYTKKLNTQGTPVTQEFWDNLEKETEGLRQEMSKDLEEVKAKVQPYLDDFQKKWQEE

MELYRQKVEPLRAELQEGARQKLHELQEKLSPLGEEMRDRARAHVDALRTHLAPYSDELRQR

LAARLEALKENGGARLAEYHAKATEHLSTLSEKAKPALEDLRQGLLPVLESFKVSFLSALEE

YTKKLNTQGTPVTQEFWDNLEKETEGLRQEMSKDLEEVKAKVQPYLDDFQKKWQEEMELYRQ

KVEPLRAELQEGARQKLHELQEKLSPLGEEMRDRARAHVDALRTHLAPYSDELRQRLAARLE

ALKENGGARLAEYHAKATEHLSTLSEKAKPALEDLRQGLLPVLESFKVSFLSALEEYTKKLN

TQLPGTGAAALEHHHHHH

NW45 (assemble ~45 nm nanodisc)
SEQ ID NO: 14

MGSSHHHHHHENLYFQGSTFSKLREQLGPVTQEFWDNLEKETEGLRQEMSKDLEEVKAKVQP

YLDDFQKKWQEEMELYRQKVEPLGEEMRDRARAHVDALRTHLAPYSDELRQRLAARLEALKE

NGGARLAEYHAKATEHLSTLSEKAKPALEDLRQGLLPVLESFKVSFLSALEEYTKKLNTQGT

PVTQEFWDNLEKETEGLRQEMSKDLEEVKAKVQPYLDDFQKKWQEEMELYRQKVEPLGEEMR

DRARAHVDALRTHLAPYSDELRQRLAARLEALKENGGARLAEYHAKATEHLSTLSEKAKPAL

EDLRQGLLPVLESFKVSFLSALEEYTKKLNTQGTPVTQEFWDNLEKETEGLRQEMSKDLEEV

KAKVQPYLDDFQKKWQEEMELYRQKVEPLGEEMRDRARAHVDALRTHLAPYSDELRQRLAAR

LEALKENGGARLAEYHAKATEHLSTLSEKAKPALEDLRQGLLPVLESFKVSFLSALEEYTKK

LNTQGTPVTQEFWDNLEKETEGLRQEMSKDLEEVKAKVQPYLDDFQKKWQEEMELYRQKVEP

LGEEMRDRARAHVDALRTHLAPYSDELRQRLAARLEALKENGGARLAEYHAKATEHLSTLSE

KAKPALEDLRQGLLPVLESFKVSFLSALEEYTKKLNTQGTPVTQEFWDNLEKETEGLRQEMS

-continued

KDLEEVKAKVQPYLDDFQKKWQEEMELYRQKVEPLGEEMRDRARAHVDALRTHLAPYSDELR

QRLAARLEALKENGGARLAEYHAKATEHLSTLSEKAKPALEDLRQGLLPVLESFKVSFLSAL

EEYTKKLNTQLPGTGAAALEHHHHHH

NW50 (assemble ~50 nm nanodisc)
                                                        SEQ ID NO: 15
MGSSHHHHHHENLYFQGSTFSKLREQLGPVTQEFWDNLEKETEGLRQEMSKDLEEVKAKVQP

YLDDFQKKWQEEMELYRQKVEPLRAELQEGARQKLHELQEKLSPLGEEMRDRARAHVDALRT

HLAPYSDELRQRLAARLEALKENGGARLAEYHAKATEHLSTLSEKAKPALEDLRQGLLPVLE

SFKVSFLSALEEYTKKLNTQGTPVTQEFWDNLEKETEGLRQEMSKDLEEVKAKVQPYLDDFQ

KKWQEEMELYRQKVEPLRAELQEGARQKLHELQEKLSPLGEEMRDRARAHVDALRTHLAPYS

DELRQRLAARLEALKENGGARLAEYHAKATEHLSTLSEKAKPALEDLRQGLLPVLESFKVSF

LSALEEYTKKLNTQGTPVTQEFWDNLEKETEGLRQEMSKDLEEVKAKVQPYLDDFQKKWQEE

MELYRQKVEPLRAELQEGARQKLHELQEKLSPLGEEMRDRARAHVDALRTHLAPYSDELRQR

LAARLEALKENGGARLAEYHAKATEHLSTLSEKAKPALEDLRQGLLPVLESFKVSFLSALEE

YTKKLNTQGTPVTQEFWDNLEKETEGLRQEMSKDLEEVKAKVQPYLDDFQKKWQEEMELYRQ

KVEPLRAELQEGARQKLHELQEKLSPLGEEMRDRARAHVDALRTHLAPYSDELRQRLAARLE

ALKENGGARLAEYHAKATEHLSTLSEKAKPALEDLRQGLLPVLESFKVSFLSALEEYTKKLN

TQGTPVTQEFWDNLEKETEGLRQEMSKDLEEVKAKVQPYLDDFQKKWQEEMELYRQKVEPLR

AELQEGARQKLHELQEKLSPLGEEMRDRARAHVDALRTHLAPYSDELRQRLAARLEALKENG

GARLAEYHAKATEHLSTLSEKAKPALEDLRQGLLPVLESFKVSFLSALEEYTKKLNTQLPGT

GAAALEHHHHHH

NW54 (assemble ~54 nm nanodisc)
                                                        SEQ ID NO: 16
MGSSHHHHHHENLYFQGSTFSKLREQLGPVTQEFWDNLEKETEGLRQEMSKDLEEVKAKVQP

YLDDFQKKWQEEMELYRQKVEPLGEEMRDRARAHVDALRTHLAPYSDELRQRLAARLEALKE

NGGARLAEYHAKATEHLSTLSEKAKPALEDLRQGLLPVLESFKVSFLSALEEYTKKLNTQGT

PVTQEFWDNLEKETEGLRQEMSKDLEEVKAKVQPYLDDFQKKWQEEMELYRQKVEPLGEEMR

DRARAHVDALRTHLAPYSDELRQRLAARLEALKENGGARLAEYHAKATEHLSTLSEKAKPAL

EDLRQGLLPVLESFKVSFLSALEEYTKKLNTQGTPVTQEFWDNLEKETEGLRQEMSKDLEEV

KAKVQPYLDDFQKKWQEEMELYRQKVEPLGEEMRDRARAHVDALRTHLAPYSDELRQRLAAR

LEALKENGGARLAEYHAKATEHLSTLSEKAKPALEDLRQGLLPVLESFKVSFLSALEEYTKK

LNTQGTPVTQEFWDNLEKETEGLRQEMSKDLEEVKAKVQPYLDDFQKKWQEEMELYRQKVEP

LGEEMRDRARAHVDALRTHLAPYSDELRQRLAARLEALKENGGARLAEYHAKATEHLSTLSE

KAKPALEDLRQGLLPVLESFKVSFLSALEEYTKKLNTQGTPVTQEFWDNLEKETEGLRQEMS

KDLEEVKAKVQPYLDDFQKKWQEEMELYRQKVEPLGEEMRDRARAHVDALRTHLAPYSDELR

QRLAARLEALKENGGARLAEYHAKATEHLSTLSEKAKPALEDLRQGLLPVLESFKVSFLSAL

EEYTKKLNTQGTPVTQEFWDNLEKETEGLRQEMSKDLEEVKAKVQPYLDDFQKKWQEEMELY

RQKVEPLGEEMRDRARAHVDALRTHLAPYSDELRQRLAARLEALKENGGARLAEYHAKATEH

LSTLSEKAKPALEDLRQGLLPVLESFKVSFLSALEEYTKKLNTQLPGTGAAALEHHHHHH

NW60 (assemble ~60 nm nanodisc)
                                                        SEQ ID NO: 17
MGSSHHHHHHENLYFQGSTFSKLREQLGPVTQEFWDNLEKETEGLRQEMSKDLEEVKAKVQP

YLDDFQKKWQEEMELYRQKVEPLRAELQEGARQKLHELQEKLSPLGEEMRDRARAHVDALRT

HLAPYSDELRQRLAARLEALKENGGARLAEYHAKATEHLSTLSEKAKPALEDLRQGLLPVLE

-continued

SFKVSFLSALEEYTKKLNTQGTPVTQEFWDNLEKETEGLRQEMSKDLEEVKAKVQPYLDDFQ

KKWQEEMELYRQKVEPLRAELQEGARQKLHELQEKLSPLGEEMRDRARAHVDALRTHLAPYS

DELRQRLAARLEALKENGGARLAEYHAKATEHLSTLSEKAKPALEDLRQGLLPVLESFKVSF

LSALEEYTKKLNTQGTPVTQEFWDNLEKETEGLRQEMSKDLEEVKAKVQPYLDDFQKKWQEE

MELYRQKVEPLRAELQEGARQKLHELQEKLSPLGEEMRDRARAHVDALRTHLAPYSDELRQR

LAARLEALKENGGARLAEYHAKATEHLSTLSEKAKPALEDLRQGLLPVLESFKVSFLSALEE

YTKKLNTQGTPVTQEFWDNLEKETEGLRQEMSKDLEEVKAKVQPYLDDFQKKWQEEMELYRQ

KVEPLRAELQEGARQKLHELQEKLSPLGEEMRDRARAHVDALRTHLAPYSDELRQRLAARLE

ALKENGGARLAEYHAKATEHLSTLSEKAKPALEDLRQGLLPVLESFKVSFLSALEEYTKKLN

TQGTPVTQEFWDNLEKETEGLRQEMSKDLEEVKAKVQPYLDDFQKKWQEEMELYRQKVEPLR

AELQEGARQKLHELQEKLSPLGEEMRDRARAHVDALRTHLAPYSDELRQRLAARLEALKENG

GARLAEYHAKATEHLSTLSEKAKPALEDLRQGLLPVLESFKVSFLSALEEYTKKLNTQGTPV

TQEFWDNLEKETEGLRQEMSKDLEEVKAKVQPYLDDFQKKWQEEMELYRQKVEPLRAELQEG

ARQKLHELQEKLSPLGEEMRDRARAHVDALRTHLAPYSDELRQRLAARLEALKENGGARLAE

YHAKATEHLSTLSEKAKPALEDLRQGLLPVLESFKVSFLSALEEYTKKLNTQLPGTGAAALE

HHHHHH

NW63 (assemble ~63 nm)
SEQ ID NO: 18

MGSSHHHHHHENLYFQGSTFSKLREQLGPVTQEFWDNLEKETEGLRQEMSKDLEEVKAKVQP

YLDDFQKKWQEEMELYRQKVEPLGEEMRDRARAHVDALRTHLAPYSDELRQRLAARLEALKE

NGGARLAEYHAKATEHLSTLSEKAKPALEDLRQGLLPVLESFKVSFLSALEEYTKKLNTQGT

PVTQEFWDNLEKETEGLRQEMSKDLEEVKAKVQPYLDDFQKKWQEEMELYRQKVEPLGEEMR

DRARAHVDALRTHLAPYSDELRQRLAARLEALKENGGARLAEYHAKATEHLSTLSEKAKPAL

EDLRQGLLPVLESFKVSFLSALEEYTKKLNTQGTPVTQEFWDNLEKETEGLRQEMSKDLEEV

KAKVQPYLDDFQKKWQEEMELYRQKVEPLGEEMRDRARAHVDALRTHLAPYSDELRQRLAAR

LEALKENGGARLAEYHAKATEHLSTLSEKAKPALEDLRQGLLPVLESFKVSFLSALEEYTKK

LNTQGTPVTQEFWDNLEKETEGLRQEMSKDLEEVKAKVQPYLDDFQKKWQEEMELYRQKVEP

LGEEMRDRARAHVDALRTHLAPYSDELRQRLAARLEALKENGGARLAEYHAKATEHLSTLSE

KAKPALEDLRQGLLPVLESFKVSFLSALEEYTKKLNTQGTPVTQEFWDNLEKETEGLRQEMS

KDLEEVKAKVQPYLDDFQKKWQEEMELYRQKVEPLGEEMRDRARAHVDALRTHLAPYSDELR

QRLAARLEALKENGGARLAEYHAKATEHLSTLSEKAKPALEDLRQGLLPVLESFKVSFLSAL

EEYTKKLNTQGTPVTQEFWDNLEKETEGLRQEMSKDLEEVKAKVQPYLDDFQKKWQEEMELY

RQKVEPLGEEMRDRARAHVDALRTHLAPYSDELRQRLAARLEALKENGGARLAEYHAKATEH

LSTLSEKAKPALEDLRQGLLPVLESFKVSFLSALEEYTKKLNTQGTPVTQEFWDNLEKETEG

LRQEMSKDLEEVKAKVQPYLDDFQKKWQEEMELYRQKVEPLGEEMRDRARAHVDALRTHLAP

YSDELRQRLAARLEALKENGGARLAEYHAKATEHLSTLSEKAKPALEDLRQGLLPVLESFKV

SFLSALEEYTKKLNTQLPGTGAAALEHHHHHH

NW70 (assemble ~70 nm)
SEQ ID NO: 19

MGSSHHHHHHENLYFQGSTFSKLREQLGPVTQEFWDNLEKETEGLRQEMSKDLEEVKAKVQP

YLDDFQKKWQEEMELYRQKVEPLRAELQEGARQKLHELQEKLSPLGEEMRDRARAHVDALRT

HLAPYSDELRQRLAARLEALKENGGARLAEYHAKATEHLSTLSEKAKPALEDLRQGLLPVLE

```
SFKVSFLSALEEYTKKLNTQGTPVTQEFWDNLEKETEGLRQEMSKDLEEVKAKVQPYLDDFQ

KKWQEEMELYRQKVEPLRAELQEGARQKLHELQEKLSPLGEEMRDRARAHVDALRTHLAPYS

DELRQRLAARLEALKENGGARLAEYHAKATEHLSTLSEKAKPALEDLRQGLLPVLESFKVSF

LSALEEYTKKLNTQGTPVTQEFWDNLEKETEGLRQEMSKDLEEVKAKVQPYLDDFQKKWQEE

MELYRQKVEPLRAELQEGARQKLHELQEKLSPLGEEMRDRARAHVDALRTHLAPYSDELRQR

LAARLEALKENGGARLAEYHAKATEHLSTLSEKAKPALEDLRQGLLPVLESFKVSFLSALEE

YTKKLNTQGTPVTQEFWDNLEKETEGLRQEMSKDLEEVKAKVQPYLDDFQKKWQEEMELYRQ

KVEPLRAELQEGARQKLHELQEKLSPLGEEMRDRARAHVDALRTHLAPYSDELRQRLAARLE

ALKENGGARLAEYHAKATEHLSTLSEKAKPALEDLRQGLLPVLESFKVSFLSALEEYTKKLN

TQGTPVTQEFWDNLEKETEGLRQEMSKDLEEVKAKVQPYLDDFQKKWQEEMELYRQKVEPLR

AELQEGARQKLHELQEKLSPLGEEMRDRARAHVDALRTHLAPYSDELRQRLAARLEALKENG

GARLAEYHAKATEHLSTLSEKAKPALEDLRQGLLPVLESFKVSFLSALEEYTKKLNTQGTPV

TQEFWDNLEKETEGLRQEMSKDLEEVKAKVQPYLDDFQKKWQEEMELYRQKVEPLRAELQEG

ARQKLHELQEKLSPLGEEMRDRARAHVDALRTHLAPYSDELRQRLAARLEALKENGGARLAE

YHAKATEHLSTLSEKAKPALEDLRQGLLPVLESFKVSFLSALEEYTKKLNTQGTPVTQEFWD

NLEKETEGLRQEMSKDLEEVKAKVQPYLDDFQKKWQEEMELYRQKVEPLRAELQEGARQKLH

ELQEKLSPLGEEMRDRARAHVDALRTHLAPYSDELRQRLAARLEALKENGGARLAEYHAKAT

EHLSTLSEKAKPALEDLRQGLLPVLESFKVSFLSALEEYTKKLNTQLPGTGAAALEHHHHHH

NW72 (assemble ~72 nm nanodisc)
                                                    SEQ ID NO: 20
MGSSHHHHHHENLYFQGSTFSKLREQLGPVTQEFWDNLEKETEGLRQEMSKDLEEVKAKVQP

YLDDFQKKWQEEMELYRQKVEPLGEEMRDRARAHVDALRTHLAPYSDELRQRLAARLEALKE

NGGARLAEYHAKATEHLSTLSEKAKPALEDLRQGLLPVLESFKVSFLSALEEYTKKLNTQGT

PVTQEFWDNLEKETEGLRQEMSKDLEEVKAKVQPYLDDFQKKWQEEMELYRQKVEPLGEEMR

DRARAHVDALRTHLAPYSDELRQRLAARLEALKENGGARLAEYHAKATEHLSTLSEKAKPAL

EDLRQGLLPVLESFKVSFLSALEEYTKKLNTQGTPVTQEFWDNLEKETEGLRQEMSKDLEEV

KAKVQPYLDDFQKKWQEEMELYRQKVEPLGEEMRDRARAHVDALRTHLAPYSDELRQRLAAR

LEALKENGGARLAEYHAKATEHLSTLSEKAKPALEDLRQGLLPVLESFKVSFLSALEEYTKK

LNTQGTPVTQEFWDNLEKETEGLRQEMSKDLEEVKAKVQPYLDDFQKKWQEEMELYRQKVEP

LGEEMRDRARAHVDALRTHLAPYSDELRQRLAARLEALKENGGARLAEYHAKATEHLSTLSE

KAKPALEDLRQGLLPVLESFKVSFLSALEEYTKKLNTQGTPVTQEFWDNLEKETEGLRQEMS

KDLEEVKAKVQPYLDDFQKKWQEEMELYRQKVEPLGEEMRDRARAHVDALRTHLAPYSDELR

QRLAARLEALKENGGARLAEYHAKATEHLSTLSEKAKPALEDLRQGLLPVLESFKVSFLSAL

EEYTKKLNTQGTPVTQEFWDNLEKETEGLRQEMSKDLEEVKAKVQPYLDDFQKKWQEEMELY

RQKVEPLGEEMRDRARAHVDALRTHLAPYSDELRQRLAARLEALKENGGARLAEYHAKATEH

LSTLSEKAKPALEDLRQGLLPVLESFKVSFLSALEEYTKKLNTQGTPVTQEFWDNLEKETEG

LRQEMSKDLEEVKAKVQPYLDDFQKKWQEEMELYRQKVEPLGEEMRDRARAHVDALRTHLAP

YSDELRQRLAARLEALKENGGARLAEYHAKATEHLSTLSEKAKPALEDLRQGLLPVLESFKV

SFLSALEEYTKKLNTQGTPVTQEFWDNLEKETEGLRQEMSKDLEEVKAKVQPYLDDFQKKWQ

EEMELYRQKVEPLGEEMRDRARAHVDALRTHLAPYSDELRQRLAARLEALKENGGARLAEYH

AKATEHLSTLSEKAKPALEDLRQGLLPVLESFKVSFLSALEEYTKKLNTQLPGTGAAALEHH

HHHH
```

-continued

NW80 (assemble ~80 nm nanodisc)
SEQ ID NO: 21
MGSSHHHHHHENLYFQGSTFSKLREQLGPVTQEFWDNLEKETEGLRQEMSKDLEEVKAKVQP

YLDDFQKKWQEEMELYRQKVEPLRAELQEGARQKLHELQEKLSPLGEEMRDRARAHVDALRT

HLAPYSDELRQRLAARLEALKENGGARLAEYHAKATEHLSTLSEKAKPALEDLRQGLLPVLE

SFKVSFLSALEEYTKKLNTQGTPVTQEFWDNLEKETEGLRQEMSKDLEEVKAKVQPYLDDFQ

KKWQEEMELYRQKVEPLRAELQEGARQKLHELQEKLSPLGEEMRDRARAHVDALRTHLAPYS

DELRQRLAARLEALKENGGARLAEYHAKATEHLSTLSEKAKPALEDLRQGLLPVLESFKVSF

LSALEEYTKKLNTQGTPVTQEFWDNLEKETEGLRQEMSKDLEEVKAKVQPYLDDFQKKWQEE

MELYRQKVEPLRAELQEGARQKLHELQEKLSPLGEEMRDRARAHVDALRTHLAPYSDELRQR

LAARLEALKENGGARLAEYHAKATEHLSTLSEKAKPALEDLRQGLLPVLESFKVSFLSALEE

YTKKLNTQGTPVTQEFWDNLEKETEGLRQEMSKDLEEVKAKVQPYLDDFQKKWQEEMELYRQ

KVEPLRAELQEGARQKLHELQEKLSPLGEEMRDRARAHVDALRTHLAPYSDELRQRLAARLE

ALKENGGARLAEYHAKATEHLSTLSEKAKPALEDLRQGLLPVLESFKVSFLSALEEYTKKLN

TQGTPVTQEFWDNLEKETEGLRQEMSKDLEEVKAKVQPYLDDFQKKWQEEMELYRQKVEPLR

AELQEGARQKLHELQEKLSPLGEEMRDRARAHVDALRTHLAPYSDELRQRLAARLEALKENG

GARLAEYHAKATEHLSTLSEKAKPALEDLRQGLLPVLESFKVSFLSALEEYTKKLNTQGTPV

TQEFWDNLEKETEGLRQEMSKDLEEVKAKVQPYLDDFQKKWQEEMELYRQKVEPLRAELQEG

ARQKLHELQEKLSPLGEEMRDRARAHVDALRTHLAPYSDELRQRLAARLEALKENGGARLAE

YHAKATEHLSTLSEKAKPALEDLRQGLLPVLESFKVSFLSALEEYTKKLNTQGTPVTQEFWD

NLEKETEGLRQEMSKDLEEVKAKVQPYLDDFQKKWQEEMELYRQKVEPLRAELQEGARQKLH

ELQEKLSPLGEEMRDRARAHVDALRTHLAPYSDELRQRLAARLEALKENGGARLAEYHAKAT

EHLSTLSEKAKPALEDLRQGLLPVLESFKVSFLSALEEYTKKLNTQGTPVTQEFWDNLEKET

EGLRQEMSKDLEEVKAKVQPYLDDFQKKWQEEMELYRQKVEPLRAELQEGARQKLHELQEKL

SPLGEEMRDRARAHVDALRTHLAPYSDELRQRLAARLEALKENGGARLAEYHAKATEHLSTL

SEKAKPALEDLRQGLLPVLESFKVSFLSALEEYTKKLNTQLPGTGAAALEHHHHHH

NW90 (assemble ~90 nm nanodisc)
SEQ ID NO: 22
MGSSHHHHHHENLYFQGSTFSKLREQLGPVTQEFWDNLEKETEGLRQEMSKDLEEVKAKVQP

YLDDFQKKWQEEMELYRQKVEPLRAELQEGARQKLHELQEKLSPLGEEMRDRARAHVDALRT

HLAPYSDELRQRLAARLEALKENGGARLAEYHAKATEHLSTLSEKAKPALEDLRQGLLPVLE

SFKVSFLSALEEYTKKLNTQGTPVTQEFWDNLEKETEGLRQEMSKDLEEVKAKVQPYLDDFQ

KKWQEEMELYRQKVEPLRAELQEGARQKLHELQEKLSPLGEEMRDRARAHVDALRTHLAPYS

DELRQRLAARLEALKENGGARLAEYHAKATEHLSTLSEKAKPALEDLRQGLLPVLESFKVSF

LSALEEYTKKLNTQGTPVTQEFWDNLEKETEGLRQEMSKDLEEVKAKVQPYLDDFQKKWQEE

MELYRQKVEPLRAELQEGARQKLHELQEKLSPLGEEMRDRARAHVDALRTHLAPYSDELRQR

LAARLEALKENGGARLAEYHAKATEHLSTLSEKAKPALEDLRQGLLPVLESFKVSFLSALEE

YTKKLNTQGTPVTQEFWDNLEKETEGLRQEMSKDLEEVKAKVQPYLDDFQKKWQEEMELYRQ

KVEPLRAELQEGARQKLHELQEKLSPLGEEMRDRARAHVDALRTHLAPYSDELRQRLAARLE

ALKENGGARLAEYHAKATEHLSTLSEKAKPALEDLRQGLLPVLESFKVSFLSALEEYTKKLN

TQGTPVTQEFWDNLEKETEGLRQEMSKDLEEVKAKVQPYLDDFQKKWQEEMELYRQKVEPLR

AELQEGARQKLHELQEKLSPLGEEMRDRARAHVDALRTHLAPYSDELRQRLAARLEALKENG

-continued

GARLAEYHAKATEHLSTLSEKAKPALEDLRQGLLPVLESFKVSFLSALEEYTKKLNTQGTPV

TQEFWDNLEKETEGLRQEMSKDLEEVKAKVQPYLDDFQKKWQEEMELYRQKVEPLRAELQEG

ARQKLHELQEKLSPLGEEMRDRARAHVDALRTHLAPYSDELRQRLAARLEALKENGGARLAE

YHAKATEHLSTLSEKAKPALEDLRQGLLPVLESFKVSFLSALEEYTKKLNTQGTPVTQEFWD

NLEKETEGLRQEMSKDLEEVKAKVQPYLDDFQKKWQEEMELYRQKVEPLRAELQEGARQKLH

ELQEKLSPLGEEMRDRARAHVDALRTHLAPYSDELRQRLAARLEALKENGGARLAEYHAKAT

EHLSTLSEKAKPALEDLRQGLLPVLESFKVSFLSALEEYTKKLNTQGTPVTQEFWDNLEKET

EGLRQEMSKDLEEVKAKVQPYLDDFQKKWQEEMELYRQKVEPLRAELQEGARQKLHELQEKL

SPLGEEMRDRARAHVDALRTHLAPYSDELRQRLAARLEALKENGGARLAEYHAKATEHLSTL

SEKAKPALEDLRQGLLPVLESFKVSFLSALEEYTKKLNTQGTPVTQEFWDNLEKETEGLRQE

MSKDLEEVKAKVQPYLDDFQKKWQEEMELYRQKVEPLRAELQEGARQKLHELQEKLSPLGEE

MRDRARAHVDALRTHLAPYSDELRQRLAARLEALKENGGARLAEYHAKATEHLSTLSEKAKP

ALEDLRQGLLPVLESFKVSFLSALEEYTKKLNTQLPGTGAAALEHHHHHH

NW100 (assemble ~100 nm nanodisc)

SEQ ID NO: 23

MGSSHHHHHHENLYFQGSTFSKLREQLGPVTQEFWDNLEKETEGLRQEMSKDLEEVKAKVQP

YLDDFQKKWQEEMELYRQKVEPLRAELQEGARQKLHELQEKLSPLGEEMRDRARAHVDALRT

HLAPYSDELRQRLAARLEALKENGGARLAEYHAKATEHLSTLSEKAKPALEDLRQGLLPVLE

SFKVSFLSALEEYTKKLNTQGTPVTQEFWDNLEKETEGLRQEMSKDLEEVKAKVQPYLDDFQ

KKWQEEMELYRQKVEPLRAELQEGARQKLHELQEKLSPLGEEMRDRARAHVDALRTHLAPYS

DELRQRLAARLEALKENGGARLAEYHAKATEHLSTLSEKAKPALEDLRQGLLPVLESFKVSF

LSALEEYTKKLNTQGTPVTQEFWDNLEKETEGLRQEMSKDLEEVKAKVQPYLDDFQKKWQEE

MELYRQKVEPLRAELQEGARQKLHELQEKLSPLGEEMRDRARAHVDALRTHLAPYSDELRQR

LAARLEALKENGGARLAEYHAKATEHLSTLSEKAKPALEDLRQGLLPVLESFKVSFLSALEE

YTKKLNTQGTPVTQEFWDNLEKETEGLRQEMSKDLEEVKAKVQPYLDDFQKKWQEEMELYRQ

KVEPLRAELQEGARQKLHELQEKLSPLGEEMRDRARAHVDALRTHLAPYSDELRQRLAARLE

ALKENGGARLAEYHAKATEHLSTLSEKAKPALEDLRQGLLPVLESFKVSFLSALEEYTKKLN

TQGTPVTQEFWDNLEKETEGLRQEMSKDLEEVKAKVQPYLDDFQKKWQEEMELYRQKVEPLR

AELQEGARQKLHELQEKLSPLGEEMRDRARAHVDALRTHLAPYSDELRQRLAARLEALKENG

GARLAEYHAKATEHLSTLSEKAKPALEDLRQGLLPVLESFKVSFLSALEEYTKKLNTQGTPV

TQEFWDNLEKETEGLRQEMSKDLEEVKAKVQPYLDDFQKKWQEEMELYRQKVEPLRAELQEG

ARQKLHELQEKLSPLGEEMRDRARAHVDALRTHLAPYSDELRQRLAARLEALKENGGARLAE

YHAKATEHLSTLSEKAKPALEDLRQGLLPVLESFKVSFLSALEEYTKKLNTQGTPVTQEFWD

NLEKETEGLRQEMSKDLEEVKAKVQPYLDDFQKKWQEEMELYRQKVEPLRAELQEGARQKLH

ELQEKLSPLGEEMRDRARAHVDALRTHLAPYSDELRQRLAARLEALKENGGARLAEYHAKAT

EHLSTLSEKAKPALEDLRQGLLPVLESFKVSFLSALEEYTKKLNTQGTPVTQEFWDNLEKET

EGLRQEMSKDLEEVKAKVQPYLDDFQKKWQEEMELYRQKVEPLRAELQEGARQKLHELQEKL

SPLGEEMRDRARAHVDALRTHLAPYSDELRQRLAARLEALKENGGARLAEYHAKATEHLSTL

SEKAKPALEDLRQGLLPVLESFKVSFLSALEEYTKKLNTQGTPVTQEFWDNLEKETEGLRQE

MSKDLEEVKAKVQPYLDDFQKKWQEEMELYRQKVEPLRAELQEGARQKLHELQEKLSPLGEE

MRDRARAHVDALRTHLAPYSDELRQRLAARLEALKENGGARLAEYHAKATEHLSTLSEKAKP

ALEDLRQGLLPVLESFKVSFLSALEEYTKKLNTQGTPVTQEFWDNLEKETEGLRQEMSKDLE

-continued

EVKAKVQPYLDDFQKKWQEEMELYRQKVEPLRAELQEGARQKLHELQEKLSPLGEEMRDRAR

AHVDALRTHLAPYSDELRQRLAARLEALKENGGARLAEYHAKATEHLSTLSEKAKPALEDLR

QGLLPVLESFKVSFLSALEEYTKKLNTQLPGTGAAALEHHHHHH

```
                                                               SEQ ID NO: 5
  1     mkaavltlav  lfltgsgarh  fwqqdeppqs  pwdrvkdlat  vyvdvlkdsg  rdyvsgfegs 61     algkqlnlkl  ldnwdsvtst  fsklreqlgp  vtqefwdnle  keteglrqem  skdleevkak 121     vqpylddfqk  kwqeemelyr  qkveplrael  gegarqklhe  lgeklsplge  emrdrarahv 181     dalrthlapy  sdelrqrlaa  rlealkengg  arlaeyhaka  tehlstlsek  akpaledlrq 241     gllpvlesfk  vsflsaleey  tkklntq
```

Example 5

Figure 19:
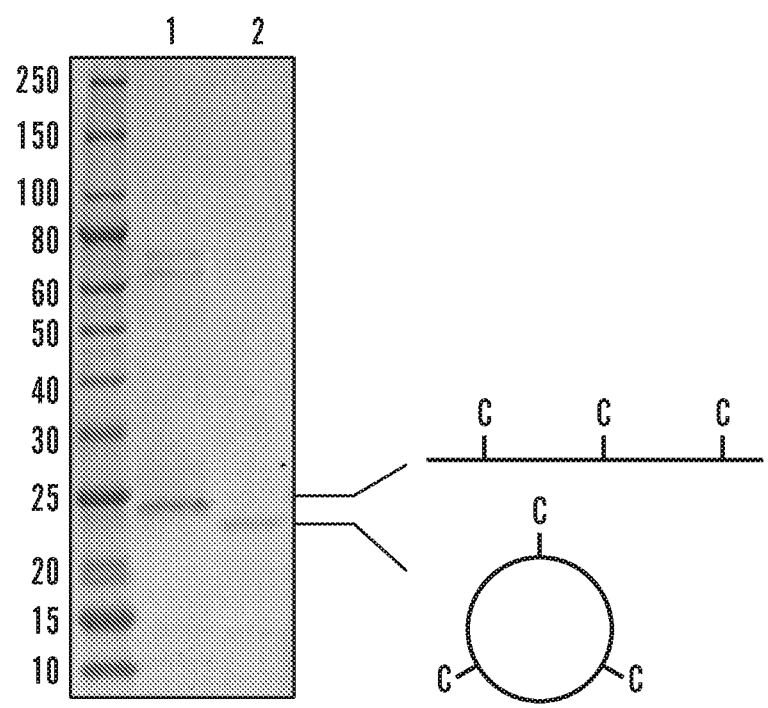
FIG. 19 depicts SDS-PAGE analysis of NW9_3 C before (lane 1) and after covalent circularization (lane 2).

A loopable membrane scaffold protein was designed based on SEQ ID NO: 2, with the inclusion of substitution mutations at residues 36, 110, and 175 (SEQ ID NO: 62, NW11_3 C). SDS-PAGE analysis of the circularized form of this protein is depicted in FIG. 19.

---

What is claimed herein is:

1. A loopable membrane scaffold protein comprising, from N-terminus to C-terminus:
   i. an N-terminal circularization domain;
   ii. a plurality of amphipathic alpha helix domains; and
   iii. a C-terminal circularization domain,
   wherein one circularization domain comprises:
   a non-polar amino acid sequence comprising at least one N-terminal glycine or alanine residue; and
   the other circularization domain comprises:
   a sequence LPXTG/A; wherein X represents any amino acid;
   wherein the loopable membrane scaffold protein has the sequence of any of SEQ ID NOs: 1-4, 6-23 and 62; or has the sequence of SEQ ID NO: 1 or 6 with the exception of a cysteine substitution at one or more residues corresponding to positions 31, 36, 137, and 153 of SEQ ID NO: 1 or 6; or has the sequence of SEQ ID NO: 2 or 7 with the exception of a cysteine substitution at one or more residues corresponding to positions 31, 36, 93, 110, 159, and 175 of SEQ ID NO: 2 or 7.

2. A covalently circularized nanodisc comprising:
   a. a phospholipid bilayer; and
   b. a looped membrane scaffold protein forming a belt around the bilayer, wherein the looped membrane scaffold protein comprises a loopable membrane scaffold protein of claim 1, wherein the N-terminal circularization domain is covalently linked to the C-terminal circularization domain.

3. The nanodisc of claim 2, wherein the diameter is greater than about 6 nm.

4. A method of making a nanodisc comprising a phospholipid bilayer; and
   a looped membrane scaffold protein forming a belt around the bilayer, wherein the looped membrane scaffold protein comprises a loopable membrane scaffold protein of claim 1, wherein the: N-terminal circularization domain is covalently linked to the C-terminal circularization domain
   the method comprising:
   a. contacting the loopable membrane scaffold protein with a sortase enzyme;
   b. contacting the looped protein produced in step (a) with solubilized phospholipids.

* * * * *

SEQUENCE LISTING

<160> NUMBER OF SEQ ID NOS: 93

<210> SEQ ID NO 1
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

```
Met Gly Ser Ser His His His His His His Glu Asn Leu Tyr Phe Gln
1               5                   10                  15

Gly Ser Thr Phe Ser Lys Leu Arg Glu Gln Leu Gly Pro Val Thr Gln
            20                  25                  30

Glu Phe Trp Asp Asn Leu Glu Lys Glu Thr Glu Gly Leu Arg Gln Glu
        35                  40                  45

Met Ser Lys Asp Leu Glu Glu Val Lys Ala Lys Val Gln Pro Tyr Leu
    50                  55                  60

Asp Asp Phe Gln Lys Lys Trp Gln Glu Glu Met Glu Leu Tyr Arg Gln
65                  70                  75                  80

Lys Val Glu Pro Leu Gly Glu Glu Met Arg Asp Arg Ala Arg Ala His
                85                  90                  95

Val Asp Ala Leu Arg Thr His Leu Ala Pro Tyr Ser Asp Glu Leu Arg
            100                 105                 110

Gln Arg Leu Ala Ala Arg Leu Glu Ala Leu Lys Glu Asn Gly Gly Ala
        115                 120                 125

Arg Leu Ala Glu Tyr His Ala Lys Ala Thr Glu His Leu Ser Thr Leu
    130                 135                 140

Ser Glu Lys Ala Lys Pro Ala Leu Glu Asp Leu Arg Gln Gly Leu Leu
145                 150                 155                 160

Pro Val Leu Glu Ser Phe Lys Val Ser Phe Leu Ser Ala Leu Glu Glu
                165                 170                 175

Tyr Thr Lys Lys Leu Asn Thr Gln Leu Pro Gly Thr Gly Ala Ala Ala
            180                 185                 190
```

```
Leu Glu His His His His His His
        195                 200
```

<210> SEQ ID NO 2
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met Gly Ser Ser His His His His Glu Asn Leu Tyr Phe Gln
1               5                   10                  15

Gly Ser Thr Phe Ser Lys Leu Arg Glu Gln Leu Gly Pro Val Thr Gln
            20                  25                  30

Glu Phe Trp Asp Asn Leu Glu Lys Glu Thr Glu Gly Leu Arg Gln Glu
        35                  40                  45

Met Ser Lys Asp Leu Glu Glu Val Lys Ala Lys Val Gln Pro Tyr Leu
    50                  55                  60

Asp Asp Phe Gln Lys Lys Trp Gln Glu Glu Met Glu Leu Tyr Arg Gln
65                  70                  75                  80

Lys Val Glu Pro Leu Arg Ala Glu Leu Gln Glu Gly Ala Arg Gln Lys
                85                  90                  95

Leu His Glu Leu Gln Glu Lys Leu Ser Pro Leu Gly Glu Glu Met Arg
            100                 105                 110

Asp Arg Ala Arg Ala His Val Asp Ala Leu Arg Thr His Leu Ala Pro
        115                 120                 125

Tyr Ser Asp Glu Leu Arg Gln Arg Leu Ala Ala Arg Leu Glu Ala Leu
    130                 135                 140

Lys Glu Asn Gly Gly Ala Arg Leu Ala Glu Tyr His Ala Lys Ala Thr
145                 150                 155                 160

Glu His Leu Ser Thr Leu Ser Glu Lys Ala Lys Pro Ala Leu Glu Asp
                165                 170                 175

Leu Arg Gln Gly Leu Leu Pro Val Leu Glu Ser Phe Lys Val Ser Phe
            180                 185                 190

Leu Ser Ala Leu Glu Glu Tyr Thr Lys Lys Leu Asn Thr Gln Leu Pro
        195                 200                 205

Gly Thr Gly Ala Ala Ala Leu Glu His His His His His
    210                 215                 220
```

<210> SEQ ID NO 3
<211> LENGTH: 582
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Met Gly Ser Ser His His His His Glu Asn Leu Tyr Phe Gln
1               5                   10                  15

Gly Ser Thr Phe Ser Lys Leu Arg Glu Gln Leu Gly Pro Val Thr Gln
            20                  25                  30

Glu Phe Trp Asp Asn Leu Glu Lys Glu Thr Glu Gly Leu Arg Gln Glu
        35                  40                  45

Met Ser Lys Asp Leu Glu Glu Val Lys Ala Lys Val Gln Pro Tyr Leu
    50                  55                  60
```

```
Asp Asp Phe Gln Lys Lys Trp Gln Glu Glu Met Glu Leu Tyr Arg Gln
 65                  70                  75                  80

Lys Val Glu Pro Leu Arg Ala Glu Leu Gln Glu Gly Ala Arg Gln Lys
                 85                  90                  95

Leu His Glu Leu Gln Glu Lys Leu Ser Pro Leu Gly Glu Glu Met Arg
            100                 105                 110

Asp Arg Ala Arg Ala His Val Asp Ala Leu Arg Thr His Leu Ala Pro
        115                 120                 125

Tyr Ser Asp Glu Leu Arg Gln Arg Leu Ala Ala Arg Leu Glu Ala Leu
    130                 135                 140

Lys Glu Asn Gly Gly Ala Arg Leu Ala Glu Tyr His Ala Lys Ala Thr
145                 150                 155                 160

Glu His Leu Ser Thr Leu Ser Glu Lys Ala Lys Pro Ala Leu Glu Asp
                165                 170                 175

Leu Arg Gln Gly Leu Leu Pro Val Leu Glu Ser Phe Lys Val Ser Phe
            180                 185                 190

Leu Ser Ala Leu Glu Glu Tyr Thr Lys Lys Leu Asn Thr Gln Gly Thr
        195                 200                 205

Pro Val Thr Gln Glu Phe Trp Asp Asn Leu Glu Lys Glu Thr Glu Gly
    210                 215                 220

Leu Arg Gln Glu Met Ser Lys Asp Leu Glu Glu Val Lys Ala Lys Val
225                 230                 235                 240

Gln Pro Tyr Leu Asp Asp Phe Gln Lys Lys Trp Gln Glu Glu Met Glu
                245                 250                 255

Leu Tyr Arg Gln Lys Val Glu Pro Leu Arg Ala Glu Leu Gln Glu Gly
            260                 265                 270

Ala Arg Gln Lys Leu His Glu Leu Gln Glu Lys Leu Ser Pro Leu Gly
        275                 280                 285

Glu Glu Met Arg Asp Arg Ala Arg Ala His Val Asp Ala Leu Arg Thr
    290                 295                 300

His Leu Ala Pro Tyr Ser Asp Glu Leu Arg Gln Arg Leu Ala Ala Arg
305                 310                 315                 320

Leu Glu Ala Leu Lys Glu Asn Gly Gly Ala Arg Leu Ala Glu Tyr His
                325                 330                 335

Ala Lys Ala Thr Glu His Leu Ser Thr Leu Ser Glu Lys Ala Lys Pro
            340                 345                 350

Ala Leu Glu Asp Leu Arg Gln Gly Leu Leu Pro Val Leu Glu Ser Phe
        355                 360                 365

Lys Val Ser Phe Leu Ser Ala Leu Glu Glu Tyr Thr Lys Lys Leu Asn
    370                 375                 380

Thr Gln Gly Thr Pro Val Thr Gln Glu Phe Trp Asp Asn Leu Glu Lys
385                 390                 395                 400

Glu Thr Glu Gly Leu Arg Gln Glu Met Ser Lys Asp Leu Glu Glu Val
                405                 410                 415

Lys Ala Lys Val Gln Pro Tyr Leu Asp Asp Phe Gln Lys Lys Trp Gln
            420                 425                 430

Glu Glu Met Glu Leu Tyr Arg Gln Lys Val Glu Pro Leu Arg Ala Glu
        435                 440                 445

Leu Gln Glu Gly Ala Arg Gln Lys Leu His Glu Leu Gln Glu Lys Leu
    450                 455                 460

Ser Pro Leu Gly Glu Glu Met Arg Asp Arg Ala Arg Ala His Val Asp
465                 470                 475                 480

Ala Leu Arg Thr His Leu Ala Pro Tyr Ser Asp Glu Leu Arg Gln Arg
```

```
                           485                 490                 495
Leu Ala Ala Arg Leu Glu Ala Leu Lys Glu Asn Gly Gly Ala Arg Leu
                500                 505                 510

Ala Glu Tyr His Ala Lys Ala Thr Glu His Leu Ser Thr Leu Ser Glu
            515                 520                 525

Lys Ala Lys Pro Ala Leu Glu Asp Leu Arg Gln Gly Leu Leu Pro Val
        530                 535                 540

Leu Glu Ser Phe Lys Val Ser Phe Leu Ser Ala Leu Glu Glu Tyr Thr
545                 550                 555                 560

Lys Lys Leu Asn Thr Gln Leu Pro Gly Thr Gly Ala Ala Leu Glu
                565                 570                 575

His His His His His His
            580

<210> SEQ ID NO 4
<211> LENGTH: 942
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gly Ser Ser His His His His His His Glu Asn Leu Tyr Phe Gln
1               5                   10                  15

Gly Ser Thr Phe Ser Lys Leu Arg Glu Gln Leu Gly Pro Val Thr Gln
            20                  25                  30

Glu Phe Trp Asp Asn Leu Glu Lys Glu Thr Glu Gly Leu Arg Gln Glu
        35                  40                  45

Met Ser Lys Asp Leu Glu Glu Val Lys Ala Lys Val Gln Pro Tyr Leu
    50                  55                  60

Asp Asp Phe Gln Lys Lys Trp Gln Glu Glu Met Glu Leu Tyr Arg Gln
65                  70                  75                  80

Lys Val Glu Pro Leu Arg Ala Glu Leu Gln Glu Gly Ala Arg Gln Lys
                85                  90                  95

Leu His Glu Leu Gln Glu Lys Leu Ser Pro Leu Gly Glu Glu Met Arg
            100                 105                 110

Asp Arg Ala Arg Ala His Val Asp Ala Leu Arg Thr His Leu Ala Pro
        115                 120                 125

Tyr Ser Asp Glu Leu Arg Gln Arg Leu Ala Ala Arg Leu Glu Ala Leu
    130                 135                 140

Lys Glu Asn Gly Gly Ala Arg Leu Ala Glu Tyr His Ala Lys Ala Thr
145                 150                 155                 160

Glu His Leu Ser Thr Leu Ser Glu Lys Ala Lys Pro Ala Leu Glu Asp
                165                 170                 175

Leu Arg Gln Gly Leu Leu Pro Val Leu Glu Ser Phe Lys Val Ser Phe
            180                 185                 190

Leu Ser Ala Leu Glu Glu Tyr Thr Lys Lys Leu Asn Thr Gln Gly Thr
        195                 200                 205

Pro Val Thr Gln Glu Phe Trp Asp Asn Leu Glu Lys Glu Thr Glu Gly
    210                 215                 220

Leu Arg Gln Glu Met Ser Lys Asp Leu Glu Glu Val Lys Ala Lys Val
225                 230                 235                 240

Gln Pro Tyr Leu Asp Asp Phe Gln Lys Lys Trp Gln Glu Glu Met Glu
                245                 250                 255
```

```
Leu Tyr Arg Gln Lys Val Glu Pro Leu Arg Ala Glu Leu Gln Glu Gly
            260                 265                 270

Ala Arg Gln Lys Leu His Glu Leu Gln Glu Lys Leu Ser Pro Leu Gly
        275                 280                 285

Glu Glu Met Arg Asp Arg Ala Arg Ala His Val Asp Ala Leu Arg Thr
    290                 295                 300

His Leu Ala Pro Tyr Ser Asp Glu Leu Arg Gln Arg Leu Ala Ala Arg
305                 310                 315                 320

Leu Glu Ala Leu Lys Glu Asn Gly Gly Ala Arg Leu Ala Glu Tyr His
                325                 330                 335

Ala Lys Ala Thr Glu His Leu Ser Thr Leu Ser Glu Lys Ala Lys Pro
            340                 345                 350

Ala Leu Glu Asp Leu Arg Gln Gly Leu Leu Pro Val Leu Glu Ser Phe
        355                 360                 365

Lys Val Ser Phe Leu Ser Ala Leu Glu Glu Tyr Thr Lys Lys Leu Asn
    370                 375                 380

Thr Gln Gly Thr Pro Val Thr Gln Glu Phe Trp Asp Asn Leu Glu Lys
385                 390                 395                 400

Glu Thr Glu Gly Leu Arg Gln Glu Met Ser Lys Asp Leu Glu Glu Val
                405                 410                 415

Lys Ala Lys Val Gln Pro Tyr Leu Asp Asp Phe Gln Lys Lys Trp Gln
            420                 425                 430

Glu Glu Met Glu Leu Tyr Arg Gln Lys Val Glu Pro Leu Arg Ala Glu
        435                 440                 445

Leu Gln Glu Gly Ala Arg Gln Lys Leu His Glu Leu Gln Glu Lys Leu
    450                 455                 460

Ser Pro Leu Gly Glu Glu Met Arg Asp Arg Ala Arg Ala His Val Asp
465                 470                 475                 480

Ala Leu Arg Thr His Leu Ala Pro Tyr Ser Asp Glu Leu Arg Gln Arg
                485                 490                 495

Leu Ala Ala Arg Leu Glu Ala Leu Lys Glu Asn Gly Gly Ala Arg Leu
            500                 505                 510

Ala Glu Tyr His Ala Lys Ala Thr Glu His Leu Ser Thr Leu Ser Glu
        515                 520                 525

Lys Ala Lys Pro Ala Leu Glu Asp Leu Arg Gln Gly Leu Leu Pro Val
    530                 535                 540

Leu Glu Ser Phe Lys Val Ser Phe Leu Ser Ala Leu Glu Glu Tyr Thr
545                 550                 555                 560

Lys Lys Leu Asn Thr Gln Gly Thr Pro Val Thr Gln Glu Phe Trp Asp
                565                 570                 575

Asn Leu Glu Lys Glu Thr Glu Gly Leu Arg Gln Glu Met Ser Lys Asp
            580                 585                 590

Leu Glu Glu Val Lys Ala Lys Val Gln Pro Tyr Leu Asp Asp Phe Gln
        595                 600                 605

Lys Lys Trp Gln Glu Glu Met Glu Leu Tyr Arg Gln Lys Val Glu Pro
    610                 615                 620

Leu Arg Ala Glu Leu Gln Glu Gly Ala Arg Gln Lys Leu His Glu Leu
625                 630                 635                 640

Gln Glu Lys Leu Ser Pro Leu Gly Glu Glu Met Arg Asp Arg Ala Arg
                645                 650                 655

Ala His Val Asp Ala Leu Arg Thr His Leu Ala Pro Tyr Ser Asp Glu
            660                 665                 670

Leu Arg Gln Arg Leu Ala Ala Arg Leu Glu Ala Leu Lys Glu Asn Gly
```

```
                675                 680                 685
Gly Ala Arg Leu Ala Glu Tyr His Ala Lys Ala Thr Glu His Leu Ser
    690                 695                 700

Thr Leu Ser Glu Lys Ala Lys Pro Ala Leu Glu Asp Leu Arg Gln Gly
705                 710                 715                 720

Leu Leu Pro Val Leu Glu Ser Phe Lys Val Ser Phe Leu Ser Ala Leu
                725                 730                 735

Glu Glu Tyr Thr Lys Lys Leu Asn Thr Gln Gly Thr Pro Val Thr Gln
            740                 745                 750

Glu Phe Trp Asp Asn Leu Glu Lys Glu Thr Glu Gly Leu Arg Gln Glu
        755                 760                 765

Met Ser Lys Asp Leu Glu Glu Val Lys Ala Lys Val Gln Pro Tyr Leu
    770                 775                 780

Asp Asp Phe Gln Lys Lys Trp Gln Glu Glu Met Glu Leu Tyr Arg Gln
785                 790                 795                 800

Lys Val Glu Pro Leu Arg Ala Glu Leu Gln Glu Gly Ala Arg Gln Lys
                805                 810                 815

Leu His Glu Leu Gln Glu Lys Leu Ser Pro Leu Gly Glu Glu Met Arg
            820                 825                 830

Asp Arg Ala Arg Ala His Val Asp Ala Leu Arg Thr His Leu Ala Pro
        835                 840                 845

Tyr Ser Asp Glu Leu Arg Gln Arg Leu Ala Ala Arg Leu Glu Ala Leu
    850                 855                 860

Lys Glu Asn Gly Gly Ala Arg Leu Ala Glu Tyr His Ala Lys Ala Thr
865                 870                 875                 880

Glu His Leu Ser Thr Leu Ser Glu Lys Ala Lys Pro Ala Leu Glu Asp
                885                 890                 895

Leu Arg Gln Gly Leu Leu Pro Val Leu Glu Ser Phe Lys Val Ser Phe
            900                 905                 910

Leu Ser Ala Leu Glu Glu Tyr Thr Lys Lys Leu Asn Thr Gln Leu Pro
        915                 920                 925

Gly Thr Gly Ala Ala Ala Leu Glu His His His His His His
    930                 935                 940

<210> SEQ ID NO 5
<211> LENGTH: 267
<212> TYPE: PRT
<213> ORGANISM: Homo sapiens

<400> SEQUENCE: 5

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110
```

```
Asp Leu Glu Glu Val Lys Ala Lys Val Gln Pro Tyr Leu Asp Asp Phe
            115                 120                 125

Gln Lys Lys Trp Gln Glu Met Glu Leu Tyr Arg Gln Lys Val Glu
130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265

<210> SEQ ID NO 6
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Gly Ser Ser His His His His His His Glu Asn Leu Tyr Phe Gln
1               5                   10                  15

Gly Ser Thr Phe Ser Lys Leu Arg Glu Gln Leu Gly Pro Val Thr Gln
            20                  25                  30

Glu Phe Trp Asp Asn Leu Glu Lys Glu Thr Glu Gly Leu Arg Gln Glu
        35                  40                  45

Met Ser Lys Asp Leu Glu Glu Val Lys Ala Lys Val Gln Pro Tyr Leu
    50                  55                  60

Asp Asp Phe Gln Lys Lys Trp Gln Glu Met Glu Leu Tyr Arg Gln
65                  70                  75                  80

Lys Val Glu Pro Leu Gly Glu Glu Met Arg Asp Arg Ala Arg Ala His
                85                  90                  95

Val Asp Ala Leu Arg Thr His Leu Ala Pro Tyr Ser Asp Glu Leu Arg
            100                 105                 110

Gln Arg Leu Ala Ala Arg Leu Glu Ala Leu Lys Glu Asn Gly Gly Ala
        115                 120                 125

Arg Leu Ala Glu Tyr His Ala Lys Ala Thr Glu His Leu Ser Thr Leu
    130                 135                 140

Ser Glu Lys Ala Lys Pro Ala Leu Glu Asp Leu Arg Gln Gly Leu Leu
145                 150                 155                 160

Pro Val Leu Glu Ser Phe Lys Val Ser Phe Leu Ser Ala Leu Glu Glu
                165                 170                 175

Tyr Thr Lys Lys Leu Asn Thr Gln Leu Pro Gly Thr Gly Ala Ala Ala
            180                 185                 190

Leu Glu His His His His His His
        195                 200
```

<210> SEQ ID NO 7
<211> LENGTH: 222
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

```
Met Gly Ser Ser His His His His His His Glu Asn Leu Tyr Phe Gln
1               5                   10                  15

Gly Ser Thr Phe Ser Lys Leu Arg Glu Gln Leu Gly Pro Val Thr Gln
            20                  25                  30

Glu Phe Trp Asp Asn Leu Glu Lys Glu Thr Glu Gly Leu Arg Gln Glu
        35                  40                  45

Met Ser Lys Asp Leu Glu Glu Val Lys Ala Lys Val Gln Pro Tyr Leu
    50                  55                  60

Asp Asp Phe Gln Lys Lys Trp Gln Glu Glu Met Glu Leu Tyr Arg Gln
65                  70                  75                  80

Lys Val Glu Pro Leu Arg Ala Glu Leu Gln Glu Gly Ala Arg Gln Lys
                85                  90                  95

Leu His Glu Leu Gln Glu Lys Leu Ser Pro Leu Gly Glu Glu Met Arg
            100                 105                 110

Asp Arg Ala Arg Ala His Val Asp Ala Leu Arg Thr His Leu Ala Pro
        115                 120                 125

Tyr Ser Asp Glu Leu Arg Gln Arg Leu Ala Ala Arg Leu Glu Ala Leu
    130                 135                 140

Lys Glu Asn Gly Gly Ala Arg Leu Ala Glu Tyr His Ala Lys Ala Thr
145                 150                 155                 160

Glu His Leu Ser Thr Leu Ser Glu Lys Ala Lys Pro Ala Leu Glu Asp
                165                 170                 175

Leu Arg Gln Gly Leu Leu Pro Val Leu Glu Ser Phe Lys Val Ser Phe
            180                 185                 190

Leu Ser Ala Leu Glu Glu Tyr Thr Lys Lys Leu Asn Thr Gln Leu Pro
        195                 200                 205

Gly Thr Gly Ala Ala Ala Leu Glu His His His His His
    210                 215                 220
```

<210> SEQ ID NO 8
<211> LENGTH: 358
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Met Gly Ser Ser His His His His His His Glu Asn Leu Tyr Phe Gln
1               5                   10                  15

Gly Ser Thr Phe Ser Lys Leu Arg Glu Gln Leu Gly Pro Val Thr Gln
            20                  25                  30

Glu Phe Trp Asp Asn Leu Glu Lys Glu Thr Glu Gly Leu Arg Gln Glu
        35                  40                  45

Met Ser Lys Asp Leu Glu Glu Val Lys Ala Lys Val Gln Pro Tyr Leu
    50                  55                  60

Asp Asp Phe Gln Lys Lys Trp Gln Glu Glu Met Glu Leu Tyr Arg Gln
65                  70                  75                  80
```

```
Lys Val Glu Pro Leu Gly Glu Met Arg Asp Arg Ala Arg Ala His
                85                  90                  95

Val Asp Ala Leu Arg Thr His Leu Ala Pro Tyr Ser Asp Glu Leu Arg
            100                 105                 110

Gln Arg Leu Ala Ala Arg Leu Glu Ala Leu Lys Glu Asn Gly Gly Ala
        115                 120                 125

Arg Leu Ala Glu Tyr His Ala Lys Ala Thr Glu His Leu Ser Thr Leu
    130                 135                 140

Ser Glu Lys Ala Lys Pro Ala Leu Glu Asp Leu Arg Gln Gly Leu Leu
145                 150                 155                 160

Pro Val Leu Glu Ser Phe Lys Val Ser Phe Leu Ser Ala Leu Glu Glu
                165                 170                 175

Tyr Thr Lys Lys Leu Asn Thr Gln Gly Thr Pro Val Thr Gln Glu Phe
            180                 185                 190

Trp Asp Asn Leu Glu Lys Glu Thr Glu Gly Leu Arg Gln Glu Met Ser
        195                 200                 205

Lys Asp Leu Glu Glu Val Lys Ala Lys Val Gln Pro Tyr Leu Asp Asp
    210                 215                 220

Phe Gln Lys Lys Trp Gln Glu Glu Met Glu Leu Tyr Arg Gln Lys Val
225                 230                 235                 240

Glu Pro Leu Gly Glu Glu Met Arg Asp Arg Ala Arg Ala His Val Asp
                245                 250                 255

Ala Leu Arg Thr His Leu Ala Pro Tyr Ser Asp Glu Leu Arg Gln Arg
            260                 265                 270

Leu Ala Ala Arg Leu Glu Ala Leu Lys Glu Asn Gly Gly Ala Arg Leu
        275                 280                 285

Ala Glu Tyr His Ala Lys Ala Thr Glu His Leu Ser Thr Leu Ser Glu
    290                 295                 300

Lys Ala Lys Pro Ala Leu Glu Asp Leu Arg Gln Gly Leu Leu Pro Val
305                 310                 315                 320

Leu Glu Ser Phe Lys Val Ser Phe Leu Ser Ala Leu Glu Glu Tyr Thr
                325                 330                 335

Lys Lys Leu Asn Thr Gln Leu Pro Gly Thr Gly Ala Ala Ala Leu Glu
            340                 345                 350

His His His His His His
        355

<210> SEQ ID NO 9
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Gly Ser Ser His His His His His His Glu Asn Leu Tyr Phe Gln
1               5                   10                  15

Gly Ser Thr Phe Ser Lys Leu Arg Glu Gln Leu Gly Pro Val Thr Gln
            20                  25                  30

Glu Phe Trp Asp Asn Leu Glu Lys Glu Thr Glu Gly Leu Arg Gln Glu
        35                  40                  45

Met Ser Lys Asp Leu Glu Glu Val Lys Ala Lys Val Gln Pro Tyr Leu
    50                  55                  60

Asp Asp Phe Gln Lys Lys Trp Gln Glu Glu Met Glu Leu Tyr Arg Gln
```

```
                65                  70                  75                  80
Lys Val Glu Pro Leu Arg Ala Glu Leu Gln Glu Gly Ala Arg Gln Lys
                85                  90                  95

Leu His Glu Leu Gln Glu Lys Leu Ser Pro Leu Gly Glu Glu Met Arg
            100                 105                 110

Asp Arg Ala Arg Ala His Val Asp Ala Leu Arg Thr His Leu Ala Pro
        115                 120                 125

Tyr Ser Asp Glu Leu Arg Gln Arg Leu Ala Ala Arg Leu Glu Ala Leu
    130                 135                 140

Lys Glu Asn Gly Gly Ala Arg Leu Ala Glu Tyr His Ala Lys Ala Thr
145                 150                 155                 160

Glu His Leu Ser Thr Leu Ser Glu Lys Ala Lys Pro Ala Leu Glu Asp
                165                 170                 175

Leu Arg Gln Gly Leu Leu Pro Val Leu Glu Ser Phe Lys Val Ser Phe
            180                 185                 190

Leu Ser Ala Leu Glu Glu Tyr Thr Lys Lys Leu Asn Thr Gln Gly Thr
        195                 200                 205

Pro Val Thr Gln Glu Phe Trp Asp Asn Leu Glu Lys Glu Thr Glu Gly
    210                 215                 220

Leu Arg Gln Glu Met Ser Lys Asp Leu Glu Glu Val Lys Ala Lys Val
225                 230                 235                 240

Gln Pro Tyr Leu Asp Asp Phe Gln Lys Lys Trp Gln Glu Glu Met Glu
                245                 250                 255

Leu Tyr Arg Gln Lys Val Glu Pro Leu Arg Ala Glu Leu Gln Glu Gly
            260                 265                 270

Ala Arg Gln Lys Leu His Glu Leu Gln Glu Lys Leu Ser Pro Leu Gly
        275                 280                 285

Glu Glu Met Arg Asp Arg Ala Arg Ala His Val Asp Ala Leu Arg Thr
    290                 295                 300

His Leu Ala Pro Tyr Ser Asp Glu Leu Arg Gln Arg Leu Ala Ala Arg
305                 310                 315                 320

Leu Glu Ala Leu Lys Glu Asn Gly Gly Ala Arg Leu Ala Glu Tyr His
                325                 330                 335

Ala Lys Ala Thr Glu His Leu Ser Thr Leu Ser Glu Lys Ala Lys Pro
            340                 345                 350

Ala Leu Glu Asp Leu Arg Gln Gly Leu Leu Pro Val Leu Glu Ser Phe
        355                 360                 365

Lys Val Ser Phe Leu Ser Ala Leu Glu Glu Tyr Thr Lys Lys Leu Asn
    370                 375                 380

Thr Gln Leu Pro Gly Thr Gly Ala Ala Ala Leu Glu His His His His
385                 390                 395                 400

His His

<210> SEQ ID NO 10
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Gly Ser Ser His His His His His His Glu Asn Leu Tyr Phe Gln
1               5                   10                  15

Gly Ser Thr Phe Ser Lys Leu Arg Glu Gln Leu Gly Pro Val Thr Gln
```

-continued

```
            20                  25                  30
Glu Phe Trp Asp Asn Leu Glu Lys Glu Thr Glu Gly Leu Arg Gln Glu
            35                  40                  45
Met Ser Lys Asp Leu Glu Glu Val Lys Ala Lys Val Gln Pro Tyr Leu
            50                  55                  60
Asp Asp Phe Gln Lys Lys Trp Gln Glu Glu Met Glu Leu Tyr Arg Gln
 65                  70                  75                  80
Lys Val Glu Pro Leu Gly Glu Glu Met Arg Asp Arg Ala Arg Ala His
                     85                  90                  95
Val Asp Ala Leu Arg Thr His Leu Ala Pro Tyr Ser Asp Glu Leu Arg
                100                 105                 110
Gln Arg Leu Ala Ala Arg Leu Glu Ala Leu Lys Glu Asn Gly Gly Ala
                115                 120                 125
Arg Leu Ala Glu Tyr His Ala Lys Ala Thr Glu His Leu Ser Thr Leu
                130                 135                 140
Ser Glu Lys Ala Lys Pro Ala Leu Glu Asp Leu Arg Gln Gly Leu Leu
145                 150                 155                 160
Pro Val Leu Glu Ser Phe Lys Val Ser Phe Leu Ser Ala Leu Glu Glu
                165                 170                 175
Tyr Thr Lys Lys Leu Asn Thr Gln Gly Thr Pro Val Thr Gln Glu Phe
                180                 185                 190
Trp Asp Asn Leu Glu Lys Glu Thr Glu Gly Leu Arg Gln Glu Met Ser
                195                 200                 205
Lys Asp Leu Glu Glu Val Lys Ala Lys Val Gln Pro Tyr Leu Asp Asp
                210                 215                 220
Phe Gln Lys Lys Trp Gln Glu Glu Met Glu Leu Tyr Arg Gln Lys Val
225                 230                 235                 240
Glu Pro Leu Gly Glu Glu Met Arg Asp Arg Ala Arg Ala His Val Asp
                245                 250                 255
Ala Leu Arg Thr His Leu Ala Pro Tyr Ser Asp Glu Leu Arg Gln Arg
                260                 265                 270
Leu Ala Ala Arg Leu Glu Ala Leu Lys Glu Asn Gly Gly Ala Arg Leu
                275                 280                 285
Ala Glu Tyr His Ala Lys Ala Thr Glu His Leu Ser Thr Leu Ser Glu
                290                 295                 300
Lys Ala Lys Pro Ala Leu Glu Asp Leu Arg Gln Gly Leu Leu Pro Val
305                 310                 315                 320
Leu Glu Ser Phe Lys Val Ser Phe Leu Ser Ala Leu Glu Glu Tyr Thr
                325                 330                 335
Lys Lys Leu Asn Thr Gln Gly Thr Pro Val Thr Gln Glu Phe Trp Asp
                340                 345                 350
Asn Leu Glu Lys Glu Thr Glu Gly Leu Arg Gln Glu Met Ser Lys Asp
                355                 360                 365
Leu Glu Glu Val Lys Ala Lys Val Gln Pro Tyr Leu Asp Asp Phe Gln
                370                 375                 380
Lys Lys Trp Gln Glu Glu Met Glu Leu Tyr Arg Gln Lys Val Glu Pro
385                 390                 395                 400
Leu Gly Glu Glu Met Arg Asp Arg Ala Arg Ala His Val Asp Ala Leu
                405                 410                 415
Arg Thr His Leu Ala Pro Tyr Ser Asp Glu Leu Arg Gln Arg Leu Ala
                420                 425                 430
Ala Arg Leu Glu Ala Leu Lys Glu Asn Gly Gly Ala Arg Leu Ala Glu
                435                 440                 445
```

Tyr His Ala Lys Ala Thr Glu His Leu Ser Thr Leu Ser Glu Lys Ala
            450                 455                 460

Lys Pro Ala Leu Glu Asp Leu Arg Gln Gly Leu Leu Pro Val Leu Glu
465                 470                 475                 480

Ser Phe Lys Val Ser Phe Leu Ser Ala Leu Glu Glu Tyr Thr Lys Lys
                485                 490                 495

Leu Asn Thr Gln Leu Pro Gly Thr Gly Ala Ala Ala Leu Glu His His
            500                 505                 510

His His His His
        515

<210> SEQ ID NO 11
<211> LENGTH: 582
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Gly Ser Ser His His His His His His Glu Asn Leu Tyr Phe Gln
1               5                   10                  15

Gly Ser Thr Phe Ser Lys Leu Arg Glu Gln Leu Gly Pro Val Thr Gln
            20                  25                  30

Glu Phe Trp Asp Asn Leu Glu Lys Glu Thr Glu Gly Leu Arg Gln Glu
        35                  40                  45

Met Ser Lys Asp Leu Glu Glu Val Lys Ala Lys Val Gln Pro Tyr Leu
    50                  55                  60

Asp Asp Phe Gln Lys Lys Trp Gln Glu Glu Met Glu Leu Tyr Arg Gln
65                  70                  75                  80

Lys Val Glu Pro Leu Arg Ala Glu Leu Gln Glu Gly Ala Arg Gln Lys
                85                  90                  95

Leu His Glu Leu Gln Glu Lys Leu Ser Pro Leu Gly Glu Glu Met Arg
            100                 105                 110

Asp Arg Ala Arg Ala His Val Asp Ala Leu Arg Thr His Leu Ala Pro
        115                 120                 125

Tyr Ser Asp Glu Leu Arg Gln Arg Leu Ala Ala Arg Leu Glu Ala Leu
    130                 135                 140

Lys Glu Asn Gly Gly Ala Arg Leu Ala Glu Tyr His Ala Lys Ala Thr
145                 150                 155                 160

Glu His Leu Ser Thr Leu Ser Glu Lys Ala Lys Pro Ala Leu Glu Asp
                165                 170                 175

Leu Arg Gln Gly Leu Leu Pro Val Leu Glu Ser Phe Lys Val Ser Phe
            180                 185                 190

Leu Ser Ala Leu Glu Glu Tyr Thr Lys Lys Leu Asn Thr Gln Gly Thr
        195                 200                 205

Pro Val Thr Gln Glu Phe Trp Asp Asn Leu Glu Lys Glu Thr Glu Gly
    210                 215                 220

Leu Arg Gln Glu Met Ser Lys Asp Leu Glu Glu Val Lys Ala Lys Val
225                 230                 235                 240

Gln Pro Tyr Leu Asp Asp Phe Gln Lys Lys Trp Gln Glu Glu Met Glu
                245                 250                 255

Leu Tyr Arg Gln Lys Val Glu Pro Leu Arg Ala Glu Leu Gln Glu Gly
            260                 265                 270

Ala Arg Gln Lys Leu His Glu Leu Gln Glu Lys Leu Ser Pro Leu Gly

```
                275                 280                 285
Glu Glu Met Arg Asp Arg Ala Arg Ala His Val Asp Ala Leu Arg Thr
290                 295                 300
His Leu Ala Pro Tyr Ser Asp Glu Leu Arg Gln Arg Leu Ala Ala Arg
305                 310                 315                 320
Leu Glu Ala Leu Lys Glu Asn Gly Gly Ala Arg Leu Ala Glu Tyr His
                325                 330                 335
Ala Lys Ala Thr Glu His Leu Ser Thr Leu Ser Glu Lys Ala Lys Pro
                340                 345                 350
Ala Leu Glu Asp Leu Arg Gln Gly Leu Leu Pro Val Leu Glu Ser Phe
                355                 360                 365
Lys Val Ser Phe Leu Ser Ala Leu Glu Glu Tyr Thr Lys Lys Leu Asn
                370                 375                 380
Thr Gln Gly Thr Pro Val Thr Gln Glu Phe Trp Asp Asn Leu Glu Lys
385                 390                 395                 400
Glu Thr Glu Gly Leu Arg Gln Glu Met Ser Lys Asp Leu Glu Glu Val
                405                 410                 415
Lys Ala Lys Val Gln Pro Tyr Leu Asp Asp Phe Gln Lys Lys Trp Gln
                420                 425                 430
Glu Glu Met Glu Leu Tyr Arg Gln Lys Val Glu Pro Leu Arg Ala Glu
                435                 440                 445
Leu Gln Glu Gly Ala Arg Gln Lys Leu His Glu Leu Gln Glu Lys Leu
                450                 455                 460
Ser Pro Leu Gly Glu Glu Met Arg Asp Arg Ala Arg Ala His Val Asp
465                 470                 475                 480
Ala Leu Arg Thr His Leu Ala Pro Tyr Ser Asp Glu Leu Arg Gln Arg
                485                 490                 495
Leu Ala Ala Arg Leu Glu Ala Leu Lys Glu Asn Gly Gly Ala Arg Leu
                500                 505                 510
Ala Glu Tyr His Ala Lys Ala Thr Glu His Leu Ser Thr Leu Ser Glu
                515                 520                 525
Lys Ala Lys Pro Ala Leu Glu Asp Leu Arg Gln Gly Leu Leu Pro Val
                530                 535                 540
Leu Glu Ser Phe Lys Val Ser Phe Leu Ser Ala Leu Glu Glu Tyr Thr
545                 550                 555                 560
Lys Lys Leu Asn Thr Gln Leu Pro Gly Thr Gly Ala Ala Ala Leu Glu
                565                 570                 575
His His His His His His
            580

<210> SEQ ID NO 12
<211> LENGTH: 674
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Gly Ser Ser His His His His His His Glu Asn Leu Tyr Phe Gln
1               5                   10                  15
Gly Ser Thr Phe Ser Lys Leu Arg Glu Gln Leu Gly Pro Val Thr Gln
                20                  25                  30
Glu Phe Trp Asp Asn Leu Glu Lys Glu Thr Glu Gly Leu Arg Gln Glu
                35                  40                  45
```

```
Met Ser Lys Asp Leu Glu Glu Val Lys Ala Lys Val Gln Pro Tyr Leu
    50              55                  60

Asp Asp Phe Gln Lys Lys Trp Gln Glu Met Glu Leu Tyr Arg Gln
65              70                  75                  80

Lys Val Glu Pro Leu Gly Glu Glu Met Arg Asp Arg Ala Arg Ala His
                85                  90                  95

Val Asp Ala Leu Arg Thr His Leu Ala Pro Tyr Ser Asp Glu Leu Arg
                100                 105                 110

Gln Arg Leu Ala Ala Arg Leu Glu Ala Leu Lys Glu Asn Gly Gly Ala
            115                 120                 125

Arg Leu Ala Glu Tyr His Ala Lys Ala Thr Glu His Leu Ser Thr Leu
        130                 135                 140

Ser Glu Lys Ala Lys Pro Ala Leu Glu Asp Leu Arg Gln Gly Leu Leu
145                 150                 155                 160

Pro Val Leu Glu Ser Phe Lys Val Ser Phe Leu Ser Ala Leu Glu Glu
                165                 170                 175

Tyr Thr Lys Lys Leu Asn Thr Gln Gly Thr Pro Val Thr Gln Glu Phe
            180                 185                 190

Trp Asp Asn Leu Glu Lys Glu Thr Glu Gly Leu Arg Gln Glu Met Ser
            195                 200                 205

Lys Asp Leu Glu Glu Val Lys Ala Lys Val Gln Pro Tyr Leu Asp Asp
210                 215                 220

Phe Gln Lys Lys Trp Gln Glu Glu Met Glu Leu Tyr Arg Gln Lys Val
225                 230                 235                 240

Glu Pro Leu Gly Glu Glu Met Arg Asp Arg Ala Arg Ala His Val Asp
                245                 250                 255

Ala Leu Arg Thr His Leu Ala Pro Tyr Ser Asp Glu Leu Arg Gln Arg
        260                 265                 270

Leu Ala Ala Arg Leu Glu Ala Leu Lys Glu Asn Gly Gly Ala Arg Leu
        275                 280                 285

Ala Glu Tyr His Ala Lys Ala Thr Glu His Leu Ser Thr Leu Ser Glu
    290                 295                 300

Lys Ala Lys Pro Ala Leu Glu Asp Leu Arg Gln Gly Leu Leu Pro Val
305                 310                 315                 320

Leu Glu Ser Phe Lys Val Ser Phe Leu Ser Ala Leu Glu Glu Tyr Thr
                325                 330                 335

Lys Lys Leu Asn Thr Gln Gly Thr Pro Val Thr Gln Glu Phe Trp Asp
            340                 345                 350

Asn Leu Glu Lys Glu Thr Glu Gly Leu Arg Gln Glu Met Ser Lys Asp
            355                 360                 365

Leu Glu Glu Val Lys Ala Lys Val Gln Pro Tyr Leu Asp Asp Phe Gln
370                 375                 380

Lys Lys Trp Gln Glu Glu Met Glu Leu Tyr Arg Gln Lys Val Glu Pro
385                 390                 395                 400

Leu Gly Glu Glu Met Arg Asp Arg Ala Arg Ala His Val Asp Ala Leu
                405                 410                 415

Arg Thr His Leu Ala Pro Tyr Ser Asp Glu Leu Arg Gln Arg Leu Ala
        420                 425                 430

Ala Arg Leu Glu Ala Leu Lys Glu Asn Gly Gly Ala Arg Leu Ala Glu
            435                 440                 445

Tyr His Ala Lys Ala Thr Glu His Leu Ser Thr Leu Ser Glu Lys Ala
    450                 455                 460

Lys Pro Ala Leu Glu Asp Leu Arg Gln Gly Leu Leu Pro Val Leu Glu
```

```
                465                 470                 475                 480
            Ser Phe Lys Val Ser Phe Leu Ser Ala Leu Glu Glu Tyr Thr Lys Lys
                                485                 490                 495
            Leu Asn Thr Gln Gly Thr Pro Val Thr Gln Glu Phe Trp Asp Asn Leu
                            500                 505                 510
            Glu Lys Glu Thr Glu Gly Leu Arg Gln Glu Met Ser Lys Asp Leu Glu
                        515                 520                 525
            Glu Val Lys Ala Lys Val Gln Pro Tyr Leu Asp Asp Phe Gln Lys Lys
                    530                 535                 540
            Trp Gln Glu Glu Met Glu Leu Tyr Arg Gln Lys Val Glu Pro Leu Gly
            545                 550                 555                 560
            Glu Glu Met Arg Asp Arg Ala Arg Ala His Val Asp Ala Leu Arg Thr
                                565                 570                 575
            His Leu Ala Pro Tyr Ser Asp Glu Leu Arg Gln Arg Leu Ala Ala Arg
                            580                 585                 590
            Leu Glu Ala Leu Lys Glu Asn Gly Gly Ala Arg Leu Ala Glu Tyr His
                        595                 600                 605
            Ala Lys Ala Thr Glu His Leu Ser Thr Leu Ser Glu Lys Ala Lys Pro
                    610                 615                 620
            Ala Leu Glu Asp Leu Arg Gln Gly Leu Leu Pro Val Leu Glu Ser Phe
            625                 630                 635                 640
            Lys Val Ser Phe Leu Ser Ala Leu Glu Glu Tyr Thr Lys Lys Leu Asn
                                645                 650                 655
            Thr Gln Leu Pro Gly Thr Gly Ala Ala Leu Glu His His His His
                            660                 665                 670
            His His

<210> SEQ ID NO 13
<211> LENGTH: 762
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Gly Ser Ser His His His His His His Glu Asn Leu Tyr Phe Gln
1               5                   10                  15
Gly Ser Thr Phe Ser Lys Leu Arg Glu Gln Leu Gly Pro Val Thr Gln
                20                  25                  30
Glu Phe Trp Asp Asn Leu Glu Lys Glu Thr Glu Gly Leu Arg Gln Glu
            35                  40                  45
Met Ser Lys Asp Leu Glu Glu Val Lys Ala Lys Val Gln Pro Tyr Leu
        50                  55                  60
Asp Asp Phe Gln Lys Lys Trp Gln Glu Glu Met Glu Leu Tyr Arg Gln
65                  70                  75                  80
Lys Val Glu Pro Leu Arg Ala Glu Leu Gln Glu Gly Ala Arg Gln Lys
                85                  90                  95
Leu His Glu Leu Gln Glu Lys Leu Ser Pro Leu Gly Glu Glu Met Arg
            100                 105                 110
Asp Arg Ala Arg Ala His Val Asp Ala Leu Arg Thr His Leu Ala Pro
        115                 120                 125
Tyr Ser Asp Glu Leu Arg Gln Arg Leu Ala Ala Arg Leu Glu Ala Leu
    130                 135                 140
Lys Glu Asn Gly Gly Ala Arg Leu Ala Glu Tyr His Ala Lys Ala Thr
```

```
                145                 150                 155                 160
Glu His Leu Ser Thr Leu Ser Glu Lys Ala Lys Pro Ala Leu Glu Asp
                        165                 170                 175

Leu Arg Gln Gly Leu Leu Pro Val Leu Glu Ser Phe Lys Val Ser Phe
                180                 185                 190

Leu Ser Ala Leu Glu Glu Tyr Thr Lys Lys Leu Asn Thr Gln Gly Thr
                195                 200                 205

Pro Val Thr Gln Glu Phe Trp Asp Asn Leu Glu Lys Glu Thr Glu Gly
            210                 215                 220

Leu Arg Gln Glu Met Ser Lys Asp Leu Glu Glu Val Lys Ala Lys Val
225                 230                 235                 240

Gln Pro Tyr Leu Asp Asp Phe Gln Lys Lys Trp Gln Glu Glu Met Glu
                    245                 250                 255

Leu Tyr Arg Gln Lys Val Glu Pro Leu Arg Ala Glu Leu Gln Glu Gly
                260                 265                 270

Ala Arg Gln Lys Leu His Glu Leu Gln Glu Lys Leu Ser Pro Leu Gly
                275                 280                 285

Glu Glu Met Arg Asp Arg Ala Arg Ala His Val Asp Ala Leu Arg Thr
        290                 295                 300

His Leu Ala Pro Tyr Ser Asp Glu Leu Arg Gln Arg Leu Ala Ala Arg
305                 310                 315                 320

Leu Glu Ala Leu Lys Glu Asn Gly Gly Ala Arg Leu Ala Glu Tyr His
                    325                 330                 335

Ala Lys Ala Thr Glu His Leu Ser Thr Leu Ser Glu Lys Ala Lys Pro
                340                 345                 350

Ala Leu Glu Asp Leu Arg Gln Gly Leu Leu Pro Val Leu Glu Ser Phe
            355                 360                 365

Lys Val Ser Phe Leu Ser Ala Leu Glu Glu Tyr Thr Lys Lys Leu Asn
                370                 375                 380

Thr Gln Gly Thr Pro Val Thr Gln Glu Phe Trp Asp Asn Leu Glu Lys
385                 390                 395                 400

Glu Thr Glu Gly Leu Arg Gln Glu Met Ser Lys Asp Leu Glu Glu Val
                    405                 410                 415

Lys Ala Lys Val Gln Pro Tyr Leu Asp Asp Phe Gln Lys Lys Trp Gln
                420                 425                 430

Glu Glu Met Glu Leu Tyr Arg Gln Lys Val Glu Pro Leu Arg Ala Glu
            435                 440                 445

Leu Gln Glu Gly Ala Arg Gln Lys Leu His Glu Leu Gln Glu Lys Leu
        450                 455                 460

Ser Pro Leu Gly Glu Glu Met Arg Asp Arg Ala Arg Ala His Val Asp
465                 470                 475                 480

Ala Leu Arg Thr His Leu Ala Pro Tyr Ser Asp Glu Leu Arg Gln Arg
                    485                 490                 495

Leu Ala Ala Arg Leu Glu Ala Leu Lys Glu Asn Gly Gly Ala Arg Leu
                500                 505                 510

Ala Glu Tyr His Ala Lys Ala Thr Glu His Leu Ser Thr Leu Ser Glu
            515                 520                 525

Lys Ala Lys Pro Ala Leu Glu Asp Leu Arg Gln Gly Leu Leu Pro Val
        530                 535                 540

Leu Glu Ser Phe Lys Val Ser Phe Leu Ser Ala Leu Glu Glu Tyr Thr
545                 550                 555                 560

Lys Lys Leu Asn Thr Gln Gly Thr Pro Val Thr Gln Glu Phe Trp Asp
                    565                 570                 575
```

```
Asn Leu Glu Lys Glu Thr Gly Leu Arg Gln Glu Met Ser Lys Asp
            580                 585                 590

Leu Glu Glu Val Lys Ala Lys Val Gln Pro Tyr Leu Asp Asp Phe Gln
        595                 600                 605

Lys Lys Trp Gln Glu Glu Met Glu Leu Tyr Arg Gln Lys Val Glu Pro
    610                 615                 620

Leu Arg Ala Glu Leu Gln Glu Gly Ala Arg Gln Lys Leu His Glu Leu
625                 630                 635                 640

Gln Glu Lys Leu Ser Pro Leu Gly Glu Glu Met Arg Asp Arg Ala Arg
                645                 650                 655

Ala His Val Asp Ala Leu Arg Thr His Leu Ala Pro Tyr Ser Asp Glu
            660                 665                 670

Leu Arg Gln Arg Leu Ala Ala Arg Leu Glu Ala Leu Lys Glu Asn Gly
        675                 680                 685

Gly Ala Arg Leu Ala Glu Tyr His Ala Lys Ala Thr Glu His Leu Ser
    690                 695                 700

Thr Leu Ser Glu Lys Ala Lys Pro Ala Leu Glu Asp Leu Arg Gln Gly
705                 710                 715                 720

Leu Leu Pro Val Leu Glu Ser Phe Lys Val Ser Phe Leu Ser Ala Leu
                725                 730                 735

Glu Glu Tyr Thr Lys Lys Leu Asn Thr Gln Leu Pro Gly Thr Gly Ala
            740                 745                 750

Ala Ala Leu Glu His His His His His His
        755                 760

<210> SEQ ID NO 14
<211> LENGTH: 832
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Gly Ser Ser His His His His His His Glu Asn Leu Tyr Phe Gln
1               5                   10                  15

Gly Ser Thr Phe Ser Lys Leu Arg Glu Gln Leu Gly Pro Val Thr Gln
            20                  25                  30

Glu Phe Trp Asp Asn Leu Glu Lys Glu Thr Glu Gly Leu Arg Gln Glu
        35                  40                  45

Met Ser Lys Asp Leu Glu Glu Val Lys Ala Lys Val Gln Pro Tyr Leu
    50                  55                  60

Asp Asp Phe Gln Lys Lys Trp Gln Glu Glu Met Glu Leu Tyr Arg Gln
65                  70                  75                  80

Lys Val Glu Pro Leu Gly Glu Glu Met Arg Asp Arg Ala Arg Ala His
                85                  90                  95

Val Asp Ala Leu Arg Thr His Leu Ala Pro Tyr Ser Asp Glu Leu Arg
            100                 105                 110

Gln Arg Leu Ala Ala Arg Leu Glu Ala Leu Lys Glu Asn Gly Gly Ala
        115                 120                 125

Arg Leu Ala Glu Tyr His Ala Lys Ala Thr Glu His Leu Ser Thr Leu
    130                 135                 140

Ser Glu Lys Ala Lys Pro Ala Leu Glu Asp Leu Arg Gln Gly Leu Leu
145                 150                 155                 160

Pro Val Leu Glu Ser Phe Lys Val Ser Phe Leu Ser Ala Leu Glu Glu
```

```
                165                 170                 175
Tyr Thr Lys Lys Leu Asn Thr Gln Gly Thr Pro Val Thr Gln Glu Phe
                180                 185                 190
Trp Asp Asn Leu Glu Lys Glu Thr Glu Gly Leu Arg Gln Glu Met Ser
                195                 200                 205
Lys Asp Leu Glu Glu Val Lys Ala Lys Val Gln Pro Tyr Leu Asp Asp
            210                 215                 220
Phe Gln Lys Lys Trp Gln Glu Met Glu Leu Tyr Arg Gln Lys Val
225                 230                 235                 240
Glu Pro Leu Gly Glu Glu Met Arg Asp Arg Ala Arg Ala His Val Asp
                245                 250                 255
Ala Leu Arg Thr His Leu Ala Pro Tyr Ser Asp Glu Leu Arg Gln Arg
            260                 265                 270
Leu Ala Ala Arg Leu Glu Ala Leu Lys Glu Asn Gly Gly Ala Arg Leu
                275                 280                 285
Ala Glu Tyr His Ala Lys Ala Thr Glu His Leu Ser Thr Leu Ser Glu
            290                 295                 300
Lys Ala Lys Pro Ala Leu Glu Asp Leu Arg Gln Gly Leu Leu Pro Val
305                 310                 315                 320
Leu Glu Ser Phe Lys Val Ser Phe Leu Ser Ala Leu Glu Glu Tyr Thr
                325                 330                 335
Lys Lys Leu Asn Thr Gln Gly Thr Pro Val Thr Gln Glu Phe Trp Asp
                340                 345                 350
Asn Leu Glu Lys Glu Thr Glu Gly Leu Arg Gln Glu Met Ser Lys Asp
            355                 360                 365
Leu Glu Glu Val Lys Ala Lys Val Gln Pro Tyr Leu Asp Asp Phe Gln
            370                 375                 380
Lys Lys Trp Gln Glu Glu Met Glu Leu Tyr Arg Gln Lys Val Glu Pro
385                 390                 395                 400
Leu Gly Glu Glu Met Arg Asp Arg Ala Arg Ala His Val Asp Ala Leu
                405                 410                 415
Arg Thr His Leu Ala Pro Tyr Ser Asp Glu Leu Arg Gln Arg Leu Ala
            420                 425                 430
Ala Arg Leu Glu Ala Leu Lys Glu Asn Gly Gly Ala Arg Leu Ala Glu
            435                 440                 445
Tyr His Ala Lys Ala Thr Glu His Leu Ser Thr Leu Ser Glu Lys Ala
        450                 455                 460
Lys Pro Ala Leu Glu Asp Leu Arg Gln Gly Leu Leu Pro Val Leu Glu
465                 470                 475                 480
Ser Phe Lys Val Ser Phe Leu Ser Ala Leu Glu Glu Tyr Thr Lys Lys
                485                 490                 495
Leu Asn Thr Gln Gly Thr Pro Val Thr Gln Glu Phe Trp Asp Asn Leu
            500                 505                 510
Glu Lys Glu Thr Glu Gly Leu Arg Gln Glu Met Ser Lys Asp Leu Glu
            515                 520                 525
Glu Val Lys Ala Lys Val Gln Pro Tyr Leu Asp Asp Phe Gln Lys Lys
        530                 535                 540
Trp Gln Glu Glu Met Glu Leu Tyr Arg Gln Lys Val Glu Pro Leu Gly
545                 550                 555                 560
Glu Glu Met Arg Asp Arg Ala Arg Ala His Val Asp Ala Leu Arg Thr
                565                 570                 575
His Leu Ala Pro Tyr Ser Asp Glu Leu Arg Gln Arg Leu Ala Ala Arg
            580                 585                 590
```

-continued

```
Leu Glu Ala Leu Lys Glu Asn Gly Gly Ala Arg Leu Ala Glu Tyr His
            595                 600                 605
Ala Lys Ala Thr Glu His Leu Ser Thr Leu Ser Glu Lys Ala Lys Pro
    610                 615                 620
Ala Leu Glu Asp Leu Arg Gln Gly Leu Leu Pro Val Leu Glu Ser Phe
625                 630                 635                 640
Lys Val Ser Phe Leu Ser Ala Leu Glu Glu Tyr Thr Lys Lys Leu Asn
                645                 650                 655
Thr Gln Gly Thr Pro Val Thr Gln Glu Phe Trp Asp Asn Leu Glu Lys
            660                 665                 670
Glu Thr Glu Gly Leu Arg Gln Glu Met Ser Lys Asp Leu Glu Glu Val
    675                 680                 685
Lys Ala Lys Val Gln Pro Tyr Leu Asp Asp Phe Gln Lys Lys Trp Gln
690                 695                 700
Glu Glu Met Glu Leu Tyr Arg Gln Lys Val Glu Pro Leu Gly Glu Glu
705                 710                 715                 720
Met Arg Asp Arg Ala Arg Ala His Val Asp Ala Leu Arg Thr His Leu
                725                 730                 735
Ala Pro Tyr Ser Asp Glu Leu Arg Gln Arg Leu Ala Ala Arg Leu Glu
            740                 745                 750
Ala Leu Lys Glu Asn Gly Gly Ala Arg Leu Ala Glu Tyr His Ala Lys
    755                 760                 765
Ala Thr Glu His Leu Ser Thr Leu Ser Glu Lys Ala Lys Pro Ala Leu
770                 775                 780
Glu Asp Leu Arg Gln Gly Leu Leu Pro Val Leu Glu Ser Phe Lys Val
785                 790                 795                 800
Ser Phe Leu Ser Ala Leu Glu Glu Tyr Thr Lys Lys Leu Asn Thr Gln
                805                 810                 815
Leu Pro Gly Thr Gly Ala Ala Leu Glu His His His His His His
            820                 825                 830

<210> SEQ ID NO 15
<211> LENGTH: 942
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Gly Ser Ser His His His His His His Glu Asn Leu Tyr Phe Gln
1               5                   10                  15
Gly Ser Thr Phe Ser Lys Leu Arg Glu Gln Leu Gly Pro Val Thr Gln
            20                  25                  30
Glu Phe Trp Asp Asn Leu Glu Lys Glu Thr Glu Gly Leu Arg Gln Glu
        35                  40                  45
Met Ser Lys Asp Leu Glu Glu Val Lys Ala Lys Val Gln Pro Tyr Leu
    50                  55                  60
Asp Asp Phe Gln Lys Lys Trp Gln Glu Glu Met Glu Leu Tyr Arg Gln
65                  70                  75                  80
Lys Val Glu Pro Leu Arg Ala Glu Leu Gln Glu Gly Ala Arg Gln Lys
                85                  90                  95
Leu His Glu Leu Gln Glu Lys Leu Ser Pro Leu Gly Glu Glu Met Arg
            100                 105                 110
Asp Arg Ala Arg Ala His Val Asp Ala Leu Arg Thr His Leu Ala Pro
```

```
            115                 120                 125
Tyr Ser Asp Glu Leu Arg Gln Arg Leu Ala Ala Arg Leu Glu Ala Leu
        130                 135                 140

Lys Glu Asn Gly Gly Ala Arg Leu Ala Glu Tyr His Ala Lys Ala Thr
145                 150                 155                 160

Glu His Leu Ser Thr Leu Ser Glu Lys Ala Lys Pro Ala Leu Glu Asp
                165                 170                 175

Leu Arg Gln Gly Leu Leu Pro Val Leu Glu Ser Phe Lys Val Ser Phe
            180                 185                 190

Leu Ser Ala Leu Glu Glu Tyr Thr Lys Lys Leu Asn Thr Gln Gly Thr
            195                 200                 205

Pro Val Thr Gln Glu Phe Trp Asp Asn Leu Glu Lys Glu Thr Glu Gly
        210                 215                 220

Leu Arg Gln Glu Met Ser Lys Asp Leu Glu Glu Val Lys Ala Lys Val
225                 230                 235                 240

Gln Pro Tyr Leu Asp Asp Phe Gln Lys Lys Trp Gln Glu Glu Met Glu
                245                 250                 255

Leu Tyr Arg Gln Lys Val Glu Pro Leu Arg Ala Glu Leu Gln Glu Gly
            260                 265                 270

Ala Arg Gln Lys Leu His Glu Leu Gln Glu Lys Leu Ser Pro Leu Gly
            275                 280                 285

Glu Glu Met Arg Asp Arg Ala Arg Ala His Val Asp Ala Leu Arg Thr
        290                 295                 300

His Leu Ala Pro Tyr Ser Asp Glu Leu Arg Gln Arg Leu Ala Ala Arg
305                 310                 315                 320

Leu Glu Ala Leu Lys Glu Asn Gly Gly Ala Arg Leu Ala Glu Tyr His
                325                 330                 335

Ala Lys Ala Thr Glu His Leu Ser Thr Leu Ser Glu Lys Ala Lys Pro
            340                 345                 350

Ala Leu Glu Asp Leu Arg Gln Gly Leu Leu Pro Val Leu Glu Ser Phe
        355                 360                 365

Lys Val Ser Phe Leu Ser Ala Leu Glu Glu Tyr Thr Lys Lys Leu Asn
        370                 375                 380

Thr Gln Gly Thr Pro Val Thr Gln Glu Phe Trp Asp Asn Leu Glu Lys
385                 390                 395                 400

Glu Thr Glu Gly Leu Arg Gln Glu Met Ser Lys Asp Leu Glu Glu Val
                405                 410                 415

Lys Ala Lys Val Gln Pro Tyr Leu Asp Asp Phe Gln Lys Lys Trp Gln
            420                 425                 430

Glu Glu Met Glu Leu Tyr Arg Gln Lys Val Glu Pro Leu Arg Ala Glu
        435                 440                 445

Leu Gln Glu Gly Ala Arg Gln Lys Leu His Glu Leu Gln Glu Lys Leu
        450                 455                 460

Ser Pro Leu Gly Glu Glu Met Arg Asp Arg Ala Arg Ala His Val Asp
465                 470                 475                 480

Ala Leu Arg Thr His Leu Ala Pro Tyr Ser Asp Glu Leu Arg Gln Arg
                485                 490                 495

Leu Ala Ala Arg Leu Glu Ala Leu Lys Glu Asn Gly Gly Ala Arg Leu
            500                 505                 510

Ala Glu Tyr His Ala Lys Ala Thr Glu His Leu Ser Thr Leu Ser Glu
        515                 520                 525

Lys Ala Lys Pro Ala Leu Glu Asp Leu Arg Gln Gly Leu Leu Pro Val
        530                 535                 540
```

```
Leu Glu Ser Phe Lys Val Ser Phe Leu Ser Ala Leu Glu Glu Tyr Thr
545                 550                 555                 560

Lys Lys Leu Asn Thr Gln Gly Thr Pro Val Thr Gln Glu Phe Trp Asp
            565                 570                 575

Asn Leu Glu Lys Glu Thr Glu Gly Leu Arg Gln Glu Met Ser Lys Asp
                580                 585                 590

Leu Glu Glu Val Lys Ala Lys Val Gln Pro Tyr Leu Asp Asp Phe Gln
            595                 600                 605

Lys Lys Trp Gln Glu Glu Met Glu Leu Tyr Arg Gln Lys Val Glu Pro
610                 615                 620

Leu Arg Ala Glu Leu Gln Glu Gly Ala Arg Gln Lys Leu His Glu Leu
625                 630                 635                 640

Gln Glu Lys Leu Ser Pro Leu Gly Glu Glu Met Arg Asp Arg Ala Arg
                645                 650                 655

Ala His Val Asp Ala Leu Arg Thr His Leu Ala Pro Tyr Ser Asp Glu
            660                 665                 670

Leu Arg Gln Arg Leu Ala Ala Arg Leu Glu Ala Leu Lys Glu Asn Gly
        675                 680                 685

Gly Ala Arg Leu Ala Glu Tyr His Ala Lys Ala Thr Glu His Leu Ser
690                 695                 700

Thr Leu Ser Glu Lys Ala Lys Pro Ala Leu Glu Asp Leu Arg Gln Gly
705                 710                 715                 720

Leu Leu Pro Val Leu Glu Ser Phe Lys Val Ser Phe Leu Ser Ala Leu
                725                 730                 735

Glu Glu Tyr Thr Lys Lys Leu Asn Thr Gln Gly Thr Pro Val Thr Gln
            740                 745                 750

Glu Phe Trp Asp Asn Leu Glu Lys Glu Thr Glu Gly Leu Arg Gln Glu
        755                 760                 765

Met Ser Lys Asp Leu Glu Glu Val Lys Ala Lys Val Gln Pro Tyr Leu
770                 775                 780

Asp Asp Phe Gln Lys Lys Trp Gln Glu Glu Met Glu Leu Tyr Arg Gln
785                 790                 795                 800

Lys Val Glu Pro Leu Arg Ala Glu Leu Gln Glu Gly Ala Arg Gln Lys
                805                 810                 815

Leu His Glu Leu Gln Glu Lys Leu Ser Pro Leu Gly Glu Glu Met Arg
            820                 825                 830

Asp Arg Ala Arg Ala His Val Asp Ala Leu Arg Thr His Leu Ala Pro
        835                 840                 845

Tyr Ser Asp Glu Leu Arg Gln Arg Leu Ala Ala Arg Leu Glu Ala Leu
850                 855                 860

Lys Glu Asn Gly Gly Ala Arg Leu Ala Glu Tyr His Ala Lys Ala Thr
865                 870                 875                 880

Glu His Leu Ser Thr Leu Ser Glu Lys Ala Lys Pro Ala Leu Glu Asp
                885                 890                 895

Leu Arg Gln Gly Leu Leu Pro Val Leu Glu Ser Phe Lys Val Ser Phe
            900                 905                 910

Leu Ser Ala Leu Glu Glu Tyr Thr Lys Lys Leu Asn Thr Gln Leu Pro
        915                 920                 925

Gly Thr Gly Ala Ala Ala Leu Glu His His His His His
930                 935                 940

<210> SEQ ID NO 16
<211> LENGTH: 990
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Met Gly Ser Ser His His His His His His Glu Asn Leu Tyr Phe Gln
1               5                   10                  15

Gly Ser Thr Phe Ser Lys Leu Arg Glu Gln Leu Gly Pro Val Thr Gln
            20                  25                  30

Glu Phe Trp Asp Asn Leu Glu Lys Glu Thr Glu Gly Leu Arg Gln Glu
        35                  40                  45

Met Ser Lys Asp Leu Glu Glu Val Lys Ala Lys Val Gln Pro Tyr Leu
    50                  55                  60

Asp Asp Phe Gln Lys Lys Trp Gln Glu Glu Met Glu Leu Tyr Arg Gln
65                  70                  75                  80

Lys Val Glu Pro Leu Gly Glu Glu Met Arg Asp Arg Ala Arg Ala His
                85                  90                  95

Val Asp Ala Leu Arg Thr His Leu Ala Pro Tyr Ser Asp Glu Leu Arg
            100                 105                 110

Gln Arg Leu Ala Ala Arg Leu Glu Ala Leu Lys Glu Asn Gly Gly Ala
        115                 120                 125

Arg Leu Ala Glu Tyr His Ala Lys Ala Thr Glu His Leu Ser Thr Leu
    130                 135                 140

Ser Glu Lys Ala Lys Pro Ala Leu Glu Asp Leu Arg Gln Gly Leu Leu
145                 150                 155                 160

Pro Val Leu Glu Ser Phe Lys Val Ser Phe Leu Ser Ala Leu Glu Glu
                165                 170                 175

Tyr Thr Lys Lys Leu Asn Thr Gln Gly Thr Pro Val Thr Gln Glu Phe
            180                 185                 190

Trp Asp Asn Leu Glu Lys Glu Thr Glu Gly Leu Arg Gln Glu Met Ser
        195                 200                 205

Lys Asp Leu Glu Glu Val Lys Ala Lys Val Gln Pro Tyr Leu Asp Asp
    210                 215                 220

Phe Gln Lys Lys Trp Gln Glu Glu Met Glu Leu Tyr Arg Gln Lys Val
225                 230                 235                 240

Glu Pro Leu Gly Glu Glu Met Arg Asp Arg Ala Arg Ala His Val Asp
                245                 250                 255

Ala Leu Arg Thr His Leu Ala Pro Tyr Ser Asp Glu Leu Arg Gln Arg
            260                 265                 270

Leu Ala Ala Arg Leu Glu Ala Leu Lys Glu Asn Gly Gly Ala Arg Leu
        275                 280                 285

Ala Glu Tyr His Ala Lys Ala Thr Glu His Leu Ser Thr Leu Ser Glu
    290                 295                 300

Lys Ala Lys Pro Ala Leu Glu Asp Leu Arg Gln Gly Leu Leu Pro Val
305                 310                 315                 320

Leu Glu Ser Phe Lys Val Ser Phe Leu Ser Ala Leu Glu Glu Tyr Thr
                325                 330                 335

Lys Lys Leu Asn Thr Gln Gly Thr Pro Val Thr Gln Glu Phe Trp Asp
            340                 345                 350

Asn Leu Glu Lys Glu Thr Glu Gly Leu Arg Gln Glu Met Ser Lys Asp
        355                 360                 365

Leu Glu Glu Val Lys Ala Lys Val Gln Pro Tyr Leu Asp Asp Phe Gln
    370                 375                 380
```

```
Lys Lys Trp Gln Glu Glu Met Glu Leu Tyr Arg Gln Lys Val Glu Pro
385                 390                 395                 400

Leu Gly Glu Glu Met Arg Asp Arg Ala Arg Ala His Val Asp Ala Leu
            405                 410                 415

Arg Thr His Leu Ala Pro Tyr Ser Asp Glu Leu Arg Gln Arg Leu Ala
        420                 425                 430

Ala Arg Leu Glu Ala Leu Lys Glu Asn Gly Gly Ala Arg Leu Ala Glu
    435                 440                 445

Tyr His Ala Lys Ala Thr Glu His Leu Ser Thr Leu Ser Glu Lys Ala
450                 455                 460

Lys Pro Ala Leu Glu Asp Leu Arg Gln Gly Leu Leu Pro Val Leu Glu
465                 470                 475                 480

Ser Phe Lys Val Ser Phe Leu Ser Ala Leu Glu Glu Tyr Thr Lys Lys
            485                 490                 495

Leu Asn Thr Gln Gly Thr Pro Val Thr Gln Glu Phe Trp Asp Asn Leu
        500                 505                 510

Glu Lys Glu Thr Glu Gly Leu Arg Gln Glu Met Ser Lys Asp Leu Glu
    515                 520                 525

Glu Val Lys Ala Lys Val Gln Pro Tyr Leu Asp Asp Phe Gln Lys Lys
530                 535                 540

Trp Gln Glu Glu Met Glu Leu Tyr Arg Gln Lys Val Glu Pro Leu Gly
545                 550                 555                 560

Glu Glu Met Arg Asp Arg Ala Arg Ala His Val Asp Ala Leu Arg Thr
            565                 570                 575

His Leu Ala Pro Tyr Ser Asp Glu Leu Arg Gln Arg Leu Ala Ala Arg
        580                 585                 590

Leu Glu Ala Leu Lys Glu Asn Gly Gly Ala Arg Leu Ala Glu Tyr His
    595                 600                 605

Ala Lys Ala Thr Glu His Leu Ser Thr Leu Ser Glu Lys Ala Lys Pro
610                 615                 620

Ala Leu Glu Asp Leu Arg Gln Gly Leu Leu Pro Val Leu Glu Ser Phe
625                 630                 635                 640

Lys Val Ser Phe Leu Ser Ala Leu Glu Glu Tyr Thr Lys Lys Leu Asn
            645                 650                 655

Thr Gln Gly Thr Pro Val Thr Gln Glu Phe Trp Asp Asn Leu Glu Lys
        660                 665                 670

Glu Thr Glu Gly Leu Arg Gln Glu Met Ser Lys Asp Leu Glu Glu Val
    675                 680                 685

Lys Ala Lys Val Gln Pro Tyr Leu Asp Asp Phe Gln Lys Lys Trp Gln
690                 695                 700

Glu Glu Met Glu Leu Tyr Arg Gln Lys Val Glu Pro Leu Gly Glu Glu
705                 710                 715                 720

Met Arg Asp Arg Ala Arg Ala His Val Asp Ala Leu Arg Thr His Leu
            725                 730                 735

Ala Pro Tyr Ser Asp Glu Leu Arg Gln Arg Leu Ala Ala Arg Leu Glu
        740                 745                 750

Ala Leu Lys Glu Asn Gly Gly Ala Arg Leu Ala Glu Tyr His Ala Lys
    755                 760                 765

Ala Thr Glu His Leu Ser Thr Leu Ser Glu Lys Ala Lys Pro Ala Leu
770                 775                 780

Glu Asp Leu Arg Gln Gly Leu Leu Pro Val Leu Glu Ser Phe Lys Val
785                 790                 795                 800
```

Ser Phe Leu Ser Ala Leu Glu Glu Tyr Thr Lys Lys Leu Asn Thr Gln
                805                 810                 815

Gly Thr Pro Val Thr Gln Glu Phe Trp Asp Asn Leu Glu Lys Glu Thr
            820                 825                 830

Glu Gly Leu Arg Gln Glu Met Ser Lys Asp Leu Glu Glu Val Lys Ala
        835                 840                 845

Lys Val Gln Pro Tyr Leu Asp Asp Phe Gln Lys Lys Trp Gln Glu Glu
850                 855                 860

Met Glu Leu Tyr Arg Gln Lys Val Glu Pro Leu Gly Glu Glu Met Arg
865                 870                 875                 880

Asp Arg Ala Arg Ala His Val Asp Ala Leu Arg Thr His Leu Ala Pro
                885                 890                 895

Tyr Ser Asp Glu Leu Arg Gln Arg Leu Ala Ala Arg Leu Glu Ala Leu
            900                 905                 910

Lys Glu Asn Gly Gly Ala Arg Leu Ala Glu Tyr His Ala Lys Ala Thr
        915                 920                 925

Glu His Leu Ser Thr Leu Ser Glu Lys Ala Lys Pro Ala Leu Glu Asp
930                 935                 940

Leu Arg Gln Gly Leu Leu Pro Val Leu Glu Ser Phe Lys Val Ser Phe
945                 950                 955                 960

Leu Ser Ala Leu Glu Glu Tyr Thr Lys Lys Leu Asn Thr Gln Leu Pro
                965                 970                 975

Gly Thr Gly Ala Ala Leu Glu His His His His His His
            980                 985                 990

<210> SEQ ID NO 17
<211> LENGTH: 1122
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 17

Met Gly Ser Ser His His His His His His Glu Asn Leu Tyr Phe Gln
1               5                   10                  15

Gly Ser Thr Phe Ser Lys Leu Arg Glu Gln Leu Gly Pro Val Thr Gln
            20                  25                  30

Glu Phe Trp Asp Asn Leu Glu Lys Glu Thr Glu Gly Leu Arg Gln Glu
        35                  40                  45

Met Ser Lys Asp Leu Glu Glu Val Lys Ala Lys Val Gln Pro Tyr Leu
    50                  55                  60

Asp Asp Phe Gln Lys Lys Trp Gln Glu Glu Met Glu Leu Tyr Arg Gln
65                  70                  75                  80

Lys Val Glu Pro Leu Arg Ala Glu Leu Gln Gly Ala Arg Gln Lys
                85                  90                  95

Leu His Glu Leu Gln Lys Leu Ser Pro Leu Gly Glu Glu Met Arg
            100                 105                 110

Asp Arg Ala Arg Ala His Val Asp Ala Leu Arg Thr His Leu Ala Pro
        115                 120                 125

Tyr Ser Asp Glu Leu Arg Gln Arg Leu Ala Ala Arg Leu Glu Ala Leu
    130                 135                 140

Lys Glu Asn Gly Gly Ala Arg Leu Ala Glu Tyr His Ala Lys Ala Thr
145                 150                 155                 160

Glu His Leu Ser Thr Leu Ser Glu Lys Ala Lys Pro Ala Leu Glu Asp
                165                 170                 175

```
Leu Arg Gln Gly Leu Leu Pro Val Leu Glu Ser Phe Lys Val Ser Phe
                180                 185                 190

Leu Ser Ala Leu Glu Glu Tyr Thr Lys Lys Leu Asn Thr Gln Gly Thr
            195                 200                 205

Pro Val Thr Gln Glu Phe Trp Asp Asn Leu Glu Lys Glu Thr Glu Gly
        210                 215                 220

Leu Arg Gln Glu Met Ser Lys Asp Leu Glu Glu Val Lys Ala Lys Val
225                 230                 235                 240

Gln Pro Tyr Leu Asp Asp Phe Gln Lys Lys Trp Gln Glu Glu Met Glu
                245                 250                 255

Leu Tyr Arg Gln Lys Val Glu Pro Leu Arg Ala Glu Leu Gln Glu Gly
            260                 265                 270

Ala Arg Gln Lys Leu His Glu Leu Gln Glu Lys Leu Ser Pro Leu Gly
        275                 280                 285

Glu Glu Met Arg Asp Arg Ala Arg Ala His Val Asp Ala Leu Arg Thr
    290                 295                 300

His Leu Ala Pro Tyr Ser Asp Glu Leu Arg Gln Arg Leu Ala Ala Arg
305                 310                 315                 320

Leu Glu Ala Leu Lys Glu Asn Gly Gly Ala Arg Leu Ala Glu Tyr His
                325                 330                 335

Ala Lys Ala Thr Glu His Leu Ser Thr Leu Ser Glu Lys Ala Lys Pro
            340                 345                 350

Ala Leu Glu Asp Leu Arg Gln Gly Leu Leu Pro Val Leu Glu Ser Phe
        355                 360                 365

Lys Val Ser Phe Leu Ser Ala Leu Glu Glu Tyr Thr Lys Lys Leu Asn
    370                 375                 380

Thr Gln Gly Thr Pro Val Thr Gln Glu Phe Trp Asp Asn Leu Glu Lys
385                 390                 395                 400

Glu Thr Glu Gly Leu Arg Gln Glu Met Ser Lys Asp Leu Glu Glu Val
                405                 410                 415

Lys Ala Lys Val Gln Pro Tyr Leu Asp Asp Phe Gln Lys Lys Trp Gln
            420                 425                 430

Glu Glu Met Glu Leu Tyr Arg Gln Lys Val Glu Pro Leu Arg Ala Glu
        435                 440                 445

Leu Gln Glu Gly Ala Arg Gln Lys Leu His Glu Leu Gln Glu Lys Leu
    450                 455                 460

Ser Pro Leu Gly Glu Glu Met Arg Asp Arg Ala Arg Ala His Val Asp
465                 470                 475                 480

Ala Leu Arg Thr His Leu Ala Pro Tyr Ser Asp Glu Leu Arg Gln Arg
                485                 490                 495

Leu Ala Ala Arg Leu Glu Ala Leu Lys Glu Asn Gly Gly Ala Arg Leu
            500                 505                 510

Ala Glu Tyr His Ala Lys Ala Thr Glu His Leu Ser Thr Leu Ser Glu
        515                 520                 525

Lys Ala Lys Pro Ala Leu Glu Asp Leu Arg Gln Gly Leu Leu Pro Val
    530                 535                 540

Leu Glu Ser Phe Lys Val Ser Phe Leu Ser Ala Leu Glu Glu Tyr Thr
545                 550                 555                 560

Lys Lys Leu Asn Thr Gln Gly Thr Pro Val Thr Gln Glu Phe Trp Asp
                565                 570                 575

Asn Leu Glu Lys Glu Thr Glu Gly Leu Arg Gln Glu Met Ser Lys Asp
            580                 585                 590
```

```
Leu Glu Glu Val Lys Ala Lys Val Gln Pro Tyr Leu Asp Asp Phe Gln
            595                 600                 605

Lys Lys Trp Gln Glu Glu Met Glu Leu Tyr Arg Gln Lys Val Glu Pro
    610                 615                 620

Leu Arg Ala Glu Leu Gln Glu Gly Ala Arg Gln Lys Leu His Glu Leu
625                 630                 635                 640

Gln Glu Lys Leu Ser Pro Leu Gly Glu Glu Met Arg Asp Arg Ala Arg
                645                 650                 655

Ala His Val Asp Ala Leu Arg Thr His Leu Ala Pro Tyr Ser Asp Glu
            660                 665                 670

Leu Arg Gln Arg Leu Ala Ala Arg Leu Glu Ala Leu Lys Glu Asn Gly
        675                 680                 685

Gly Ala Arg Leu Ala Glu Tyr His Ala Lys Ala Thr Glu His Leu Ser
    690                 695                 700

Thr Leu Ser Glu Lys Ala Lys Pro Ala Leu Glu Asp Leu Arg Gln Gly
705                 710                 715                 720

Leu Leu Pro Val Leu Glu Ser Phe Lys Val Ser Phe Leu Ser Ala Leu
                725                 730                 735

Glu Glu Tyr Thr Lys Lys Leu Asn Thr Gln Gly Thr Pro Val Thr Gln
            740                 745                 750

Glu Phe Trp Asp Asn Leu Glu Lys Glu Thr Glu Gly Leu Arg Gln Glu
        755                 760                 765

Met Ser Lys Asp Leu Glu Glu Val Lys Ala Lys Val Gln Pro Tyr Leu
    770                 775                 780

Asp Asp Phe Gln Lys Lys Trp Gln Glu Glu Met Glu Leu Tyr Arg Gln
785                 790                 795                 800

Lys Val Glu Pro Leu Arg Ala Glu Leu Gln Glu Gly Ala Arg Gln Lys
                805                 810                 815

Leu His Glu Leu Gln Glu Lys Leu Ser Pro Leu Gly Glu Glu Met Arg
            820                 825                 830

Asp Arg Ala Arg Ala His Val Asp Ala Leu Arg Thr His Leu Ala Pro
        835                 840                 845

Tyr Ser Asp Glu Leu Arg Gln Arg Leu Ala Ala Arg Leu Glu Ala Leu
    850                 855                 860

Lys Glu Asn Gly Gly Ala Arg Leu Ala Glu Tyr His Ala Lys Ala Thr
865                 870                 875                 880

Glu His Leu Ser Thr Leu Ser Glu Lys Ala Lys Pro Ala Leu Glu Asp
                885                 890                 895

Leu Arg Gln Gly Leu Leu Pro Val Leu Glu Ser Phe Lys Val Ser Phe
            900                 905                 910

Leu Ser Ala Leu Glu Glu Tyr Thr Lys Lys Leu Asn Thr Gln Gly Thr
        915                 920                 925

Pro Val Thr Gln Glu Phe Trp Asp Asn Leu Glu Lys Glu Thr Glu Gly
    930                 935                 940

Leu Arg Gln Glu Met Ser Lys Asp Leu Glu Glu Val Lys Ala Lys Val
945                 950                 955                 960

Gln Pro Tyr Leu Asp Asp Phe Gln Lys Lys Trp Gln Glu Glu Met Glu
                965                 970                 975

Leu Tyr Arg Gln Lys Val Glu Pro Leu Arg Ala Glu Leu Gln Glu Gly
            980                 985                 990

Ala Arg Gln Lys Leu His Glu Leu  Gln Glu Lys Leu Ser  Pro Leu Gly
        995                 1000                1005

Glu Glu  Met Arg Asp Arg Ala  Arg Ala His Val Asp  Ala Leu Arg
```

```
            1010                1015                1020

Thr His Leu Ala Pro Tyr Ser Asp Glu Leu Arg Gln Arg Leu Ala
        1025                1030                1035

Ala Arg Leu Glu Ala Leu Lys Glu Asn Gly Gly Ala Arg Leu Ala
        1040                1045                1050

Glu Tyr His Ala Lys Ala Thr Glu His Leu Ser Thr Leu Ser Glu
        1055                1060                1065

Lys Ala Lys Pro Ala Leu Glu Asp Leu Arg Gln Gly Leu Leu Pro
        1070                1075                1080

Val Leu Glu Ser Phe Lys Val Ser Phe Leu Ser Ala Leu Glu Glu
        1085                1090                1095

Tyr Thr Lys Lys Leu Asn Thr Gln Leu Pro Gly Thr Gly Ala Ala
        1100                1105                1110

Ala Leu Glu His His His His His His
        1115                1120

<210> SEQ ID NO 18
<211> LENGTH: 1148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Gly Ser Ser His His His His His His Glu Asn Leu Tyr Phe Gln
1               5                   10                  15

Gly Ser Thr Phe Ser Lys Leu Arg Glu Gln Leu Gly Pro Val Thr Gln
                20                  25                  30

Glu Phe Trp Asp Asn Leu Glu Lys Glu Thr Glu Gly Leu Arg Gln Glu
            35                  40                  45

Met Ser Lys Asp Leu Glu Glu Val Lys Ala Lys Val Gln Pro Tyr Leu
        50                  55                  60

Asp Asp Phe Gln Lys Lys Trp Gln Glu Glu Met Glu Leu Tyr Arg Gln
65                  70                  75                  80

Lys Val Glu Pro Leu Gly Glu Glu Met Arg Asp Arg Ala Arg Ala His
                85                  90                  95

Val Asp Ala Leu Arg Thr His Leu Ala Pro Tyr Ser Asp Glu Leu Arg
            100                 105                 110

Gln Arg Leu Ala Ala Arg Leu Glu Ala Leu Lys Glu Asn Gly Gly Ala
        115                 120                 125

Arg Leu Ala Glu Tyr His Ala Lys Ala Thr Glu His Leu Ser Thr Leu
    130                 135                 140

Ser Glu Lys Ala Lys Pro Ala Leu Glu Asp Leu Arg Gln Gly Leu Leu
145                 150                 155                 160

Pro Val Leu Glu Ser Phe Lys Val Ser Phe Leu Ser Ala Leu Glu Glu
                165                 170                 175

Tyr Thr Lys Lys Leu Asn Thr Gln Gly Thr Pro Val Thr Gln Glu Phe
            180                 185                 190

Trp Asp Asn Leu Glu Lys Glu Thr Glu Gly Leu Arg Gln Glu Met Ser
        195                 200                 205

Lys Asp Leu Glu Glu Val Lys Ala Lys Val Gln Pro Tyr Leu Asp Asp
    210                 215                 220

Phe Gln Lys Lys Trp Gln Glu Glu Met Glu Leu Tyr Arg Gln Lys Val
225                 230                 235                 240
```

-continued

Glu Pro Leu Gly Glu Met Arg Asp Arg Ala Arg Ala His Val Asp
                245                 250                 255

Ala Leu Arg Thr His Leu Ala Pro Tyr Ser Asp Glu Leu Arg Gln Arg
            260                 265                 270

Leu Ala Ala Arg Leu Glu Ala Leu Lys Glu Asn Gly Gly Ala Arg Leu
        275                 280                 285

Ala Glu Tyr His Ala Lys Ala Thr Glu His Leu Ser Thr Leu Ser Glu
    290                 295                 300

Lys Ala Lys Pro Ala Leu Glu Asp Leu Arg Gln Gly Leu Leu Pro Val
305                 310                 315                 320

Leu Glu Ser Phe Lys Val Ser Phe Leu Ser Ala Leu Glu Glu Tyr Thr
                325                 330                 335

Lys Lys Leu Asn Thr Gln Gly Thr Pro Val Thr Gln Glu Phe Trp Asp
            340                 345                 350

Asn Leu Glu Lys Glu Thr Glu Gly Leu Arg Gln Glu Met Ser Lys Asp
        355                 360                 365

Leu Glu Glu Val Lys Ala Lys Val Gln Pro Tyr Leu Asp Asp Phe Gln
    370                 375                 380

Lys Lys Trp Gln Glu Glu Met Glu Leu Tyr Arg Gln Lys Val Glu Pro
385                 390                 395                 400

Leu Gly Glu Glu Met Arg Asp Arg Ala Arg Ala His Val Asp Ala Leu
                405                 410                 415

Arg Thr His Leu Ala Pro Tyr Ser Asp Glu Leu Arg Gln Arg Leu Ala
            420                 425                 430

Ala Arg Leu Glu Ala Leu Lys Glu Asn Gly Gly Ala Arg Leu Ala Glu
        435                 440                 445

Tyr His Ala Lys Ala Thr Glu His Leu Ser Thr Leu Ser Glu Lys Ala
    450                 455                 460

Lys Pro Ala Leu Glu Asp Leu Arg Gln Gly Leu Leu Pro Val Leu Glu
465                 470                 475                 480

Ser Phe Lys Val Ser Phe Leu Ser Ala Leu Glu Glu Tyr Thr Lys Lys
                485                 490                 495

Leu Asn Thr Gln Gly Thr Pro Val Thr Gln Glu Phe Trp Asp Asn Leu
            500                 505                 510

Glu Lys Glu Thr Glu Gly Leu Arg Gln Glu Met Ser Lys Asp Leu Glu
        515                 520                 525

Glu Val Lys Ala Lys Val Gln Pro Tyr Leu Asp Asp Phe Gln Lys Lys
    530                 535                 540

Trp Gln Glu Glu Met Glu Leu Tyr Arg Gln Lys Val Glu Pro Leu Gly
545                 550                 555                 560

Glu Glu Met Arg Asp Arg Ala Arg Ala His Val Asp Ala Leu Arg Thr
                565                 570                 575

His Leu Ala Pro Tyr Ser Asp Glu Leu Arg Gln Arg Leu Ala Ala Arg
            580                 585                 590

Leu Glu Ala Leu Lys Glu Asn Gly Gly Ala Arg Leu Ala Glu Tyr His
        595                 600                 605

Ala Lys Ala Thr Glu His Leu Ser Thr Leu Ser Glu Lys Ala Lys Pro
    610                 615                 620

Ala Leu Glu Asp Leu Arg Gln Gly Leu Leu Pro Val Leu Glu Ser Phe
625                 630                 635                 640

Lys Val Ser Phe Leu Ser Ala Leu Glu Glu Tyr Thr Lys Lys Leu Asn
                645                 650                 655

Thr Gln Gly Thr Pro Val Thr Gln Glu Phe Trp Asp Asn Leu Glu Lys

-continued

```
              660             665            670
Glu Thr Glu Gly Leu Arg Gln Glu Met Ser Lys Asp Leu Glu Glu Val
            675             680            685
Lys Ala Lys Val Gln Pro Tyr Leu Asp Asp Phe Gln Lys Lys Trp Gln
            690             695            700
Glu Glu Met Glu Leu Tyr Arg Gln Lys Val Glu Pro Leu Gly Glu Glu
705             710             715            720
Met Arg Asp Arg Ala Arg Ala His Val Asp Ala Leu Arg Thr His Leu
            725             730            735
Ala Pro Tyr Ser Asp Glu Leu Arg Gln Arg Leu Ala Ala Arg Leu Glu
            740             745            750
Ala Leu Lys Glu Asn Gly Gly Ala Arg Leu Ala Glu Tyr His Ala Lys
            755             760            765
Ala Thr Glu His Leu Ser Thr Leu Ser Glu Lys Ala Lys Pro Ala Leu
            770             775            780
Glu Asp Leu Arg Gln Gly Leu Leu Pro Val Leu Glu Ser Phe Lys Val
785             790             795            800
Ser Phe Leu Ser Ala Leu Glu Glu Tyr Thr Lys Lys Leu Asn Thr Gln
            805             810            815
Gly Thr Pro Val Thr Gln Glu Phe Trp Asp Asn Leu Glu Lys Glu Thr
            820             825            830
Glu Gly Leu Arg Gln Glu Met Ser Lys Asp Leu Glu Glu Val Lys Ala
            835             840            845
Lys Val Gln Pro Tyr Leu Asp Asp Phe Gln Lys Lys Trp Gln Glu Glu
            850             855            860
Met Glu Leu Tyr Arg Gln Lys Val Glu Pro Leu Gly Glu Glu Met Arg
865             870             875            880
Asp Arg Ala Arg Ala His Val Asp Ala Leu Arg Thr His Leu Ala Pro
            885             890            895
Tyr Ser Asp Glu Leu Arg Gln Arg Leu Ala Ala Arg Leu Glu Ala Leu
            900             905            910
Lys Glu Asn Gly Gly Ala Arg Leu Ala Glu Tyr His Ala Lys Ala Thr
            915             920            925
Glu His Leu Ser Thr Leu Ser Glu Lys Ala Lys Pro Ala Leu Glu Asp
            930             935            940
Leu Arg Gln Gly Leu Leu Pro Val Leu Glu Ser Phe Lys Val Ser Phe
945             950             955            960
Leu Ser Ala Leu Glu Glu Tyr Thr Lys Lys Leu Asn Thr Gln Gly Thr
            965             970            975
Pro Val Thr Gln Glu Phe Trp Asp Asn Leu Glu Lys Glu Thr Glu Gly
            980             985            990
Leu Arg Gln Glu Met Ser Lys Asp  Leu Glu Glu Val Lys  Ala Lys Val
            995              1000              1005
Gln Pro Tyr Leu Asp Asp Phe  Gln Lys Lys Trp Gln  Glu Glu Met
            1010             1015             1020
Glu Leu Tyr Arg Gln Lys Val  Glu Pro Leu Gly Glu  Glu Met Arg
            1025             1030             1035
Asp Arg Ala Arg Ala His Val  Asp Ala Leu Arg Thr  His Leu Ala
            1040             1045             1050
Pro Tyr Ser Asp Glu Leu Arg  Gln Arg Leu Ala Ala  Arg Leu Glu
            1055             1060             1065
Ala Leu Lys Glu Asn Gly Gly  Ala Arg Leu Ala Glu  Tyr His Ala
            1070             1075             1080
```

```
Lys Ala Thr Glu His Leu Ser Thr Leu Ser Glu Lys Ala Lys Pro
    1085                1090                1095

Ala Leu Glu Asp Leu Arg Gln Gly Leu Leu Pro Val Leu Glu Ser
    1100                1105                1110

Phe Lys Val Ser Phe Leu Ser Ala Leu Glu Glu Tyr Thr Lys Lys
    1115                1120                1125

Leu Asn Thr Gln Leu Pro Gly Thr Gly Ala Ala Ala Leu Glu His
    1130                1135                1140

His His His His His
    1145

<210> SEQ ID NO 19
<211> LENGTH: 1302
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Gly Ser Ser His His His His His His Glu Asn Leu Tyr Phe Gln
1               5                   10                  15

Gly Ser Thr Phe Ser Lys Leu Arg Glu Gln Leu Gly Pro Val Thr Gln
                20                  25                  30

Glu Phe Trp Asp Asn Leu Glu Lys Glu Thr Glu Gly Leu Arg Gln Glu
            35                  40                  45

Met Ser Lys Asp Leu Glu Glu Val Lys Ala Lys Val Gln Pro Tyr Leu
50                  55                  60

Asp Asp Phe Gln Lys Lys Trp Gln Glu Glu Met Glu Leu Tyr Arg Gln
65                  70                  75                  80

Lys Val Glu Pro Leu Arg Ala Glu Leu Gln Glu Gly Ala Arg Gln Lys
                85                  90                  95

Leu His Glu Leu Gln Glu Lys Leu Ser Pro Leu Gly Glu Glu Met Arg
            100                 105                 110

Asp Arg Ala Arg Ala His Val Asp Ala Leu Arg Thr His Leu Ala Pro
        115                 120                 125

Tyr Ser Asp Glu Leu Arg Gln Arg Leu Ala Ala Arg Leu Glu Ala Leu
    130                 135                 140

Lys Glu Asn Gly Gly Ala Arg Leu Ala Glu Tyr His Ala Lys Ala Thr
145                 150                 155                 160

Glu His Leu Ser Thr Leu Ser Glu Lys Ala Lys Pro Ala Leu Glu Asp
                165                 170                 175

Leu Arg Gln Gly Leu Leu Pro Val Leu Glu Ser Phe Lys Val Ser Phe
            180                 185                 190

Leu Ser Ala Leu Glu Glu Tyr Thr Lys Lys Leu Asn Thr Gln Gly Thr
        195                 200                 205

Pro Val Thr Gln Glu Phe Trp Asp Asn Leu Glu Lys Glu Thr Glu Gly
    210                 215                 220

Leu Arg Gln Glu Met Ser Lys Asp Leu Glu Glu Val Lys Ala Lys Val
225                 230                 235                 240

Gln Pro Tyr Leu Asp Asp Phe Gln Lys Lys Trp Gln Glu Glu Met Glu
                245                 250                 255

Leu Tyr Arg Gln Lys Val Glu Pro Leu Arg Ala Glu Leu Gln Glu Gly
            260                 265                 270

Ala Arg Gln Lys Leu His Glu Leu Gln Glu Lys Leu Ser Pro Leu Gly
```

```
              275                 280                 285
Glu Glu Met Arg Asp Arg Ala Arg Ala His Val Asp Ala Leu Arg Thr
290                 295                 300

His Leu Ala Pro Tyr Ser Asp Glu Leu Arg Gln Arg Leu Ala Ala Arg
305                 310                 315                 320

Leu Glu Ala Leu Lys Glu Asn Gly Gly Ala Arg Leu Ala Glu Tyr His
                    325                 330                 335

Ala Lys Ala Thr Glu His Leu Ser Thr Leu Ser Glu Lys Ala Lys Pro
                340                 345                 350

Ala Leu Glu Asp Leu Arg Gln Gly Leu Leu Pro Val Leu Glu Ser Phe
            355                 360                 365

Lys Val Ser Phe Leu Ser Ala Leu Glu Glu Tyr Thr Lys Lys Leu Asn
        370                 375                 380

Thr Gln Gly Thr Pro Val Thr Gln Glu Phe Trp Asp Asn Leu Glu Lys
385                 390                 395                 400

Glu Thr Glu Gly Leu Arg Gln Glu Met Ser Lys Asp Leu Glu Glu Val
                    405                 410                 415

Lys Ala Lys Val Gln Pro Tyr Leu Asp Asp Phe Gln Lys Lys Trp Gln
                420                 425                 430

Glu Glu Met Glu Leu Tyr Arg Gln Lys Val Glu Pro Leu Arg Ala Glu
            435                 440                 445

Leu Gln Glu Gly Ala Arg Gln Lys Leu His Glu Leu Gln Glu Lys Leu
        450                 455                 460

Ser Pro Leu Gly Glu Glu Met Arg Asp Arg Ala Arg Ala His Val Asp
465                 470                 475                 480

Ala Leu Arg Thr His Leu Ala Pro Tyr Ser Asp Glu Leu Arg Gln Arg
                    485                 490                 495

Leu Ala Ala Arg Leu Glu Ala Leu Lys Glu Asn Gly Gly Ala Arg Leu
                500                 505                 510

Ala Glu Tyr His Ala Lys Ala Thr Glu His Leu Ser Thr Leu Ser Glu
            515                 520                 525

Lys Ala Lys Pro Ala Leu Glu Asp Leu Arg Gln Gly Leu Leu Pro Val
        530                 535                 540

Leu Glu Ser Phe Lys Val Ser Phe Leu Ser Ala Leu Glu Glu Tyr Thr
545                 550                 555                 560

Lys Lys Leu Asn Thr Gln Gly Thr Pro Val Thr Gln Glu Phe Trp Asp
                    565                 570                 575

Asn Leu Glu Lys Glu Thr Glu Gly Leu Arg Gln Glu Met Ser Lys Asp
                580                 585                 590

Leu Glu Glu Val Lys Ala Lys Val Gln Pro Tyr Leu Asp Asp Phe Gln
            595                 600                 605

Lys Lys Trp Gln Glu Glu Met Glu Leu Tyr Arg Gln Lys Val Glu Pro
        610                 615                 620

Leu Arg Ala Glu Leu Gln Glu Gly Ala Arg Gln Lys Leu His Glu Leu
625                 630                 635                 640

Gln Glu Lys Leu Ser Pro Leu Gly Glu Glu Met Arg Asp Arg Ala Arg
                    645                 650                 655

Ala His Val Asp Ala Leu Arg Thr His Leu Ala Pro Tyr Ser Asp Glu
                660                 665                 670

Leu Arg Gln Arg Leu Ala Ala Arg Leu Glu Ala Leu Lys Glu Asn Gly
            675                 680                 685

Gly Ala Arg Leu Ala Glu Tyr His Ala Lys Ala Thr Glu His Leu Ser
        690                 695                 700
```

```
Thr Leu Ser Glu Lys Ala Lys Pro Ala Leu Glu Asp Leu Arg Gln Gly
705                 710                 715                 720

Leu Leu Pro Val Leu Glu Ser Phe Lys Val Ser Phe Leu Ser Ala Leu
                725                 730                 735

Glu Glu Tyr Thr Lys Lys Leu Asn Thr Gln Gly Thr Pro Val Thr Gln
            740                 745                 750

Glu Phe Trp Asp Asn Leu Glu Lys Glu Thr Glu Gly Leu Arg Gln Glu
        755                 760                 765

Met Ser Lys Asp Leu Glu Glu Val Lys Ala Lys Val Gln Pro Tyr Leu
770                 775                 780

Asp Asp Phe Gln Lys Lys Trp Gln Glu Glu Met Glu Leu Tyr Arg Gln
785                 790                 795                 800

Lys Val Glu Pro Leu Arg Ala Glu Leu Gln Glu Gly Ala Arg Gln Lys
                805                 810                 815

Leu His Glu Leu Gln Glu Lys Leu Ser Pro Leu Gly Glu Glu Met Arg
            820                 825                 830

Asp Arg Ala Arg Ala His Val Asp Ala Leu Arg Thr His Leu Ala Pro
        835                 840                 845

Tyr Ser Asp Glu Leu Arg Gln Arg Leu Ala Ala Arg Leu Glu Ala Leu
850                 855                 860

Lys Glu Asn Gly Gly Ala Arg Leu Ala Glu Tyr His Ala Lys Ala Thr
865                 870                 875                 880

Glu His Leu Ser Thr Leu Ser Glu Lys Ala Lys Pro Ala Leu Glu Asp
                885                 890                 895

Leu Arg Gln Gly Leu Leu Pro Val Leu Glu Ser Phe Lys Val Ser Phe
            900                 905                 910

Leu Ser Ala Leu Glu Glu Tyr Thr Lys Lys Leu Asn Thr Gln Gly Thr
        915                 920                 925

Pro Val Thr Gln Glu Phe Trp Asp Asn Leu Glu Lys Glu Thr Glu Gly
    930                 935                 940

Leu Arg Gln Glu Met Ser Lys Asp Leu Glu Glu Val Lys Ala Lys Val
945                 950                 955                 960

Gln Pro Tyr Leu Asp Asp Phe Gln Lys Lys Trp Gln Glu Glu Met Glu
                965                 970                 975

Leu Tyr Arg Gln Lys Val Glu Pro Leu Arg Ala Glu Leu Gln Glu Gly
            980                 985                 990

Ala Arg Gln Lys Leu His Glu Leu  Gln Glu Lys Leu Ser  Pro Leu Gly
            995                 1000                1005

Glu Glu  Met Arg Asp Arg Ala  Arg Ala His Val Asp  Ala Leu Arg
        1010                1015                1020

Thr His  Leu Ala Pro Tyr Ser  Asp Glu Leu Arg Gln  Arg Leu Ala
        1025                1030                1035

Ala Arg  Leu Glu Ala Leu Lys  Glu Asn Gly Gly Ala  Arg Leu Ala
        1040                1045                1050

Glu Tyr  His Ala Lys Ala Thr  Glu His Leu Ser Thr  Leu Ser Glu
        1055                1060                1065

Lys Ala  Lys Pro Ala Leu Glu  Asp Leu Arg Gln Gly  Leu Leu Pro
        1070                1075                1080

Val Leu  Glu Ser Phe Lys Val  Ser Phe Leu Ser Ala  Leu Glu Glu
        1085                1090                1095

Tyr Thr  Lys Lys Leu Asn Thr  Gln Gly Thr Pro Val  Thr Gln Glu
        1100                1105                1110
```

```
Phe Trp Asp Asn Leu Glu Lys Glu Thr Glu Gly Leu Arg Gln Glu
    1115                1120                1125

Met Ser Lys Asp Leu Glu Glu Val Lys Ala Lys Val Gln Pro Tyr
    1130                1135                1140

Leu Asp Asp Phe Gln Lys Lys Trp Gln Glu Glu Met Glu Leu Tyr
    1145                1150                1155

Arg Gln Lys Val Glu Pro Leu Arg Ala Glu Leu Gln Glu Gly Ala
    1160                1165                1170

Arg Gln Lys Leu His Glu Leu Gln Glu Lys Leu Ser Pro Leu Gly
    1175                1180                1185

Glu Glu Met Arg Asp Arg Ala Arg Ala His Val Asp Ala Leu Arg
    1190                1195                1200

Thr His Leu Ala Pro Tyr Ser Asp Glu Leu Arg Gln Arg Leu Ala
    1205                1210                1215

Ala Arg Leu Glu Ala Leu Lys Glu Asn Gly Gly Ala Arg Leu Ala
    1220                1225                1230

Glu Tyr His Ala Lys Ala Thr Glu His Leu Ser Thr Leu Ser Glu
    1235                1240                1245

Lys Ala Lys Pro Ala Leu Glu Asp Leu Arg Gln Gly Leu Leu Pro
    1250                1255                1260

Val Leu Glu Ser Phe Lys Val Ser Phe Leu Ser Ala Leu Glu Glu
    1265                1270                1275

Tyr Thr Lys Lys Leu Asn Thr Gln Leu Pro Gly Thr Gly Ala Ala
    1280                1285                1290

Ala Leu Glu His His His His His His
    1295                1300

<210> SEQ ID NO 20
<211> LENGTH: 1306
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Gly Ser Ser His His His His His His Glu Asn Leu Tyr Phe Gln
1               5                   10                  15

Gly Ser Thr Phe Ser Lys Leu Arg Glu Gln Leu Gly Pro Val Thr Gln
                20                  25                  30

Glu Phe Trp Asp Asn Leu Glu Lys Glu Thr Glu Gly Leu Arg Gln Glu
            35                  40                  45

Met Ser Lys Asp Leu Glu Glu Val Lys Ala Lys Val Gln Pro Tyr Leu
        50                  55                  60

Asp Asp Phe Gln Lys Lys Trp Gln Glu Glu Met Glu Leu Tyr Arg Gln
65                  70                  75                  80

Lys Val Glu Pro Leu Gly Glu Glu Met Arg Asp Arg Ala Arg Ala His
                85                  90                  95

Val Asp Ala Leu Arg Thr His Leu Ala Pro Tyr Ser Asp Glu Leu Arg
            100                 105                 110

Gln Arg Leu Ala Ala Arg Leu Glu Ala Leu Lys Glu Asn Gly Gly Ala
        115                 120                 125

Arg Leu Ala Glu Tyr His Ala Lys Ala Thr Glu His Leu Ser Thr Leu
    130                 135                 140

Ser Glu Lys Ala Lys Pro Ala Leu Glu Asp Leu Arg Gln Gly Leu Leu
145                 150                 155                 160
```

Pro Val Leu Glu Ser Phe Lys Val Ser Phe Leu Ser Ala Leu Glu Glu
                165                 170                 175

Tyr Thr Lys Lys Leu Asn Thr Gln Gly Thr Pro Val Thr Gln Glu Phe
                180                 185                 190

Trp Asp Asn Leu Glu Lys Glu Thr Glu Gly Leu Arg Gln Glu Met Ser
                195                 200                 205

Lys Asp Leu Glu Glu Val Lys Ala Lys Val Gln Pro Tyr Leu Asp Asp
                210                 215                 220

Phe Gln Lys Lys Trp Gln Glu Met Glu Leu Tyr Arg Gln Lys Val
225                 230                 235                 240

Glu Pro Leu Gly Glu Glu Met Arg Asp Arg Ala Arg Ala His Val Asp
                245                 250                 255

Ala Leu Arg Thr His Leu Ala Pro Tyr Ser Asp Glu Leu Arg Gln Arg
                260                 265                 270

Leu Ala Ala Arg Leu Glu Ala Leu Lys Glu Asn Gly Gly Ala Arg Leu
                275                 280                 285

Ala Glu Tyr His Ala Lys Ala Thr Glu His Leu Ser Thr Leu Ser Glu
                290                 295                 300

Lys Ala Lys Pro Ala Leu Glu Asp Leu Arg Gln Gly Leu Leu Pro Val
305                 310                 315                 320

Leu Glu Ser Phe Lys Val Ser Phe Leu Ser Ala Leu Glu Glu Tyr Thr
                325                 330                 335

Lys Lys Leu Asn Thr Gln Gly Thr Pro Val Thr Gln Glu Phe Trp Asp
                340                 345                 350

Asn Leu Glu Lys Glu Thr Glu Gly Leu Arg Gln Glu Met Ser Lys Asp
                355                 360                 365

Leu Glu Glu Val Lys Ala Lys Val Gln Pro Tyr Leu Asp Asp Phe Gln
                370                 375                 380

Lys Lys Trp Gln Glu Glu Met Glu Leu Tyr Arg Gln Lys Val Glu Pro
385                 390                 395                 400

Leu Gly Glu Glu Met Arg Asp Arg Ala Arg Ala His Val Asp Ala Leu
                405                 410                 415

Arg Thr His Leu Ala Pro Tyr Ser Asp Glu Leu Arg Gln Arg Leu Ala
                420                 425                 430

Ala Arg Leu Glu Ala Leu Lys Glu Asn Gly Gly Ala Arg Leu Ala Glu
                435                 440                 445

Tyr His Ala Lys Ala Thr Glu His Leu Ser Thr Leu Ser Glu Lys Ala
                450                 455                 460

Lys Pro Ala Leu Glu Asp Leu Arg Gln Gly Leu Leu Pro Val Leu Glu
465                 470                 475                 480

Ser Phe Lys Val Ser Phe Leu Ser Ala Leu Glu Glu Tyr Thr Lys Lys
                485                 490                 495

Leu Asn Thr Gln Gly Thr Pro Val Thr Gln Glu Phe Trp Asp Asn Leu
                500                 505                 510

Glu Lys Glu Thr Glu Gly Leu Arg Gln Glu Met Ser Lys Asp Leu Glu
                515                 520                 525

Glu Val Lys Ala Lys Val Gln Pro Tyr Leu Asp Asp Phe Gln Lys Lys
                530                 535                 540

Trp Gln Glu Glu Met Glu Leu Tyr Arg Gln Lys Val Glu Pro Leu Gly
545                 550                 555                 560

Glu Glu Met Arg Asp Arg Ala Arg Ala His Val Asp Ala Leu Arg Thr
                565                 570                 575

-continued

```
His Leu Ala Pro Tyr Ser Asp Glu Leu Arg Gln Arg Leu Ala Ala Arg
            580                 585                 590

Leu Glu Ala Leu Lys Glu Asn Gly Gly Ala Arg Leu Ala Glu Tyr His
        595                 600                 605

Ala Lys Ala Thr Glu His Leu Ser Thr Leu Ser Glu Lys Ala Lys Pro
    610                 615                 620

Ala Leu Glu Asp Leu Arg Gln Gly Leu Leu Pro Val Leu Glu Ser Phe
625                 630                 635                 640

Lys Val Ser Phe Leu Ser Ala Leu Glu Glu Tyr Thr Lys Lys Leu Asn
                645                 650                 655

Thr Gln Gly Thr Pro Val Thr Gln Glu Phe Trp Asp Asn Leu Glu Lys
            660                 665                 670

Glu Thr Glu Gly Leu Arg Gln Glu Met Ser Lys Asp Leu Glu Glu Val
        675                 680                 685

Lys Ala Lys Val Gln Pro Tyr Leu Asp Asp Phe Gln Lys Lys Trp Gln
    690                 695                 700

Glu Glu Met Glu Leu Tyr Arg Gln Lys Val Glu Pro Leu Gly Glu Glu
705                 710                 715                 720

Met Arg Asp Arg Ala Arg Ala His Val Asp Ala Leu Arg Thr His Leu
                725                 730                 735

Ala Pro Tyr Ser Asp Glu Leu Arg Gln Arg Leu Ala Ala Arg Leu Glu
            740                 745                 750

Ala Leu Lys Glu Asn Gly Gly Ala Arg Leu Ala Glu Tyr His Ala Lys
        755                 760                 765

Ala Thr Glu His Leu Ser Thr Leu Ser Glu Lys Ala Lys Pro Ala Leu
    770                 775                 780

Glu Asp Leu Arg Gln Gly Leu Leu Pro Val Leu Glu Ser Phe Lys Val
785                 790                 795                 800

Ser Phe Leu Ser Ala Leu Glu Glu Tyr Thr Lys Lys Leu Asn Thr Gln
                805                 810                 815

Gly Thr Pro Val Thr Gln Glu Phe Trp Asp Asn Leu Glu Lys Glu Thr
            820                 825                 830

Glu Gly Leu Arg Gln Glu Met Ser Lys Asp Leu Glu Glu Val Lys Ala
        835                 840                 845

Lys Val Gln Pro Tyr Leu Asp Asp Phe Gln Lys Lys Trp Gln Glu Glu
    850                 855                 860

Met Glu Leu Tyr Arg Gln Lys Val Glu Pro Leu Gly Glu Glu Met Arg
865                 870                 875                 880

Asp Arg Ala Arg Ala His Val Asp Ala Leu Arg Thr His Leu Ala Pro
                885                 890                 895

Tyr Ser Asp Glu Leu Arg Gln Arg Leu Ala Ala Arg Leu Glu Ala Leu
            900                 905                 910

Lys Glu Asn Gly Gly Ala Arg Leu Ala Glu Tyr His Ala Lys Ala Thr
        915                 920                 925

Glu His Leu Ser Thr Leu Ser Glu Lys Ala Lys Pro Ala Leu Glu Asp
    930                 935                 940

Leu Arg Gln Gly Leu Leu Pro Val Leu Glu Ser Phe Lys Val Ser Phe
945                 950                 955                 960

Leu Ser Ala Leu Glu Glu Tyr Thr Lys Lys Leu Asn Thr Gln Gly Thr
                965                 970                 975

Pro Val Thr Gln Glu Phe Trp Asp Asn Leu Glu Lys Glu Thr Glu Gly
            980                 985                 990

Leu Arg Gln Glu Met Ser Lys Asp  Leu Glu Glu Val Lys  Ala Lys Val
```

Gln Pro Tyr Leu Asp Asp Phe Gln Lys Lys Trp Gln Glu Glu Met
        995                 1000                1005

Glu Leu Tyr Arg Gln Lys Val Glu Pro Leu Gly Glu Glu Met Arg
    1010                1015                1020

Asp Arg Ala Arg Ala His Val Asp Ala Leu Arg Thr His Leu Ala
    1025                1030                1035

Pro Tyr Ser Asp Glu Leu Arg Gln Arg Leu Ala Ala Arg Leu Glu
    1040                1045                1050

Ala Leu Lys Glu Asn Gly Gly Ala Arg Leu Ala Glu Tyr His Ala
    1055                1060                1065

Lys Ala Thr Glu His Leu Ser Thr Leu Ser Glu Lys Ala Lys Pro
    1070                1075                1080

Ala Leu Glu Asp Leu Arg Gln Gly Leu Leu Pro Val Leu Glu Ser
    1085                1090                1095

Phe Lys Val Ser Phe Leu Ser Ala Leu Glu Glu Tyr Thr Lys Lys
    1100                1105                1110

Leu Asn Thr Gln Gly Thr Pro Val Thr Gln Glu Phe Trp Asp Asn
    1115                1120                1125

Leu Glu Lys Glu Thr Glu Gly Leu Arg Gln Glu Met Ser Lys Asp
    1130                1135                1140

Leu Glu Glu Val Lys Ala Lys Val Gln Pro Tyr Leu Asp Asp Phe
    1145                1150                1155

Gln Lys Lys Trp Gln Glu Glu Met Glu Leu Tyr Arg Gln Lys Val
    1160                1165                1170

Glu Pro Leu Gly Glu Glu Met Arg Asp Arg Ala Arg Ala His Val
    1175                1180                1185

Asp Ala Leu Arg Thr His Leu Ala Pro Tyr Ser Asp Glu Leu Arg
    1190                1195                1200

Gln Arg Leu Ala Ala Arg Leu Glu Ala Leu Lys Glu Asn Gly Gly
    1205                1210                1215

Ala Arg Leu Ala Glu Tyr His Ala Lys Ala Thr Glu His Leu Ser
    1220                1225                1230

Thr Leu Ser Glu Lys Ala Lys Pro Ala Leu Glu Asp Leu Arg Gln
    1235                1240                1245

Gly Leu Leu Pro Val Leu Glu Ser Phe Lys Val Ser Phe Leu Ser
    1250                1255                1260

Ala Leu Glu Glu Tyr Thr Lys Lys Leu Asn Thr Gln Leu Pro Gly
    1265                1270                1275

Thr Gly Ala Ala Ala Leu Glu His His His His His
    1280                1285                1290

<210> SEQ ID NO 21
<211> LENGTH: 1482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Gly Ser Ser His His His His His His Glu Asn Leu Tyr Phe Gln
1               5                   10                  15

Gly Ser Thr Phe Ser Lys Leu Arg Glu Gln Leu Gly Pro Val Thr Gln
            20                  25                  30

```
Glu Phe Trp Asp Asn Leu Glu Lys Glu Thr Glu Gly Leu Arg Gln Glu
         35                  40                  45

Met Ser Lys Asp Leu Glu Glu Val Lys Ala Lys Val Gln Pro Tyr Leu
 50                  55                  60

Asp Asp Phe Gln Lys Lys Trp Gln Glu Met Glu Leu Tyr Arg Gln
 65                  70                  75                  80

Lys Val Glu Pro Leu Arg Ala Glu Leu Gln Glu Gly Ala Arg Gln Lys
                 85                  90                  95

Leu His Glu Leu Gln Glu Lys Leu Ser Pro Leu Gly Glu Glu Met Arg
             100                 105                 110

Asp Arg Ala Arg Ala His Val Asp Ala Leu Arg Thr His Leu Ala Pro
             115                 120                 125

Tyr Ser Asp Glu Leu Arg Gln Arg Leu Ala Ala Arg Leu Glu Ala Leu
 130                 135                 140

Lys Glu Asn Gly Gly Ala Arg Leu Ala Glu Tyr His Ala Lys Ala Thr
145                 150                 155                 160

Glu His Leu Ser Thr Leu Ser Glu Lys Ala Lys Pro Ala Leu Glu Asp
                 165                 170                 175

Leu Arg Gln Gly Leu Leu Pro Val Leu Glu Ser Phe Lys Val Ser Phe
                 180                 185                 190

Leu Ser Ala Leu Glu Glu Tyr Thr Lys Lys Leu Asn Thr Gln Gly Thr
             195                 200                 205

Pro Val Thr Gln Glu Phe Trp Asp Asn Leu Glu Lys Glu Thr Glu Gly
             210                 215                 220

Leu Arg Gln Glu Met Ser Lys Asp Leu Glu Glu Val Lys Ala Lys Val
225                 230                 235                 240

Gln Pro Tyr Leu Asp Asp Phe Gln Lys Lys Trp Gln Glu Glu Met Glu
                 245                 250                 255

Leu Tyr Arg Gln Lys Val Glu Pro Leu Arg Ala Glu Leu Gln Glu Gly
             260                 265                 270

Ala Arg Gln Lys Leu His Glu Leu Gln Glu Lys Leu Ser Pro Leu Gly
             275                 280                 285

Glu Glu Met Arg Asp Arg Ala Arg Ala His Val Asp Ala Leu Arg Thr
290                 295                 300

His Leu Ala Pro Tyr Ser Asp Glu Leu Arg Gln Arg Leu Ala Ala Arg
305                 310                 315                 320

Leu Glu Ala Leu Lys Glu Asn Gly Gly Ala Arg Leu Ala Glu Tyr His
                 325                 330                 335

Ala Lys Ala Thr Glu His Leu Ser Thr Leu Ser Glu Lys Ala Lys Pro
             340                 345                 350

Ala Leu Glu Asp Leu Arg Gln Gly Leu Leu Pro Val Leu Glu Ser Phe
             355                 360                 365

Lys Val Ser Phe Leu Ser Ala Leu Glu Glu Tyr Thr Lys Lys Leu Asn
370                 375                 380

Thr Gln Gly Thr Pro Val Thr Gln Glu Phe Trp Asp Asn Leu Glu Lys
385                 390                 395                 400

Glu Thr Glu Gly Leu Arg Gln Glu Met Ser Lys Asp Leu Glu Glu Val
                 405                 410                 415

Lys Ala Lys Val Gln Pro Tyr Leu Asp Asp Phe Gln Lys Lys Trp Gln
             420                 425                 430

Glu Glu Met Glu Leu Tyr Arg Gln Lys Val Glu Pro Leu Arg Ala Glu
             435                 440                 445

Leu Gln Glu Gly Ala Arg Gln Lys Leu His Glu Leu Gln Glu Lys Leu
```

```
              450                 455                 460
Ser Pro Leu Gly Glu Glu Met Arg Asp Arg Ala Arg Ala His Val Asp
465                 470                 475                 480

Ala Leu Arg Thr His Leu Ala Pro Tyr Ser Asp Glu Leu Arg Gln Arg
                485                 490                 495

Leu Ala Ala Arg Leu Glu Ala Leu Lys Glu Asn Gly Gly Ala Arg Leu
            500                 505                 510

Ala Glu Tyr His Ala Lys Ala Thr Glu His Leu Ser Thr Leu Ser Glu
        515                 520                 525

Lys Ala Lys Pro Ala Leu Glu Asp Leu Arg Gln Gly Leu Leu Pro Val
    530                 535                 540

Leu Glu Ser Phe Lys Val Ser Phe Leu Ser Ala Leu Glu Glu Tyr Thr
545                 550                 555                 560

Lys Lys Leu Asn Thr Gln Gly Thr Pro Val Thr Gln Glu Phe Trp Asp
                565                 570                 575

Asn Leu Glu Lys Glu Thr Glu Gly Leu Arg Gln Glu Met Ser Lys Asp
            580                 585                 590

Leu Glu Glu Val Lys Ala Lys Val Gln Pro Tyr Leu Asp Asp Phe Gln
        595                 600                 605

Lys Lys Trp Gln Glu Glu Met Glu Leu Tyr Arg Gln Lys Val Glu Pro
    610                 615                 620

Leu Arg Ala Glu Leu Gln Glu Gly Ala Arg Gln Lys Leu His Glu Leu
625                 630                 635                 640

Gln Glu Lys Leu Ser Pro Leu Gly Glu Glu Met Arg Asp Arg Ala Arg
                645                 650                 655

Ala His Val Asp Ala Leu Arg Thr His Leu Ala Pro Tyr Ser Asp Glu
            660                 665                 670

Leu Arg Gln Arg Leu Ala Ala Arg Leu Glu Ala Leu Lys Glu Asn Gly
        675                 680                 685

Gly Ala Arg Leu Ala Glu Tyr His Ala Lys Ala Thr Glu His Leu Ser
    690                 695                 700

Thr Leu Ser Glu Lys Ala Lys Pro Ala Leu Glu Asp Leu Arg Gln Gly
705                 710                 715                 720

Leu Leu Pro Val Leu Glu Ser Phe Lys Val Ser Phe Leu Ser Ala Leu
                725                 730                 735

Glu Glu Tyr Thr Lys Lys Leu Asn Thr Gln Gly Thr Pro Val Thr Gln
            740                 745                 750

Glu Phe Trp Asp Asn Leu Glu Lys Glu Thr Glu Gly Leu Arg Gln Glu
        755                 760                 765

Met Ser Lys Asp Leu Glu Glu Val Lys Ala Lys Val Gln Pro Tyr Leu
    770                 775                 780

Asp Asp Phe Gln Lys Lys Trp Gln Glu Glu Met Glu Leu Tyr Arg Gln
785                 790                 795                 800

Lys Val Glu Pro Leu Arg Ala Glu Leu Gln Glu Gly Ala Arg Gln Lys
                805                 810                 815

Leu His Glu Leu Gln Glu Lys Leu Ser Pro Leu Gly Glu Glu Met Arg
            820                 825                 830

Asp Arg Ala Arg Ala His Val Asp Ala Leu Arg Thr His Leu Ala Pro
        835                 840                 845

Tyr Ser Asp Glu Leu Arg Gln Arg Leu Ala Ala Arg Leu Glu Ala Leu
    850                 855                 860

Lys Glu Asn Gly Gly Ala Arg Leu Ala Glu Tyr His Ala Lys Ala Thr
865                 870                 875                 880
```

```
Glu His Leu Ser Thr Leu Ser Glu Lys Ala Lys Pro Ala Leu Glu Asp
            885                 890                 895

Leu Arg Gln Gly Leu Leu Pro Val Leu Glu Ser Phe Lys Val Ser Phe
        900                 905                 910

Leu Ser Ala Leu Glu Glu Tyr Thr Lys Lys Leu Asn Thr Gln Gly Thr
        915                 920                 925

Pro Val Thr Gln Glu Phe Trp Asp Asn Leu Glu Lys Glu Thr Glu Gly
    930                 935                 940

Leu Arg Gln Glu Met Ser Lys Asp Leu Glu Glu Val Lys Ala Lys Val
945                 950                 955                 960

Gln Pro Tyr Leu Asp Asp Phe Gln Lys Lys Trp Gln Glu Glu Met Glu
                965                 970                 975

Leu Tyr Arg Gln Lys Val Glu Pro Leu Arg Ala Glu Leu Gln Glu Gly
            980                 985                 990

Ala Arg Gln Lys Leu His Glu Leu  Gln Glu Lys Leu Ser  Pro Leu Gly
            995                 1000                1005

Glu Glu  Met Arg Asp Arg Ala  Arg Ala His Val Asp  Ala Leu Arg
    1010                1015                1020

Thr His  Leu Ala Pro Tyr Ser  Asp Glu Leu Arg Gln  Arg Leu Ala
    1025                1030                1035

Ala Arg  Leu Glu Ala Leu Lys  Glu Asn Gly Gly Ala  Arg Leu Ala
    1040                1045                1050

Glu Tyr  His Ala Lys Ala Thr  Glu His Leu Ser Thr  Leu Ser Glu
    1055                1060                1065

Lys Ala  Lys Pro Ala Leu Glu  Asp Leu Arg Gln Gly  Leu Leu Pro
    1070                1075                1080

Val Leu  Glu Ser Phe Lys Val  Ser Phe Leu Ser Ala  Leu Glu Glu
    1085                1090                1095

Tyr Thr  Lys Lys Leu Asn Thr  Gln Gly Thr Pro Val  Thr Gln Glu
    1100                1105                1110

Phe Trp  Asp Asn Leu Glu Lys  Glu Thr Glu Gly Leu  Arg Gln Glu
    1115                1120                1125

Met Ser  Lys Asp Leu Glu Glu  Val Lys Ala Lys Val  Gln Pro Tyr
    1130                1135                1140

Leu Asp  Asp Phe Gln Lys Lys  Trp Gln Glu Glu Met  Glu Leu Tyr
    1145                1150                1155

Arg Gln  Lys Val Glu Pro Leu  Arg Ala Glu Leu Gln  Glu Gly Ala
    1160                1165                1170

Arg Gln  Lys Leu His Glu Leu  Gln Glu Lys Leu Ser  Pro Leu Gly
    1175                1180                1185

Glu Glu  Met Arg Asp Arg Ala  Arg Ala His Val Asp  Ala Leu Arg
    1190                1195                1200

Thr His  Leu Ala Pro Tyr Ser  Asp Glu Leu Arg Gln  Arg Leu Ala
    1205                1210                1215

Ala Arg  Leu Glu Ala Leu Lys  Glu Asn Gly Gly Ala  Arg Leu Ala
    1220                1225                1230

Glu Tyr  His Ala Lys Ala Thr  Glu His Leu Ser Thr  Leu Ser Glu
    1235                1240                1245

Lys Ala  Lys Pro Ala Leu Glu  Asp Leu Arg Gln Gly  Leu Leu Pro
    1250                1255                1260

Val Leu  Glu Ser Phe Lys Val  Ser Phe Leu Ser Ala  Leu Glu Glu
    1265                1270                1275
```

```
Tyr Thr Lys Lys Leu Asn Thr Gln Gly Thr Pro Val Thr Gln Glu
    1280                1285                1290

Phe Trp Asp Asn Leu Glu Lys Glu Thr Glu Gly Leu Arg Gln Glu
    1295                1300                1305

Met Ser Lys Asp Leu Glu Glu Val Lys Ala Lys Val Gln Pro Tyr
    1310                1315                1320

Leu Asp Asp Phe Gln Lys Lys Trp Gln Glu Glu Met Glu Leu Tyr
    1325                1330                1335

Arg Gln Lys Val Glu Pro Leu Arg Ala Glu Leu Gln Glu Gly Ala
    1340                1345                1350

Arg Gln Lys Leu His Glu Leu Gln Glu Lys Leu Ser Pro Leu Gly
    1355                1360                1365

Glu Glu Met Arg Asp Arg Ala Arg Ala His Val Asp Ala Leu Arg
    1370                1375                1380

Thr His Leu Ala Pro Tyr Ser Asp Glu Leu Arg Gln Arg Leu Ala
    1385                1390                1395

Ala Arg Leu Glu Ala Leu Lys Glu Asn Gly Gly Ala Arg Leu Ala
    1400                1405                1410

Glu Tyr His Ala Lys Ala Thr Glu His Leu Ser Thr Leu Ser Glu
    1415                1420                1425

Lys Ala Lys Pro Ala Leu Glu Asp Leu Arg Gln Gly Leu Leu Pro
    1430                1435                1440

Val Leu Glu Ser Phe Lys Val Ser Phe Leu Ser Ala Leu Glu Glu
    1445                1450                1455

Tyr Thr Lys Lys Leu Asn Thr Gln Leu Pro Gly Thr Gly Ala Ala
    1460                1465                1470

Ala Leu Glu His His His His His His
    1475                1480

<210> SEQ ID NO 22
<211> LENGTH: 1662
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Gly Ser Ser His His His His His His Glu Asn Leu Tyr Phe Gln
1               5                   10                  15

Gly Ser Thr Phe Ser Lys Leu Arg Glu Gln Leu Gly Pro Val Thr Gln
                20                  25                  30

Glu Phe Trp Asp Asn Leu Glu Lys Glu Thr Glu Gly Leu Arg Gln Glu
            35                  40                  45

Met Ser Lys Asp Leu Glu Glu Val Lys Ala Lys Val Gln Pro Tyr Leu
        50                  55                  60

Asp Asp Phe Gln Lys Lys Trp Gln Glu Glu Met Glu Leu Tyr Arg Gln
65                  70                  75                  80

Lys Val Glu Pro Leu Arg Ala Glu Leu Gln Glu Gly Ala Arg Gln Lys
                85                  90                  95

Leu His Glu Leu Gln Glu Lys Leu Ser Pro Leu Gly Glu Glu Met Arg
            100                 105                 110

Asp Arg Ala Arg Ala His Val Asp Ala Leu Arg Thr His Leu Ala Pro
        115                 120                 125

Tyr Ser Asp Glu Leu Arg Gln Arg Leu Ala Ala Arg Leu Glu Ala Leu
    130                 135                 140
```

```
Lys Glu Asn Gly Gly Ala Arg Leu Ala Glu Tyr His Ala Lys Ala Thr
145                 150                 155                 160

Glu His Leu Ser Thr Leu Ser Glu Lys Ala Lys Pro Ala Leu Glu Asp
            165                 170                 175

Leu Arg Gln Gly Leu Leu Pro Val Leu Glu Ser Phe Lys Val Ser Phe
            180                 185                 190

Leu Ser Ala Leu Glu Glu Tyr Thr Lys Lys Leu Asn Thr Gln Gly Thr
            195                 200                 205

Pro Val Thr Gln Glu Phe Trp Asp Asn Leu Glu Lys Glu Thr Glu Gly
            210                 215                 220

Leu Arg Gln Glu Met Ser Lys Asp Leu Glu Glu Val Lys Ala Lys Val
225                 230                 235                 240

Gln Pro Tyr Leu Asp Asp Phe Gln Lys Lys Trp Gln Glu Glu Met Glu
            245                 250                 255

Leu Tyr Arg Gln Lys Val Glu Pro Leu Arg Ala Glu Leu Gln Glu Gly
            260                 265                 270

Ala Arg Gln Lys Leu His Glu Leu Gln Glu Lys Leu Ser Pro Leu Gly
            275                 280                 285

Glu Glu Met Arg Asp Arg Ala Arg Ala His Val Asp Ala Leu Arg Thr
            290                 295                 300

His Leu Ala Pro Tyr Ser Asp Glu Leu Arg Gln Arg Leu Ala Ala Arg
305                 310                 315                 320

Leu Glu Ala Leu Lys Glu Asn Gly Gly Ala Arg Leu Ala Glu Tyr His
            325                 330                 335

Ala Lys Ala Thr Glu His Leu Ser Thr Leu Ser Glu Lys Ala Lys Pro
            340                 345                 350

Ala Leu Glu Asp Leu Arg Gln Gly Leu Leu Pro Val Leu Glu Ser Phe
            355                 360                 365

Lys Val Ser Phe Leu Ser Ala Leu Glu Glu Tyr Thr Lys Lys Leu Asn
            370                 375                 380

Thr Gln Gly Thr Pro Val Thr Gln Glu Phe Trp Asp Asn Leu Glu Lys
385                 390                 395                 400

Glu Thr Glu Gly Leu Arg Gln Glu Met Ser Lys Asp Leu Glu Glu Val
            405                 410                 415

Lys Ala Lys Val Gln Pro Tyr Leu Asp Asp Phe Gln Lys Lys Trp Gln
            420                 425                 430

Glu Glu Met Glu Leu Tyr Arg Gln Lys Val Glu Pro Leu Arg Ala Glu
            435                 440                 445

Leu Gln Glu Gly Ala Arg Gln Lys Leu His Glu Leu Gln Glu Lys Leu
            450                 455                 460

Ser Pro Leu Gly Glu Glu Met Arg Asp Arg Ala Arg Ala His Val Asp
465                 470                 475                 480

Ala Leu Arg Thr His Leu Ala Pro Tyr Ser Asp Glu Leu Arg Gln Arg
            485                 490                 495

Leu Ala Ala Arg Leu Glu Ala Leu Lys Glu Asn Gly Gly Ala Arg Leu
            500                 505                 510

Ala Glu Tyr His Ala Lys Ala Thr Glu His Leu Ser Thr Leu Ser Glu
            515                 520                 525

Lys Ala Lys Pro Ala Leu Glu Asp Leu Arg Gln Gly Leu Leu Pro Val
            530                 535                 540

Leu Glu Ser Phe Lys Val Ser Phe Leu Ser Ala Leu Glu Glu Tyr Thr
545                 550                 555                 560
```

Lys Lys Leu Asn Thr Gln Gly Thr Pro Val Thr Gln Glu Phe Trp Asp
            565                 570                 575

Asn Leu Glu Lys Glu Thr Glu Gly Leu Arg Gln Glu Met Ser Lys Asp
            580                 585                 590

Leu Glu Glu Val Lys Ala Lys Val Gln Pro Tyr Leu Asp Asp Phe Gln
            595                 600                 605

Lys Lys Trp Gln Glu Glu Met Glu Leu Tyr Arg Gln Lys Val Glu Pro
            610                 615                 620

Leu Arg Ala Glu Leu Gln Glu Gly Ala Arg Gln Lys Leu His Glu Leu
625                 630                 635                 640

Gln Glu Lys Leu Ser Pro Leu Gly Glu Glu Met Arg Asp Arg Ala Arg
            645                 650                 655

Ala His Val Asp Ala Leu Arg Thr His Leu Ala Pro Tyr Ser Asp Glu
            660                 665                 670

Leu Arg Gln Arg Leu Ala Ala Arg Leu Glu Ala Leu Lys Glu Asn Gly
            675                 680                 685

Gly Ala Arg Leu Ala Glu Tyr His Ala Lys Ala Thr Glu His Leu Ser
            690                 695                 700

Thr Leu Ser Glu Lys Ala Lys Pro Ala Leu Glu Asp Leu Arg Gln Gly
705                 710                 715                 720

Leu Leu Pro Val Leu Glu Ser Phe Lys Val Ser Phe Leu Ser Ala Leu
            725                 730                 735

Glu Glu Tyr Thr Lys Lys Leu Asn Thr Gln Gly Thr Pro Val Thr Gln
            740                 745                 750

Glu Phe Trp Asp Asn Leu Glu Lys Glu Thr Glu Gly Leu Arg Gln Glu
            755                 760                 765

Met Ser Lys Asp Leu Glu Glu Val Lys Ala Lys Val Gln Pro Tyr Leu
770                 775                 780

Asp Asp Phe Gln Lys Lys Trp Gln Glu Glu Met Glu Leu Tyr Arg Gln
785                 790                 795                 800

Lys Val Glu Pro Leu Arg Ala Glu Leu Gln Glu Gly Ala Arg Gln Lys
            805                 810                 815

Leu His Glu Leu Gln Glu Lys Leu Ser Pro Leu Gly Glu Glu Met Arg
            820                 825                 830

Asp Arg Ala Arg Ala His Val Asp Ala Leu Arg Thr His Leu Ala Pro
835                 840                 845

Tyr Ser Asp Glu Leu Arg Gln Arg Leu Ala Ala Arg Leu Glu Ala Leu
850                 855                 860

Lys Glu Asn Gly Gly Ala Arg Leu Ala Glu Tyr His Ala Lys Ala Thr
865                 870                 875                 880

Glu His Leu Ser Thr Leu Ser Glu Lys Ala Lys Pro Ala Leu Glu Asp
            885                 890                 895

Leu Arg Gln Gly Leu Leu Pro Val Leu Glu Ser Phe Lys Val Ser Phe
            900                 905                 910

Leu Ser Ala Leu Glu Glu Tyr Thr Lys Lys Leu Asn Thr Gln Gly Thr
            915                 920                 925

Pro Val Thr Gln Glu Phe Trp Asp Asn Leu Glu Lys Glu Thr Glu Gly
            930                 935                 940

Leu Arg Gln Glu Met Ser Lys Asp Leu Glu Glu Val Lys Ala Lys Val
945                 950                 955                 960

Gln Pro Tyr Leu Asp Asp Phe Gln Lys Lys Trp Gln Glu Glu Met Glu
            965                 970                 975

Leu Tyr Arg Gln Lys Val Glu Pro Leu Arg Ala Glu Leu Gln Glu Gly

-continued

```
            980                 985                 990
Ala Arg Gln Lys Leu His Glu Leu  Gln Glu Lys Leu Ser  Pro Leu Gly
        995                 1000                1005

Glu Glu Met Arg Asp Arg Ala  Arg Ala His Val Asp  Ala Leu Arg
1010                1015                1020

Thr His Leu Ala Pro Tyr Ser  Asp Glu Leu Arg Gln  Arg Leu Ala
1025                1030                1035

Ala Arg Leu Glu Ala Leu Lys  Glu Asn Gly Gly Ala  Arg Leu Ala
1040                1045                1050

Glu Tyr His Ala Lys Ala Thr  Glu His Leu Ser Thr  Leu Ser Glu
1055                1060                1065

Lys Ala Lys Pro Ala Leu Glu  Asp Leu Arg Gln Gly  Leu Leu Pro
1070                1075                1080

Val Leu Glu Ser Phe Lys Val  Ser Phe Leu Ser Ala  Leu Glu Glu
1085                1090                1095

Tyr Thr Lys Lys Leu Asn Thr  Gln Gly Thr Pro Val  Thr Gln Glu
1100                1105                1110

Phe Trp Asp Asn Leu Glu Lys  Glu Thr Glu Gly Leu  Arg Gln Glu
1115                1120                1125

Met Ser Lys Asp Leu Glu Glu  Val Lys Ala Lys Val  Gln Pro Tyr
1130                1135                1140

Leu Asp Asp Phe Gln Lys Lys  Trp Gln Glu Glu Met  Glu Leu Tyr
1145                1150                1155

Arg Gln Lys Val Glu Pro Leu  Arg Ala Glu Leu Gln  Glu Gly Ala
1160                1165                1170

Arg Gln Lys Leu His Glu Leu  Gln Glu Lys Leu Ser  Pro Leu Gly
1175                1180                1185

Glu Glu Met Arg Asp Arg Ala  Arg Ala His Val Asp  Ala Leu Arg
1190                1195                1200

Thr His Leu Ala Pro Tyr Ser  Asp Glu Leu Arg Gln  Arg Leu Ala
1205                1210                1215

Ala Arg Leu Glu Ala Leu Lys  Glu Asn Gly Gly Ala  Arg Leu Ala
1220                1225                1230

Glu Tyr His Ala Lys Ala Thr  Glu His Leu Ser Thr  Leu Ser Glu
1235                1240                1245

Lys Ala Lys Pro Ala Leu Glu  Asp Leu Arg Gln Gly  Leu Leu Pro
1250                1255                1260

Val Leu Glu Ser Phe Lys Val  Ser Phe Leu Ser Ala  Leu Glu Glu
1265                1270                1275

Tyr Thr Lys Lys Leu Asn Thr  Gln Gly Thr Pro Val  Thr Gln Glu
1280                1285                1290

Phe Trp Asp Asn Leu Glu Lys  Glu Thr Glu Gly Leu  Arg Gln Glu
1295                1300                1305

Met Ser Lys Asp Leu Glu Glu  Val Lys Ala Lys Val  Gln Pro Tyr
1310                1315                1320

Leu Asp Asp Phe Gln Lys Lys  Trp Gln Glu Glu Met  Glu Leu Tyr
1325                1330                1335

Arg Gln Lys Val Glu Pro Leu  Arg Ala Glu Leu Gln  Glu Gly Ala
1340                1345                1350

Arg Gln Lys Leu His Glu Leu  Gln Glu Lys Leu Ser  Pro Leu Gly
1355                1360                1365

Glu Glu Met Arg Asp Arg Ala  Arg Ala His Val Asp  Ala Leu Arg
1370                1375                1380
```

Thr His Leu Ala Pro Tyr Ser Asp Glu Leu Arg Gln Arg Leu Ala
    1385            1390                1395

Ala Arg Leu Glu Ala Leu Lys Glu Asn Gly Gly Ala Arg Leu Ala
    1400            1405                1410

Glu Tyr His Ala Lys Ala Thr Glu His Leu Ser Thr Leu Ser Glu
    1415            1420                1425

Lys Ala Lys Pro Ala Leu Glu Asp Leu Arg Gln Gly Leu Leu Pro
    1430            1435                1440

Val Leu Glu Ser Phe Lys Val Ser Phe Leu Ser Ala Leu Glu Glu
    1445            1450                1455

Tyr Thr Lys Lys Leu Asn Thr Gln Gly Thr Pro Val Thr Gln Glu
    1460            1465                1470

Phe Trp Asp Asn Leu Glu Lys Glu Thr Glu Gly Leu Arg Gln Glu
    1475            1480                1485

Met Ser Lys Asp Leu Glu Glu Val Lys Ala Lys Val Gln Pro Tyr
    1490            1495                1500

Leu Asp Asp Phe Gln Lys Lys Trp Gln Glu Glu Met Glu Leu Tyr
    1505            1510                1515

Arg Gln Lys Val Glu Pro Leu Arg Ala Glu Leu Gln Glu Gly Ala
    1520            1525                1530

Arg Gln Lys Leu His Glu Leu Gln Glu Lys Leu Ser Pro Leu Gly
    1535            1540                1545

Glu Glu Met Arg Asp Arg Ala Arg Ala His Val Asp Ala Leu Arg
    1550            1555                1560

Thr His Leu Ala Pro Tyr Ser Asp Glu Leu Arg Gln Arg Leu Ala
    1565            1570                1575

Ala Arg Leu Glu Ala Leu Lys Glu Asn Gly Gly Ala Arg Leu Ala
    1580            1585                1590

Glu Tyr His Ala Lys Ala Thr Glu His Leu Ser Thr Leu Ser Glu
    1595            1600                1605

Lys Ala Lys Pro Ala Leu Glu Asp Leu Arg Gln Gly Leu Leu Pro
    1610            1615                1620

Val Leu Glu Ser Phe Lys Val Ser Phe Leu Ser Ala Leu Glu Glu
    1625            1630                1635

Tyr Thr Lys Lys Leu Asn Thr Gln Leu Pro Gly Thr Gly Ala Ala
    1640            1645                1650

Ala Leu Glu His His His His His His
    1655            1660

<210> SEQ ID NO 23
<211> LENGTH: 1842
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Gly Ser Ser His His His His His His Glu Asn Leu Tyr Phe Gln
1               5                   10                  15

Gly Ser Thr Phe Ser Lys Leu Arg Glu Gln Leu Gly Pro Val Thr Gln
                20                  25                  30

Glu Phe Trp Asp Asn Leu Glu Lys Glu Thr Glu Gly Leu Arg Gln Glu
            35                  40                  45

Met Ser Lys Asp Leu Glu Glu Val Lys Ala Lys Val Gln Pro Tyr Leu

-continued

```
                50                  55                  60
Asp Asp Phe Gln Lys Lys Trp Gln Glu Glu Met Glu Leu Tyr Arg Gln
 65                  70                  75                  80

Lys Val Glu Pro Leu Arg Ala Glu Leu Gln Glu Gly Ala Arg Gln Lys
                    85                  90                  95

Leu His Glu Leu Gln Glu Lys Leu Ser Pro Leu Gly Glu Glu Met Arg
                100                 105                 110

Asp Arg Ala Arg Ala His Val Asp Ala Leu Arg Thr His Leu Ala Pro
                115                 120                 125

Tyr Ser Asp Glu Leu Arg Gln Arg Leu Ala Ala Arg Leu Glu Ala Leu
                130                 135                 140

Lys Glu Asn Gly Gly Ala Arg Leu Ala Glu Tyr His Ala Lys Ala Thr
145                 150                 155                 160

Glu His Leu Ser Thr Leu Ser Glu Lys Ala Lys Pro Ala Leu Glu Asp
                165                 170                 175

Leu Arg Gln Gly Leu Leu Pro Val Leu Glu Ser Phe Lys Val Ser Phe
                180                 185                 190

Leu Ser Ala Leu Glu Glu Tyr Thr Lys Lys Leu Asn Thr Gln Gly Thr
                195                 200                 205

Pro Val Thr Gln Glu Phe Trp Asp Asn Leu Glu Lys Glu Thr Glu Gly
                210                 215                 220

Leu Arg Gln Glu Met Ser Lys Asp Leu Glu Glu Val Lys Ala Lys Val
225                 230                 235                 240

Gln Pro Tyr Leu Asp Asp Phe Gln Lys Lys Trp Gln Glu Glu Met Glu
                245                 250                 255

Leu Tyr Arg Gln Lys Val Glu Pro Leu Arg Ala Glu Leu Gln Glu Gly
                260                 265                 270

Ala Arg Gln Lys Leu His Glu Leu Gln Glu Lys Leu Ser Pro Leu Gly
                275                 280                 285

Glu Glu Met Arg Asp Arg Ala Arg Ala His Val Asp Ala Leu Arg Thr
                290                 295                 300

His Leu Ala Pro Tyr Ser Asp Glu Leu Arg Gln Arg Leu Ala Ala Arg
305                 310                 315                 320

Leu Glu Ala Leu Lys Glu Asn Gly Gly Ala Arg Leu Ala Glu Tyr His
                325                 330                 335

Ala Lys Ala Thr Glu His Leu Ser Thr Leu Ser Glu Lys Ala Lys Pro
                340                 345                 350

Ala Leu Glu Asp Leu Arg Gln Gly Leu Leu Pro Val Leu Glu Ser Phe
                355                 360                 365

Lys Val Ser Phe Leu Ser Ala Leu Glu Glu Tyr Thr Lys Lys Leu Asn
                370                 375                 380

Thr Gln Gly Thr Pro Val Thr Gln Glu Phe Trp Asp Asn Leu Glu Lys
385                 390                 395                 400

Glu Thr Glu Gly Leu Arg Gln Glu Met Ser Lys Asp Leu Glu Glu Val
                405                 410                 415

Lys Ala Lys Val Gln Pro Tyr Leu Asp Asp Phe Gln Lys Lys Trp Gln
                420                 425                 430

Glu Glu Met Glu Leu Tyr Arg Gln Lys Val Glu Pro Leu Arg Ala Glu
                435                 440                 445

Leu Gln Glu Gly Ala Arg Gln Lys Leu His Glu Leu Gln Glu Lys Leu
                450                 455                 460

Ser Pro Leu Gly Glu Glu Met Arg Asp Arg Ala Arg Ala His Val Asp
465                 470                 475                 480
```

```
Ala Leu Arg Thr His Leu Ala Pro Tyr Ser Asp Glu Leu Arg Gln Arg
            485                 490                 495

Leu Ala Ala Arg Leu Glu Ala Leu Lys Glu Asn Gly Gly Ala Arg Leu
            500                 505                 510

Ala Glu Tyr His Ala Lys Ala Thr Glu His Leu Ser Thr Leu Ser Glu
            515                 520                 525

Lys Ala Lys Pro Ala Leu Glu Asp Leu Arg Gln Gly Leu Leu Pro Val
        530                 535                 540

Leu Glu Ser Phe Lys Val Ser Phe Leu Ser Ala Leu Glu Glu Tyr Thr
545                 550                 555                 560

Lys Lys Leu Asn Thr Gln Gly Thr Pro Val Thr Gln Glu Phe Trp Asp
                565                 570                 575

Asn Leu Glu Lys Glu Thr Glu Gly Leu Arg Gln Glu Met Ser Lys Asp
            580                 585                 590

Leu Glu Glu Val Lys Ala Lys Val Gln Pro Tyr Leu Asp Asp Phe Gln
            595                 600                 605

Lys Lys Trp Gln Glu Glu Met Glu Leu Tyr Arg Gln Lys Val Glu Pro
        610                 615                 620

Leu Arg Ala Glu Leu Gln Glu Gly Ala Arg Gln Lys Leu His Glu Leu
625                 630                 635                 640

Gln Glu Lys Leu Ser Pro Leu Gly Glu Glu Met Arg Asp Arg Ala Arg
                645                 650                 655

Ala His Val Asp Ala Leu Arg Thr His Leu Ala Pro Tyr Ser Asp Glu
            660                 665                 670

Leu Arg Gln Arg Leu Ala Ala Arg Leu Glu Ala Leu Lys Glu Asn Gly
            675                 680                 685

Gly Ala Arg Leu Ala Glu Tyr His Ala Lys Ala Thr Glu His Leu Ser
        690                 695                 700

Thr Leu Ser Glu Lys Ala Lys Pro Ala Leu Glu Asp Leu Arg Gln Gly
705                 710                 715                 720

Leu Leu Pro Val Leu Glu Ser Phe Lys Val Ser Phe Leu Ser Ala Leu
                725                 730                 735

Glu Glu Tyr Thr Lys Lys Leu Asn Thr Gln Gly Thr Pro Val Thr Gln
            740                 745                 750

Glu Phe Trp Asp Asn Leu Glu Lys Glu Thr Glu Gly Leu Arg Gln Glu
            755                 760                 765

Met Ser Lys Asp Leu Glu Glu Val Lys Ala Lys Val Gln Pro Tyr Leu
        770                 775                 780

Asp Asp Phe Gln Lys Lys Trp Gln Glu Glu Met Glu Leu Tyr Arg Gln
785                 790                 795                 800

Lys Val Glu Pro Leu Arg Ala Glu Leu Gln Glu Gly Ala Arg Gln Lys
                805                 810                 815

Leu His Glu Leu Gln Glu Lys Leu Ser Pro Leu Gly Glu Glu Met Arg
            820                 825                 830

Asp Arg Ala Arg Ala His Val Asp Ala Leu Arg Thr His Leu Ala Pro
            835                 840                 845

Tyr Ser Asp Glu Leu Arg Gln Arg Leu Ala Ala Arg Leu Glu Ala Leu
        850                 855                 860

Lys Glu Asn Gly Gly Ala Arg Leu Ala Glu Tyr His Ala Lys Ala Thr
865                 870                 875                 880

Glu His Leu Ser Thr Leu Ser Glu Lys Ala Lys Pro Ala Leu Glu Asp
                885                 890                 895
```

```
Leu Arg Gln Gly Leu Leu Pro Val Leu Glu Ser Phe Lys Val Ser Phe
            900                 905                 910

Leu Ser Ala Leu Glu Glu Tyr Thr Lys Lys Leu Asn Thr Gln Gly Thr
        915                 920                 925

Pro Val Thr Gln Glu Phe Trp Asp Asn Leu Glu Lys Glu Thr Glu Gly
    930                 935                 940

Leu Arg Gln Glu Met Ser Lys Asp Leu Glu Glu Val Lys Ala Lys Val
945                 950                 955                 960

Gln Pro Tyr Leu Asp Asp Phe Gln Lys Lys Trp Gln Glu Glu Met Glu
                965                 970                 975

Leu Tyr Arg Gln Lys Val Glu Pro Leu Arg Ala Glu Leu Gln Glu Gly
            980                 985                 990

Ala Arg Gln Lys Leu His Glu Leu Gln Glu Lys Leu Ser Pro Leu Gly
        995                 1000                1005

Glu Glu Met Arg Asp Arg Ala Arg Ala His Val Asp Ala Leu Arg
    1010                1015                1020

Thr His Leu Ala Pro Tyr Ser Asp Glu Leu Arg Gln Arg Leu Ala
    1025                1030                1035

Ala Arg Leu Glu Ala Leu Lys Glu Asn Gly Gly Ala Arg Leu Ala
    1040                1045                1050

Glu Tyr His Ala Lys Ala Thr Glu His Leu Ser Thr Leu Ser Glu
    1055                1060                1065

Lys Ala Lys Pro Ala Leu Glu Asp Leu Arg Gln Gly Leu Leu Pro
    1070                1075                1080

Val Leu Glu Ser Phe Lys Val Ser Phe Leu Ser Ala Leu Glu Glu
    1085                1090                1095

Tyr Thr Lys Lys Leu Asn Thr Gln Gly Thr Pro Val Thr Gln Glu
    1100                1105                1110

Phe Trp Asp Asn Leu Glu Lys Glu Thr Glu Gly Leu Arg Gln Glu
    1115                1120                1125

Met Ser Lys Asp Leu Glu Glu Val Lys Ala Lys Val Gln Pro Tyr
    1130                1135                1140

Leu Asp Asp Phe Gln Lys Lys Trp Gln Glu Glu Met Glu Leu Tyr
    1145                1150                1155

Arg Gln Lys Val Glu Pro Leu Arg Ala Glu Leu Gln Glu Gly Ala
    1160                1165                1170

Arg Gln Lys Leu His Glu Leu Gln Glu Lys Leu Ser Pro Leu Gly
    1175                1180                1185

Glu Glu Met Arg Asp Arg Ala Arg Ala His Val Asp Ala Leu Arg
    1190                1195                1200

Thr His Leu Ala Pro Tyr Ser Asp Glu Leu Arg Gln Arg Leu Ala
    1205                1210                1215

Ala Arg Leu Glu Ala Leu Lys Glu Asn Gly Gly Ala Arg Leu Ala
    1220                1225                1230

Glu Tyr His Ala Lys Ala Thr Glu His Leu Ser Thr Leu Ser Glu
    1235                1240                1245

Lys Ala Lys Pro Ala Leu Glu Asp Leu Arg Gln Gly Leu Leu Pro
    1250                1255                1260

Val Leu Glu Ser Phe Lys Val Ser Phe Leu Ser Ala Leu Glu Glu
    1265                1270                1275

Tyr Thr Lys Lys Leu Asn Thr Gln Gly Thr Pro Val Thr Gln Glu
    1280                1285                1290

Phe Trp Asp Asn Leu Glu Lys Glu Thr Glu Gly Leu Arg Gln Glu
```

```
            1295                1300                1305
Met Ser Lys Asp Leu Glu Glu Val Lys Ala Lys Val Gln Pro Tyr
    1310                1315                1320

Leu Asp Asp Phe Gln Lys Lys Trp Gln Glu Glu Met Glu Leu Tyr
    1325                1330                1335

Arg Gln Lys Val Glu Pro Leu Arg Ala Glu Leu Gln Glu Gly Ala
    1340                1345                1350

Arg Gln Lys Leu His Glu Leu Gln Glu Lys Leu Ser Pro Leu Gly
    1355                1360                1365

Glu Glu Met Arg Asp Arg Ala Arg Ala His Val Asp Ala Leu Arg
    1370                1375                1380

Thr His Leu Ala Pro Tyr Ser Asp Glu Leu Arg Gln Arg Leu Ala
    1385                1390                1395

Ala Arg Leu Glu Ala Leu Lys Glu Asn Gly Gly Ala Arg Leu Ala
    1400                1405                1410

Glu Tyr His Ala Lys Ala Thr Glu His Leu Ser Thr Leu Ser Glu
    1415                1420                1425

Lys Ala Lys Pro Ala Leu Glu Asp Leu Arg Gln Gly Leu Leu Pro
    1430                1435                1440

Val Leu Glu Ser Phe Lys Val Ser Phe Leu Ser Ala Leu Glu Glu
    1445                1450                1455

Tyr Thr Lys Lys Leu Asn Thr Gln Gly Thr Pro Val Thr Gln Glu
    1460                1465                1470

Phe Trp Asp Asn Leu Glu Lys Glu Thr Glu Gly Leu Arg Gln Glu
    1475                1480                1485

Met Ser Lys Asp Leu Glu Glu Val Lys Ala Lys Val Gln Pro Tyr
    1490                1495                1500

Leu Asp Asp Phe Gln Lys Lys Trp Gln Glu Glu Met Glu Leu Tyr
    1505                1510                1515

Arg Gln Lys Val Glu Pro Leu Arg Ala Glu Leu Gln Glu Gly Ala
    1520                1525                1530

Arg Gln Lys Leu His Glu Leu Gln Glu Lys Leu Ser Pro Leu Gly
    1535                1540                1545

Glu Glu Met Arg Asp Arg Ala Arg Ala His Val Asp Ala Leu Arg
    1550                1555                1560

Thr His Leu Ala Pro Tyr Ser Asp Glu Leu Arg Gln Arg Leu Ala
    1565                1570                1575

Ala Arg Leu Glu Ala Leu Lys Glu Asn Gly Gly Ala Arg Leu Ala
    1580                1585                1590

Glu Tyr His Ala Lys Ala Thr Glu His Leu Ser Thr Leu Ser Glu
    1595                1600                1605

Lys Ala Lys Pro Ala Leu Glu Asp Leu Arg Gln Gly Leu Leu Pro
    1610                1615                1620

Val Leu Glu Ser Phe Lys Val Ser Phe Leu Ser Ala Leu Glu Glu
    1625                1630                1635

Tyr Thr Lys Lys Leu Asn Thr Gln Gly Thr Pro Val Thr Gln Glu
    1640                1645                1650

Phe Trp Asp Asn Leu Glu Lys Glu Thr Glu Gly Leu Arg Gln Glu
    1655                1660                1665

Met Ser Lys Asp Leu Glu Glu Val Lys Ala Lys Val Gln Pro Tyr
    1670                1675                1680

Leu Asp Asp Phe Gln Lys Lys Trp Gln Glu Glu Met Glu Leu Tyr
    1685                1690                1695
```

```
Arg Gln Lys Val Glu Pro Leu Arg Ala Glu Leu Gln Glu Gly Ala
    1700                1705                1710

Arg Gln Lys Leu His Glu Leu Gln Glu Lys Leu Ser Pro Leu Gly
    1715                1720                1725

Glu Glu Met Arg Asp Arg Ala Arg Ala His Val Asp Ala Leu Arg
    1730                1735                1740

Thr His Leu Ala Pro Tyr Ser Asp Glu Leu Arg Gln Arg Leu Ala
    1745                1750                1755

Ala Arg Leu Glu Ala Leu Lys Glu Asn Gly Gly Ala Arg Leu Ala
    1760                1765                1770

Glu Tyr His Ala Lys Ala Thr Glu His Leu Ser Thr Leu Ser Glu
    1775                1780                1785

Lys Ala Lys Pro Ala Leu Glu Asp Leu Arg Gln Gly Leu Leu Pro
    1790                1795                1800

Val Leu Glu Ser Phe Lys Val Ser Phe Leu Ser Ala Leu Glu Glu
    1805                1810                1815

Tyr Thr Lys Lys Leu Asn Thr Gln Leu Pro Gly Thr Gly Ala Ala
    1820                1825                1830

Ala Leu Glu His His His His His His
    1835                1840

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Gly or Ala

<400> SEQUENCE: 24

Leu Pro Gly Thr Xaa
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Gly or Ala

<400> SEQUENCE: 25

Leu Pro Ser Thr Xaa
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Gly or Ala
```

```
<400> SEQUENCE: 26

Leu Pro Glu Thr Xaa
1               5

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Trp Phe Lys Ala Phe Tyr Asp Lys Leu Ala Glu Lys Phe Lys Glu
1               5                   10                  15

Ala Phe

<210> SEQ ID NO 28
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Phe Leu Lys Ala Phe Tyr Asp Lys Val Ala Glu Lys Phe Lys Glu
1               5                   10                  15

Ala Ala Pro Asp Trp Phe Lys Ala Phe Tyr Asp Lys Val Ala Glu Lys
            20                  25                  30

Phe Lys Glu Ala Phe
        35

<210> SEQ ID NO 29
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Leu Ala Leu Arg Leu Ala Leu Lys Ala Phe Lys Ala Ala Leu Lys
1               5                   10                  15

Leu Ala

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Leu Ala Leu Asp Leu Ala Leu Arg Ala Phe Lys Ala Ala Trp Lys
1               5                   10                  15

Leu Ala

<210> SEQ ID NO 31
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 31

Glu Leu Ala Trp Asp Leu Ala Phe Glu Ala Leu Asp Ala Glu Leu Lys
1               5                   10                  15

Leu Asp

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Phe Leu Lys Leu Leu Lys Lys Phe Leu Lys Leu Phe Lys Lys Leu Leu
1               5                   10                  15

Lys Leu Phe

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Trp Leu Lys Leu Leu Lys Lys Trp Leu Lys Leu Trp Lys Lys Leu Leu
1               5                   10                  15

Lys Leu

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Leu Leu Lys Phe Leu Lys Arg Leu Leu Lys Leu Leu Lys Asp Leu Trp
1               5                   10                  15

Lys Leu Leu

<210> SEQ ID NO 35
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Trp Glu Ala Ala Phe Ala Glu Ala Leu Ala Glu Ala Trp Ala Glu His
1               5                   10                  15

Leu Ala Glu Ala Leu Ala Glu Ala Val Glu Ala Leu Ala Ala
                20                  25                  30

<210> SEQ ID NO 36
<211> LENGTH: 30
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 37
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Ala Phe Ala Arg Ala Leu Ala Arg Ala Leu Lys Ala Leu Ala Arg
1               5                   10                  15

Ala Leu Lys Ala Leu Ala Arg
            20

<210> SEQ ID NO 38
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Leu Phe Glu Ala Leu Leu Glu Leu Leu Glu Ser Leu Trp Glu Leu
1               5                   10                  15

Leu Leu Glu Ala
            20

<210> SEQ ID NO 39
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Lys Leu Leu Lys Leu Leu Leu Lys Leu Trp Lys Lys Leu Leu Lys Leu
1               5                   10                  15

Leu Lys

<210> SEQ ID NO 40
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Trp Leu Lys Ala Phe Tyr Asp Lys Val Ala Glu Lys Leu Lys Glu
1               5                   10                  15

Ala Phe
```

<210> SEQ ID NO 41
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asp Trp Phe Lys Ala Phe Tyr Asp Lys Val Ala Glu Lys Phe Lys Glu
1               5                   10                  15

Ala Phe

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Val Pro Arg Gly Ser
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any large or medium hydrophobic residue
<220> FEATURE:
<221> NAME/KEY: MOD_RES
<222> LOCATION: (7)..(7)
<223> OTHER INFORMATION: Gly or Ala

<400> SEQUENCE: 43

Glu Xaa Leu Tyr Xaa Gln Xaa
1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Pro Gly Thr Gly Ser
1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 45

Leu Pro Gly Thr Ser Gly
1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Pro Ser Thr Gly Ser
1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Pro Ser Thr Ser Gly
1               5

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Pro Gly Thr
1

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Leu Pro Ser Thr
1

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Leu Pro Glu Thr
1

<210> SEQ ID NO 51
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 51

Leu Pro Xaa Thr Gly
1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Ser Thr Phe Ser Lys
1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Pro Gly Thr Gly
1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 54

His His His His His His
1               5

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Asn Thr Gln Leu Pro Gly Thr Gly His His His His His His
1               5                   10                  15

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(3)
<223> OTHER INFORMATION: Any amino acid

<400> SEQUENCE: 56

Leu Pro Xaa Thr Ala
1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Pro Gly Thr Ala
1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Pro Ser Thr Gly
1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Leu Pro Ser Thr Ala
1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Leu Pro Glu Thr Gly
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Leu Pro Glu Thr Ala
1               5
```

<210> SEQ ID NO 62
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Gly Ser Ser His His His His His His Glu Asn Leu Tyr Phe Gln
1               5                   10                  15

Gly Ser Thr Phe Ser Lys Leu Arg Glu Gln Leu Gly Pro Val Thr Gln
            20                  25                  30

Glu Phe Trp Cys Asn Leu Glu Lys Glu Thr Glu Gly Leu Arg Gln Glu
        35                  40                  45

Met Ser Lys Asp Leu Glu Glu Val Lys Ala Lys Val Gln Pro Tyr Leu
    50                  55                  60

Asp Asp Phe Gln Lys Lys Trp Gln Glu Glu Met Glu Leu Tyr Arg Gln
65                  70                  75                  80

Lys Val Glu Pro Leu Arg Ala Glu Leu Gln Glu Gly Ala Arg Gln Lys
                85                  90                  95

Leu His Glu Leu Gln Glu Lys Leu Ser Pro Leu Gly Glu Cys Met Arg
            100                 105                 110

Asp Arg Ala Arg Ala His Val Asp Ala Leu Arg Thr His Leu Ala Pro
        115                 120                 125

Tyr Ser Asp Glu Leu Arg Gln Arg Leu Ala Ala Arg Leu Glu Ala Leu
    130                 135                 140

Lys Glu Asn Gly Gly Ala Arg Leu Ala Glu Tyr His Ala Lys Ala Thr
145                 150                 155                 160

Glu His Leu Ser Thr Leu Ser Glu Lys Ala Lys Pro Ala Leu Cys Asp
                165                 170                 175

Leu Arg Gln Gly Leu Leu Pro Val Leu Glu Ser Phe Lys Val Ser Phe
            180                 185                 190

Leu Ser Ala Leu Glu Glu Tyr Thr Lys Lys Leu Asn Thr Gln Leu Pro
        195                 200                 205

Gly Thr Gly Ala Ala Ala Leu Glu His His His His His
    210                 215                 220

<210> SEQ ID NO 63
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(5)
<223> OTHER INFORMATION: This region may encompass 1-5 residues
<220> FEATURE:
<221> NAME/KEY: MISC_FEATURE
<222> LOCATION: (6)..(10)
<223> OTHER INFORMATION: This region may encompass 1-5 residues
<220> FEATURE:
<221> NAME/KEY: MISC_FEATURE
<222> LOCATION: (11)..(15)
<223> OTHER INFORMATION: This region may encompass 1-5 residues
<220> FEATURE:
<221> NAME/KEY: MISC_FEATURE
<222> LOCATION: (16)..(20)
<223> OTHER INFORMATION: This region may encompass 1-5 residues
<220> FEATURE:

```
<221> NAME/KEY: MISC_FEATURE
<222> LOCATION: (21)..(25)
<223> OTHER INFORMATION: This region may encompass 1-5 residues
<220> FEATURE:
<221> NAME/KEY: MISC_FEATURE
<222> LOCATION: (26)..(30)
<223> OTHER INFORMATION: This region may encompass 1-5 residues
<220> FEATURE:
<221> NAME/KEY: MISC_FEATURE
<222> LOCATION: (31)..(35)
<223> OTHER INFORMATION: This region may encompass 1-5 residues
<220> FEATURE:
<221> NAME/KEY: MISC_FEATURE
<222> LOCATION: (36)..(40)
<223> OTHER INFORMATION: This region may encompass 1-5 residues
<220> FEATURE:
<221> NAME/KEY: MISC_FEATURE
<222> LOCATION: (41)..(45)
<223> OTHER INFORMATION: This region may encompass 1-5 residues
<220> FEATURE:
<221> NAME/KEY: MISC_FEATURE
<222> LOCATION: (46)..(50)
<223> OTHER INFORMATION: This region may encompass 1-5 residues
<220> FEATURE:
<221> NAME/KEY: MISC_FEATURE
<222> LOCATION: (1)..(50)
<223> OTHER INFORMATION: This sequence may encompass 1-5 "Gly1-5 Ser1-5"
      repeating units, wherein some positions may be absent

<400> SEQUENCE: 63

Gly Gly Gly Gly Gly Ser Ser Ser Ser Ser Gly Gly Gly Gly Gly Ser
1               5                   10                  15

Ser Ser Ser Ser Gly Gly Gly Gly Gly Ser Ser Ser Ser Ser Gly Gly
            20                  25                  30

Gly Gly Gly Ser Ser Ser Ser Ser Gly Gly Gly Gly Gly Ser Ser Ser
        35                  40                  45

Ser Ser
    50

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Gly Gly Gly Ser
1               5

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Thr Gly Glu Lys Pro
1               5

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 66

Gly Gly Arg Arg
1

<210> SEQ ID NO 67
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(25)
<223> OTHER INFORMATION: This sequence may encompass 1-5 "Gly Gly Gly
      Gly Ser" repeating units

<400> SEQUENCE: 67

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 68
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Glu Gly Lys Ser Ser Gly Ser Gly Ser Glu Ser Lys Val Asp
1               5                   10

<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Glu Ser Gly Ser Val Ser Ser Glu Gln Leu Ala Gln Phe Arg Ser
1               5                   10                  15

Leu Asp

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Gly Arg Arg Gly Gly Gly Ser
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                                   peptide

<400> SEQUENCE: 71

Leu Arg Gln Arg Asp Gly Glu Arg Pro
1               5

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Leu Arg Gln Lys Asp Gly Gly Gly Ser Glu Arg Pro
1               5                   10

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Leu Arg Gln Lys Asp Gly Gly Gly Ser Gly Gly Gly Ser Glu Arg Pro
1               5                   10                  15

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Ser Thr Ser Gly Ser Gly Lys Pro Gly Ser Gly Glu Gly Ser Thr
1               5                   10                  15

Lys Gly

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 75

Leu Ala Xaa Thr Gly
1               5

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76
```

```
Leu Ser Glu Thr Gly
1               5

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 77

Leu Pro Xaa Ser Gly
1               5

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 78

Leu Pro Xaa Cys Gly
1               5

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 79

Leu Pro Xaa Ala Gly
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Ser Thr Phe Ser Lys Leu
1               5

<210> SEQ ID NO 81
<211> LENGTH: 20
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 81

Lys Leu Asn Thr Gln Leu Pro Gly Thr Ala Ala Ala Leu Glu His His
1               5                   10                  15

His His His His
            20

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Lys Leu Asn Thr Gln Leu Pro Gly Thr Gly Ser Thr Phe Ser Lys Leu
1               5                   10                  15

Arg

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Ala Leu Glu His His His His His His
1               5                   10

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Lys Leu Asn Thr Gln Leu Pro Gly Thr Gly Ser Thr Phe Ser Lys
1               5                   10                  15

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Asn Thr Gln Leu Pro Gly Thr Ala Ala
1               5

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

```
Asn Thr Gln Leu Pro Gly Thr Gly Ser Thr
1               5                   10
```

<210> SEQ ID NO 87
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

```
Leu Glu Glu Tyr Thr Lys Lys Leu Asn Thr Gln Leu Pro Gly Thr Gly
1               5                   10                  15

Ser Thr Phe Ser Lys Leu Arg Glu Gln Leu
            20                  25
```

<210> SEQ ID NO 88
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (53)..(53)
<223> OTHER INFORMATION: Any amino acid

<400> SEQUENCE: 88

```
Leu Glu Glu Lys Leu Asn Thr Gln Leu Pro Xaa Thr Gly Ser Thr Phe
1               5                   10                  15

Ser Lys Leu Arg Glu Leu Glu Glu Lys Leu Asn Thr Gln Leu Pro Xaa
            20                  25                  30

Thr Gly Ser Thr Phe Ser Lys Leu Arg Glu Leu Glu Glu Lys Leu Asn
        35                  40                  45

Thr Gln Leu Pro Xaa Thr Gly Ser Thr Phe Ser Lys Leu Arg Glu
    50                  55                  60
```

<210> SEQ ID NO 89
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

```
Leu Glu Glu Tyr Thr Lys Lys Leu Asn Thr Gln Leu Pro Gly Thr Gly
1               5                   10                  15

Ser Thr Phe Ser Lys Leu Arg Glu Leu Glu Glu Lys Leu Asn Thr Gln
            20                  25                  30

Leu Pro Gly Thr Gly Ser Thr Phe Ser Lys Leu Arg Glu
        35                  40                  45
```

<210> SEQ ID NO 90
<211> LENGTH: 184
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 90

```
Gly Ser Thr Phe Ser Lys Leu Arg Glu Gln Leu Gly Pro Val Thr Gln
1               5                   10                  15

Glu Phe Trp Asp Asn Leu Glu Lys Glu Thr Glu Gly Leu Arg Gln Glu
            20                  25                  30

Met Ser Lys Asp Leu Glu Glu Val Lys Ala Lys Val Gln Pro Tyr Leu
        35                  40                  45

Asp Asp Phe Gln Lys Lys Trp Gln Glu Glu Met Glu Leu Tyr Arg Gln
    50                  55                  60

Lys Val Glu Pro Leu Gly Glu Glu Met Arg Asp Arg Ala Arg Ala His
65                  70                  75                  80

Val Asp Ala Leu Arg Thr His Leu Ala Pro Tyr Ser Asp Glu Leu Arg
                85                  90                  95

Gln Arg Leu Ala Ala Arg Leu Glu Ala Leu Lys Glu Asn Gly Gly Ala
            100                 105                 110

Arg Leu Ala Glu Tyr His Ala Lys Ala Thr Glu His Leu Ser Thr Leu
        115                 120                 125

Ser Glu Lys Ala Lys Pro Ala Leu Glu Asp Leu Arg Gln Gly Leu Leu
    130                 135                 140

Pro Val Leu Glu Ser Phe Lys Val Ser Phe Leu Ser Ala Leu Glu Glu
145                 150                 155                 160

Tyr Thr Lys Lys Leu Asn Thr Gln Leu Pro Gly Thr Gly Ala Ala Ala
                165                 170                 175

Leu Glu His His His His His His
            180
```

<210> SEQ ID NO 91
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

```
Leu Asn Thr Gln Leu Pro Gly Thr Gly Ser Thr Phe Ser Lys
1               5                   10
```

<210> SEQ ID NO 92
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

```
Gly Ser Thr Phe Ser Lys Leu Arg Glu Gln Leu Gly Pro Val Thr Gln
1               5                   10                  15

Glu Phe Trp Asp Asn Leu Glu Lys Glu Thr Glu Gly Leu Arg Gln Glu
            20                  25                  30

Met Ser Lys Asp Leu Glu Glu Val Lys Ala Lys Val Gln Pro Tyr Leu
        35                  40                  45

Asp Asp Phe Gln Lys Lys Trp Gln Glu Glu Met Glu Leu Tyr Arg Gln
    50                  55                  60
```

```
Lys Val Glu Pro Leu Arg Ala Glu Leu Gln Glu Gly Ala Arg Gln Lys
 65                  70                  75                  80

Leu His Glu Leu Gln Glu Lys Leu Ser Pro Leu Gly Glu Glu Met Arg
             85                  90                  95

Asp Arg Ala Arg Ala His Val Asp Ala Leu Arg Thr His Leu Ala Pro
            100                 105                 110

Tyr Ser Asp Glu Leu Arg Gln Arg Leu Ala Ala Arg Leu Glu Ala Leu
            115                 120                 125

Lys Glu Asn Gly Gly Ala Arg Leu Ala Glu Tyr His Ala Lys Ala Thr
130                 135                 140

Glu His Leu Ser Thr Leu Ser Glu Lys Ala Lys Pro Ala Leu Glu Asp
145                 150                 155                 160

Leu Arg Gln Gly Leu Leu Pro Val Leu Glu Ser Phe Lys Val Ser Phe
                165                 170                 175

Leu Ser Ala Leu Glu Glu Tyr Thr Lys Lys Leu Asn Thr Gln Gly Thr
            180                 185                 190

Pro Val Thr Gln Glu Phe Trp Asp Asn Leu Glu Lys Glu Thr Glu Gly
            195                 200                 205

Leu Arg Gln Glu Met Ser Lys Asp Leu Glu Glu Val Lys Ala Lys Val
            210                 215                 220

Gln Pro Tyr Leu Asp Asp Phe Gln Lys Lys Trp Gln Glu Glu Met Glu
225                 230                 235                 240

Leu Tyr Arg Gln Lys Val Glu Pro Leu Arg Ala Glu Leu Gln Glu Gly
                245                 250                 255

Ala Arg Gln Lys Leu His Glu Leu Gln Glu Lys Leu Ser Pro Leu Gly
            260                 265                 270

Glu Glu Met Arg Asp Arg Ala Arg Ala His Val Asp Ala Leu Arg Thr
            275                 280                 285

His Leu Ala Pro Tyr Ser Asp Glu Leu Arg Gln Arg Leu Ala Ala Arg
290                 295                 300

Leu Glu Ala Leu Lys Glu Asn Gly Gly Ala Arg Leu Ala Glu Tyr His
305                 310                 315                 320

Ala Lys Ala Thr Glu His Leu Ser Thr Leu Ser Glu Lys Ala Lys Pro
                325                 330                 335

Ala Leu Glu Asp Leu Arg Gln Gly Leu Leu Pro Val Leu Glu Ser Phe
            340                 345                 350

Lys Val Ser Phe Leu Ser Ala Leu Glu Glu Tyr Thr Lys Lys Leu Asn
            355                 360                 365

Thr Gln Gly Thr Pro Val Thr Gln Glu Phe Trp Asp Asn Leu Glu Lys
            370                 375                 380

Glu Thr Glu Gly Leu Arg Gln Glu Met Ser Lys Asp Leu Glu Glu Val
385                 390                 395                 400

Lys Ala Lys Val Gln Pro Tyr Leu Asp Asp Phe Gln Lys Lys Trp Gln
                405                 410                 415

Glu Glu Met Glu Leu Tyr Arg Gln Lys Val Glu Pro Leu Arg Ala Glu
            420                 425                 430

Leu Gln Glu Gly Ala Arg Gln Lys Leu His Glu Leu Gln Glu Lys Leu
            435                 440                 445

Ser Pro Leu Gly Glu Glu Met Arg Asp Arg Ala Arg Ala His Val Asp
            450                 455                 460

Ala Leu Arg Thr His Leu Ala Pro Tyr Ser Asp Glu Leu Arg Gln Arg
465                 470                 475                 480
```

```
Leu Ala Ala Arg Leu Glu Ala Leu Lys Glu Asn Gly Gly Ala Arg Leu
                485                 490                 495

Ala Glu Tyr His Ala Lys Ala Thr Glu His Leu Ser Thr Leu Ser Glu
            500                 505                 510

Lys Ala Lys Pro Ala Leu Glu Asp Leu Arg Gln Gly Leu Leu Pro Val
        515                 520                 525

Leu Glu Ser Phe Lys Val Ser Phe Leu Ser Ala Leu Glu Glu Tyr Thr
    530                 535                 540

Lys Lys Leu Asn Thr Gln Leu Pro Gly Thr Gly Ala Ala Ala Leu Glu
545                 550                 555                 560

His His His His His His
                565

<210> SEQ ID NO 93
<211> LENGTH: 926
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gly Ser Thr Phe Ser Lys Leu Arg Glu Gln Leu Gly Pro Val Thr Gln
1               5                   10                  15

Glu Phe Trp Asp Asn Leu Glu Lys Glu Thr Glu Gly Leu Arg Gln Glu
            20                  25                  30

Met Ser Lys Asp Leu Glu Glu Val Lys Ala Lys Val Gln Pro Tyr Leu
        35                  40                  45

Asp Asp Phe Gln Lys Lys Trp Gln Glu Glu Met Glu Leu Tyr Arg Gln
    50                  55                  60

Lys Val Glu Pro Leu Arg Ala Glu Leu Gln Glu Gly Ala Arg Gln Lys
65                  70                  75                  80

Leu His Glu Leu Gln Glu Lys Leu Ser Pro Leu Gly Glu Glu Met Arg
                85                  90                  95

Asp Arg Ala Arg Ala His Val Asp Ala Leu Arg Thr His Leu Ala Pro
            100                 105                 110

Tyr Ser Asp Glu Leu Arg Gln Arg Leu Ala Ala Arg Leu Glu Ala Leu
        115                 120                 125

Lys Glu Asn Gly Gly Ala Arg Leu Ala Glu Tyr His Ala Lys Ala Thr
    130                 135                 140

Glu His Leu Ser Thr Leu Ser Glu Lys Ala Lys Pro Ala Leu Glu Asp
145                 150                 155                 160

Leu Arg Gln Gly Leu Leu Pro Val Leu Glu Ser Phe Lys Val Ser Phe
                165                 170                 175

Leu Ser Ala Leu Glu Glu Tyr Thr Lys Lys Leu Asn Thr Gln Gly Thr
            180                 185                 190

Pro Val Thr Gln Glu Phe Trp Asp Asn Leu Glu Lys Glu Thr Glu Gly
        195                 200                 205

Leu Arg Gln Glu Met Ser Lys Asp Leu Glu Glu Val Lys Ala Lys Val
    210                 215                 220

Gln Pro Tyr Leu Asp Asp Phe Gln Lys Lys Trp Gln Glu Glu Met Glu
225                 230                 235                 240

Leu Tyr Arg Gln Lys Val Glu Pro Leu Arg Ala Glu Leu Gln Glu Gly
                245                 250                 255

Ala Arg Gln Lys Leu His Glu Leu Gln Glu Lys Leu Ser Pro Leu Gly
            260                 265                 270
```

```
Glu Glu Met Arg Asp Arg Ala Arg Ala His Val Asp Ala Leu Arg Thr
            275                 280                 285

His Leu Ala Pro Tyr Ser Asp Glu Leu Arg Gln Arg Leu Ala Ala Arg
            290                 295                 300

Leu Glu Ala Leu Lys Glu Asn Gly Gly Ala Arg Leu Ala Glu Tyr His
305                 310                 315                 320

Ala Lys Ala Thr Glu His Leu Ser Thr Leu Ser Glu Lys Ala Lys Pro
                325                 330                 335

Ala Leu Glu Asp Leu Arg Gln Gly Leu Leu Pro Val Leu Glu Ser Phe
            340                 345                 350

Lys Val Ser Phe Leu Ser Ala Leu Glu Glu Tyr Thr Lys Lys Leu Asn
            355                 360                 365

Thr Gln Gly Thr Pro Val Thr Gln Glu Phe Trp Asp Asn Leu Glu Lys
            370                 375                 380

Glu Thr Glu Gly Leu Arg Gln Glu Met Ser Lys Asp Leu Glu Glu Val
385                 390                 395                 400

Lys Ala Lys Val Gln Pro Tyr Leu Asp Asp Phe Gln Lys Lys Trp Gln
                405                 410                 415

Glu Glu Met Glu Leu Tyr Arg Gln Lys Val Glu Pro Leu Arg Ala Glu
            420                 425                 430

Leu Gln Glu Gly Ala Arg Gln Lys Leu His Glu Leu Gln Glu Lys Leu
            435                 440                 445

Ser Pro Leu Gly Glu Glu Met Arg Asp Arg Ala Arg Ala His Val Asp
            450                 455                 460

Ala Leu Arg Thr His Leu Ala Pro Tyr Ser Asp Glu Leu Arg Gln Arg
465                 470                 475                 480

Leu Ala Ala Arg Leu Glu Ala Leu Lys Glu Asn Gly Gly Ala Arg Leu
                485                 490                 495

Ala Glu Tyr His Ala Lys Ala Thr Glu His Leu Ser Thr Leu Ser Glu
            500                 505                 510

Lys Ala Lys Pro Ala Leu Glu Asp Leu Arg Gln Gly Leu Leu Pro Val
            515                 520                 525

Leu Glu Ser Phe Lys Val Ser Phe Leu Ser Ala Leu Glu Glu Tyr Thr
            530                 535                 540

Lys Lys Leu Asn Thr Gln Gly Thr Pro Val Thr Gln Glu Phe Trp Asp
545                 550                 555                 560

Asn Leu Glu Lys Glu Thr Glu Gly Leu Arg Gln Glu Met Ser Lys Asp
                565                 570                 575

Leu Glu Glu Val Lys Ala Lys Val Gln Pro Tyr Leu Asp Asp Phe Gln
            580                 585                 590

Lys Lys Trp Gln Glu Glu Met Glu Leu Tyr Arg Gln Lys Val Glu Pro
            595                 600                 605

Leu Arg Ala Glu Leu Gln Glu Gly Ala Arg Gln Lys Leu His Glu Leu
            610                 615                 620

Gln Glu Lys Leu Ser Pro Leu Gly Glu Glu Met Arg Asp Arg Ala Arg
625                 630                 635                 640

Ala His Val Asp Ala Leu Arg Thr His Leu Ala Pro Tyr Ser Asp Glu
                645                 650                 655

Leu Arg Gln Arg Leu Ala Ala Arg Leu Glu Ala Leu Lys Glu Asn Gly
            660                 665                 670

Gly Ala Arg Leu Ala Glu Tyr His Ala Lys Ala Thr Glu His Leu Ser
            675                 680                 685
```

-continued

```
Thr Leu Ser Glu Lys Ala Lys Pro Ala Leu Glu Asp Leu Arg Gln Gly
    690             695             700

Leu Leu Pro Val Leu Glu Ser Phe Lys Val Ser Phe Leu Ser Ala Leu
705             710             715             720

Glu Glu Tyr Thr Lys Lys Leu Asn Thr Gln Gly Thr Pro Val Thr Gln
            725             730             735

Glu Phe Trp Asp Asn Leu Glu Lys Glu Thr Glu Gly Leu Arg Gln Glu
            740             745             750

Met Ser Lys Asp Leu Glu Glu Val Lys Ala Lys Val Gln Pro Tyr Leu
        755             760             765

Asp Asp Phe Gln Lys Lys Trp Gln Glu Met Glu Leu Tyr Arg Gln
770             775             780

Lys Val Glu Pro Leu Arg Ala Glu Leu Gln Glu Gly Ala Arg Gln Lys
785             790             795             800

Leu His Glu Leu Gln Glu Lys Leu Ser Pro Leu Gly Glu Glu Met Arg
                805             810             815

Asp Arg Ala Arg Ala His Val Asp Ala Leu Arg Thr His Leu Ala Pro
            820             825             830

Tyr Ser Asp Glu Leu Arg Gln Arg Leu Ala Ala Arg Leu Glu Ala Leu
            835             840             845

Lys Glu Asn Gly Gly Ala Arg Leu Ala Glu Tyr His Ala Lys Ala Thr
850             855             860

Glu His Leu Ser Thr Leu Ser Glu Lys Ala Lys Pro Ala Leu Glu Asp
865             870             875             880

Leu Arg Gln Gly Leu Leu Pro Val Leu Glu Ser Phe Lys Val Ser Phe
            885             890             895

Leu Ser Ala Leu Glu Glu Tyr Thr Lys Lys Leu Asn Thr Gln Leu Pro
            900             905             910

Gly Thr Gly Ala Ala Ala Leu Glu His His His His His
            915             920             925
```